(12) United States Patent
Zhang et al.

(10) Patent No.: US 11,679,108 B2
(45) Date of Patent: Jun. 20, 2023

(54) AROMATIC HETEROCYCLIC COMPOUND, AND PHARMACEUTICAL COMPOSITION AND USE THEREOF

(71) Applicant: GUANGZHOU HENOVCOM BIOSCIENCE CO., LTD., Guangzhou (CN)

(72) Inventors: Jiancun Zhang, Guangzhou (CN); Qingan Zou, Guangzhou (CN); Yanwei Chen, Guangzhou (CN); Ning Kang, Guangzhou (CN); Lijun Zhang, Guangzhou (CN); Yang Hu, Guangzhou (CN); Jufu Zhang, Guangzhou (CN)

(73) Assignee: GUANGZHOU HENOVCOM BIOSCIENCE CO., LTD., Guangzhou (CN)

( * ) Notice: Subject to any disclaimer, the term of this patent is extended or adjusted under 35 U.S.C. 154(b) by 0 days.

(21) Appl. No.: 17/057,782

(22) PCT Filed: May 22, 2019

(86) PCT No.: PCT/CN2019/087974
§ 371 (c)(1),
(2) Date: Nov. 23, 2020

(87) PCT Pub. No.: WO2019/223721
PCT Pub. Date: Nov. 28, 2019

(65) Prior Publication Data
US 2022/0088008 A1 Mar. 24, 2022

(30) Foreign Application Priority Data
May 24, 2018 (CN) .......................... 201810508922.1

(51) Int. Cl.
| | |
|---|---|
| *A61K 31/496* | (2006.01) |
| *A61K 31/433* | (2006.01) |
| *A61K 31/438* | (2006.01) |
| *A61K 31/454* | (2006.01) |
| *A61K 31/499* | (2006.01) |
| *A61K 31/4995* | (2006.01) |
| *A61K 31/5377* | (2006.01) |
| *A61K 31/5386* | (2006.01) |
| *C07D 513/04* | (2006.01) |
| *C07D 519/00* | (2006.01) |

(52) U.S. Cl.
CPC .......... *A61K 31/496* (2013.01); *A61K 31/433* (2013.01); *A61K 31/438* (2013.01); *A61K 31/454* (2013.01); *A61K 31/499* (2013.01); *A61K 31/4995* (2013.01); *A61K 31/5377* (2013.01); *A61K 31/5386* (2013.01); *C07D 513/04* (2013.01); *C07D 519/00* (2013.01)

(58) Field of Classification Search
CPC .............. A61K 31/5386; A61K 31/438; A61K 31/433; A61K 31/496
See application file for complete search history.

(56) References Cited

FOREIGN PATENT DOCUMENTS

| | | |
|---|---|---|
| CN | 104903327 A | 9/2015 |
| CN | 105143218 A | 12/2015 |
| CN | 105143221 A | 12/2015 |
| CN | 105339370 A | 2/2016 |

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995. (Year: 1995).*
International Search Report for PCT/CN2019/087974 dated Aug. 13, 2019.
Eliel, Ernest L.: Stereochemistry of Organic Compounds; John Wiley & Sons, Inc., A Wiley-Interscience Publication.
Parker, Sybil P.: McGraw-Hill Dictionary of Chemical Terms, 3d Ed.

* cited by examiner

*Primary Examiner* — Marcos L Sznaidman
(74) *Attorney, Agent, or Firm* — Schmeiser, Olsen & Watts, LLP

(57) ABSTRACT

Provided are novel heteroaromatic compound as an Autotaxin inhibitor, a pharmaceutical composition comprising the compound, and a use thereof in a treatment of a disease with a pathological feature of Autotaxin overexpression in a mammal, wherein the compound is according to formula (I), or a pharmaceutically acceptable salt, hydrate, solvate, stereoisomer, tautomer, nitrogen oxide, metabolite, prodrug, or mixture thereof; wherein each of $R^1$, $Ar^1$, $Ar^2$, $Ar^3$, W, Y, Z, and Cy is defined in the present disclosure.

19 Claims, No Drawings

AROMATIC HETEROCYCLIC COMPOUND, AND PHARMACEUTICAL COMPOSITION AND USE THEREOF

CROSS-REFERENCE TO RELATED APPLICATIONS

This application claims priority to PCT Application No. PCT/CN2019/087974, having a filing date of May 22, 2019, which is based on Chinese Application No. 201810508922.1, having a filing date of May 24, 2018, the entire contents both of which are hereby incorporated by reference.

FIELD OF TECHNOLOGY

The following relates to the technical field of pharmaceutical chemistry, particularly, it relates to a novel heteroaromatic compound as an Autotaxin (ATX) inhibitor, a pharmaceutical composition comprising the compound and a use thereof in a treatment of a disease with a pathological feature of ATX overexpression.

BACKGROUND

Autotaxin (ATX) was first isolated from A2058 melanoma cells in 1992, and is called "autocrine motility factor" and is a secreted glycoprotein. ATX has phosphodiesterase (PDE) activity and is a member of the extracellular pyrophosphatase/phosphodiesterase (ENPP) family. ATX also has lysophospholipase D (lysoPLD) activity and can catalyze the production of lysophosphatidic acid (LPA) using lysophosphatidylcholine (LPC) as a substrate. LPA is not only a precursor for phospholipid synthesis, but also can cause a wide range of biological effects through various signal transduction pathways. Once LPA is produced, it can be mediated by six cell surface-specific receptor proteins (LPA1-6), namely G protein-coupled receptors (GPCR). According to endothelial cell differentiation genes (Edg) and ventricular region genes, LPA1-6 are named as LPA1/Edg-2/VZG-1, LPA2/Edg-4, LPA3/Edg-7, LPA4/p2y9/GPR23, LPA5/GPR92 and LPA6/p2Y5, respectively, and each of the receptors is mediated by Ga proteins (Gs, Gi, Gq, and G12/13), which further triggers a series of cell signaling cascades. The main pathway includes the hydrolysis of phosphatidylinositol diphosphate (PIP2), which triggers the release of intracellular calcium ions and the activation of protein kinase C (PKC); which inhibits the adenylate cyclase (cAMP) signaling pathway; which activates the pathways of Ras-MAPK, MERK, and ERK to regulate the cell proliferation; which activates the phosphoinositide PI3K-AKT pathway to regulate cell survival and apoptosis; finally, which activates the Rho pathway to regulate cytoskeleton remodeling, shape changes and cell migration activities. Under many pathological conditions, especially in tumor cells, ATX has a high expression, resulting in excessive concentration of LPA. In tumor cells, the LPA concentration can increase to 10 mol/L, which is much higher than the normal level of 100 nmol/L. An excessive amount of LPA increases the production of vascular endothelial growth factor (VEGF) and promotes angiogenesis, which reduces the expression of tumor suppressor p53, and increases tumor cell survival and metastasis. The ATX-LPA signaling pathway involves many physiological and pathological processes, and thus has important links with many serious diseases, mainly including cardiovascular disease, autoimmune disease, cancer, fibrotic disease, inflammatory disease, nervous system disease, pain, etc. LPA has multiple functions in tumor formation, promoting tumor cell growth, angiogenesis, metastasis and the emergence of drug resistance. Therefore, reducing the concentration of LPA is beneficial to the treatment and control of tumors. Correspondingly, inhibiting the activity of AXT and blocking the production pathway of LPA are research hotspots in the treatment of many serious diseases.

With the deepening of research on ATX, many new inhibitors targeting it have emerged, wherein cancer and fibrotic diseases are the most concentrated research. Fibrotic diseases are mainly idiopathic pulmonary fibrosis (IPF) and hepatic fibrosis. IPF is a fatal disease that shows as diffuse alveolitis and alveolar structural disorders, and leads to the progressive development of pulmonary interstitial fibrosis. The prognosis is poor, and the average survival time is 2 to 5 years. IPF may be the most closely linked disease with the ATX-LPA pathway, because in lung tissues, the highest expression of ATX is concentrated in bronchial epithelial cells and alveolar macrophages, which can be juxtaposed to fibroblast foci.

At present, GLPG-1690 as an Autotaxin inhibitor has entered a phase II clinical trial, for the treatment of idiopathic pulmonary fibrosis; the concentration of ATX in serum is closely related to hepatic fibrosis and the stiffness of liver, and is one of the best indicators for predicting liver cirrhosis. In addition, ATX has a high expression in many tumor tissues, including melanoma, non-small cell lung cancer, liver cancer, kidney cancer, breast cancer, thyroid cancer, ovarian cancer and Hodgkin's lymphoma. LPA/ATX can promote cell invasion and metastasis during the growth of tumor cells. Therefore, ATX inhibitors block the signal transduction pathway and provide a new way for clinical treatment of cancer and fibrotic diseases.

Compared with the conventional kinase inhibitors, the ATX inhibitors affect multiple signal pathways related to cell proliferation, growth and apoptosis while they are inhibiting the activity of ATX, and they have a better inhibiting effect on some drug-resistant tumors, and are closely related to the fibrogenesis of multiple organs, and they are an important target for the research and development of drugs for novel fibrotic diseases.

The present disclosure provides a novel heteroaromatic compound, which has a good inhibiting activity against ATX. The compound of the present disclosure has an excellent efficacy, a pharmaceutical property and/or a toxicological property and a well clinical prospect.

SUMMARY

An aspect relates to a new compound which can effectively inhibit the activity of ATX, and be used to prepare a medicament for the treatment of a disease with a pathological feature of ATX over-expression, such as cancer, fibrotic disease (for example, idiopathic pulmonary fibrosis or hepatic fibrosis), metabolic disease, myelodysplastic syndrome, cardiovascular disease, autoimmune disease, inflammatory disease, nervous system disease or pain. An aspect relates to providing a method of preparing the compounds of the present disclosure, which are used to treat the disease in a mammal, especially human, and a pharmaceutical composition including these compounds.

It is an aspect to provide a novel heteroaromatic compound of formula (I), or a pharmaceutically acceptable salt, hydrate, solvate, stereoisomer, tautomer, nitrogen oxide, metabolite, prodrug, or mixture thereof:

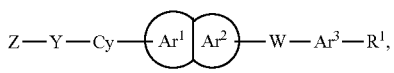
(I)

wherein,

W is —N(R$^{1a}$)—, —O—, —S—, —S(=O)$_{1-2}$—, —C(=O)—, —(C(R$^{2a}$)(R$^{2b}$))$_{1-4}$—, —N(R$^{1a}$)(C(R$^{2a}$)(R$^{2b}$))$_{14}$—, —N(R$^{1a}$)C(=O)—, or —O(C(R$^{2a}$)(R$^{2b}$))$_{1-4}$—;

each of Ar$^1$ and Ar$^2$ is independently five-membered heteroaryl, wherein Ar$^1$ and Ar$^2$ are each optionally substituted with 1, 2, or 3 R$^2$;

Ar$^3$ is aryl, or heteroaryl, wherein Ar$^3$ is optionally substituted with 1, 2, 3, or 4 R$^3$;

Cy is cycloalkyl, heterocyclyl, spiro bicyclic, spiro heterobicyclic, fused bicyclic, fused heterobicyclic, bridged cyclic, bridged heterocyclic, aryl, or heteroaryl, wherein Cy is optionally substituted with 1, 2, 3, or 4 R$^4$;

Y is -(L$^1$-W$^1$)$_m$-L$^2$-;

L$^1$ is absent, or L$^1$ is —O—, —C(=O)—, —N(R$^i$)—, —N(R$^h$)C(=O)—, or —S(=O)$_{0-2}$—;

W$^1$ is C$_{1-4}$ alkylene, wherein C$_{1-4}$ alkylene is optionally substituted with 1, 2, 3, or 4 groups independently selected from H, F, Cl, Br, I, —OH, —NH$_2$, —NO$_2$, —CN, or C$_{1-6}$ alkoxy;

L$^2$ is absent, or L$^2$ is —O—, —C(=O)—, —OC(=O)—, —C(=O)O—, —C(=O)—C(=O)—, —C(=O)—C(=O)N(R$^a$)—, —N(R$^b$)—, —C(=O)N(R$^c$)—, —N(R$^c$)C(=O)—, —C(=O)N(R$^c$)—R$^{15}$—C(=O)O—, —C(=O)N(R$^c$)—R$^{15}$—C(=O)N(R$^a$)—, —N(R$^d$)C(=O)N(R$^c$)—, —N(R$^g$)C(=O)O—, —S(=O)$_{0-2}$—, —S(=O)$_{1-2}$N(R$^e$)—, —N(R$^f$)S(=O)$_{1-2}$—, or —N(R$^f$)S(=O)$_{1-2}$—R$^{15}$—N(R$^a$)—;

Z is H, —CN, alkyl, alkenyl, alkynyl, haloalkyl, cycloalkyl, heteroalkyl, heterocyclyl, heterocyclylalkyl, cycloalkylalkyl, spiro bicyclic, spiro heterobicyclic, fused bicyclic, fused heterobicyclic, bridged cyclic, bridged heterocyclic, aryl, or heteroaryl, wherein each of alkyl, alkenyl, alkynyl, haloalkyl, cycloalkyl, heterocyclyl, heterocyclylalkyl, cycloalkylalkyl, spiro bicyclic, spiro heterobicyclic, fused bicyclic, fused heterobicyclic, bridged cyclic, bridged heterocyclic, aryl, and heteroaryl is optionally substituted with one or more R$^5$;

R$^1$ is alkyl, alkenyl, alkynyl, aryl, heteroaryl, cycloalkyl, or heterocyclyl, wherein R$^1$ is optionally substituted with 1, 2, 3, or 4 R$^6$;

each R$^2$ is independently H, —CN, —NO$_2$, —OH, —NH$_2$, F, Cl, Br, I, alkyl, alkenyl, alkynyl, haloalkyl, cyanoalkyl, hydroxyalkyl, alkoxy, alkoxyalkyl, aralkoxyalkyl, aryloxyalkyl, —S(=O)$_{0-2}$R$^7$, —C(=O)R$^8$, —OS(=O)$_{1-2}$R$^{7a}$, —OC(=O)R$^{8a}$, —C(=O)OR$^{8a}$, —N(R$^{9a}$)C(=O)R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R$^8$, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, or —R$^{14}$—N(R$^{13}$)C(=O)NR$^{13a}$R$^{13b}$;

each of R$^{2a}$ and R$^{2b}$ is independently H, —CN, —OH, —NH$_2$, F, Cl, Br, I, alkyl, alkenyl, alkynyl, haloalkyl, cyanoalkyl, hydroxyalkyl, alkoxyl, aryl, aralkyl, heteroaryl, or heteroarylalkyl;

each R$^3$ is independently H, —CN, —NO$_2$, —OH, —NH$_2$, F, Cl, Br, I, alkyl, alkenyl, alkynyl, haloalkyl, cyanoalkyl, hydroxyalkyl, alkoxyl, —S(=O)$_{0-2}$R$^7$, —C(=O)R$^8$, —OS(=O)$_{1-2}$R$^{7a}$, —OC(=O)R$^{8a}$, —C(=O)OR$^{8a}$, —N(R$^{9a}$)C(=O)R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R$^8$, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, or —R$^{14}$—N(R$^{13}$)C(=O)NR$^{13a}$R$^{13b}$;

each R$^4$ is independently H, oxo (C=O), —CN, —NO$_2$, —OH, —NH$_2$, F, Cl, Br, I, alkyl, alkenyl, alkynyl, haloalkyl, cyanoalkyl, hydroxyalkyl, alkoxyl, —S(=O)$_{0-2}$R$^7$, —C(=O)R$^8$, —OS(=O)$_{1-2}$R$^{7a}$, —C(=O)OR$^{8a}$, —OC(=O)R$^{8a}$, —N(R$^{9a}$)C(=O)R$^9$, —C(=O)NR$^{9a}$R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R$^8$, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, or —R$^{14}$—N(R$^{13}$)C(=O)NR$^{13a}$R$^{13b}$;

each R$^5$ is independently H, oxo (C=O), —CN, —NO$_2$, —OH, —NH$_2$, F, Cl, Br, I, alkyl, alkenyl, alkynyl, alkylamino, haloalkyl, cyanoalkyl, hydroxyalkyl, alkoxyl, aryl, aralkyl, —S(=O)$_{0-2}$R$^7$, —C(=O)R$^8$, —OS(=O)$_{1-2}$R$^{7a}$, —OC(=O)R$^{8a}$, —C(=O)OR$^{8a}$, —N(R$^{9a}$)C(=O)R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R$^8$, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, or —R$^{14}$—N(R$^{13}$)C(=O)NR$^{13a}$R$^{13b}$;

each R$^6$ is independently H, —CN, —NO$_2$, —OH, —NH$_2$, F, Cl, Br, I, alkyl, alkenyl, alkynyl, haloalkyl, cyanoalkyl, hydroxyalkyl, alkoxyl, —S(=O)$_{0-2}$R$^7$, —C(=O)R$^8$, —OS(=O)$_{1-2}$R$^{7a}$, —OC(=O)R$^{8a}$, —C(=O)OR$^{8a}$, —N(R$^{9a}$)C(=O)R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R$^8$, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, or —R$^{14}$—N(R$^{13}$)C(=O)NR$^{13a}$R$^{13b}$;

R$^7$, R$^{7a}$, R$^8$, R$^{8a}$, R$^9$, and R$^{12a}$ are, independently in each instance, H, C$_{1-6}$ alkyl, C$_{2-6}$ alkenyl, C$_{2-6}$ alkynyl, C$_{1-6}$ haloalkyl, C$_{1-6}$ cyanoalkyl, aryl, aralkyl, heteroaryl, heteroarylalkyl, cycloalkyl, cycloalkylalkyl, heterocyclyl, or heterocyclylalkyl;

R$^{9a}$, R$^{10}$, and R$^{10a}$ are, independently in each instance, H, C$_{1-6}$ alkyl, C$_{2-6}$ alkenyl, C$_{2-6}$ alkynyl, C$_{1-6}$ cyanoalkyl, or C$_{1-6}$ haloalkyl;

R$^{11}$ and R$^{11a}$ are, independently in each instance, H, C$_{1-6}$ alkyl, C$_{2-6}$ alkenyl, C$_{2-6}$ alkynyl, C$_{1-6}$ haloalkyl, C$_{1-6}$ cyanoalkyl, or aralkyl;

R$^{12}$, R$^{13}$, R$^{13a}$, and R$^{13b}$ are, independently in each instance, H, C$_{1-6}$ alkyl, C$_{2-6}$ alkenyl, C$_{2-6}$ alkynyl, C$_{1-6}$ cyanoalkyl, or C$_{1-6}$ haloalkyl;

R$^{1a}$ is independently H, alkyl, alkenyl, alkynyl, haloalkyl, cyanoalkyl, hydroxyalkyl, cycloalkyl, cycloalkylalkyl, aryl, or aralkyl;

R$^a$, R$^b$, R$^c$, R$^d$, R$^e$, R$^f$, R$^g$, R$^h$, and R$^i$ are, independently in each instance, H, alkyl, alkenyl, alkynyl, cyanoalkyl, haloalkyl, R$^{16}$—C(=O)—, or cycloalkylalkyl;

R$^{14}$ and R$^{15}$ are, independently in each instance, alkylene, alkenylene, alkynylene, cyanoalkylene, or haloalkylene;

R$^{16}$ is H, C$_{1-6}$ alkyl, or C$_{1-6}$ haloalkyl; and m is 0, 1, or 2.

It is another aspect to provide a pharmaceutical composition, comprising the compound of the present disclosure or a pharmaceutically acceptable salt, hydrate, solvate, stereoisomer, tautomer, nitrogen oxide, metabolite, prodrug thereof, and a pharmaceutically acceptable excipient, diluent, or carrier.

In some examples, the pharmaceutical composition of the present disclosure further comprises an additional therapeutic agent.

It is another aspect to provide a use of the compound or the pharmaceutical composition of the present disclosure in the preparation of a medicament for preventing or treating a disease with a pathological feature of Autotaxin (ATX) overexpression in a mammal.

In some examples, the disease with a pathological feature of Autotaxin overexpression comprises: cancer, fibrotic disease, metabolic disease, myelodysplastic syndrome, cardiovascular disease, autoimmune disease, inflammatory disease, nervous system disease, or pain.

In some examples, the disease with a pathological feature of Autotaxin overexpression is idiopathic pulmonary fibrosis or hepatic fibrosis.

DETAILED DESCRIPTION

Definition and General Terms

All the scientific and technological terms used in the present disclosure have the same meaning as commonly understood by those skilled in the art to which the present disclosure belongs, unless otherwise stated. All patents and publications related to the present disclosure are incorporated into embodiments of the present invention by reference in their entirety.

Unless otherwise stated, the following definitions used herein shall be applied. For the purpose of the present disclosure, Periodic Table with all the elements in CAS version is consistent with "Handbook of Chemistry and Physics", 75th edition, 1994. In addition, the general principles of organic chemistry can refer to the descriptions in "*Organic Chemistry*", Thomas Sorrell, University Science Books, Sausalito: 1999, and "*March's Advanced Organic Chemistry*" by Michael B. Smith and Jerry March, John Wiley & Sons, New York: 2007, the entire contents of which are incorporated herein by reference.

Unless otherwise stated or there is an obvious conflict in context, the articles "a", "an" and "the" used herein are intended to include "at least one" or "one or more". Therefore, these articles used herein refer to articles of one or more than one (i.e. at least one) objects. For example, "a component" means one or more components, that is, more than one component may be considered to be applied or used in the example of the technical solution.

The term "mammal" used herein refers to for example primates (such as, humans, male or female), cows, sheep, goats, horses, swine, dogs, cats, rabbits, rats, mice, fishes, or birds, etc. In some examples, the mammal is a primate. In other examples, the primate is a human.

The term "patient" used herein refers to humans (including adults and children) or other animals. In some examples, the "patient" refers to humans.

The term "comprise" is an open-ended expression, and it comprises the content specified in the present disclosure, but does not exclude other aspects.

"Stereoisomers" refer to compounds having the same chemical structure, but different arrangement of the atoms or groups in space. The stereoisomers include enantiomers, diastereomers, conformational isomers (rotational isomers), geometrical isomers (cis/trans isomers), atropisomers, etc.

"Chiral" refers to a molecule that can not overlap with its mirror image; and "achiral" refers to a molecule that can overlap with its mirror image.

"Enantiomer" refers to two isomers of a compound that can not overlap, but are mirror images of each other.

"Diastereoisomer" refers to stereoisomers that have two or more chiral centers and whose molecules are not mirror images of each other. Diastereoisomers have different physical properties, such as melting points, boiling points, spectral properties and reactivity. Diastereomeric mixtures can be separated by high-resolution analytical procedures such as electrophoresis and chromatography, such as HPLC.

The stereochemical definitions and rules used in the present disclosure generally follow S. P. Parker, Ed., *McGraw-Hill Dictionary of Chemical Terms*(1984) McGraw-Hill Book Company, New York; and Eliel, E. and Wilen, S., "*Stereochemistry of Organic Compounds*", John Wiley & Sons, Inc., New York, 1994.

Many organic compounds exist in an optically active form, that is, they have the capacity of rotating a plane of plane-polarized light. When optically active compounds are described, the prefixes D and L or R and S are used to indicate an absolute configuration of the molecule with respect to one or more of its chiral centers. The prefixes d and l or (+) and (−) are symbols referring to the rotation of plane-polarized light caused by a compound, wherein (−) or l indicates that the compound is left-handed, and the compounds prefixed with (+) or d are right-handed. A specific stereoisomer is an enantiomer, and a mixture of such isomers is called an enantiomeric mixture. The mixture of enantiomer at a ratio of 50 to 50 is called a racemic mixture or a racemate, which occurs when there is no stereoselection or stereospecificity in a chemical reaction or process.

Any asymmetric atoms (e.g., carbon, etc.) of a compound disclosed herein can exist in racemic or enantiomerically enriched form, such as (R)-configuration, (S)-configuration, or (R, S)-configuration. In some examples, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)-configuration or (S)-configuration.

According to the selection of starting materials and methods, the compound of the present disclosure may exist in a form of one or a mixture of the possible isomers, such as a mixture of a racemate and a diastereomer (which depends on the amount of asymmetric carbon atoms). Optically active (R)-isomers or (S)-isomers can be prepared by using chiral synthons or chiral reagents, or can be separated by using conventional techniques. If the compound includes a double bond, the substituent may be in the E-configuration or Z-configuration; if the compound includes a disubstituted cycloalkyl, the substituent of the cycloalkyl may have a cis or trans configuration.

Based on differences in the physicochemical properties of components, the resulting mixture of any stereoisomers can be separated into pure or substantially pure geometric isomers, enantiomers, or diastereomers, for example, by chromatography, and/or fractional crystallization.

Any racemates of resulting products or intermediates can be separated into optical enantiomers by using any methods well-known by ones skilled in the art, for example, the resulting diastereoisomeric salt can be separated. Racemic products can also be separated by chiral chromatography, such as high-performance liquid chromatography (HPLC) using a chiral adsorbent. In particular, enantiomers can be prepared by asymmetric synthesis, for example, referring to Jacques, et al., *Enantiomers, Racemates and Resolutions* (Wiley Interscience, New York, 1981); *Principles of Asymmetric Synthesis* (2nd Ed. Robert E. Gawley, Jeffrey Aubé, Elsevier, Oxford, U K, 2012); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972); *Chiral Separation Techniques: A Practical Approach* (Subramanian, G. Ed., Wiley-VCH Verlag GmbH & Co. KGaA, Weinheim, Germany, 2007.

The term "tautomer" or "tautomeric form" refers to structural isomers with different energies which may be converted into each other by crossing a lower energy barrier. If tautomerization occurs possibly (such as in solution), the chemical equilibrium of the tautomers can be reached. For example, protontautomers (also called as prototropic tautomers) may interconvert, such as ketone-enol isomerization and imine-enylamine isomerization, through proton transfer. Valence tautomers may interconvert through recombination of bonding electrons. A specific example of ketone-enol tautomerism is the tautomerism of pentane-2,4-diketone and 4-hydroxypent-3-ene-2-one. Another example of the tautomerism is phenol-ketone tautomerism. A specific example of phenol-ketone tautomerism is the tautomerism of tautomers of pyridine-4-ol and pyridine-4(1H)-one. Unless otherwise indicated, all tautomeric forms of the compounds of the present disclosure are within the scope of the disclosure.

"Pharmaceutically acceptable" refers to some compounds, materials, compositions and/or preparations, which within reasonable medical judgements, are suitable for contact with patients' tissues without excessive toxicity, irritation, allergic reactions, or other problems and complications corresponding to a reasonable benefit/risk ratio, and are effectively used for the intended purpose.

As described in the present disclosure, the compound of the present disclosure is optionally substituted with one or more substituents, such as the compound of general formula above, or like special examples, subclasses in the examples and a class of compounds included in the present disclosure.

In general, the term "substituted" means that one or more hydrogen atoms in a given structure are replaced by a specified substituent. Unless otherwise stated, one substituted group can have a substituent at each substitutable position of the group. When more than one position in the given structural formula can be substituted by one or more substituents selected from a specific group, then the substituents can be substituted at each position with the same or different substitutions.

The term "unsubstituted" indicates that the specified group does not have any substituent.

The term "optionally substituted . . . with" and the term "unsubstituted or substituted . . . with" are interchangeable, that is, the structure is unsubstituted or substituted with one or more substituents of the present disclosure. The substituents of the present disclosure include, but are not limited to, D, F, Cl, Br, I, $N_3$, CN, $NO_2$, OH, SH, $NH_2$, alkyl, haloalkyl, alkenyl, alkynyl, alkoxy, alkylamino, hydroxyalkyl, cyanoalkyl, cycloalkyl, heterocyclyl, aryl, heteroaryl, $—S(=O)_{0-2}$ $R^7$, $—C(=O)R^8$, $—OS(=O)_{1-2}R^{7a}$, $—OC(=O)R^{8a}$, $—C(=O)OR^{8a}$, $—N(R^{9a})C(=O)R^9$, $—C(=O)NR^{9a}R^9$, $—OC(=O)NR^{10}R^{10a}$, $—NR^{11}R^{11a}$, $—N(R^{12})S(=O)_{1-2}R^{12a}$, $—N(R^{13})C(=O)NR^{13a}R^{13b}$, $—R^{14}—S(=O)_{0-2}R^7$, $—R^{14}—C(=O)R^8$, $—R^{14}—OS(=O)_{1-2}R^{7a}$, $—R^{14}—OC(=O)R^{8a}$, $—R^{14}—N(R^{9a})C(=O)R^9$, $—R^{14}—OC(=O)NR^{10}R^{10a}$, $—R^{14}—NR^{11}R^{11a}$, $—R^{14}—N(R^{12})S$ $(=O)_{1-2}R^{12a}$, $—R^{14}—N(R^{13})C(=O)NR^{13a}R^{13b}$, etc., wherein each of $R^7$, $R^{7a}$, $R^8$, $R^{8a}$, $R^9$, $R^{9a}$, $R^{10}$, $R^{10a}$, $R^{11}$, $R^{11a}$, $R^{12}$, $R^{12a}$, $R^{13}$, $R^{13a}$, $R^{13b}$, and $R^{14}$ is defined as described in the present disclosure.

In addition, it should be noted that, unless otherwise expressly stated, the description ways used in the present disclosure such as "each of . . . is independently selected from . . . " and "are each independently selected from" and " . . . are independently" are interchangeable and should be understood in broad sense. It may mean that specific options expressed on the same symbol in different groups do not affect each other, and it also may mean that specific options expressed on the same symbol in the same group do not affect each other.

In each part of the description of the present disclosure, the substituents of the compounds disclosed in the present disclosure are disclosed according to the type or scope of the group. In particular, the present disclosure includes each independent subcombination of each member of the type and scope of these groups. For example, the term "$C_{1-6}$ alkyl" specifically refers to independently disclosed methyl, ethyl, $C_3$ alkyl, $C_4$ alkyl, $C_5$ alkyl, and $C_6$ alkyl.

In each part of the description of the present disclosure, the term linking substituent is described. When said structure clearly needs a linking group, the Markush variables listed for the group should be understood as the linking group. For example, if the structure requires a linking group and the Markush group definition of the variable lists "alkyl" or "aryl", it should be understood that the "alkyl" or "aryl" respectively represents a linked alkylene group or arylene group.

The term "alkyl" or "alkyl group" used herein means a saturated linear or branched monovalent hydrocarbon group containing 1 to 20 carbon atoms, wherein the alkyl group may be optionally substituted with one or more substituents described herein. Unless otherwise specified, the alkyl group contains 1 to 20 carbon atoms. In one example, the alkyl group contains 1 to 12 carbon atoms; in another example, the alkyl group contains 1 to 6 carbon atoms; in a further example, the alkyl group contains 1 to 4 carbon atoms; in yet another example, the alkyl group contains 1 to 3 carbon atoms. The alkyl group may be optionally substituted with one or more substituents described herein.

Examples of the alkyl group include, but are not limited to, methyl (Me, $—CH_3$), ethyl (Et, $—CH_2CH_3$), n-propyl (n-Pr, $—CH_2CH_2CH_3$), isopropyl (i-Pr, $—CH(CH_3)_2$), n-butyl (n-Bu, $—CH_2CH_2CH_2CH_3$), isobutyl (i-Bu, $—CH_2CH(CH_3)_2$), sec-butyl (s-Bu, $—CH(CH_3)CH_2CH_3$), tert-butyl (t-Bu, $—C(CH_3)_3$), n-pentyl ($—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), n-hexyl ($—CH_2CH_2CH_2CH_2CH_2CH_3$), 2-hexyl ($—CH(CH_3)CH_2CH_2CH_2CH_3$), 3-hexyl ($—CH(CH_2CH_3)(CH_2CH_2CH_3)$), 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH_2CH_3)_2$), 2-methyl-3-pentyl ($—CH(CH_2CH_3)CH(CH_3)_2$), 2,3-dimethyl-2-butyl ($—C(CH_3)_2CH(CH_3)_2$), 3,3-dimethyl-2-butyl ($—CH(CH_3)C(CH_3)_3$), n-heptyl, n-octyl, etc.

The term "alkylene" refers to a saturated divalent hydrocarbyl group obtained by removing two hydrogen atoms from a saturated linear or branched hydrocarbyl. Unless otherwise specified, the alkylene group contains 1 to 12 carbon atoms. In one example, the alkylene group contains 1 to 6 carbon atoms; in another example, the alkylene group contains 1 to 4 carbon atoms; in a further example, the alkylene group contains 1 to 3 carbon atoms; in yet another example, the alkylene group contains 1 to 2 carbon atoms. Examples of the alkylene group include methylene (—$CH_2$—), ethylene (—$CH_2CH_2$—), isopropylene (—CH($CH_3$)$CH_2$—), etc. The alkylene group may be optionally substituted with one or more substituents described herein.

The term "alkenyl" means a linear or branched monovalent hydrocarbyl group containing 2 to 12 carbon atoms, wherein there is at least one unsaturation point, that is, a carbon-carbon $sp^2$ double bond, which includes "cis" and "trans" configurations, or "E" and "Z" configurations. In one example, the alkenyl group contains 2 to 8 carbon atoms; in another example, the alkenyl group contains 2 to 6 carbon atoms; in yet another example, the alkenyl group contains 2 to 4 carbon atoms. Examples of alkenyl group include, but are not limited to, vinyl (—CH=$CH_2$), allyl (—$CH_2$CH=$CH_2$), etc. The alkenyl group may be optionally substituted with one or more substituents described herein.

The term "alkenylene" means a linear or branched divalent hydrocarbon group containing 2 to 12 carbon atoms, wherein there is at least one unsaturation point, that is, a carbon-carbon $sp^2$ double bond, which includes "cis" and "trans" configurations, or "E" and "Z" configurations. Unless otherwise specified, the alkenylene group contains 2 to 12 carbon atoms. In one example, the alkenylene group contains 2 to 6 carbon atoms; in another example, the alkenylene group contains 2 to 4 carbon atoms; in a further example, the alkenylene group contains 2 to 3 carbon atoms; in yet another example, the alkenylene group contains 2 carbon atoms. Examples of the alkenylene group include vinylene (—CH=CH—), allylidene (—$CH_2$CH=CH—), etc. The alkenylene group may be optionally substituted with one or more substituents described herein.

The term "alkynyl" means a linear or branched monovalent hydrocarbon group containing 2 to 12 carbon atoms, wherein there is at least one unsaturation point, that is, a carbon-carbon sp triple bond. In one example, the alkynyl group contains 2 to 8 carbon atoms; in another embodiment, the alkynyl group contains 2 to 6 carbon atoms; in yet another embodiment, the alkynyl group contains 2 to 4 carbon atoms. Examples of alkynyl group include, but are not limited to, ethynyl (—C≡CH), propargyl (—$CH_2$C≡CH), 1-propynyl (—C≡C—$CH_3$), etc. The alkynyl group may be optionally substituted with one or more substituents described herein.

The term "alkynylene" means a linear or branched divalent hydrocarbon group containing 2 to 12 carbon atoms, wherein there is at least one unsaturation point, that is, a carbon-carbon sp triple bond. In one example, the alkynylene group contains 2 to 8 carbon atoms; in another example, the alkynylene group contains 2 to 6 carbon atoms; in a further example, the alkynylene group contains 2 to 4 carbon atoms. Examples of alkynylene group include, but are not limited to, ethynylene (—C≡C—), propynylene (—$CH_2$C≡C—), etc. The alkynylene group may be optionally substituted with one or more substituents described in the embodiments of the invention.

The term "alkoxy" means that the alkyl group is connected to the rest of the molecule through an oxygen atom, wherein the alkyl group has the definition as described herein. Unless otherwise specified, the alkoxy group contains 1 to 12 carbon atoms. In one example, the alkoxy group contains 1 to 6 carbon atoms; in another example, the alkoxy group contains 1 to 4 carbon atoms; in a further example, the alkoxy group contains 1 to 3 carbon atoms. The alkoxy group may be optionally substituted with one or more substituents described herein.

Examples of alkoxy group include, but are not limited to, methoxy (MeO, —$OCH_3$), ethoxy (EtO, —$OCH_2CH_3$), 1-propoxy (n-PrO, n-propoxy, —$OCH_2CH_2CH_3$), 2-propoxy (i-PrO, i-propoxy, —OCH($CH_3$)$_2$), 1-butoxy (n-BuO, n-butoxy, —$OCH_2CH_2CH_2CH_3$), 2-methyl-1-propoxy (i-BuO, i-butoxy, —$OCH_2$CH($CH_3$)$_2$), 2-butoxy (s-BuO, s-butoxy, —OCH($CH_3$)$CH_2CH_3$), 2-methyl-2-propoxy (t-BuO, t-butoxy, —OC($CH_3$)$_3$), 1-pentoxy (n-pentoxy, —$OCH_2CH_2CH_2CH_2CH_3$), 2-pentyloxy (—OCH($CH_3$)$CH_2CH_2CH_3$), 3-pentyloxy (—OCH($CH_2CH_3$)$_2$), 2-methyl-2-butoxy (—OC($CH_3$)$_2CH_2CH_3$), 3-methyl-2-butoxy (—OCH($CH_3$)CH($CH_3$)$_2$), 3-methyl-1-butoxy (—$OCH_2CH_2$CH($CH_3$)$_2$), 2-methyl-1-butoxy (—$OCH_2$CH($CH_3$)$CH_2CH_3$), etc.

The term "haloalkyl", "haloalkenyl" or "haloalkoxy" means an alkyl, alkenyl or alkoxy group substituted with one or more halogen atoms. Examples of the haloalkyl, haloalkenyl, or haloalkoxy group include, but are not limited to, trifluoromethyl, trifluoroethyl, 2,2,3,3-tetrafluoropropyl, trifluoromethoxy, etc.

The term "hydroxyalkyl" used herein means that an alkyl group is substituted with one or more hydroxy groups, wherein the alkyl group is defined as described herein. Examples of the hydroxyalkyl group include, but are not limited to, hydroxy ethyl, 2-hydroxypropyl, hydroxymethyl, etc.

The term "heteroalkyl" means that one or more heteroatoms can be inserted in the alkyl chain, wherein the alkyl group and the heteroatom are defined as described herein. Unless otherwise specified, the heteroalkyl group contains 1 to 10 carbon atoms. In another example, the heteroalkyl group contains 1 to 8 carbon atoms. In a further example, the heteroalkyl group contains 1 to 6 carbon atoms. In yet another example, the heteroalkyl group contains 1 to 4 carbon atoms, and in an alternative example, the heteroalkyl group contains 1 to 3 carbon atoms. Examples of the heteroalkyl group include, but are not limited to, $CH_3OCH_2$—, $CH_3CH_2OCH_2$—, $CH_3SCH_2$—, ($CH_3$)$_2NCH_2$—, ($CH_3$)$_2CH_2OCH_2$—, $CH_3OCH_2CH_2$—, $CH_3CH_2OCH_2CH_2$—, etc.

The term "cycloalkyl" used herein, unless otherwise specified, refers to a monovalent saturated or partially unsaturated (but not aromatic) monocyclic or polycyclic hydrocarbon. In some examples, the cycloalkyl group may be a bridged or unbridged, spiro cyclic or non-spiro cyclic, and/or fused or non-fused bicyclic. In some examples, the cycloalkyl group includes 3 to 10 carbon atoms, i.e. $C_3$ to $C_{10}$ cycloalkyl. In some examples, the cycloalkyl group has 3 to 15 ($C_{3-15}$), 3 to 10 ($C_{3-10}$), or 3 to 7 ($C_{3-7}$) carbon atoms. In some examples, the cycloalkyl group is monocyclic or bicyclic. In some embodiments, the cycloalkyl group is monocyclic. In some examples, the cycloalkyl group is bicyclic. In some examples, the cycloalkyl group is tricyclic. In some examples, the cycloalkyl group is fully saturated. In some examples, the cycloalkyl group is partially saturated. In some examples, the cycloalkyl group is cyclopropyl, cyclobutyl, cyclopentyl, cyclohexyl, cycloheptyl, bicyclo[2.1.1]hexyl, bicyclo[2.2.1]heptyl, decahydronaphthyl, or adamantyl. When a cycloalkyl group is substituted, it can be on any ring, that is, on any aromatic or non-aromatic ring contained by the cycloalkyl group, and it is independently substituted with one or more substituents described herein.

The terms "heterocyclyl" and "heterocycle" are used interchangeably herein, and unless otherwise specified, they refer to a monovalent monocyclic non-aromatic ring system and/or polycyclic ring system containing at least one non-aromatic ring; wherein the non-aromatic monocyclic atoms comprise one or more heteroatoms (in some examples, there being 1, 2, 3, or 4 heteroatoms) independently selected from O, $S(O)_{0-2}$ and N, and the remaining ring atoms are all carbon atoms; and wherein the ring atoms in the polycyclic ring system comprise one or more heteroatoms (in some examples, there being 1, 2, 3, or 4 heteroatoms) independently selected from O, $S(O)_{0-2}$ and N, and the remaining ring atoms are all carbon atoms. In some examples, the heterocyclyl contains 1 or 2 heteroatoms, which are nitrogen atoms. In some examples, the heterocyclyl is polycyclic and contains one heteroatom in a non-aromatic ring, or contains one heteroatom in an aromatic ring, or contains two heteroatoms in an aromatic ring, or contains two heteroatoms, one an aromatic ring and the other in a non-aromatic ring. In some examples, the heterocyclyl group has 3 to 20, 3 to 15, 3 to 10, 3 to 8, 4 to 7, or 5 to 6 ring atoms. In some examples, the heterocyclyl group is a monocyclic, bicyclic, tricyclic, or tetracyclic ring system. In some examples, the heterocyclyl group may be a bridged or unbridged, spiro cyclic or non-spiro cyclic, and/or fused or non-fused bicyclic. One or more nitrogen atoms and sulfur atoms can be optionally oxidized, and one or more nitrogen atoms can be optionally quaternized, and one or more carbon atoms can be optionally substituted with

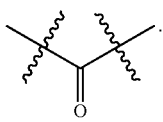

Some rings may be partially or fully saturated, or aromatic, provided that the heterocycle is not fully aromatic. The monocyclic heterocycle and polycyclic heterocycle may be connected to the main structure at any heteroatoms or carbon atoms that result in a steady compound. The polycyclic heterocyclyl can be connected to the main structure through any ring, including any aromatic or non-aromatic ring, regardless of whether the ring contains a heteroatom or not. In some examples, the heterocyclyl is a "heterocycloalkyl group", which is 1) a saturated or partially unsaturated (but not aromatic) monovalent monocyclic group containing at least one heterocycloatom as described herein, or 2) saturated or partially unsaturated (but not aromatic) monovalent bicyclyl or tricyclic group, wherein at least one ring contains at least one heteroatom as described herein. When the heterocyclyl and heterocycloalkyl group are substituted, they can be substituted on any ring, that is, on any aromatic or non-aromatic ring contained by the heterocyclyl and heterocycloalkyl group. In some examples, such heterocyclyl group includes, but is not limited to, epoxyethanyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, benzodioxanyl, benzodioxolyl, benzofuranone, benzopyranone, benzopyranyl, dihydrobenzofuranyl, benzotetrahydrothienyl, benzothiopyranyl, benzoxazinyl, O-carbolinyl, benzopyranyl, chromonyl, cinnolyl, coumaryl, decahydroquinolinyl, decahydroisoquinolinyl, dihydrobenzisothiazinyl, dihydrobenzisoxazinyl, dihydrofuranyl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithiopyranyl, furanonyl, imidazolidinyl, 2,4-dioxo-imidazolidinyl, imidazolinyl, indolinyl, 2-oxo-indolinyl, isobenzotetrahydrofuranyl, isobenzotetrahydrothienyl, isobenzodihydropyranyl, isocoumarinyl, isodihydroindolyl (isoindolinyl), 1-oxo-isodihydroindolyl, 1,3-dioxo-isodihydroindolyl, isothiazolidinyl, isoxazolidinyl, 3-oxo-isoxazolidinyl, morpholinyl, 3,5-dioxo-morpholinyl, octahydroindolyl, octahydroisoindolyl, 1-oxo-octahydroisoindolyl, 1,3-dioxo-hexahydroisoindolyl, oxazolidinonyl, oxazolidinyl, oxiranyl, piperazinyl, 2,6-dioxo-piperazinyl, piperidinyl, 2,6-dioxo-piperidinyl, 4-piperidinone, 2-oxopyrrolidinyl, 2,5-dioxopyrrolidinyl, quinuclidinyl, tetrahydroisoquinolinyl, 3,5-dioxo-thiomorpholinyl, thiazolidinyl, 2,4-dioxo-thiazolidinyl, tetrahydroquinolinyl, phenothiazinyl, phenoxazinyl, xanthene and 1,3,5-trithiocyclohexyl. Examples of the —CH$_2$— group in the heterocyclyl substituted with —C(=O)— include, but are not limited to, 2-oxopyrrolidinyl, oxo-1,3-thiazolidinyl, 2-piperidone, 3,5-dioxopiperidinyl and pyrimidinedione. Examples of sulfur atom oxidized in the heterocyclyl include, but are not limited to, sulfolanyl and a 1,1-dioxothiomorpholinyl. The heterocyclyl may be optionally substituted with one or more substituents described herein.

In one example, the heterocyclyl is a heterocyclyl composed of 3 to 8 atoms, and refers to a saturated or partially unsaturated monocyclic ring containing 3 to 8 ring atoms, wherein at least one ring atom is selected from nitrogen, sulfur and oxygen atoms. Unless otherwise specified, the heterocyclyl consisting of 3 to 8 atoms may be a carbon group or a nitrogen group, and the —CH$_2$— group may be optionally substituted with —C(=O)—. The sulfur atom of the ring can optionally be oxidized to S-oxide. The nitrogen atom of the ring can optionally be oxidized to an N-oxide. Examples of heterocyclyl consisting of 3 to 8 atoms include, but are not limited to, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl. Examples of —CH$_2$— group in the heterocyclyl substituted with —C(=O)— include, but are not limited to, 2-oxopyrrolidinyl, oxo-1,3-thiazolidinyl, 2-piperidinonyl, 3,5-dioxopiperidinyl and pyrimidinedionyl. Examples of sulfur atom in the heterocyclyl oxidized include, but are not limited to, sulfolanyl and 1,1-dioxothiomorpholinyl. The heterocyclyl consisting of 3 to 8 atoms can be optionally substituted with one or more substituents described herein.

In one example, the heterocyclyl is a heterocyclyl consisting of 3 to 6 atoms, and refers to a saturated or partially unsaturated monocyclic ring containing 3 to 6 ring atoms, wherein at least one ring atom is selected from nitrogen, sulfur and oxygen atoms. Unless otherwise specified, the heterocyclyl consisting of 3 to 6 atoms may be a carbon group or a nitrogen group, and the —CH$_2$— group may be optionally substituted with —C(=O)—. The sulfur atom of the ring can optionally be oxidized to S-oxide. The nitrogen atom of the ring can optionally be oxidized to an N-oxide. The heterocyclyl consisting of 3 to 6 atoms can be optionally substituted with one or more substituents described herein.

In another example, the heterocyclyl is a heterocyclyl consisting of 5 to 6 atoms, and refers to a saturated or partially unsaturated monocyclic ring containing 5 to 6 ring atoms, wherein at least one ring atom is selected from nitrogen, sulfur and oxygen atoms. Unless otherwise specified, the heterocyclyl consisting of 5 to 6 atoms may be a carbon group or a nitrogen group, and the —CH$_2$— group may be optionally substituted with —C(=O)—. The sulfur atom of the ring can optionally be oxidized to S-oxide. The nitrogen atom of the ring can optionally be oxidized to an N-oxide. Examples of heterocyclyl consisting of 5 to 6 atoms include, but are not limited to, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxocyclopentyl, dithiocyclopentyl, 2-oxopyrrolidinyl, oxo-1,3-thiazolidinyl, sulfolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, 2-piperidinonyl, 3,5-dioxopiperidinyl and pyrimidinedionyl, 1,1-dioxylthiomorpholinyl. The heterocyclyl consisting of 5 to 6 atoms may be optionally substituted with one or more substituents described herein.

The term "cycloalkylalkyl" means that the alkyl group may be substituted with one or more cycloalkyl groups, wherein the cycloalkyl and alkyl are defined as described herein. Examples of cycloalkylalkyl include, but are not limited to, cyclopropylmethyl, cyclopropylethyl, cyclopropylpropyl, cyclobutylmethyl, cyclobutylethyl, cyclopentylmethyl, cyclopentylethyl, cyclopentylpropyl, cyclohexylethyl, etc.

The term "heterocyclylalkyl" includes heterocyclyl-substituted alkyl; the term "heterocyclylalkoxy" includes heterocyclyl-substituted alkoxy, wherein the oxygen atom is connected to the rest of the molecule; the term "heterocyclylalkylamino" includes heterocyclyl-substituted alkylamino, wherein the nitrogen atom is connected to the rest of the molecule, wherein heterocyclyl, alkyl group, alkoxy group and alkylamino group are all defined as described herein. Examples of heterocyclylalkylamino include, but are not limited to, azetidine-1-ylmethyl, azetidine-1-ylethyl, azetidine-1-ylpropyl, pyrrol-1-ylmethyl, pyrrol-1-ylethyl, pyrrol-1-ylpropyl, morpholin-4-ylethyl, morpholin-4-ylethoxy, piperazin-4-ylethoxy, piperidin-4-ylethylamino, etc.

The terms "fused bicyclic ring", "fused ring", "fused bicyclic", "fused cyclyl" refer to saturated or unsaturated fused ring systems, involving non-aromatic bicyclic systems, as shown in formula (a1), that is, ring B and ring B' share a bond. Such a system may contain independent or conjugated unsaturation point, but its core structure does not contain aromatic or heteroaromatic rings (but aromatics can be used as substituents on it). Each ring of the fused bicyclic is either carbocyclic or heteroalicyclic. Examples of the fused bicyclic include, but are not limited to, hexahydro-furo[3,2-b]furan, 2,3,3a,4,7,7a-hexahydro-1H-indene, 7-azabicyclo[2.3.0]heptane, fused bicyclo[3.3.0]octane, fused bicyclo[3.1.0]hexane, all of which are contained within the fused bicyclic. The fused bicyclic may be substituted or unsubstituted, wherein the substituent may be, but are not limited to, D, F, Cl, Br, I, N$_3$, CN, NO$_2$, OH, SH, NH$_2$, oxo, alkyl, haloalkyl, alkenyl, alkynyl, alkoxy, alkylamino, hydroxyalkyl, cyanoalkyl, cycloalkyl, heterocyclyl, aryl, heteroaryl, —S(=O)$_{0-2}$R$^7$, —C(=O)R$^8$, —OS(=O)$_{1-2}$R$^{7a}$, —OC(=O)R$^{8a}$, —C(=O)OR$^{8a}$, —N(R$^{9a}$)C(=O)R$^9$, —C(=O)NR$^{9a}$R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, —R$^{14}$—N(R$^{13}$)C(=O)NR$^{13a}$R$^{13b}$ etc., wherein R$^7$, R$^{7a}$, R$^8$, R$^{8a}$, R$^9$, R$^{9a}$, R$^{10}$, R$^{10a}$, R$^{11}$, R$^{11a}$, R$^{12}$, R$^{12a}$, R$^{13}$, R$^{13a}$, R$^{13b}$ and R$^{14}$ are defined as described herein.

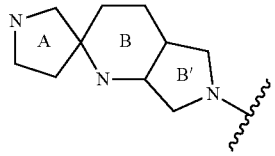

(a1)

The term "fused heterobicyclic" refers to saturated or unsaturated fused ring systems or bridged systems, involving non-aromatic bicyclyl systems or bridged systems. Such a system may contain independent or conjugated unsaturation point, but its core structure does not contain aromatic or heteroaromatic rings (but aromatics can be used as substituents on it), and at least one ring system contains one or more heteroatoms, wherein each ring system contains 3 to 7 membered ring, that is, it contains 1 to 6 carbon atoms and 1 to 3 heteroatoms selected from N, O, P, S, wherein the S or P is optionally substituted with one or more oxygen atoms to obtain a group such as SO, SO$_2$, PO, PO$_2$. Examples of the fused heterobicyclic include, but are not limited to, hexahydro-furo[3,2-b]furan, 7-azabicyclo[2.3.0]heptane, 2-azabicyclo[2.2.1]heptane, octahydropyrrole[3,2,-b]pyrrole, octahydropyrrole[3,4,-c]pyrrole, octahydro-1H-pyrrole[3,2,-b]pyrrole, etc. The fused heterobicyclic may be substituted or unsubstituted, wherein the substituted groups are, but not limited to, D, F, Cl, Br, I, N$_3$, CN, NO$_2$, OH, SH, NH$_2$, oxo, alkyl, haloalkyl, alkenyl, alkynyl, alkoxy, alkylamino, hydroxyalkyl, cyanoalkyl, cycloalkyl, heterocyclyl, aryl, heteroaryl, —S(=O)$_{0-2}$R$^7$, —C(=O)R$^8$, —OS(=O)$_{1-2}$R$^{7a}$, —OC(=O)R$^{8a}$, —C(=O)OR$^{8a}$, —N(R$^{9a}$)C(=O)R$^9$, —C(=O)NR$^{9a}$R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, —R$^{14}$—N(R$^{13}$)C(=O)NR$^{13a}$R$^{13b}$ etc., wherein R$^7$, R$^{7a}$, R$^8$, R$^{8a}$, R$^9$, R$^{9a}$, R$^{10}$, R$^{10a}$, R$^{11}$, R$^{11a}$, R$^{12}$, R$^{12a}$, R$^{13}$, R$^{13a}$, R$^{13b}$ and R$^{14}$ are defined as described herein.

The terms "spiro group", "spiro", "spiro bicyclic", "spiro bicycle" means that one ring originates from a special cyclic carbon on another ring. For example, ring A and ring B share a carbon atom in two saturated ring systems and are called "spiro". Each ring in the spiro is either carbocyclic or heteroalicyclic. Examples of the spiro include, but are not limited to, 2,7-diazaspiro[4.4]nonane-2-yl, 7-oxo-2-azaspiro[4.5]decane-2-yl, 4-azaspiro[2.4]heptane-5-yl, 4-oxaspiro[2.4]heptane-5-yl, 5-azaspiro[2.4]heptane-5-yl, spiro[2.4]heptan-5-yl, spiro[4.4]nonyl, 7-hydroxy-5-azaspiro[2.4]heptane-5-yl, etc. The spiro bicyclic may be substituted or unsubstituted, wherein the substituents are, but not limited to, D, F, Cl, Br, I, N$_3$, CN, NO$_2$, OH, SH, NH$_2$, oxo, alkyl, haloalkyl, alkenyl, alkynyl, alkoxy, alkylamino, hydroxyalkyl, cyanoalkyl, cycloalkyl, heterocyclyl, aryl, heteroaryl, —S(=O)$_{0-2}$R$^7$, —C(=O)R$^8$, —OS(=O)$_{1-2}$R$^{7a}$, —OC(=O)R$^{8a}$, —C(=O)OR$^{8a}$, —N(R$^{9a}$)C(=O)R$^9$, —C(=O)NR$^{9a}$R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R$^8$, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, —R$^{14}$—N(R$^{13}$)C(=O)NR$^{13a}$R$^{13b}$, etc., wherein R$^7$, R$^{7a}$, R$^8$, R$^{8a}$, R$^9$, R$^{9a}$, R$^{10}$, R$^{10a}$, R$^{11}$, R$^{11a}$, R$^{12}$, R$^{12a}$, R$^{13}$, R$^{13a}$, R$^{13b}$ and R$^{14}$ are defined as described herein.

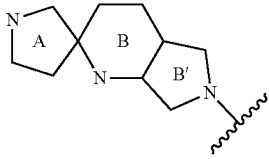

(a1)

The term "spiro bicycloalkylene" means that system has two connection points connected to the rest of the molecule, wherein the spiro bicycloalkylene is defined as described herein.

The term "spiro heterobicyclic" means that one ring originates from a special cyclic carbon on another ring. For example, as described above, ring A and ring B share one carbon atom in two saturated ring systems and are called "spiro cyclic", and at least one ring system contains one or more heteroatoms, wherein each ring system contains 3 to 7 membered ring, that is, it contains 1 to 6 carbon atoms and 1 to 3 heteroatoms selected from N, O, P, S, wherein the S or P is optionally substituted with one or more oxygen atoms to obtain a group such as SO, SO$_2$, PO, PO$_2$. Examples of the spiro heterobicyclic include, but are not limited to, 4-azaspiro[2.4]heptan-5-yl, 4-oxaspiro[2.4]heptan-5-yl, 5-azaspiro[2.4]heptan-5-yl, 7-hydroxy-5-azaspiro[2.4]heptan-5-yl, 2,6-diazaspiro[3.3]heptane, 2,6-diazaspiro[3.4]octane, 1,6-diazaspiro[3.4]octane, 2,7-diazaspiro[3.5]nonane, 1,7-diazaspiro[3.5]nonane, 3,9-diazaspiro[5.5]undecane, etc. The spiro heterobicyclic may be substituted or unsubstituted, wherein the substituents may be, but not limited to, D, F, Cl, Br, I, N$_3$, CN, NO$_2$, OH, SH, NH$_2$, oxo, alkyl, haloalkyl, alkenyl, alkynyl, alkoxy, alkylamino, hydroxyalkyl, cyanoalkyl, cycloalkyl, heterocyclyl, aryl, heteroaryl, —S(=O)$_{0-2}$R$^7$, —C(=O)R$^8$, —OS(=O)$_{1-2}$R$^{7a}$, —OC(=O)R$^{8a}$, —C(=O)OR$^{8a}$, —N(R$^{9a}$)C(=O)R$^9$, —C(=O)NR$^{9a}$R$^9$, —OC(=O)NR$^{10}$R$^{10a}$, —NR$^{11}$R$^{11a}$, —N(R$^{12}$)S(=O)$_{1-2}$R$^{2a}$, —N(R$^{13}$)C(=O)NR$^{13a}$R$^{13b}$, —R$^{14}$—S(=O)$_{0-2}$R$^7$, —R$^{14}$—C(=O)R, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, —R$^{14}$—N(R$^{13}$)C(=O)NR$^{13a}$R$^{13b}$, etc., wherein R$^7$, R$^{7a}$, R$^8$, R$^{8a}$, R$^9$, R$^{9a}$, R$^{10}$, R$^{10a}$, R$^{11}$, R$^{11a}$, R$^{12}$, R$^{12a}$, R$^{13}$, R$^{13a}$, R$^{13b}$ and R$^{14}$ are defined as described herein.

The term "bridged cyclic" used herein refers to saturated or unsaturated bridged-ring system, involving non-aromatic bridged-ring system, as shown in formula (a2), that is, Ring A1 and Ring A2 share a alkyl chain or a heteroalkyl chain, wherein j is 1, 2, 3, or 4. Such system may contain independent or conjugated unsaturation point, but its core structure does not contain aromatic or heteroaromatic ring (but aromatics can be used as substituents on it). Each ring of the bridged cyclic is either carbocyclic or heteroalicyclic. Examples of the bridged cyclic include, but are not limited to, bicyclo[2.2.1]heptane, 2-azabicyclo[2.2.1]heptane, 1,2,3,4,4a,5,8,8a-octahydronaphthalene, which are all included in the fused bicyclic system or within the bridged-ring system. The bridged cyclic may be substituted or unsubstituted, wherein the substituents may be, but not limited to, D, F, Cl, Br, I, N$_3$, CN, NO$_2$, OH, SH, NH$_2$, oxo, alkyl, haloalkyl, alkenyl, alkynyl, alkoxy, alkylamino, hydroxyalkyl, cyanoalkyl, cycloalkyl, heterocyclyl, aryl, heteroaryl, —S(=O)$_{0-2}$R$^7$, —C(=O)R$^8$, —OS(=O)$_{1-2}$R$^{7a}$, —OC(=O)R$^{8a}$, —C(=O)OR$^{8a}$, —N(R$^{9a}$)C(=O)R$^9$, —C(=O)NR$^{9a}$R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R$^8$, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, —R$^{14}$—N(R$^{13}$)C(=O)NR$^{13a}$R$^{13b}$, etc, wherein the X$^3$, R$^7$, R$^{7a}$, R$^8$, R$^{8a}$, R$^9$, R$^{9a}$, R$^{10}$, R$^{10a}$, R$^{11}$, R$^{11a}$, R$^{12}$, R$^{12a}$, R$^{13}$, R$^{13a}$, R$^{13b}$ and R$^{14}$ are defined as described herein.

(a2)

The term "bridged heterocyclic" means saturated or unsaturated bridged-ring system, involving non-aromatic bridged-ring system. Such system may contain independent or conjugated unsaturation point, but its core structure does not contain aromatic or heteroaromatic ring (but aromatics can be used as substituents on it), and at least one ring system contains one or more heteroatoms, wherein each ring system contains 3 to 7 membered ring, that is, it contains 1 to 6 carbon atoms and 1 to 3 heteroatoms selected from N, O, P, S, wherein the S or P is optionally substituted with one or more oxygen atoms to obtain a group such as SO, SO$_2$, PO, PO$_2$. Examples of the bridged heterocyclic include, but are not limited to, 2-azabicyclo[2.2.1]heptane, (1R,5S)-3,6-diazabicyclo[3.1.1]heptane, 2,5-diazabicyclo[2.2.1]heptane, (1R,5S)-8-azabicyclo[3.2.1]octane, etc. The bridged heterocyclic may be substituted or unsubstituted, wherein the substituents may be, but not limited to, D, F, Cl, Br, I, N$_3$, CN, NO$_2$, OH, SH, NH$_2$, oxo, alkyl, haloalkyl, alkenyl, alkynyl, alkoxy, alkylamino, hydroxyalkyl, cyanoalkyl, cycloalkyl, heterocyclyl, aryl, heteroaryl, —S(=O)$_{0-2}$R$^7$, —C(=O)R$^8$, —OS(=O)$_{1-2}$R$^{7a}$, —OC(=O)R$^{8a}$, —C(=O)OR$^{8a}$, —N(R$^{9a}$)C(=O)R$^9$, —C(=O)NR$^{9a}$R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R$^8$, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, R$^{14}$—N(R$^{13}$)C(=O)NR$^{13a}$R$^{13b}$ etc, wherein R$^7$, R$^{7a}$, R$^8$, R$^{8a}$, R$^9$, R$^{9a}$, R$^{10}$, R$^{10a}$, R$^{11}$, R$^{11a}$, R$^{12}$, R$^{12a}$, R$^{13}$, R$^{13a}$, R$^{13b}$ and R$^{14}$ are defined as described herein.

As described in the present disclosure, there are two connection points connected to the rest of the molecule, as shown in formula (a3) or (a4), which means either E end or E' end is connected to the rest of the molecule, i.e. the connection of the two ends can be interchangeable.

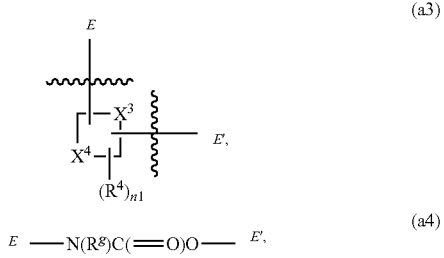

(a3)

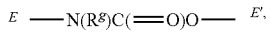

E—N(R$^g$)C(=O)O—E', (a4)

The term "consisting of n atoms" typically describes the number of ring atoms in the molecule, and the number of ring atoms in the molecule is n, wherein n is an integer. For example, piperidinyl is a heterocycloalkyl group consisting of 6 atoms, and 1,2,3,4-tetrahydronaphthalene is a cycloalkyl group consisting of 10 atoms. The term "unsaturated" as used herein means that the group has one or more unsaturated degrees.

The term "heteroatom" refers to O, S, N, P and Si, comprising N, S, P in any oxidation state; primary, secondary, tertiary and quaternary ammonium salt forms; or the form wherein the hydrogen on the nitrogen atom in the heterocycle is substituted, for example, N (like N in 3,4-dihydro-2H-pyrrolyl), NH (like NH in pyrrolidinyl) or NR (like NR in N-substituted pyrrolidinyl).

The term "halogen" refers to fluorine (F), chlorine (Cl), bromine (Br) or iodine (I).

The term "aryl" used herein, unless otherwise specified, refers to a monovalent $C_6 \sim C_{14}$ carbocyclyl system containing at least one aromatic ring, wherein the aromatic ring system is monocyclic, bicyclic, or tricyclic. The aryl group can be connected to the main structure through any of its rings, that is, any aromatic or non-aromatic ring. In some examples, the aryl group is phenyl, naphthyl, bicyclo[4.2.0]octyl-1,3,5-trienyl, indanyl, fluorenyl, or tetrahydronaphthyl. When the aryl group is substituted, it can be substituted on any ring, that is, on any aromatic or non-aromatic ring contained by the aryl group. In some or any examples, aryl is phenyl, naphthyl, tetrahydronaphthyl, fluorenyl, or indanyl; the aryl group, such as said phenyl, naphthyl, tetrahydronaphthyl, fluorenyl, and indanyl is independently optionally substituted with one or more substituents described herein, and in some examples, the aryl includes substituents each of which is independently selected from D, F, Cl, Br, I, $N_3$, CN, $NO_2$, OH, SH, $NH_2$, alkyl, haloalkyl, alkenyl, alkynyl, alkoxy, alkylamino, hydroxyalkyl, cyanoalkyl, cycloalkyl, heterocyclyl, aryl, heteroaryl, —S(=O)$_{0-2}R^7$, —C(=O)R$^8$, —OS(=O)$_{1-2}R^{7a}$, —OC(=O)R$^{8a}$, —C(=O)OR$^{8a}$, —N(R$^{9a}$)C(=O)R$^9$, —C(=O)NR$^{9a}R^9$, —OC(=O)NR$^{10}R^{10a}$, —NR$^{11}R^{11a}$, —N(R$^{12}$)S(=O)$_{1-2}R^{12a}$, —N(R$^{13}$)C(=O)NR$^{13a}R^{13b}$, —R$^{14}$—S(=O)$_{0-2}R^7$, —R$^{14}$—C(=O)R, —R$^{14}$—OS(=O)$_{1-2}R^{7a}$, —R$^{14}$—OC(=O)R$^{8a}$, —R$^{14}$—N(R$^{9a}$)C(=O)R$^9$, —R$^{14}$—OC(=O)NR$^{10}R^{10a}$, —R$^{14}$—NR$^{11}R^{11a}$, —R$^{14}$—N(R$^{12}$)S(=O)$_{1-2}R^{12a}$, —R$^{14}$—N(R$^{13}$)C(=O)NR$^{13a}R^{13b}$ etc, wherein R$^7$, R$^{7a}$, R$^8$, R$^{8a}$, R$^9$, R$^{9a}$, R$^{10}$, R$^{10a}$, R$^{11}$, R$^{11a}$, R$^{12}$, R$^{12a}$, R$^{13}$, R$^{13a}$, R$^{13b}$ and R$^{14}$ are defined as described herein.

The term "aralkyl" used herein, unless otherwise specified, refers to alkyl group substituted with one or two aryl group as defined herein, wherein alkyl group is a connection point of attachment to the rest of the molecule. In some examples, aralkyl is benzyl, pheneth-1-yl, pheneth-2-yl, diphenylmethyl, 2,2-diphenylethyl, 3,3-diphenylpropyl, and 3-phenylpropyl, each of which is optionally substituted on the ring with one or more substituents as described herein.

The term "heteroaryl" as used herein, unless otherwise specified, refers to a monovalent monocyclic or polycyclic aromatic group, wherein ring atoms comprise at least one heteroatom (in some examples, there being 1, 2, 3, or 4 heteroatoms) independently selected from O, S(O)$_{0-2}$ and N in the ring. The heteroaryl group is connected to the rest of the molecule through any atoms in the ring system in consideration of its valence rules. In some examples, each ring of a heteroaryl group may contains 1 or 2 O atoms, 1 or 2 S atoms, and/or 1 to 4 N atoms, or a combination thereof, provided that the total number of heteroatoms in each ring is 4 or less, and each ring contains at least 1 carbon atom. In some examples, the heteroaryl group has 5 to 20, 5 to 15, or 5 to 10 ring atoms. When the heteroaryl group is substituted, it can be substituted on any ring. In certain examples, monocyclic heteroaryl groups include, but are not limited to, furyl, imidazolyl, isothiazolyl, isoxazolyl, oxadiazolyl, oxazolyl, pyrazinyl, pyrazolyl, pyridazinyl, pyridinyl, pyrimidinyl, pyrrolyl, thiadiazolyl, thiazolyl, thienyl, tetrazolyl, triazinyl and triazolyl. In certain examples, bicyclic heteroaryl groups include, but are not limited to, benzofuranyl, benzimidazolyl, benzisoxazolyl, benzopyranyl, benzothiadiazolyl, benzothiazolyl, benzothienyl, benzotriazolyl, benzoxazolyl, furopyridyl, imidazopyridyl, imidazothiazolyl, indazinyl, indolyl, indazolyl, isobenzofuryl, isobenzothienyl, isoindolyl, isoquinolinyl, isothiazolyl, naphthyridinyl, oxazolopyridyl, phthalazinyl, pteridinyl, purinyl, pyridopyridyl, pyrrolepyridyl, quinolinyl, quinoxalinyl, quinazolinyl, thiadiazolopyrimidinyl and thienopyridinyl. In certain examples, tricyclic heteroaryl groups include, but are not limited to, acridinyl, benzindolyl, carbazolyl, dibenzofuranyl, perimidinyl, phenanthrolinyl, phenanthridinyl and phenazinyl. In some or any examples, the heteroaryl group is indolyl, furyl, pyridyl, pyrimidinyl, imidazolyl, or pyrazolyl; each of which is optionally substituted with 1, 2, 3, or 4 groups defined as described herein. In some examples, the heteroaryl group includes substituents independently selected from D, F, Cl, Br, I, $N_3$, CN, $NO_2$, OH, SH, $NH_2$, alkyl, haloalkyl, alkenyl, alkynyl, alkoxy, alkylamino, hydroxyalkyl, cyanoalkyl, cycloalkyl, heterocyclyl, aryl, heteroaryl, —S(=O)$_{0-2}R^7$, —C(=O)R$^8$, —OS(=O)$_{1-2}R^{7a}$, —OC(=O)R$^{8a}$, —C(=O)OR$^{8a}$, —N(R$^{9a}$)C(=O)R$^9$, —C(=O)NR$^{9a}R^9$, —OC(=O)NR$^{10}R^{10a}$, —NR$^{11}R^{11a}$, —N(R$^{12}$)S(=O)$_{1-2}R^{12a}$, —N(R$^{13}$)C(=O)NR$^{13a}R^{13b}$, —R$^{14}$—S(=O)$_{0-2}R^7$, —R$^{14}$—C(=O)R$^8$, —R$^{14}$—OS(=O)$_{1-2}R^{7a}$, —R$^{14}$—OC(=O)R$^{8a}$, —R$^{14}$—N(R$^{9a}$)C(=O)R$^9$, —R$^{14}$—OC(=O)NR$^{10}R^{10a}$, —R$^{14}$—NR$^{11}R^{11a}$, —R$^{14}$—N(R$^{12}$)S(=O)$_{1-2}R^{12a}$, —R$^{14}$—N(R$^{13}$)C(=O)NR$^{13a}R^{13b}$, etc., wherein each of R$^7$, R$^{7a}$, R$^8$, R$^{8a}$, R$^9$, R$^{9a}$, R$^{10}$, R$^{10a}$, R$^{11}$, R$^{11a}$, R$^{12}$, R$^{12a}$, R$^{13}$, R$^{13a}$, R$^{13b}$, and R$^{14}$ is defined as described herein.

The term "heteroarylalkyl" as used in the present disclosure, unless otherwise specified, refers to an alkyl group substituted with one or two heteroaryl groups as defined herein, wherein the alkyl group is the connection point for connecting with the rest of the molecule. Examples of the heteroarylalkyl group include, but are not limited to, imidazole-2-methyl, thiazole-2-methyl, furan-2-ethyl, indole-3-methyl, etc.; each of which optionally is substituted on any rings with one or more substituents as described herein.

The term "alkylamino" includes "N-alkylamino" and "N,N-dialkylamino", wherein each amino group is independently substituted with one or two alkyl groups. In some examples, the alkylamino group is a lower alkylamino group with one or two $C_{1-6}$ alkyl groups attached to the nitrogen atom. In other examples, the alkylamino group is a $C_{1-3}$ lower alkylamino group. Suitable alkylamino groups can be monoalkylamino or dialkylamino. Examples of the alkylamino groups include, but are not limited to, N-methylamino, N-ethylamino, N, N-dimethylamino, N, N-diethylamino, etc.

The term "aminoalkyl" includes $C_{1-10}$ linear or branched alkyl groups substituted with one or more amino groups. In some examples, the aminoalkyl group is a $C_{1-6}$ "lower aminoalkyl group" substituted with one or more amino groups. In other examples, the aminoalkyl group is a $C_{1-4}$ "lower aminoalkyl" substituted with one or more amino groups. Such examples include, but are not limited to, aminomethyl, aminoethyl, aminopropyl, aminobutyl and aminohexyl.

The term "cyanoalkyl" includes $C_{1-10}$ straight or branched chain alkyl groups substituted with one or more cyano groups. In some examples, the cyanoalkyl group is a $C_{1-6}$ "lower cyanoalkyl" substituted with one or more cyano groups, and in other examples, the cyanoalkyl group is a $C_{1-4}$ "lower cyanoalkyl group" substituted with one or more cyano groups. Such examples include, but are not limited to, $CNCH_2$—, $CNCH_2CH_2$—, $CNCH_2CH_2CH_2$—, $CNCH_2CHCNCH_2$—, etc.

As described in the present disclosure, the ring system (as shown in the FIGURE below) formed by attaching a substituent through drawing a bond to the central ring represents that the substituent can be substituted at any substitutable position on any rings. For example, formula b represents that any position on ring A or ring B that may be substituted, such as formula c, d, e, f, g, h, i, j, k, l, m, n, o, p, q, etc.

b
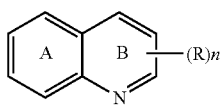

c
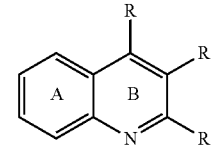

d
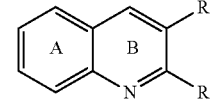

e
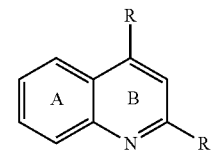

f
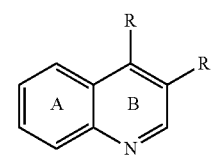

g
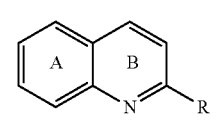

h
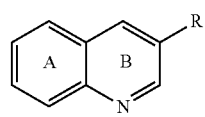

i
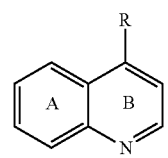

j
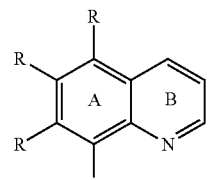

k
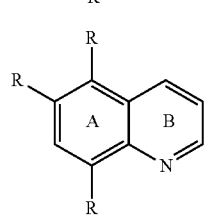

l
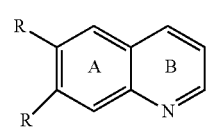

m
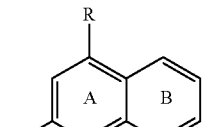

n
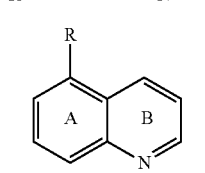

o
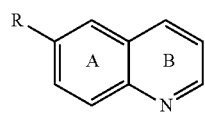

p
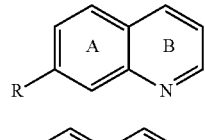

q
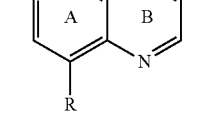

The term "prodrug" as used in the present disclosure represents a compound which is converted into a compound shown in formula (I) in vivo. Such conversion is affected by the hydrolysis of the prodrug in the blood or the enzymatic conversion of the prodrug into the maternal structure in the blood or tissues. The prodrug compounds of the present disclosure can be esters. In the present disclosure, esters which can be used as prodrugs include phenyl esters, aliphatic ($C_1$~$C_{24}$) esters, acyloxymethyl esters, carbonate, carbamic acid ester and amino acid esters. For example, a compound in the present disclosure contains a hydroxyl group, which can be acylated to obtain a compound in the form of a prodrug. Other prodrug forms include phosphate esters. For example, these phosphate ester compounds are obtained by phosphorylation of the parent hydroxyl group. For a complete discussion of prodrugs, refer to the following documents: T. Higuchi and V. Stella, *Pro-drugs as Novel Delivery Systems*, Vol. 14 *of the A.C.S. Symposium Series*, Edward B. Roche, ed., *Bioreversible Carriers in Drug Design*, American Pharmaceutical Association and Pergamon Press, 1987, J Rautio et al., *Prodrugs: Design and Clinical Applications, Nature Review Drug Discovery*, 2008, 7, 255-270, and S. J. Hecker et al., *Prodrugs of Phosphates and Phosphonates, Journal of Medicinal Chemistry*, 2008, 51, 2328-2345.

"Metabolite" refers to the product obtained by the metabolism of a specific compound or its salt in the body. The metabolites of a compound can be identified by techniques well-known in the art, and its activity can be characterized by experimental methods as described in the present disclosure. Such products can be obtained by oxidizing, reducing, hydrolyzing, amidating, deamidating, esterifying, degreasing, enzymatic cleavage, etc. of the administered compound. Correspondingly, the present disclosure includes the metabolites of the compound, including the metabolites produced by fully contacting the compound of the present disclosure with mammals for a period.

The term "pharmaceutically acceptable salt" used in the present disclosure refers to organic salts and inorganic salts of the compound of the present disclosure. The pharmaceutically acceptable salts are well known for one skilled in the field, as described in the literature: S. M Berge et al., describe pharmaceutically acceptable salts in detail in *J. Pharmaceutical Sciences*, 1977, 66: 1-19. The pharmaceutically acceptable non-toxic salts formed by acid include, but are not limited to, inorganic acid salts formed by reaction with amino groups such as hydrochloride, hydrobromide, phosphate, sulfate, and perchlorate, and organic acid salts, such as acetate, oxalate, maleate, tartrate, citrate, succinate, malonate, or other salts formed by methods described in books and literatures such as ion exchange. Other pharmaceutically acceptable salts include adipate, alginate, ascorbate, aspartate, benzene sulfonate, benzoate, bisulfate, borate, butyrate, camphanate, camphorsulfonate, cyclopentylpropionate, digluconate, laurylsulfonate, ethanesulfonate, formate, fumarate, gluceptate, glycerophosphate, gluconate, hemisulfate, enanthate, hexanoate, hydriodate, 2-hydroxyethanesulfonate, lactobionate, lactate, laurate, laurylsulfate, malate, malonate, mesylate, 2-naphthalenesulfonate, nicotinate, nitrate, oleate, palmitate, embonate, pectate, persulphate, 3-phenylpropionate, picrate, pivalate, propionate, stearate, thiocyanate, tosilate, undecanoate, valerate, etc. The salts obtained by reaction with suitable alkali include alkaline metal, alkaline earth metal, ammonium and $N^+(C_1$~$C_4$ alkyl)$_4$ salts. The present disclosure also designs the quaternary ammonium salt formed by any compound containing the N group. Water-soluble or oil-soluble or dispersed products can be obtained by quaternization. The alkaline metal or alkaline earth metal salts include sodium, lithium, potassium, calcium, magnesium, etc. The pharmaceutically acceptable salts further include appropriate, non-toxic ammonium, quaternary ammonium salts and amine cation formed by anti-equilibrium ion, such as halides, hydroxides, carboxylates, sulfates, phosphates, nitrates, $C_{1-8}$ sulfonates and aromatic sulfonates.

The "solvate" of the present disclosure refers to the association complex formed by one or more solvent molecules and the compounds of the present disclosure. The solvents that form solvates include, but are not limited to, water, isopropanol, ethanol, methanol, dimethyl sulfoxide, ethyl acetate, acetic acid, and aminoethanol. The term "hydrate" refers to an association complex formed by the solvent molecule, which is water.

When the solvent is water, the term "hydrate" can be used. In some examples, a compound of the present disclosure can be connected to one water molecule, such as monohydrate; in further examples, a compound of the present disclosure can be connected to more than one water molecules, such as dihydrate, and in yet another examples, a compound of the present disclosure can be connected to less than one water molecule, such as hemihydrate. It should be noted that the hydrates of the present disclosure retain the biologically effectiveness of the compound in its non-hydrated form.

The term "treating" any diseases or symptoms used herein refers to remedy the diseases or symptoms (i.e. easing or preventing or relieving the diseases or the development of at least one symptom) in some examples. In further examples, "treating" refers to the alleviation or improvement of at least one physical parameter, including physical parameters that the patients ignore. In further examples, "treating" refers to the regulation of a disease or symptoms physically (for example, stabilizing perceptible symptoms) or physiologically (for example, stabilizing physical parameters) or both. In other examples, "treating" refers to preventing or delaying the onset, occurrence, or worsening of a disease or symptoms.

SUMMARY

An aspect relates to a heteroaromatic compound that can effectively inhibit the activity of ATX, and can be used to prepare a medicament for the treatment of a disease with a pathological feature of ATX over-expression, such as cancer, fibrotic disease (for example, idiopathic pulmonary fibrosis or hepatic fibrosis), metabolic disease, myelodysplastic syndrome, cardiovascular disease, autoimmune disease, inflammatory disease, nervous system disease, or pain.

It is an aspect to provide a compound of formula (I), or a pharmaceutically acceptable salt, hydrate, solvate, stereoisomer, tautomer, nitrogen oxide, metabolite, prodrug, or mixture thereof:

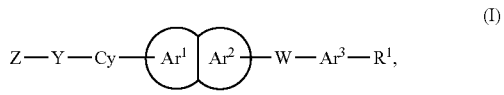

(I)

wherein,

W is —N($R^{1a}$)—, —O—, —S—, —S(=O)$_{1-2}$—, —C(=O)—, —(C($R^{2a}$)($R^{2b}$))$_{1-4}$—, —N($R^{1a}$)(C($R^{2a}$)($R^{2b}$))$_{1-4}$—, —N($R^{1a}$)C(=O)—, or —O(C($R^{2a}$)($R^{2b}$))$_{1-4}$—;

each of $Ar^1$ and $Ar^2$ is independently five-membered heteroaryl, wherein $Ar^1$ and $Ar^2$ are each optionally substituted with 1, 2, or 3 $R^2$;

$Ar^3$ is aryl, or heteroaryl, wherein $Ar^3$ is optionally substituted with 1, 2, 3, or 4 $R^3$;

Cy is cycloalkyl, heterocyclyl, spiro bicyclic, spiro heterobicyclic, fused bicyclic, fused heterobicyclic, bridged cyclic, bridged heterocyclic, aryl or heteroaryl, wherein Cy is optionally substituted with 1, 2, 3, or 4 $R^4$;

Y is -($L^1$-$W^1$)$_m$-$L^2$-;

$L^1$ is absent, or $L^1$ is —O—, —C(=O)—, —N($R^i$)—, —N($R^h$)C(=O)—, or —S(=O)$_{0-2}$—;

$W^1$ is $C_{1-4}$ alkylene, wherein $C_{1-4}$ alkylene is optionally substituted with 1, 2, 3, or 4 groups independently selected from H, F, Cl, Br, I, —OH, —NH$_2$, —NO$_2$, —CN, or $C_{1-6}$ alkoxy; $L^2$ is absent, or $L^2$ is —O—, —C(=O)—, —OC(=O)—, —C(=O)O—, —C(=O)—C(=O)—, —C(=O)—C(=O)N($R^a$)—, —N($R^b$)—, —C(=O)N($R^c$)—, —N($R^c$)C(=O)—, —C(=O)N($R^c$)—$R^{15}$—C(=O)O—, —C(=O)N($R^c$)—$R^{15}$—C(=O)N($R^a$)—, —N($R^d$)C(=O)N($R^c$)—, —N($R^g$)C(=O)O—, —S(=O)$_{0-2}$—, —S(=O)$_{1-2}$N($R^e$)—, —N($R^f$)S(=O)$_{1-2}$—, or —N($R^f$)S(=O)$_{1-2}$—$R^{15}$—N($R^a$)—;

Z is H, —CN, alkyl, alkenyl, alkynyl, haloalkyl, cycloalkyl, heterocyclyl, heterocyclylalkyl, cycloalkylalkyl, Spiro bicyclic, Spiro heterobicyclic, fused bicyclic, fused heterobicyclic, bridged cyclic, bridged heterocyclic, aryl, or heteroaryl, wherein each of alkyl, alkenyl, alkynyl, haloalkyl, cycloalkyl, heterocyclyl, heterocyclylalkyl, cycloalkylalkyl, spiro bicyclic, spiro heterobicyclic, fused bicyclic, fused heterobicyclic, bridged cyclic, bridged heterocyclic, aryl, and heteroaryl is optionally substituted with one or more $R^5$;

$R^1$ is alkyl, alkenyl, alkynyl, aryl, heteroaryl, cycloalkyl, or heterocyclyl, wherein $R^1$ is optionally substituted with 1, 2, 3, or 4 $R^6$;

each $R^2$ is independently H, —CN, —NO$_2$, —OH, —NH$_2$, F, Cl, Br, I, alkyl, alkenyl, alkynyl, haloalkyl, cyanoalkyl, hydroxyalkyl, alkoxy, alkoxyalkyl, aralkoxyalkyl, aryloxyalkyl, haloalkoxy, —S(=O)$_{0-2}$$R^7$, —C(=O)$R^8$, —OS(=O)$_{1-2}$$R^{7a}$, —OC(=O)$R^{8a}$, —C(=O)O$R^{8a}$, —N($R^{9a}$)C(=O)$R^9$, —OC(=O)N$R^{10}$$R^{10a}$, —N$R^{11}$$R^{11a}$, —N($R^{12}$)S(=O)$_{1-2}$$R^{12a}$, —N($R^{13}$)C(=O)N$R^{13a}$$R^{13b}$, —$R^{14}$—S(=O)$_{0-2}$$R^7$, —$R^{14}$—C(=O)$R^8$, —$R^{14}$—OS(=O)$_{1-2}$$R^{7a}$, —$R^{14}$—OC(=O)$R^{8a}$, —$R^{14}$—N($R^{9a}$)C(=O)$R^9$, —$R^{14}$—OC(=O)N$R^{10}$$R^{10a}$, —$R^{14}$—N$R^{11}$$R^{11a}$, —$R^{14}$—N($R^{12}$)S(=O)$_{1-2}$$R^{12a}$, or —$R^{14}$—N($R^{13}$)C(=O)N$R^{13a}$$R^{13b}$;

each of $R^{2a}$ and $R^{2b}$ is independently H, —CN, —OH, —NH$_2$, F, Cl, Br, I, alkyl, alkenyl, alkynyl, haloalkyl, cyanoalkyl, hydroxyalkyl, alkoxyl, haloalkoxy, aryl, aralkyl, heteroaryl, or heteroarylalkyl;

each $R^3$ is independently H, —CN, —NO$_2$, —OH, —NH$_2$, F, Cl, Br, I, alkyl, alkenyl, alkynyl, haloalkyl, cyanoalkyl, hydroxyalkyl, alkoxyl, haloalkoxy, —S(=O)$_{0-2}$$R^7$, —C(=O)$R^8$, —OS(=O)$_{1-2}$$R^{7a}$, —OC(=O)$R^{8a}$, —C(=O)O$R^{8a}$, —N($R^{9a}$)C(=O)$R^9$, —OC(=O)N$R^{10}$$R^{10a}$, —N$R^{11}$$R^{11a}$, —N($R^{12}$)S(=O)$_{1-2}$$R^{12a}$, —N($R^{13}$)C(=O)N$R^{13a}$$R^{13b}$, —$R^{14}$—S(=O)$_{0-2}$$R^7$, —$R^{14}$—C(=O)$R^8$, —$R^{14}$—OS(=O)$_{1-2}$$R^{7a}$, —$R^{14}$—OC(=O)$R^{8a}$, —$R^{14}$—N($R^{9a}$)C(=O)$R^9$, —$R^{14}$—OC(=O)N$R^{10}$$R^{10a}$, —$R^{14}$—N$R^{11}$$R^{11a}$, —$R^{14}$—N($R^{12}$)S(=O)$_{1-2}$$R^{12a}$, or —$R^{14}$—N($R^{13}$)C(=O)N$R^{13a}$$R^{13b}$;

each $R^4$ is independently H, oxo (C=O), —CN, —NO$_2$, —OH, —NH$_2$, F, Cl, Br, I, alkyl, alkenyl, alkynyl, haloalkyl, cyanoalkyl, hydroxyalkyl, alkoxyl, haloalkoxy, —S(=O)$_{0-2}$$R^7$, —C(=O)$R^8$, —OS(=O)$_{1-2}$$R^{7a}$, —C(=O)O$R^{8a}$, —OC(=O)$R^{8a}$, —N($R^{9a}$)C(=O)$R^9$, —C(=O)N$R^{9a}$$R^9$, —OC(=O)N$R^{10}$$R^{10a}$, —N$R^{11}$$R^{11a}$, —N($R^{12}$)S(=O)$_{1-2}$$R^{12a}$, —N($R^{13}$)C(=O)N$R^{13a}$$R^{13b}$, —$R^{14}$—S(=O)$_{0-2}$$R^7$, —$R_{14}$—C(=O)$R^8$, —$R^{14}$—OS(=O)$_{1-2}$$R^{7a}$, —$R^{14}$—OC(=O)$R^{8a}$, —$R^{14}$—N($R^{9a}$)C(=O)$R^9$, —$R^{14}$—OC(=O)N$R^{10}$$R^{10a}$, —$R^{14}$—N$R^{11}$$R^{11a}$, —$R^{14}$—N($R^{12}$)S(=O)$_{1-2}$$R^{12a}$, or —$R^{14}$—N($R^{13}$)C(=O)N$R^{13a}$$R^{13b}$;

each $R^5$ is independently H, oxo (C=O), —CN, —NO$_2$, —OH, —NH$_2$, F, Cl, Br, I, alkyl, alkenyl, alkynyl, haloalkyl, cyanoalkyl, hydroxyalkyl, alkoxyl, haloalkoxy, aryl, aralkyl, —S(=O)$_{0-2}$$R^7$, —C(=O)$R^8$, —OS(=O)$_{1-2}$$R^{7a}$, —OC(=O)$R^{8a}$, —C(=O)O$R^{8a}$, —N($R^{9a}$)C(=O)$R^9$, —OC(=O)N$R^{10}$$R^{10a}$, —N$R^{11}$$R^{11a}$, —N($R^{12}$)S(=O)$_{1-2}$$R^{12a}$, —N($R^{13}$)C(=O)N$R^{13a}$$R^{13b}$, —$R^{14}$—S(=O)$_{0-2}$$R^7$, —$R^{14}$—C(=O)$R^8$, —$R^{14}$—OS(=O)$_{1-2}$$R^{7a}$, —$R^{14}$—OC(=O)$R^{8a}$, —$R^{14}$—N($R^{9a}$)C(=O)$R^9$, —$R^{14}$—OC(=O)N$R^{10}$$R^{10a}$, —$R^{14}$—N$R^{11}$$R^{11a}$, —$R^{14}$—N($R^{12}$)S(=O)$_{1-2}$$R^{12a}$, or —$R^{14}$—N($R^{13}$)C(=O)N$R^{13a}$$R^{13b}$;

each $R^6$ is independently H, —CN, —NO$_2$, —OH, —NH$_2$, F, Cl, Br, I, alkyl, alkenyl, alkynyl, haloalkyl, cyanoalkyl, hydroxyalkyl, alkoxyl, haloalkoxy, —S(=O)$_{0-2}$$R^7$, —C(=O)$R^8$, —OS(=O)$_{1-2}$$R^{7a}$, —OC(=O)$R^{8a}$, —C(=O)O$R^{8a}$, —N($R^{9a}$)C(=O)$R^9$, —OC(=O)N$R^{10}$$R^{10a}$, —N$R^{11}$$R^{11a}$, —N($R^{12}$)S(=O)$_{1-2}$$R^{12a}$, —N($R^{13}$)C(=O)N$R^{13a}$$R^{13b}$, —$R^{14}$—S(=O)$_{0-2}$$R^7$, —$R^{14}$—C(=O)$R^8$, —$R^{14}$—OS(=O)$_{1-2}$$R^{7a}$, —$R^{14}$—OC(=O)$R^{8a}$, —$R^{14}$—N($R^{9a}$)C(=O)$R^9$, —$R^{14}$—OC(=O)N$R^{10}$$R^{10a}$, —$R^{14}$—N$R^{11}$$R^{11a}$, —$R^{14}$—N($R^{12}$)S(=O)$_{1-2}$$R^{12a}$, or —$R^{14}$—N($R^{13}$)C(=O)N$R^{13a}$$R^{13b}$;

$R^7$, $R^{7a}$, $R^8$, $R^{8a}$, $R^9$, and $R^{12a}$ are, independently in each instance, H, $C_{1-6}$ alkyl, $C_{2-6}$ alkenyl, $C_{2-6}$ alkynyl, $C_{1-6}$ haloalkyl, $C_{1-6}$ cyanoalkyl, aryl, aralkyl, heteroaryl, heteroarylalkyl, cycloalkyl, cycloalkylalkyl, heterocyclyl, or heterocyclylalkyl;

$R^{9a}$, $R^{10}$, and $R^{10a}$ are, independently in each instance, H, $C_{1-6}$ alkyl, $C_{2-6}$ alkenyl, $C_{2-6}$ alkynyl, $C_{1-6}$ cyanoalkyl, or $C_{1-6}$ haloalkyl;

$R^{11}$ and $R^{11a}$ are, independently in each instance, H, $C_{1-6}$ alkyl, $C_{2-6}$ alkenyl, $C_{2-6}$ alkynyl, $C_{1-6}$ haloalkyl, $C_{1-6}$ cyanoalkyl, or aralkyl;

$R^{12}$, $R^{13}$, $R^{13a}$, and $R^{13b}$ are, independently in each instance, H, $C_{1-6}$ alkyl, $C_{2-6}$ alkenyl, $C_{2-6}$ alkynyl, $C_{1-6}$ cyanoalkyl, or $C_{1-6}$ haloalkyl;

$R^{1a}$ is independently H, alkyl, alkenyl, alkynyl, haloalkyl, cyanoalkyl, hydroxyalkyl, cycloalkyl, cycloalkylalkyl, aryl, or aralkyl;

$R^a$, $R^b$, $R^c$, $R^d$, $R^e$, $R^f$, $R^g$, $R^h$, and $R^i$ are, independently in each instance, H, alkyl, alkenyl, alkynyl, cyanoalkyl, haloalkyl, $R^{16}$—C(=O)—, or cycloalkylalkyl;

$R^{14}$ and $R^{15}$ are, independently in each instance, alkylene, alkenylene, alkynylene, cyanoalkylene, or haloalkylene;

$R^{16}$ is H, $C_{1-6}$ alkyl, or $C_{1-6}$ haloalkyl; and m is 0, 1, or 2.

In some examples, $Ar^3$ is $C_{6-10}$ aryl, or $C_{1-9}$ heteroaryl, wherein $Ar^3$ is optionally substituted with 1, 2,3, or 4 $R^3$.

In other examples, $Ar^3$ is

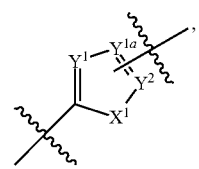

wherein, $X^1$ is —O—, —S—, —N($R^3$)—, —N=C($R^3$)—, —C($R^3$)=N—, or —C($R^3$)=C($R^3$)—; and each of $Y^1$, $Y^{1a}$, and $Y^2$ is independently —N—, —CH—, or —C($R^3$)—.

In other examples, $Ar^3$ is

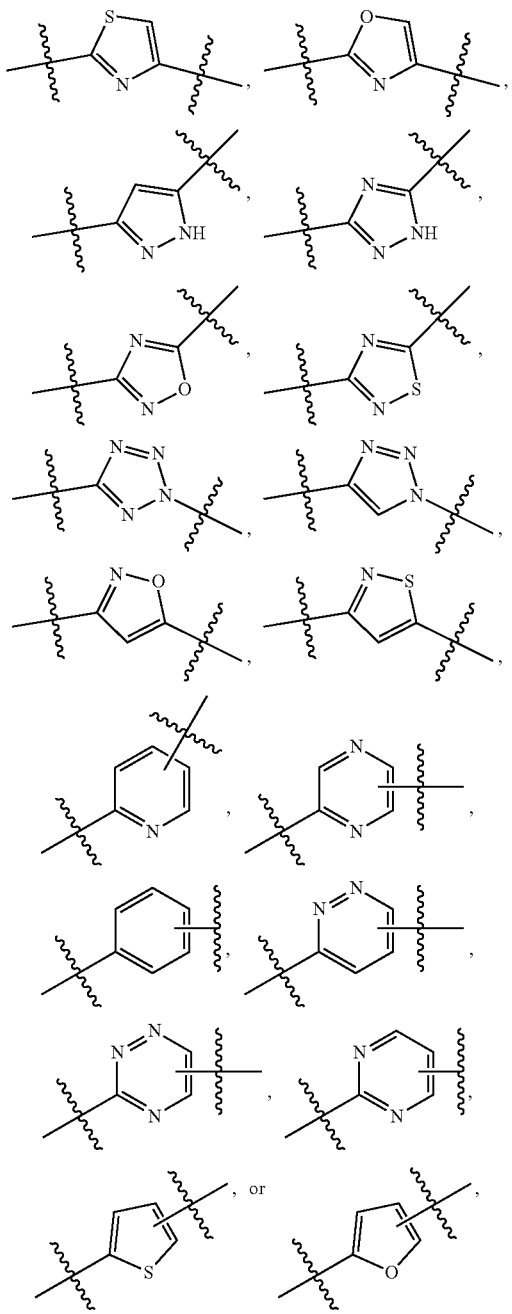

wherein, $Ar^3$ is optionally substituted with 0, 1, or 2 $R^3$.

In some examples, the compound is according to formula (Ia):

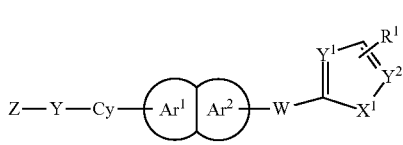

(Ia)

wherein, $X^1$ is —O—, —S—, —N($R^3$)—, —N=C($R^3$)—, —C($R^3$)=N—, or —C($R^3$)=C($R^3$)—; and each of $Y^1$ and $Y^2$ is independently —N—, or —C($R^3$)—;

or a pharmaceutically acceptable salt, hydrate, solvate, stereoisomer, tautomer, nitrogen oxide, metabolite, prodrug, or mixture thereof.

In some examples, the ring

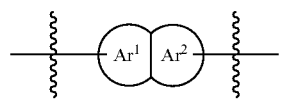

composed of $Ar^1$ and $Ar^2$ is

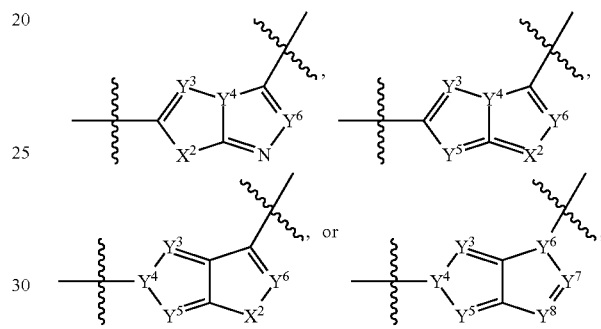

wherein, $X^2$ is —O—, —S—, C($R^2$)($R^{2c}$), or —N($R^{2d}$)—;

each of $Y^3$, $Y^4$, $Y^5$, $Y^6$, $Y^7$, and $Y^8$ is independently —N—, or —C($R^2$)—;

$R^{2c}$ is H, —CN, —NO$_2$, —OH, —NH$_2$, F, Cl, Br, I, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, $C_{1-4}$ alkoxy, $C_{1-4}$ alkoxy-$C_{1-4}$ alkyl, aralkoxy-$C_{1-4}$ alkyl, $C_{6-10}$ aryloxy-$C_{1-4}$ alkyl, —S(=O)$_{0-2}$R$^7$, —C(=O)R$^8$, —OS(=O)$_{1-2}$R$^{7a}$, —OC(=O)R$^{8a}$, —N(R$^{9a}$)C(=O)R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R$^8$, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, or —R$^{14}$—N(R$^{13}$)C(=O)NR$^{13a}$R$^{13b}$;

$R^{2d}$ is H, $C_{1-4}$ alkyl, $C_{2-4}$ alkenyl, $C_{2-4}$ alkynyl, $C_{1-4}$ cyanoalkyl, $C_{1-4}$ haloalkyl, $C_{1-4}$ hydroxyalkyl, $C_{1-4}$ alkoxy-$C_{1-4}$ alkyl, aralkoxy-$C_{1-4}$ alkyl, $C_{6-10}$ aryloxy-$C_{1-4}$ alkyl, —S(=O)$_{0-2}$R$^7$, —C(=O)R$^8$, —OS(=O)$_{1-2}$R$^{7a}$, —OC(=O)R$^{8a}$, or —OC(=O)NR$^{10}$R$^{10a}$, —R$^{14}$—S(=O)$_{0-2}$R$^7$, —R$^{14}$—C(=O)R$^8$, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, or —R$^{14}$—N(R$^{13}$)C(=O)NR$^{13a}$R$^{13b}$; and each $R^{14}$ is independently $C_{1-4}$ alkylene, $C_{2-4}$ alkenylene, $C_{2-4}$ alkynylene, $C_{1-4}$ cyanoalkylene, or $C_{1-4}$ haloalkylene.

In other examples, the ring

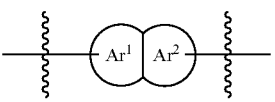

composed of Ar¹ and Ar² is

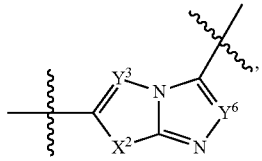

wherein,

X² is —O—, —S—, —C(R²)(R²ᶜ)—, or —N(R²ᵈ)—;
Y³ is —N—, or —C(R²)—;
Y⁶ is —N—, or —C(R²)—;
$R^{2c}$ is H, —CN, —NO₂, —OH, —NH₂, F, Cl, Br, I, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, $C_{1-4}$ alkoxy, $C_{1-4}$ alkoxy-$C_{1-4}$ alkyl, aralkoxy-$C_{1-4}$ alkyl, $C_{6-10}$ aryloxy-$C_{1-4}$ alkyl, —S(=O)$_{0-2}$R⁷, —C(=O)R⁸, —OS(=O)$_{1-2}$R⁷ᵃ, —OC(=O)R⁸ᵃ, —N(R⁹ᵃ)C(=O)R⁹, —OC(=O)NR¹⁰R¹⁰ᵃ, —NR¹¹R¹¹ᵃ, —N(R¹²)S(=O)$_{1-2}$R¹²ᵃ, —N(R¹³)C(=O)NR¹³ᵃR¹³ᵇ, —R¹⁴—S(=O)$_{0-2}$R⁷, —R¹⁴—C(=O)R⁸, —R¹⁴—OS(=O)$_{1-2}$R⁷ᵃ, —R¹⁴—OC(=O)R⁸ᵃ, —R¹⁴—N(R⁹ᵃ)C(=O)R⁹, —R¹⁴—OC(=O)NR¹⁰R¹⁰ᵃ, —R¹⁴—NR¹¹R¹¹ᵃ, —R¹⁴—N(R¹²)S(=O)$_{1-2}$R¹²ᵃ, or —R¹⁴—N(R¹³)C(=O)NR¹³ᵃR¹³ᵇ;

$R^{2d}$ is H, $C_{1-4}$ alkyl, $C_{2-4}$ alkenyl, $C_{2-4}$ alkynyl, $C_{1-4}$ cyanoalkyl, $C_{1-4}$ haloalkyl, $C_{1-4}$ hydroxyalkyl, —S(=O)$_{0-2}$R⁷, —C(=O)R⁸, —OS(=O)$_{1-2}$R⁷ᵃ, —OC(=O)R⁸ᵃ, —OC(=O)NR¹⁰R¹⁰ᵃ, —R¹⁴—S(=O)$_{0-2}$R⁷, —R¹⁴—C(=O)R⁸, —R¹⁴—OS(=O)$_{1-2}$R⁷ᵃ, —R¹⁴—OC(=O)R⁸ᵃ, —R¹⁴—N(R⁹ᵃ)C(=O)R⁹, —R¹⁴—OC(=O)NR¹⁰R¹⁰ᵃ, —R¹⁴—NR¹¹R¹¹ᵃ, —R¹⁴—N(R¹²)S(=O)$_{1-2}$R¹²ᵃ, or —R¹⁴—N(R¹³)C(=O)NR¹³ᵃR¹³ᵇ; and each R¹⁴ is independently $C_{1-4}$ alkylene, $C_{2-4}$ alkenylene, $C_{2-4}$ alkynylene, $C_{1-4}$ cyanoalkylene, or $C_{1-4}$ haloalkylene.

In other examples, the ring

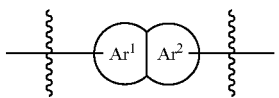

composed of Ar¹ and Ar² is

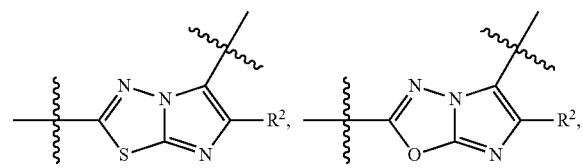

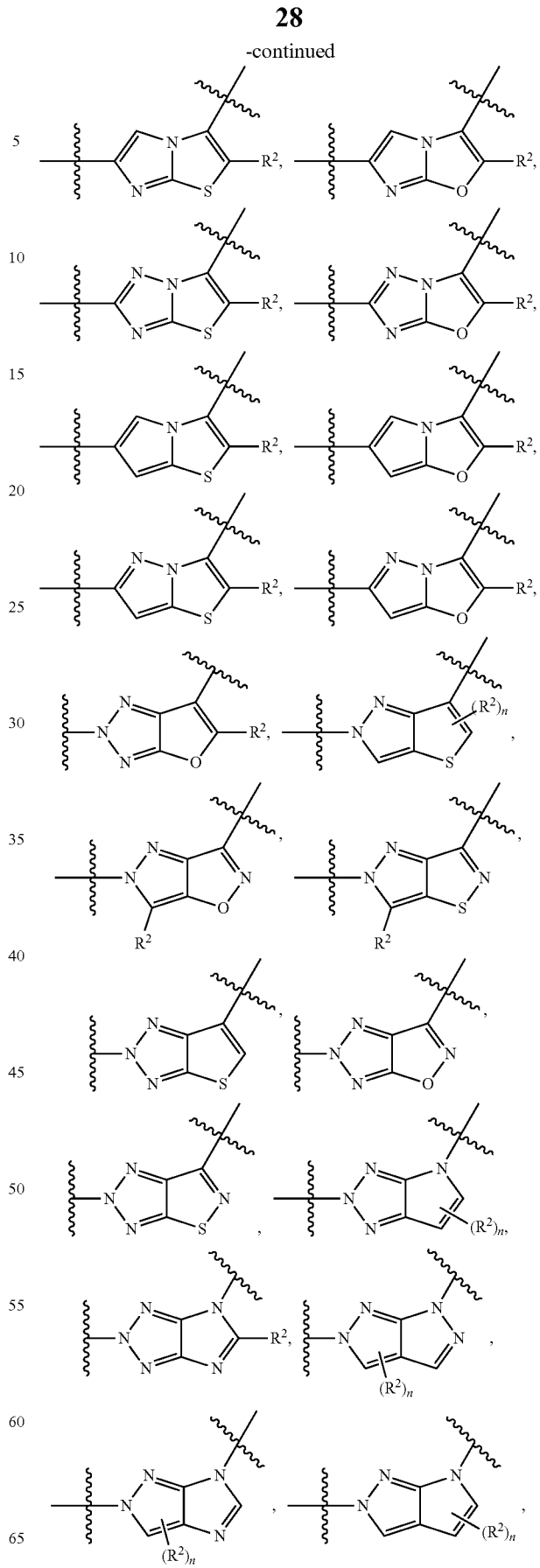

-continued

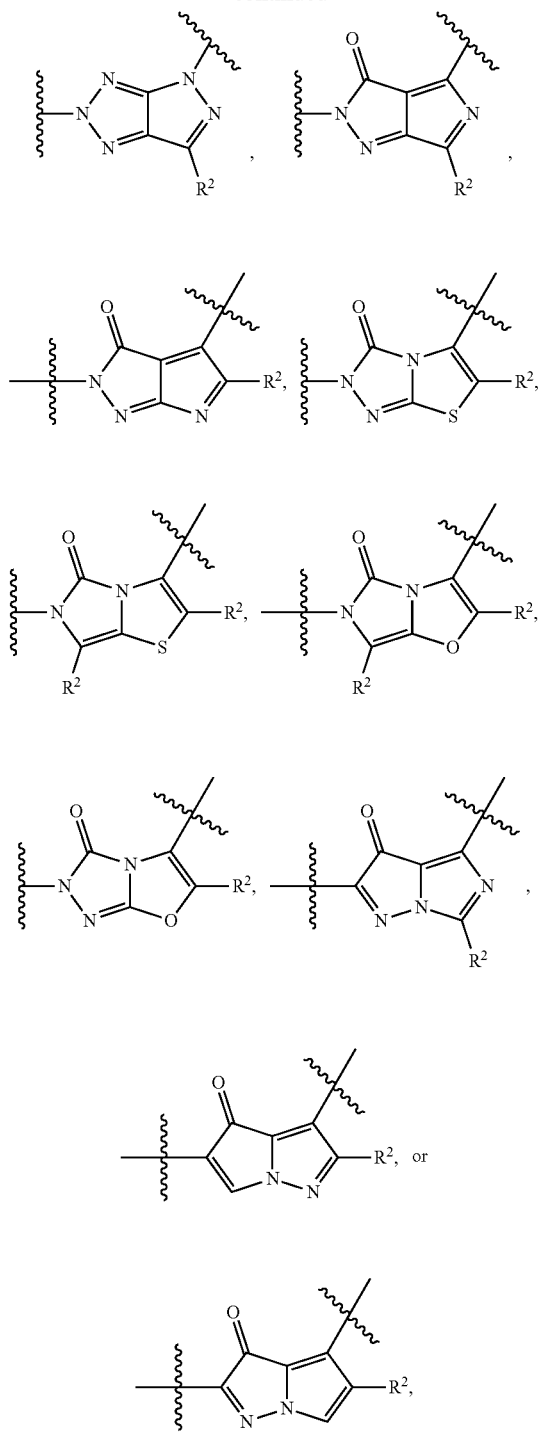

wherein, n is 0, 1, or 2.

In some examples, R¹ is $C_{6-10}$ aryl, $C_{1-9}$ heteroaryl, $C_{3-8}$ cycloalkyl, or $C_{2-9}$ heterocyclyl, and wherein R¹ is optionally substituted with 1, 2, 3, or 4 R⁶.

In some examples, R¹ is $C_{6-10}$ aryl, $C_{1-9}$ heteroaryl, $C_{3-6}$ cycloalkyl, or $C_{2-7}$ heterocyclyl, and wherein R¹ is optionally substituted with 1, 2, 3, or 4 R⁶.

In further examples, R¹ is phenyl, or pyridyl, and wherein phenyl is optionally substituted with 1, 2, 3, or 4 R⁶.

In some example, the compound is according to formula (Ib):

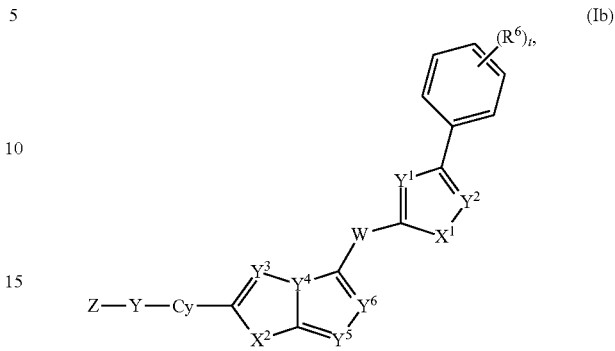

wherein,
X¹ is —O—, —S—, —N(R³)—, —N=C(R³)—, —C(R³)=N—, or —C(R³)=C(R³)—;
X² is —O—, —S—, C(R²)(R²ᶜ), or —N(R²ᵈ)—;
each of Y¹ and Y² is independently —N—, or —C(R³)—;
each of Y³, Y⁴, Y⁵, and Y⁶ is independently —N—, or —C(R²)—;
t is 0, 1, 2, 3, or 4;
R²ᶜ is H, —CN, —NO₂, —OH, —NH₂, F, Cl, Br, I, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, $C_{1-4}$ alkoxy, $C_{1-4}$ alkoxy-$C_{1-4}$ alkyl, aralkoxy-$C_{1-4}$ alkyl, $C_{6-10}$ aryloxy-$C_{1-4}$ alkyl, —S(=O)₀₋₂R⁷, —C(=O)R⁸, —OS(=O)₁₋₂R⁷ᵃ, —OC(=O)R⁸ᵃ, —N(R⁹ᵃ)C(=O)R⁹, —OC(=O)NR¹⁰R¹⁰ᵃ, —NR¹¹R¹¹ᵃ, —N(R¹²)S(=O)₁₋₂R¹²ᵃ, —N(R¹³)C(=O)NR¹³ᵃR¹³ᵇ, —R¹⁴—S(=O)₀₋₂R⁷, —R¹⁴—C(=O)R⁸, —R¹⁴—OS(=O)₁₋₂R⁷ᵃ, —R¹⁴—OC(=O)R⁸ᵃ, —R¹⁴—N(R⁹ᵃ)C(=O)R⁹, —R¹⁴—OC(=O)NR¹⁰R¹⁰ᵃ, —R¹⁴—NR¹¹R¹¹ᵃ, —R¹⁴—N(R¹²)S(=O)₁₋₂R¹²ᵃ, or —R¹⁴—N(R¹³)C(=O)NR¹³ᵃR¹³ᵇ;
R²ᵈ is H, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, —S(=O)₀₋₂R⁷, —C(=O)R⁸, —OS(=O)₁₋₂R⁷ᵃ, —OC(=O)R⁸ᵃ, —OC(=O)NR¹⁰R¹⁰ᵃ, —R¹⁴—S(=O)₀₋₂R⁷, —R¹⁴—C(=O)R⁸, —R¹⁴—OS(=O)₁₋₂R⁷ᵃ, —R¹⁴—OC(=O)R⁸ᵃ, —R¹⁴—N(R⁹ᵃ)C(=O)R⁹, —R¹⁴—OC(=O)NR¹⁰R¹⁰ᵃ, —R¹⁴—NR¹¹R¹¹ᵃ, —R¹⁴—N(R¹²)S(=O)₁₋₂R¹²ᵃ, or —R¹⁴—N(R¹³)C(=O)NR¹³ᵃR¹³ᵇ; and
each R¹⁴ is independently $C_{1-4}$ alkylene, $C_{2-4}$ alkenylene, $C_{2-4}$ alkynylene, $C_{1-4}$ cyanoalkylene, or $C_{1-4}$ haloalkylene; and or a pharmaceutically acceptable salt, hydrate, solvate, stereoisomer, tautomer, nitrogen oxide, metabolite, prodrug, or mixture thereof.

In some examples, W is —N(R¹ᵃ)—, or —C(R²ᵃ)(R²ᵇ)—; R¹ᵃ is H, $C_{1-4}$ alkyl, or $C_{1-4}$ haloalkyl; each of R²ᵃ and R²ᵇ is independently H, —CN, —OH, —NH₂, F, Cl, Br, I, $C_{1-4}$ alkyl, $C_{1-4}$ haloalkyl, $C_{1-4}$ cyanoalkyl, $C_{1-4}$ hydroxyalkyl, $C_{1-4}$ alkoxy, $C_{6-10}$ aryl, $C_{6-10}$ aryl-$C_{1-4}$ alkyl, $C_{1-9}$ heteroaryl, or $C_{1-9}$ heteroaryl-$C_{1-4}$ alkyl.

In some examples, W is —N(R¹ᵃ)—; R¹ᵃ is H, methyl, ethyl, propyl, —CF₃, or —CH₂CF₃.

In some examples, wherein,
X¹ is —O—, —S—, —N(R³)—, —N=C(R³)—, —C(R³)=N—, or —C(R³)=C(R³)—;
each of Y¹ and Y² is independently —N—, or —C(R³)—;
each R³ is independently H, —CN, —NO₂, —OH, —NH₂, F, Cl, Br, I, $C_{1-4}$ alkyl, $C_{1-4}$ haloalkyl, $C_{1-4}$ cyanoalkyl, $C_{1-4}$ hydroxyalkyl, $C_{1-4}$ alkoxy, $—S(=O)_{0-2}R^7$, $—C(=O)R^8$, $—OS(=O)_{1-2}R^{7a}$, $—OC(=O)R^{8a}$, $—N(R^{9a})C(=O)R^9$, $—OC(=O)NR^{10}R^{10a}$, $—NR^{11}R^{11a}$, $—N(R^{12})S(=O)_{1-2}R^{12a}$, $—N(R^{13})C(=O)NR^{13a}R^{13b}$, $—R^{14}—S(=O)_{0-2}R^7$, $—R^{14}—C(=O)R^8$, $—R^{14}—OS(=O)_{1-2}R^{7a}$, $—R^{14}—OC(=O)R^{8a}$, $—R^{14}—N(R^{9a})C(=O)R^9$, $—R^{14}—OC(=O)NR^{10}R^{10a}$, $—R^{14}—NR^{11}R^{11a}$, $—R^{14}—N(R^{12})S(=O)_{1-2}R^{12a}$, or $—R^{14}—N(R^{13})C(=O)NR^{13a}R^{13b}$;

$R^7$, $R^{7a}$, $R^8$, $R^{8a}$, $R^9$, and $R^{12a}$ are, independently in each instance, H, $C_{1-4}$ alkyl, $C_{2-4}$ alkenyl, $C_{2-4}$ alkynyl, $C_{1-4}$ haloalkyl, $C_{1-4}$ cyanoalkyl, aryl, aralkyl, heteroaryl, heteroarylalkyl, cycloalkyl, cycloalkylalkyl, heterocyclyl, or heterocyclylalkyl;

$R^{9a}$, $R^{10}$, and $R^{10a}$ are, independently in each instance, H, $C_{1-4}$ alkyl, $C_{2-4}$ alkenyl, $C_{2-4}$ alkynyl, $C_{1-4}$ cyanoalkyl, or $C_{1-4}$ haloalkyl;

$R^{11}$ and $R^{11a}$ are, independently in each instance, H, $C_{1-4}$ alkyl, $C_{2-4}$ alkenyl, $C_{2-4}$ alkynyl, $C_{1-4}$ haloalkyl, $C_{1-4}$ cyanoalkyl, or $C_{6-10}$ aryl-$C_{1-6}$ alkyl;

$R^{12}$, $R^{13}$, $R^{13a}$, and $R^{13b}$ are, independently in each instance, H, $C_{1-4}$ alkyl, $C_{2-4}$ alkenyl, $C_{2-4}$ alkynyl, $C_{1-4}$ cyanoalkyl, or $C_{1-4}$ haloalkyl; and each $R^{14}$ is independently $C_{1-4}$ alkylene, $C_{2-4}$ alkenylene, $C_{2-4}$ alkynylene, $C_{1-4}$ cyanoalkylene, or $C_{1-4}$ haloalkylene.

In some examples, the compound is according to formula (Ic):

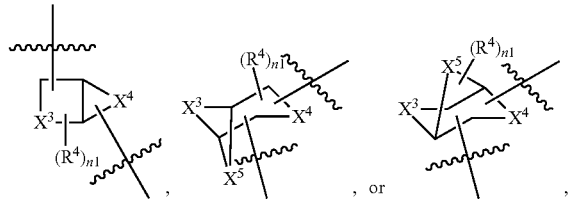
(Ic)

wherein,
$R^{1a}$ is H, $C_{1-4}$ alkyl, or $C_{1-4}$ haloalkyl; and
t is 0, 1, 2, 3, or 4;

or a pharmaceutically acceptable salt, hydrate, solvate, stereoisomer, tautomer, nitrogen oxide, metabolite, prodrug, or mixture thereof.

In some examples, Cy is $C_{3-8}$ cycloalkyl, $C_{2-7}$ heterocyclyl, $C_{5-12}$ spiro bicyclic, $C_{5-12}$ spiro heterobicyclic, $C_{5-12}$ fused bicyclic, $C_{5-12}$ fused heterobicyclic, $C_{5-12}$ bridged cyclic, $C_{5-12}$ bridged heterocyclic, $C_{6-10}$ aryl, or $C_{1-9}$ heteroaryl, wherein Cy is optionally substituted with 1, 2, 3, or 4 $R^4$.

In some examples, Cy is

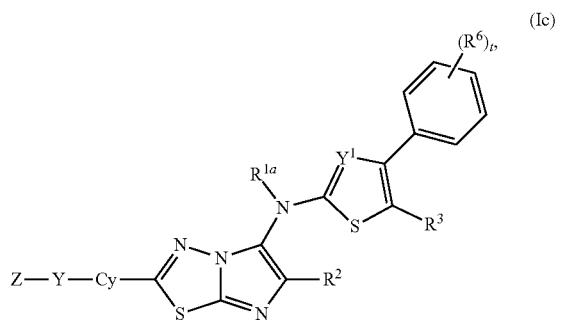

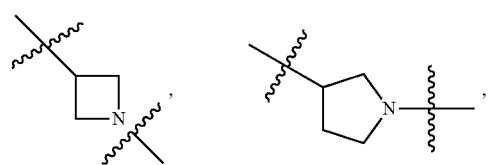

wherein,
each of $X^3$, $X^4$, and $X^5$ is independently $—O—$, $—S—$, $—NH—$, $—(CH_2)_{m1}—NH—(CH_2)_{m2}—$, $—(CH_2)_{m1}—O—(CH_2)_{m2}—$, $—(CH_2)_{m1}—S—(CH_2)_{m2}—$, or $—(CH_2)_{m3}—$;
each m1 is independently 1, 2, 3, or 4;
each m2 is independently 0, 1, 2, 3, or 4;
each m3 is independently 1, 2, 3, or 4; and
n1 is 0, 1, 2, 3, or 4.

In some examples, Cy is

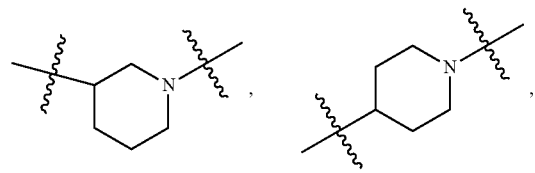

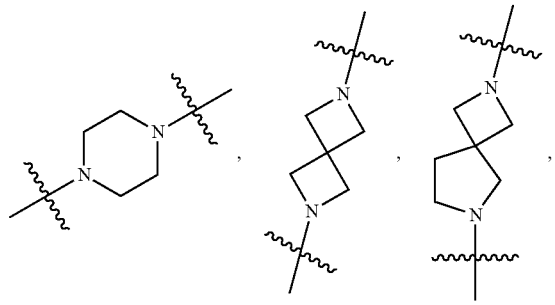

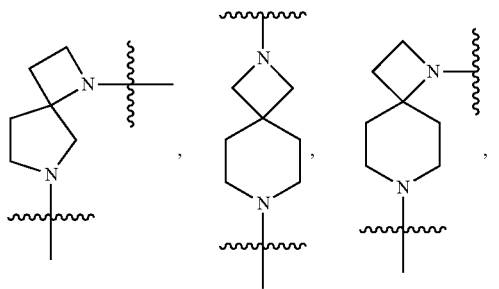

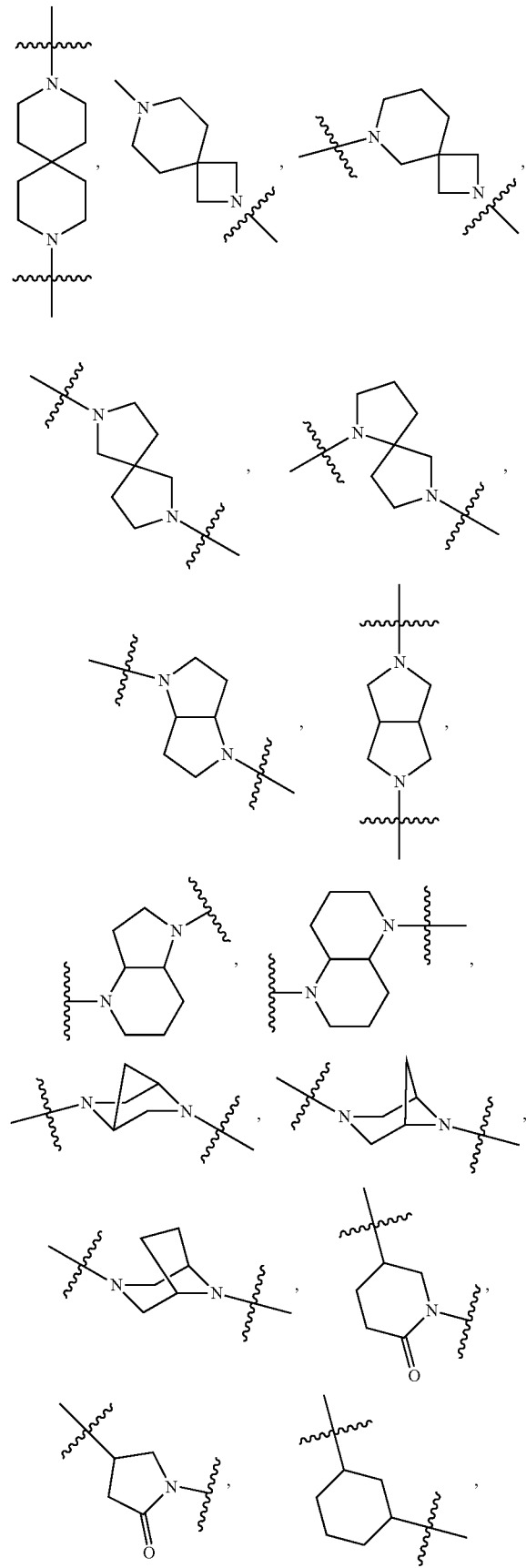

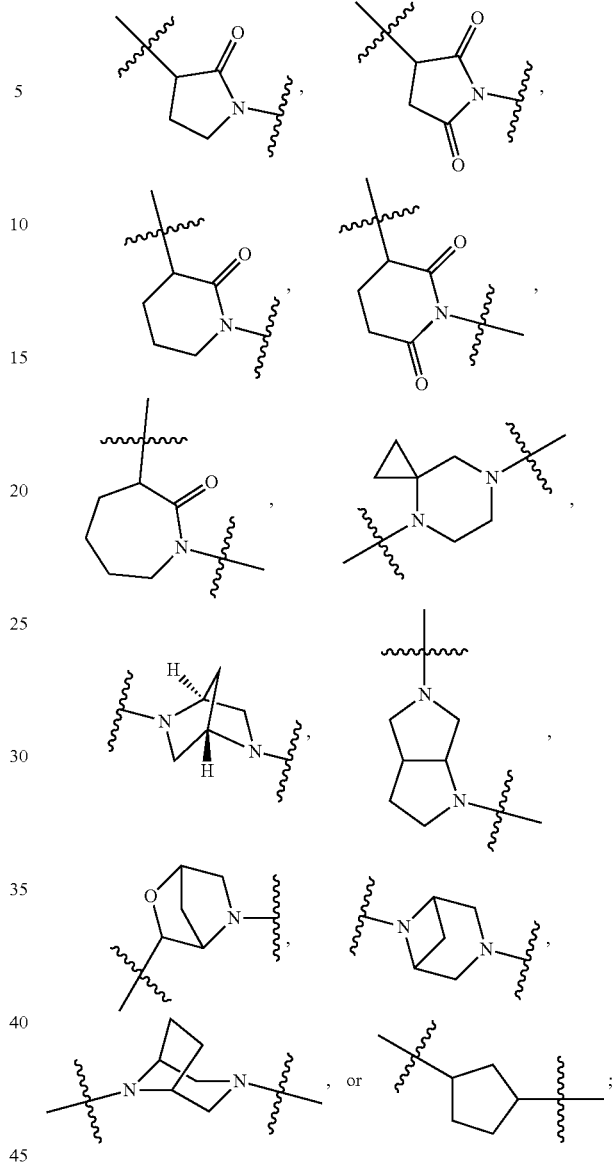

wherein, Cy is optionally substituted with 1, 2, 3, or 4 $R^4$.
In some examples,
Y is -($L^1$-$W^1$)$_m$-$L^2$-;
$L^1$ is absent, or $L^1$ is —O—, —C(=O)—, —N($R^i$)—, —N($R^h$)C(=O), or —S(=O)$_{0-2}$—;
$W^1$ is $C_{1-6}$ alkylene, wherein $C_{1-6}$ alkylene is optionally substituted with 1, 2, 3, or 4 groups independently selected from H, F, Cl, Br, —OH, —NH$_2$, —NO$_2$, —CN, or $C_{1-4}$ alkoxy;
$L^2$ is absent, or $L^2$ is —O—, —C(=O)—, —OC(=O)—, —C(=O)O—, —C(=O)—C(=O)—, —C(=O)—C(=O)N($R^a$)—, —N($R^b$)—, —C(=O)N($R^c$)—, —N($R^c$)C(=O)—, —N($R^d$)C(=O)N($R^e$)—, —C(=O)N($R^c$)—$R^{15}$—C(=O)O—, —C(=O)N($R^c$)—$R^{15}$—C(=O)N($R^a$)—, —N($R^g$)C(=O)O—, —S(=O)$_{0-2}$—, —S(=O)$_{1-2}$N($R^e$)—, —N($R^f$)S(=O)$_{1-2}$—, or —N($R^f$)S(=O)$_{1-2}$—$R^{15}$—N($R^a$)—;

$R^a$, $R^b$, $R^c$, $R^d$, $R^e$, $R^f$, $R^g$, $R^h$, and $R^i$ are, independently in each instance, H, $C_{1-6}$ alkyl, $C_{2-6}$ alkenyl, $C_{2-6}$ alkynyl, $C_{1-6}$ cyanoalkyl, $C_{1-6}$ hydroxyalkyl, $C_{1-6}$ haloalkyl, $R^{16}$—C(=O)—, or $C_{3-6}$ cycloalkyl-$C_{1-4}$ alkyl;

$R^{15}$ is $C_{1-6}$ alkylene;
$R^{16}$ is H, $C_{1-6}$ alkyl, or $C_{1-6}$ haloalkyl; and
m is 0, 1, or 2.

In some examples,
Y is -(L$^1$-W$^1$)$_m$-L$^2$-;
L$^1$ is absent, or L$^1$ is —O—, —C(=O)—, —N(R$^i$)—, —N(R$^h$)C(=O), or —S(=O)$_{0-2}$—;
W$^1$ is $C_{1-4}$ alkylene, wherein $C_{1-4}$ alkylene is optionally substituted with 1, 2, 3, or 4 groups independently selected from H, F, Cl, Br, —OH, —NH$_2$, —NO$_2$, —CN, or $C_{1-4}$ alkoxy;
L$^2$ is absent, or L$^2$ is —O—, —C(=O)—, —OC(=O)—, —C(=O)O—, —C(=O)—C(=O)—, —C(=O)—C(=O)N(R$^a$)—, —N(R$^b$)—, —C(=O)N(R$^c$)—, —N(R$^c$)C(=O)—, —N(R$^d$)C(=O)N(R$^c$)—, —C(=O)N(R$^c$)—R$^{15}$—C(=O)O—, —C(=O)N(R$^c$)—R$^{15}$—C(=O)N(R$^a$)—, —N(R$^g$)C(=O)O—, —S(=O)$_{0-2}$—, —S(=O)$_{1-2}$N(R$^e$)—, —N(R$^f$)S(=O)$_{1-2}$—, or —N(R$^f$)S(=O)$_{1-2}$—R$^{15}$—N(R$^a$)—;
R$^a$, R$^b$, R$^c$, R$^d$, R$^e$, R$^f$, R$^g$, R$^h$, and R$^i$ are, independently in each instance, H, $C_{1-4}$ alkyl, $C_{2-4}$ alkenyl, $C_{2-4}$ alkynyl, $C_{1-4}$ cyanoalkyl, $C_{1-4}$ hydroxyalkyl, $C_{1-4}$ haloalkyl, R$^{16}$—C(=O)—, or $C_{3-6}$ cycloalkyl-$C_{1-4}$ alkyl;
R$^{15}$ is $C_{1-6}$ alkylene;
R$^{16}$ is H, $C_{1-4}$ alkyl, or $C_{1-4}$ haloalkyl; and
m is 0, 1, or 2.

In some examples,
Y is -(L$^1$-W$^1$)$_m$-L$^2$-;
L$^1$ is absent, or L$^1$ is —O—, —C(=O)—, —N(R$^i$)—, —N(R$^h$)C(O), or —S(=O)$_{0-2}$—;
W$^1$ is $C_{1-4}$ alkylene, wherein $C_{1-4}$ alkylene is optionally substituted with 1, 2, 3, or 4 groups independently selected from H, F, Cl, Br, —OH, —NH$_2$, —NO$_2$, —CN, or $C_{1-4}$ alkoxy;
L$^2$ is absent, or L$^2$ is —O—, —C(=O)—, —OC(=O)—, —C(=O)O—, —C(=O)—C(=O)—, —C(=O)—C(=O)N(R$^a$)—, —N(R$^b$)—, —C(=O)N(R$^c$)—, —N(R$^c$)C(=O)—, —N(R$^d$)C(=O)N(R$^c$)—, —C(=O)N(R$^c$)—R$^{15}$—C(=O)O—, —C(=O)N(R$^c$)—R$^{15}$—C(=O)N(R$^a$)—, —N(R$^g$)C(=O)O—, —S(=O)$_{0-2}$—, —S(=O)$_{1-2}$N(R$^e$)—, —N(R$^f$)S(=O)$_{1-2}$—, or —N(R$^f$)S(=O)$_{1-2}$—R$^{15}$—N(R$^a$)—;
R$^a$, R$^b$, R$^c$, R$^d$, R$^e$, R$^f$, R$^g$, R$^h$, and R$^i$ are, independently in each instance, H, methyl, ethyl, propyl, CNCH$_2$—, CNCH$_2$CH$_2$—, HOCH$_2$CH$_2$—, —CF$_3$, —CH$_2$CF$_3$, $C_{1-4}$ haloalkyl, cyclopropylmethyl, R$^{16}$—C(=O)—, or cyclopropylethyl;
R$^{15}$ is methylene, ethylidene, propylidene, or butylidene;
R$^{16}$ is H, methyl, ethyl, propyl, butyl, —CF$_3$, or CH$_2$CF$_3$; and
m is 0, 1 or 2.

In some examples, Z is H, —CN, $C_{1-4}$ alkyl, $C_{2-4}$ alkenyl, $C_{2-4}$ alkynyl, $C_{1-4}$ haloalkyl, $C_{3-8}$ cycloalkyl, $C_{2-7}$ heterocyclyl, $C_{2-7}$ heterocyclyl-$C_{1-4}$ alkyl, $C_{3-8}$ cycloalkyl-$C_{1-4}$ alkyl, $C_{5-12}$ spiro bicyclic, $C_{5-12}$ spiro heterobicyclic, $C_{5-12}$ fused bicyclic, $C_{5-12}$ fused heterobicyclic, $C_{5-12}$ bridged cyclic, $C_{5-12}$ bridged heterocyclic, $C_{6-10}$ aryl, or $C_{1-9}$ heteroaryl, wherein each of $C_{1-4}$ alkyl, $C_{2-4}$ alkenyl, $C_{2-4}$ alkynyl, $C_{1-4}$ haloalkyl, $C_{3-8}$ cycloalkyl, $C_{2-7}$ heterocyclyl, $C_{2-7}$ heterocyclyl-$C_{1-4}$ alkyl, $C_{3-8}$ cycloalkyl-$C_{1-4}$ alkyl, $C_{5-12}$ spiro bicyclyl, $C_{5-12}$ spiro heterobicyclic, $C_{5-12}$ fused bicyclic, $C_{5-12}$ fused heterobicyclic, $C_{5-12}$ bridged cyclic, $C_{5-12}$ bridged heterocyclic, $C_{6-10}$ aryl, and $C_{1-9}$ heteroaryl is optionally substituted with one or more R$^5$.

In some examples, Z is H, —CN, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, —$C_{1-4}$ alkyl-NR$^{11}$R$^{11a}$, or $C_{3-6}$ cycloalkyl, or Z is:

wherein, X$^6$ is N, or CH$_2$;
X$^7$ is —O—, —S—, —NH—, —(CH$_2$)$_{m4}$—NH—(CH$_2$)$_{m5}$—, —(CH$_2$)$_{m4}$—O—(CH$_2$)$_{m5}$—, —(CH$_2$)$_{m4}$—S—(CH$_2$)$_{m5}$—, or —(CH$_2$)$_{m6}$—;
each m4 is independently 1, 2, 3, or 4;
each m5 is independently 0, 1, 2, 3, or 4;
each m6 is independently 1, 2, 3, or 4; and
n2 is 0, 1, 2, 3, or 4.

In further examples, Z is H, —CN, methyl, ethyl, propyl, tert-butyl, —CF$_3$, —CH$_2$CF$_3$, —CH$_2$CH$_2$CN, or —CH$_2$CH$_2$OH, or Z is In some examples,
each R$^2$ is independently H, —CN, —NO$_2$, —OH, —NH$_2$, F, Cl, Br, I, $C_{1-6}$ alkyl, $C_{2-6}$ alkenyl, $C_{2-6}$ alkynyl, $C_{1-6}$ haloalkyl, $C_{1-6}$ cyanoalkyl, $C_{1-6}$ hydroxyalkyl, $C_{1-6}$ alkoxy, $C_{1-6}$ alkoxy-$C_{1-6}$ alkyl, $C_{6-10}$ aryl-$C_{1-6}$ alkoxy-$C_{1-6}$ alkyl, $C_{6-10}$ aryloxy-$C_{1-6}$ alkyl, —S(=O)$_{0-2}$R$^7$, —C(=O)R$^8$, —OS(=O)$_{1-2}$R$^{7a}$, —OC(=O)R$^{8a}$, —N(R$^{9a}$)C(=O)R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R$^8$, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, or —R$^{14}$—N(R$^{13}$)C(=O)NR$^{13a}$R$^{13b}$.

In further examples,
each R$^2$ is independently H, —CN, —NO$_2$, OH, —NH$_2$, F, Cl, Br, I, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, $C_{1-4}$ alkoxy, $C_{1-4}$ alkoxy-$C_{1-4}$ alkyl, $C_{6-10}$ aryl-$C_{1-4}$ alkoxy-$C_{1-4}$ alkyl, $C_{6-10}$ aryloxy-$C_{1-4}$ alkyl, —S(=O)$_{0-2}$R$^7$, —C(=O)R$^8$, —OS(=O)$_{1-2}$R$^{7a}$, —OC(=O)R$^{8a}$, —N(R$^{9a}$)C(=O)R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R$^8$, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, or —R$^{14}$—N(R$^{13}$)C(=O)NR$^{13a}$R$^{13b}$.

In further examples, each R$^2$ is independently H, —CN, —NO$_2$, OH, —NH$_2$, F, Cl, Br, I, methyl, ethyl, propyl, methoxymethyl, methoxyethyl, methoxypropyl, ethoxymethyl, ethoxyethyl, benzyloxymethyl, benzyloxyethyl, phenoxymethyl, phenoxyethyl, —CH$_2$CH$_2$CN, —CH$_2$CH$_2$OH, —CH$_2$OH, —CF$_3$, —CH$_2$CF$_3$, or —CH$_2$CH$_2$C(=O)NH$_2$.

In some examples, each R$^3$ is independently H, —CN, —NO$_2$, OH, —NH$_2$, F, Cl, Br, I, C$_{1-6}$ alkyl, C$_{2-6}$ alkenyl, C$_{2-6}$ alkynyl, C$_{1-6}$ haloalkyl, C$_{1-6}$ cyanoalkyl, C$_{1-6}$ hydroxyalkyl, C$_{1-6}$ alkoxy, —S(=O)$_{0-2}$R$^7$, —C(=O)R$^8$, —OS(=O)$_{1-2}$R$^{7a}$, —OC(=O)R$^{8a}$, —N(R$^{9a}$)C(=O)R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R$^8$, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, or —R$^{14}$—N(R$^{13}$)C(=O)NR$^{13a}$R$^{13b}$.

In further examples, each R$^3$ is independently H, —CN, —NO$_2$, OH, —NH$_2$, F, Cl, Br, I, C$_{1-4}$ alkyl, C$_{2-4}$ alkenyl, C$_{2-4}$ alkynyl, C$_{1-4}$ haloalkyl, C$_{1-4}$ cyanoalkyl, C$_{1-4}$ hydroxyalkyl, C$_{1-4}$ alkoxy, —S(=O)$_{0-2}$R$^7$, —C(=O)R$^8$, —OS(=O)$_{1-2}$R$^{7a}$, —OC(=O)R$^{8a}$, —N(R$^{9a}$)C(=O)R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R$^8$, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, or —R$^{14}$—N(R$^{13}$)C(=O)NR$^{13a}$R$^{13b}$.

In further examples, each R$^3$ is independently H, —CN, —NO$_2$, OH, —NH$_2$, F, Cl, Br, I, methyl, ethyl, propyl, butyl, tert-butyl, trifluoromethyl, trifluoroethyl, —CH$_2$CH$_2$CN, —CH$_2$CH$_2$OH, —CH$_2$CH$_2$C(=O)NH$_2$, methoxy, ethoxy, —S(=O)$_{0-2}$R$^7$, —C(=O)R$^8$, —OS(=O)$_{1-2}$R$^{7a}$, —OC(=O)R$^{8a}$, —N(R$^{9a}$)C(=O)R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R$^8$, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, or —R$^{14}$—N(R$^{13}$)C(=O)NR$^{13a}$R$^{13b}$.

In some examples, each R$^4$ is independently H, oxo (C=O), —CN, —NO$_2$, —OH, —NH$_2$, F, Cl, Br, I, C$_{1-6}$ alkyl, C$_{2-6}$ alkenyl, C$_{2-6}$ alkynyl, C$_{1-6}$ haloalkyl, C$_{1-6}$ cyanoalkyl, C$_{1-6}$ hydroxyalkyl, C$_{1-6}$ alkoxy, —S(=O)$_{0-2}$R$^7$, —C(=O)R$^8$, —OS(=O)$_{1-2}$R$^{7a}$, —C(=O)OR$^{8a}$, —OC(=O)R$^{8a}$, —N(R$^{9a}$)C(=O)R$^9$, —C(=O)NR$^{9a}$R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R$^8$, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, or —R$^{14}$—N(R$^{13}$)C(=O)NR$^{13a}$R$^{13b}$.

In further examples, each R$^4$ is independently H, oxo (C=O), —CN, —NO$_2$, —OH, —NH$_2$, F, Cl, Br, I, C$_{1-4}$ alkyl, C$_{2-4}$ alkenyl, C$_{2-4}$ alkynyl, C$_{1-4}$ haloalkyl, C$_{1-4}$ cyanoalkyl, C$_{1-4}$ hydroxyalkyl, C$_{1-4}$ alkoxy, —S(=O)$_{0-2}$R$^7$, —C(=O)R$^8$, —OS(=O)$_{1-2}$R$^{7a}$, —C(=O)OR$^{8a}$, —OC(=O)R$^{8a}$, —N(R$^{9a}$)C(=O)R$^9$, —C(=O)NR$^{9a}$R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R$^8$, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, or —R$^{14}$—N(R$^{13}$)C(=O)NR$^{13a}$R$^{13b}$.

In some examples, each R$^4$ is independently H, oxo (C=O), —CN, —NO$_2$, —OH, —NH$_2$, F, Cl, Br, I, methyl, ethyl, propyl, butyl, tert-butyl, trifluoromethyl, trifluoroethyl, —CH$_2$CH$_2$CN, —CH$_2$CH$_2$OH, —CH$_2$OH, —CH$_2$CH$_2$C(=O)NH$_2$, methoxy, ethoxy, —S(=O)$_{0-2}$R$^7$, —C(=O)R$^8$, —OS(=O)$_{1-2}$R$^{7a}$, —C(=O)OR$^{8a}$, —OC(=O)R$^{8a}$, —N(R$^{9a}$)C(=O)R$^9$, —C(=O)NR$^{9a}$R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R$^8$, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, or —R$^{14}$—N(R$^{13}$)C(=O)NR$^{13a}$R$^{13b}$.

In some examples, each R$^5$ is independently H, oxo (C=O), —CN, —NO$_2$, —OH, —NH$_2$, F, Cl, Br, I, C$_{1-6}$ alkyl, C$_{2-6}$ alkenyl, C$_{2-6}$ alkynyl, C$_{1-6}$ alkylamino, C$_{1-6}$ haloalkyl, C$_{1-6}$ cyanoalkyl, C$_{1-6}$ hydroxyalkyl, C$_{1-6}$ alkoxy, C$_{6-10}$ aryl, C$_{6-10}$ aryl-C$_{1-4}$ alkyl, —S(=O)$_{0-2}$R$^7$, —C(=O)R$^8$, —OS(=O)$_{1-2}$R$^{7a}$, —OC(=O)R$^{8a}$, —C(=O)OR$^{8a}$, —N(R$^{9a}$)C(=O)R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R$^8$, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, or —R$^{14}$—N(R$^{13}$)C(=O)NR$^{13a}$R$^{13b}$.

In further examples, each R$^5$ is independently H, oxo (C=O), —CN, —NO$_2$, —OH, —NH$_2$, F, Cl, Br, I, C$_{1-4}$ alkyl, C$_{2-4}$ alkenyl, C$_{2-4}$ alkynyl, C$_{1-4}$ alkylamino, C$_{1-4}$ haloalkyl, C$_{1-4}$ cyanoalkyl, C$_{1-4}$ hydroxyalkyl, C$_{1-4}$ alkoxy, C$_{6-10}$ aryl, C$_{6-10}$ aryl-C$_{1-4}$ alkyl, —S(=O)$_{0-2}$R$^7$, —C(=O)R$^8$, —OS(=O)$_{1-2}$R$^{7a}$, —OC(=O)R$^{8a}$, —C(=O)OR$^{8a}$, —N(R$^{9a}$)C(=O)R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, or —R$^{14}$—N(R$^{13}$)C(=O)NR$^{13a}$R$^{13b}$.

In further examples, each R$^5$ is independently H, oxo (C=O), —CN, —NO$_2$, —OH, —NH$_2$, F, Cl, Br, I, methyl, ethyl, propyl, butyl, tert-butyl, trifluoromethyl, trifluoroethyl, —CH$_2$CH$_2$CN, —CH$_2$CH$_2$OH, —CH$_2$CH$_2$C(=O)NH$_2$, methoxy, ethoxy, phenyl, benzyl, phenethyl, —S(=O)$_{0-2}$R$^7$, —C(=O)R$^8$, —OS(=O)$_{1-2}$R$^{7a}$, —OC(=O)R$^{8a}$, —C(=O)OR$^{8a}$, —N(R$^{9a}$)C(=O)R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R$^8$, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, or —R$^{14}$—N(R$^{13}$)C(=O)NR$^{13a}$R$^{13b}$.

In some examples, each R$^6$ is independently H, —CN, —NO$_2$, —OH, —NH$_2$, F, Cl, Br, I, C$_{1-6}$ alkyl, C$_{2-6}$ alkenyl, C$_{2-6}$ alkynyl, C$_{1-6}$ haloalkyl, C$_{1-6}$ cyanoalkyl, C$_{1-6}$ hydroxyalkyl, C$_{1-6}$ alkoxy, —S(=O)$_{0-2}$R$^7$, —C(=O)R$^8$, —OS(=O)$_{1-2}$R$^{7a}$, —OC(=O)R$^{8a}$, —N(R$^{9a}$)C(=O)R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R$^8$, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, or —R$^{14}$—N(R$^{13}$)C(=O)NR$^{13a}$R$^{13b}$.

In further examples, each R$^6$ is independently H, —CN, —NO$_2$, —OH, —NH$_2$, F, Cl, Br, I, C$_{1-4}$ alkyl, C$_{2-4}$ alkenyl, C$_{2-4}$ alkynyl, C$_{1-4}$ haloalkyl, C$_{1-4}$ cyanoalkyl, C$_{1-4}$ hydroxyalkyl, C$_{1-4}$ alkoxy, —S(=O)$_{0-2}$R$^7$, —C(=O)R$^8$, —OS(=O)$_{1-2}$R$^{7a}$, —OC(=O)R$^{8a}$, —N(R$^{9a}$)C(=O)R$^9$, —OC(=O)NR$^{10}$R$^{10a}$, —NR$^{11}$R$^{11a}$, —N(R$^{12}$)S(=O)$_{1-2}$R$^{12a}$, —N(R$^{13}$)C(=O)NR$^{13a}$R$^{13b}$, —R$^{14}$—S(=O)$_{0-2}$R$^7$, —R$^{14}$—C(=O)R$^8$, —R$^{14}$—OS(=O)$_{1-2}$R$^{7a}$, —R$^{14}$—OC(=O)R$^{8a}$, —R$^{14}$—N(R$^{9a}$)C(=O)R$^9$, —R$^{14}$—OC(=O)NR$^{10}$R$^{10a}$, —R$^{14}$—NR$^{11}$R$^{11a}$, —R$^{14}$—N(R$^{12}$)S(=O)$_{1-2}$R$^{12a}$, or —R$^{14}$—N(R$^{13}$)C(=O)NR$^{13a}$R$^{13b}$.

In further examples, each R$^6$ is independently H, —CN, F, Cl, Br, I, methyl, ethyl, propyl, tert-butyl, methoxy, ethoxy, —OCH$_2$CF$_3$, —CF$_3$, —CH$_2$CF$_3$, —CH$_2$CH$_2$CN, —CH$_2$CH$_2$OH, —C(=O)CH$_3$, —C(=O)CF$_3$, —C(=O)OCH$_3$, —C(=O)NH$_2$, or —NHC(=O)CH$_3$.

In some examples,

R$^7$, R$^{7a}$, R$^8$, R$^{8a}$, R$^9$, and R$^{12a}$ are, independently in each instance, H, C$_{1-6}$ alkyl, C$_{1-6}$ haloalkyl, C$_{1-6}$ cyanoalkyl, C$_{2-6}$ alkenyl, C$_{2-6}$ alkynyl, C$_{6-10}$ aryl, C$_{6-10}$ aryl-C$_{1-6}$ alkyl, C$_{1-9}$ heteroaryl, C$_{1-9}$ heteroaryl-C$_{1-6}$ alkyl, C$_{3-8}$ cycloalkyl, C$_{3-8}$ cycloalkyl-C$_{1-6}$ alkyl, C$_{2-9}$ heterocyclyl, or C$_{2-9}$ heterocyclyl-C$_{1-6}$ alkyl;

R$^{9a}$, R$^{10}$, and R$^{10a}$ are, independently in each instance, H, C$_{1-6}$ alkyl, C$_{2-6}$ alkenyl, C$_{2-6}$ alkynyl, C$_{1-6}$ cyanoalkyl, or C$_{1-6}$ haloalkyl;

R$^{11}$ and R$^{11a}$ are, independently in each instance, H, C$_{1-6}$ alkyl, C$_{2-6}$ alkenyl, C$_{2-6}$ alkynyl, C$_{1-6}$ haloalkyl, C$_{1-6}$ cyanoalkyl, or C$_{6-10}$ aryl-C$_{1-6}$ alkyl;

R$^{12}$, R$^{13}$, R$^{13a}$, and R$^{13b}$ are, independently in each instance, H, C$_{1-6}$ alkyl, C$_{2-6}$ alkenyl, C$_{2-6}$ alkynyl, C$_{1-6}$ cyanoalkyl, or C$_{1-6}$ haloalkyl; and R$^{14}$ is each independently C$_{1-6}$ alkylene, C$_{2-6}$ alkenylene, C$_{2-6}$ alkynylene, C$_{1-6}$ cyanoalkylene, or C$_{1-6}$ haloalkylene.

In other examples,

R$^7$, R$^{7a}$, R$^8$, R$^{8a}$, R$^9$, and R$^{12a}$ are, independently in each instance, H, C$_{1-4}$ alkyl, C$_{1-4}$ haloalkyl, C$_{1-4}$ cyanoalkyl, C$_{2-4}$ alkenyl, C$_{2-4}$ alkynyl, C$_{6-10}$ aryl, C$_{6-10}$ aryl-C$_{1-4}$ alkyl, C$_{1-9}$ heteroaryl, C$_{1-9}$ heteroaryl-C$_{1-4}$ alkyl, C$_{3-8}$ cycloalkyl, C$_{3-8}$ cycloalkyl-C$_{1-4}$ alkyl, C$_{2-7}$ heterocyclyl, or C$_{2-7}$ heterocyclyl-C$_{1-4}$ alkyl;

R$^{9a}$, R$^{10}$, and R$^{10a}$ are, independently in each instance, H, C$_{1-4}$ alkyl, C$_{2-4}$ alkenyl, C$_{2-4}$ alkynyl, C$_{1-4}$ cyanoalkyl, or C$_{1-4}$ haloalkyl;

R$^{11}$ and R$^{11a}$ is independently H, C$_{1-4}$ alkyl, C$_{2-4}$ alkenyl, C$_{2-4}$ alkynyl, C$_{1-4}$ haloalkyl, C$_{1-4}$ cyanoalkyl, or C$_{6-10}$ aryl-C$_{1-4}$ alkyl;

R$^{12}$, R$^{13}$, R$^{13a}$, and R$^{13b}$ are, independently in each instance, H, C$_{1-4}$ alkyl, C$_{2-4}$ alkenyl, C$_{2-4}$ alkynyl, C$_{1-4}$ cyanoalkyl, or C$_{1-4}$ haloalkyl; and each R$^{14}$ is independently C$_{1-4}$ alkylene, C$_{2-4}$ alkenylene, C$_{2-4}$ alkynylene, C$_{1-4}$ cyanoalkylene, or C$_{1-4}$ haloalkylene.

In other examples, wherein,

R$^7$, R$^{7a}$, R$^8$, R$^{8a}$, R$^9$, and R$^{12a}$ are, independently in each instance, H, methyl, ethyl, propyl, tert-butyl, —CF$_3$, —CH$_2$CF$_3$, —CH$_2$CH$_2$CN, —CH$_2$CH$_2$OH, ethylene, propenyl, ethynyl, phenyl, benzyl, phenethyl, C$_{1-9}$ heteroaryl, C$_{1-9}$ heteroaryl-C$_{1-4}$ alkyl, C$_{3-8}$ cycloalkyl, C$_{3-8}$ cycloalkyl-C$_{1-4}$ alkyl, C$_{2-7}$ heterocyclyl, or C$_{2-7}$ heterocyclyl-C$_{1-4}$ alkyl;

R$^{9a}$, R$^{10}$, and R$^{10a}$ are, independently in each instance, H, methyl, ethyl, propyl, tert-butyl, —CF$_3$, —CH$_2$CF$_3$, —CH$_2$CH$_2$CN, ethylene, propenyl, or ethynyl;

R$^{11}$ and R$^{11a}$ are, independently in each instance, H, methyl, ethyl, propyl, tert-butyl, —CF$_3$, —CH$_2$CF$_3$, —CH$_2$CH$_2$CN, ethylene, propenyl, ethynyl, benzyl, or phenethyl;

R$^{12}$, R$^{13}$, R$^{13a}$, and R$^{13b}$ are, independently in each instance, H, methyl, ethyl, propyl, tert-butyl, —CF$_3$, —CH$_2$CF$_3$, —CH$_2$CH$_2$CN, ethylene, propenyl, or ethynyl; and each R$^{14}$ is independently methylene, ethylidene, propylidene, butylidene, ethenylidene, propenylidene, ethynylene, —CH$_2$CH(CN)—, or —CH$_2$CH(F)—.

In some examples, the compound is according to any one of formulas (Id) to (Ig)

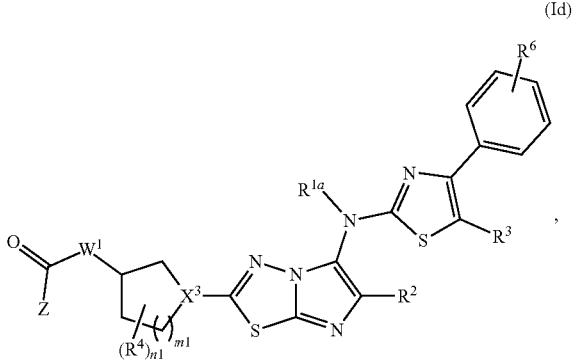

(Id)

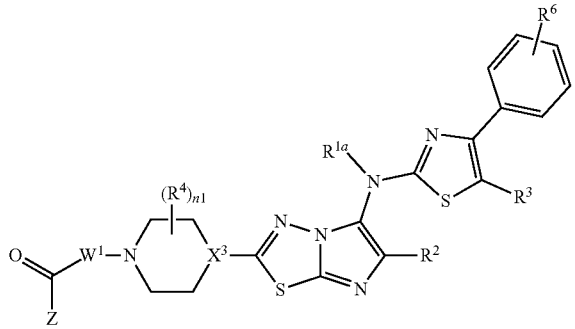

(Ie)

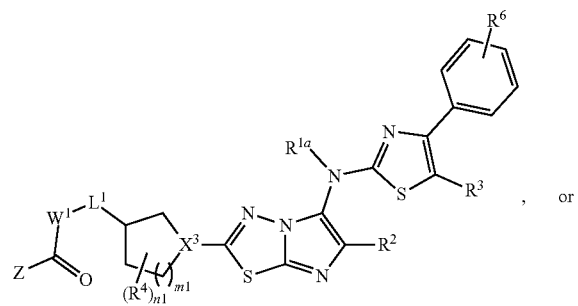

(If) , or

-continued (Ig)

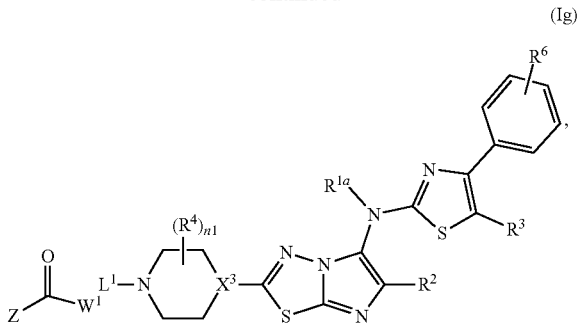

wherein, $R^{1a}$ is H, methyl, ethyl, propyl, —CF$_3$, or —CH$_2$CF$_3$;

each of $R^2$ and $R^3$ is independently H, —CN, F, Cl, Br, methyl, ethyl, propyl, methoxymethyl, methoxyethyl, methoxypropyl, ethoxymethyl, ethoxyethyl, benzyloxymethyl, benzyloxyethyl, —CF$_3$, —CH$_2$CF$_3$, —CH$_2$CH$_2$CN, —CH$_2$CH$_2$OH, or —CH$_2$CH$_2$C(=O)NH$_2$;

$R^4$ is H, oxo (=O), —CN, F, Cl, Br, I, methyl, ethyl, propyl, tert-butyl, methoxy, ethyoxyl, —OCH$_2$CF$_3$, —CF$_3$, —CH$_2$CF$_3$, —CH$_2$CH$_2$CN, —CH$_2$CH$_2$OH, —CH$_2$OH, —C(=O)CH$_3$, —C(=O)CF$_3$, —C(=O)OCH$_3$, —C(=O)NH$_2$, —C(=O)NHCH$_3$, —C(=O)NHCH$_2$CH$_3$, or —NHC(=O)CH$_3$;

$R^6$ is H, —CN, F, Cl, Br, I, methyl, ethyl, propyl, tert-butyl, methoxy, ethyoxyl, —OCH$_2$CF$_3$, —CF$_3$, —CH$_2$CF$_3$, —CH$_2$CH$_2$CN, —CH$_2$CH$_2$OH, —C(=O)CH$_3$, —C(=O)CF$_3$, —C(=O)OCH$_3$, —C(=O)NH$_2$, or —NHC(=O)CH$_3$;

$X^3$ is N, or CH;

$L^1$ is absent, or $L^1$ is —O—, —C(=O)—, —N(R$^i$)—, —N(R$^h$)C(=O)—, or —S(=O)$_{0\text{-}2}$—;

$W^1$ is $C_{1\text{-}4}$ alkylene, wherein $C_{1\text{-}4}$ alkylene is optionally substituted with 1, 2, 3, or 4 groups independently selected from H, F, Cl, Br, —OH, —NH$_2$, —NO$_2$, —CN, or $C_{1\text{-}4}$ alkoxy;

each of $R^h$ and $R^i$ is independently H, methyl, ethyl, propyl, tert-butyl, $C_{2\text{-}4}$ alkenyl, $C_{2\text{-}4}$ alkynyl, $C_{1\text{-}4}$ cyanoalkyl, $C_{1\text{-}4}$ hydroxyalkyl, $C_{1\text{-}4}$ haloalkyl, or cyclopropylmethyl, HC(=O)—, CH$_3$C(=O)—, or cyclopropylethyl;

m1 is 1, 2, 3, or 4;

n1 is 0, 1, 2, 3, or 4; and

Z is defined as herein;

or a pharmaceutically acceptable salt, hydrate, solvate, stereoisomer, tautomer, nitrogen oxide, metabolite, prodrug, or mixture thereof.

In some examples, the compound of the present disclosure is a compound having one of the following structures:

(1)

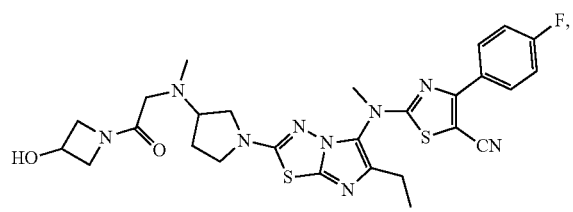

(2)

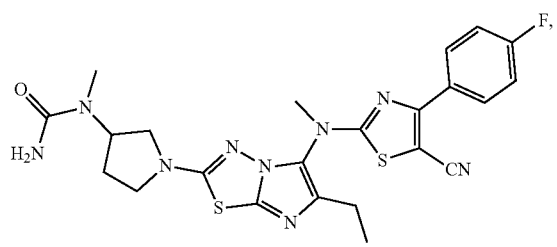

(3)

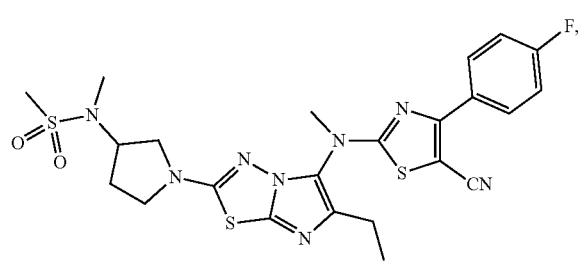

(4)

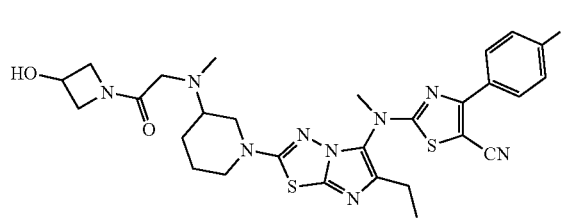

(5)

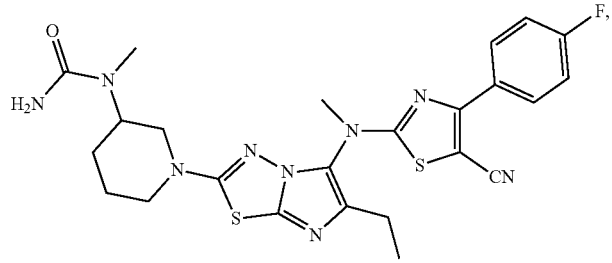

-continued
(6)
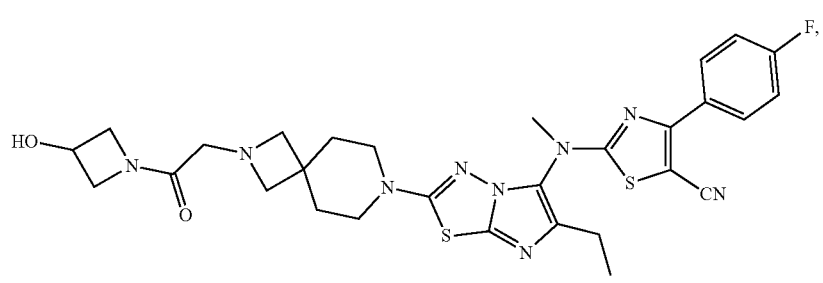
(7)
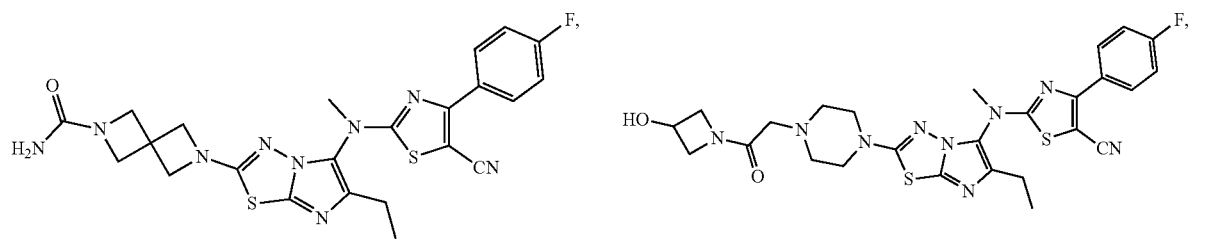
(8)
(9)
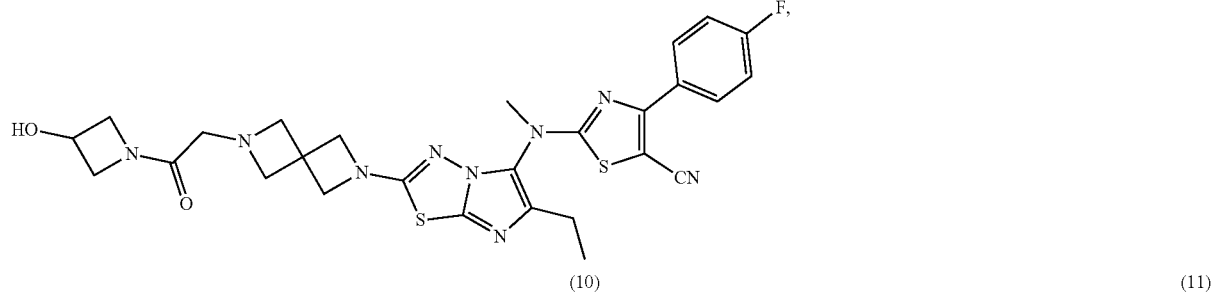
(10)
(11)
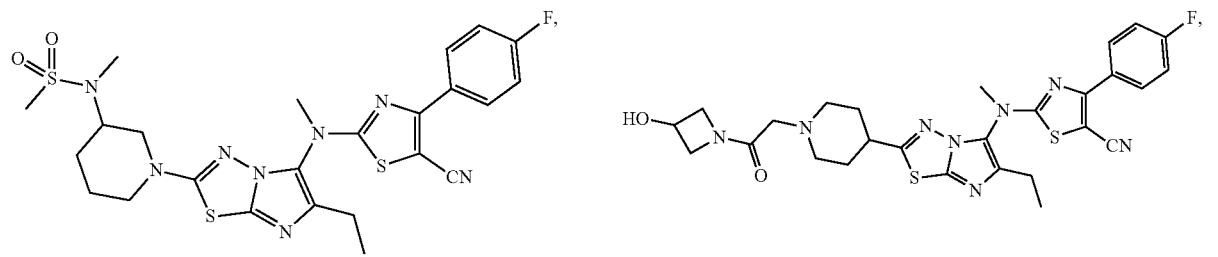
(12)
(13)
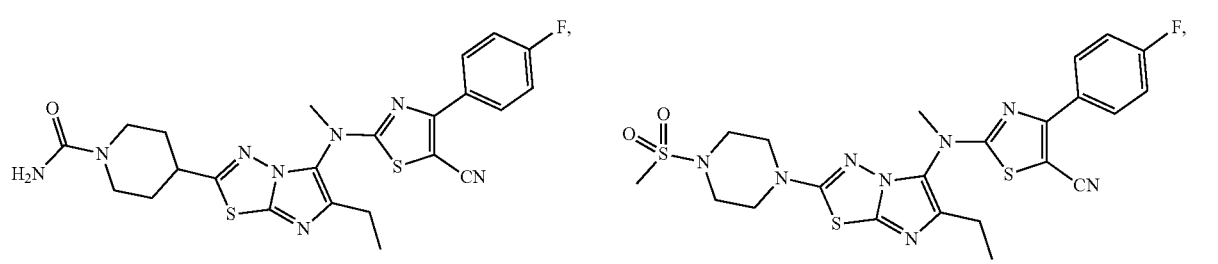
(14)
(15)
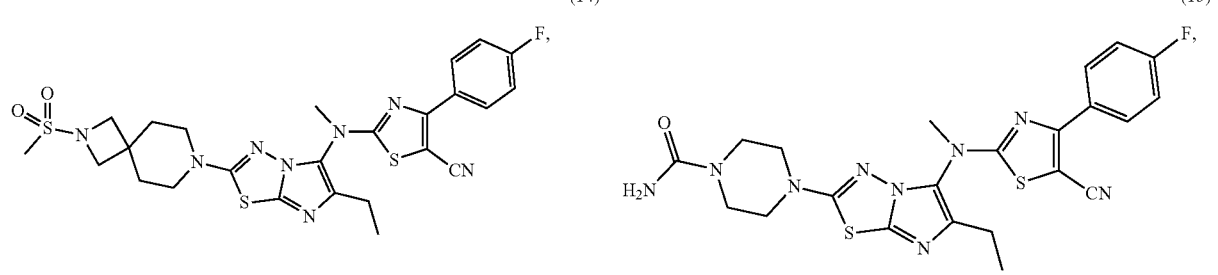

-continued
(16)
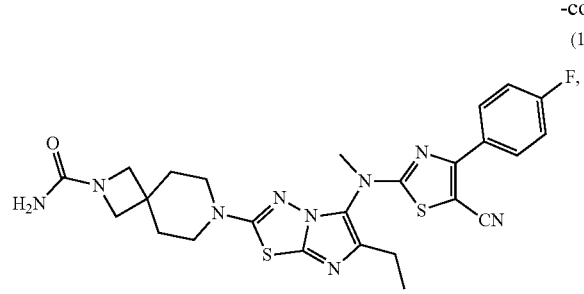
(17)
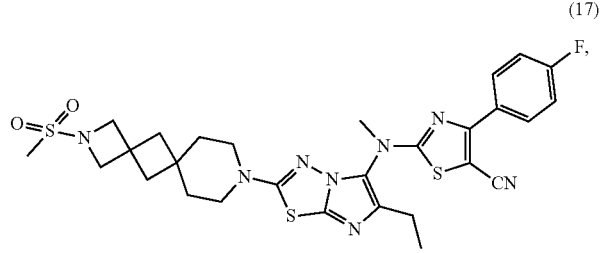
(18)
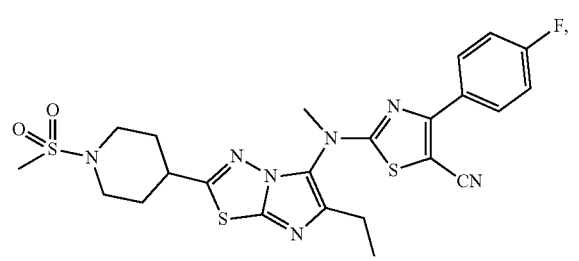
(19)
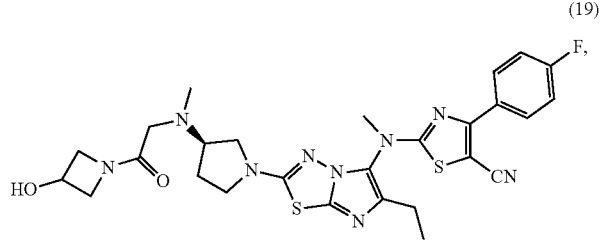
(20)
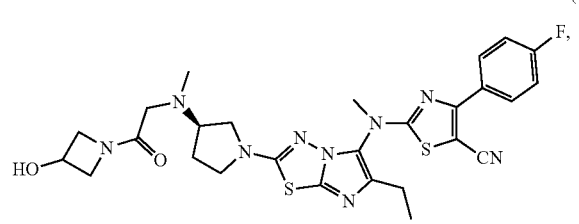
(21)
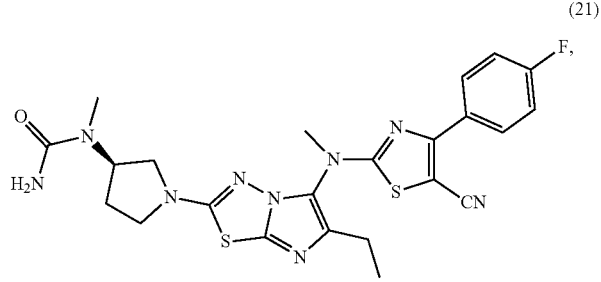
(22)
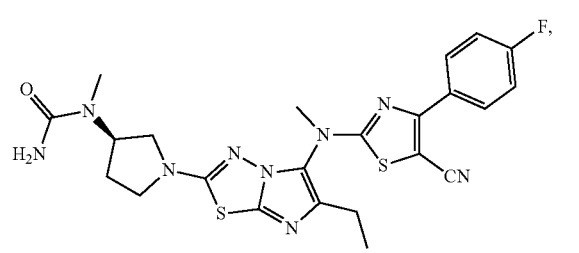
(23)
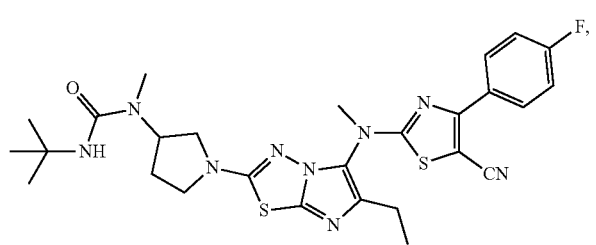
(24)
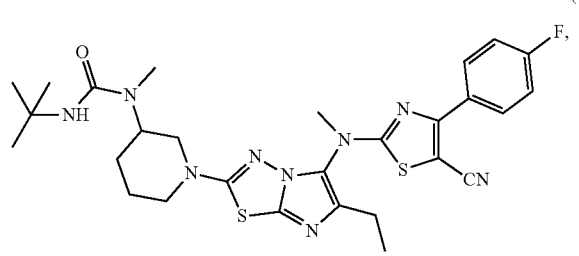
(25)
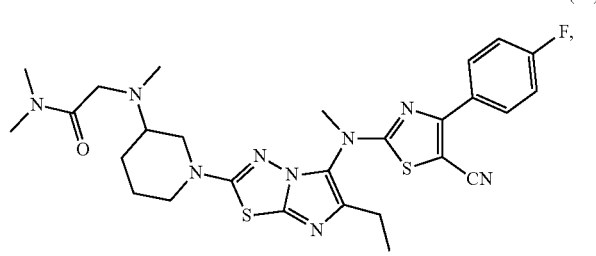
(26)
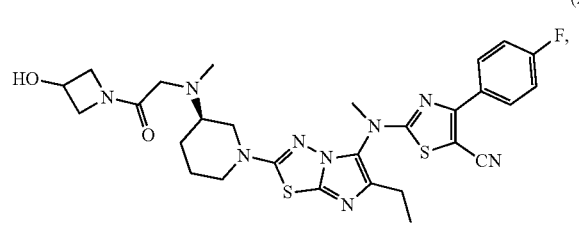
(27)
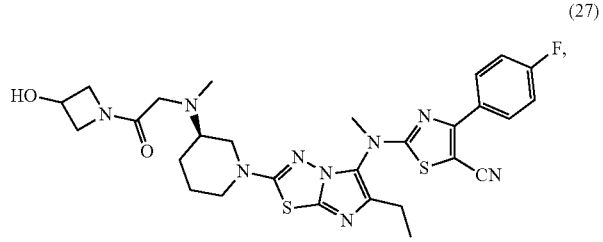

(28)
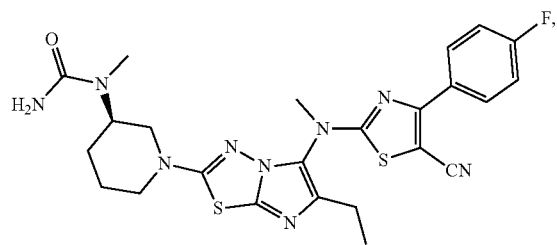
(29)
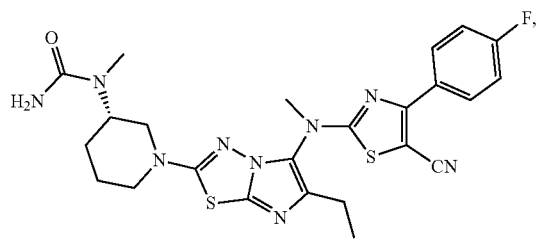
(30)
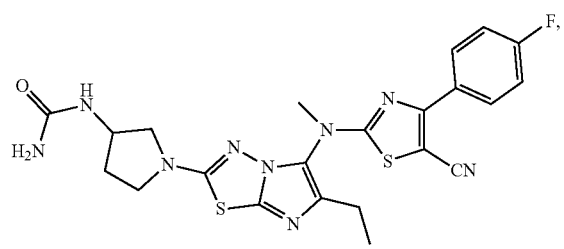
(31)
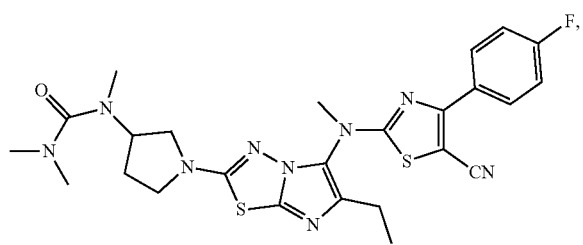
(32)
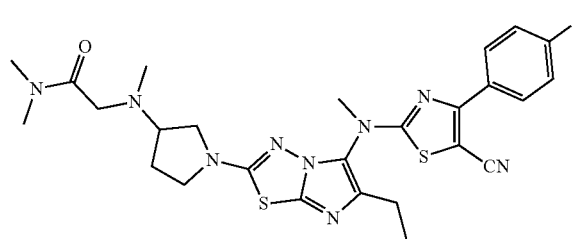
(33)
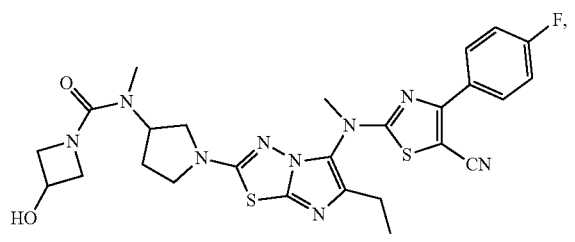
(34)
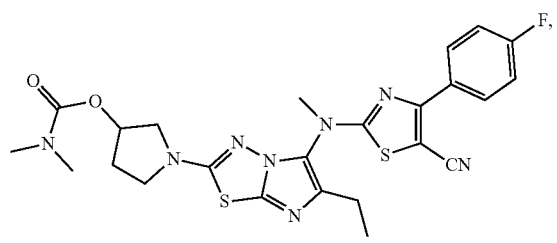
(35)
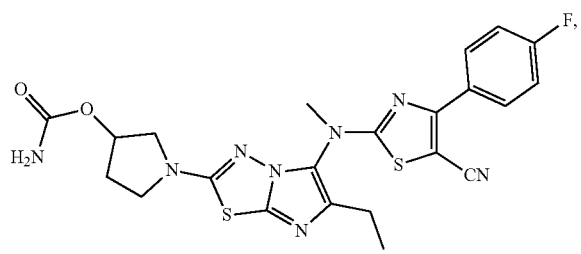
(36)
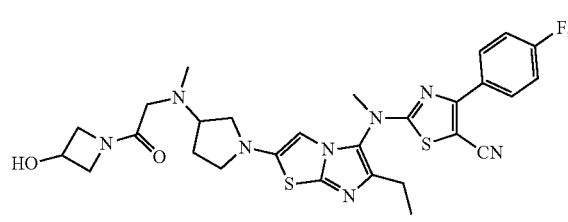
(37)
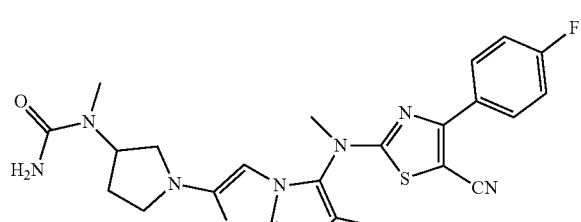
(38)
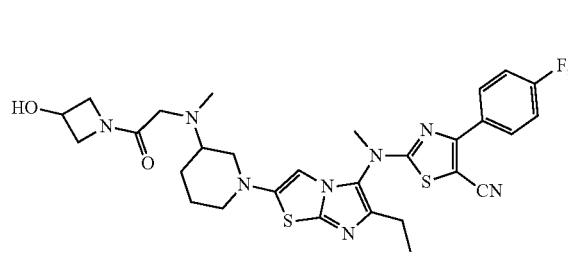
(39)
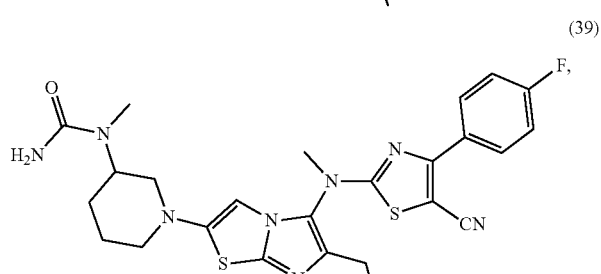

-continued
(40)
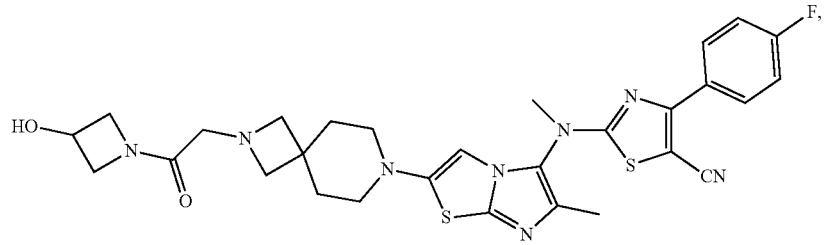
(41)
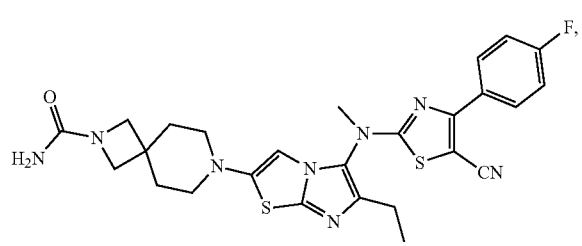
(42)
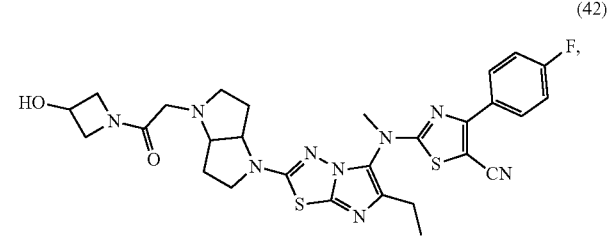
(43)
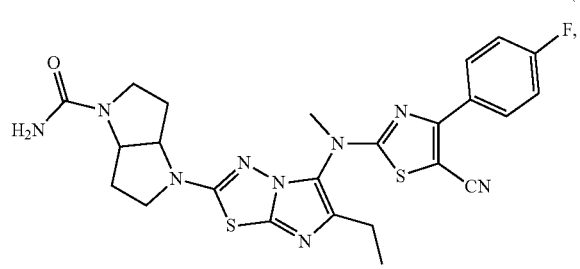
(44)
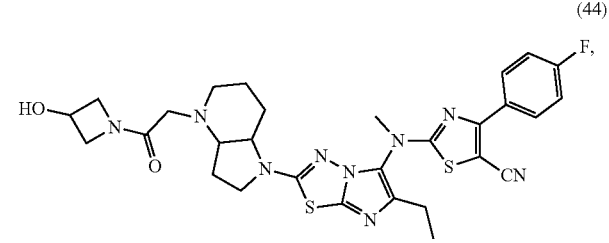
(45)
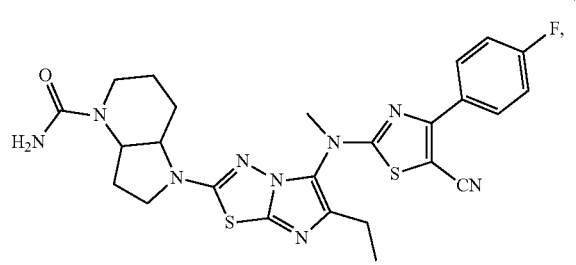
(46)
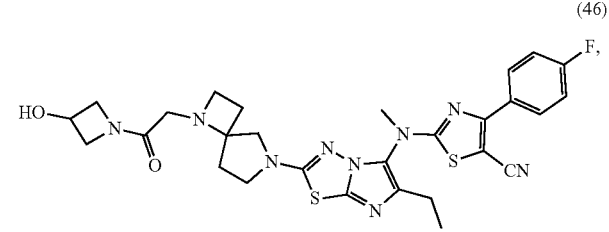
(47)
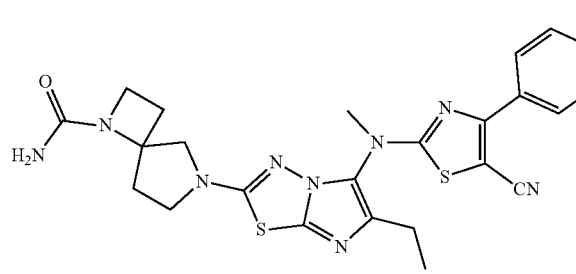
(48)
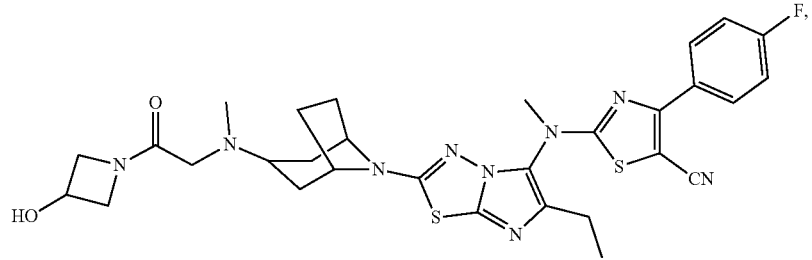

-continued
(49)
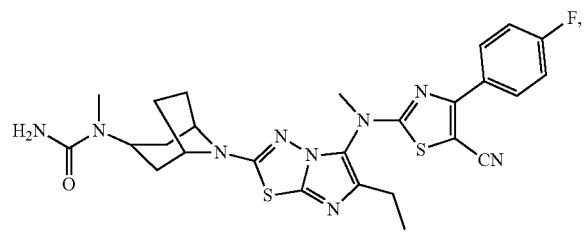
(50)
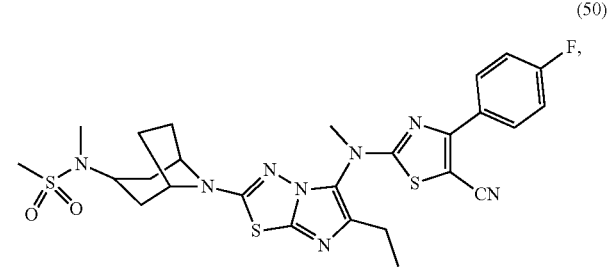
(51)
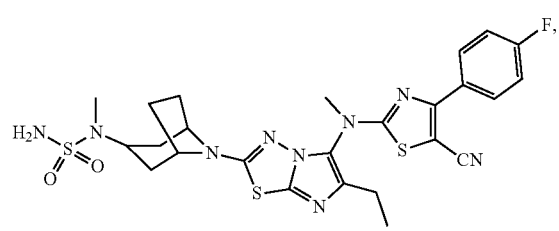
(52)
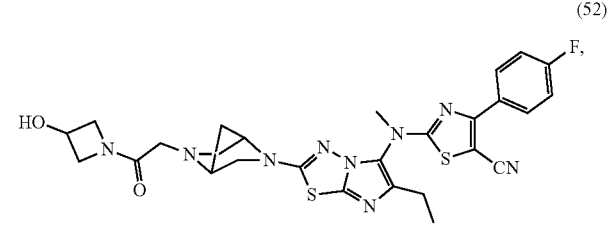
(53)
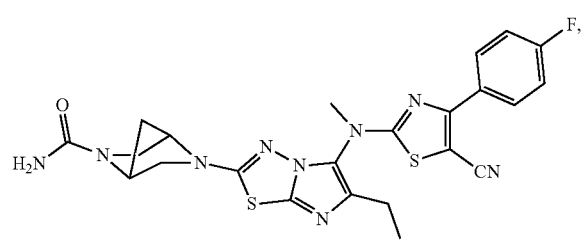
(54)
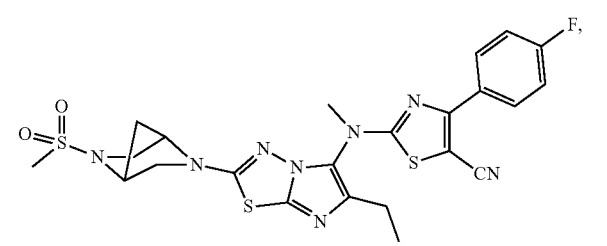
(55)
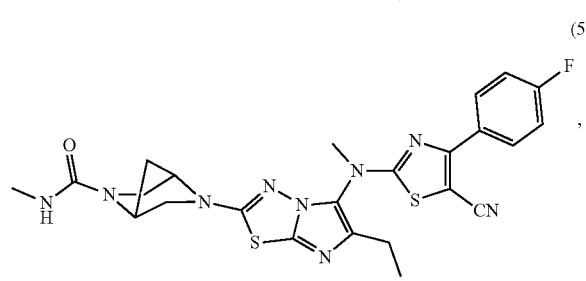
(56)
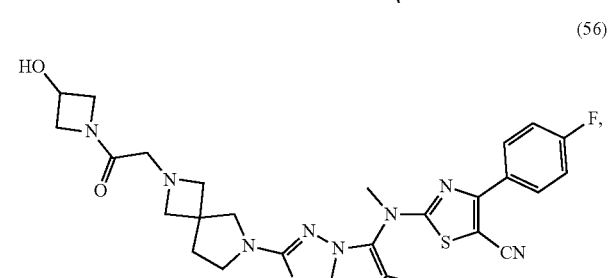
(57)
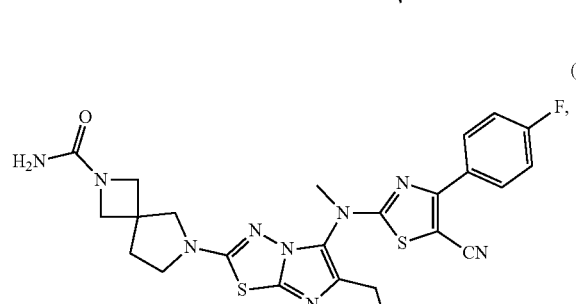
(58)
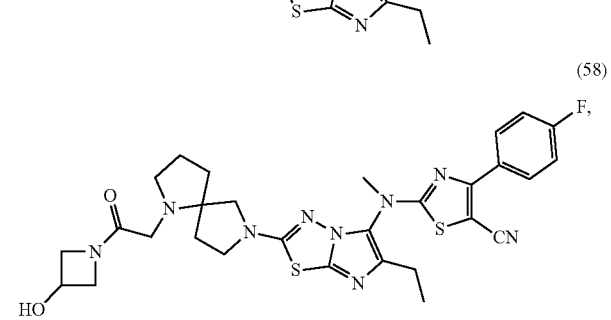
(59)
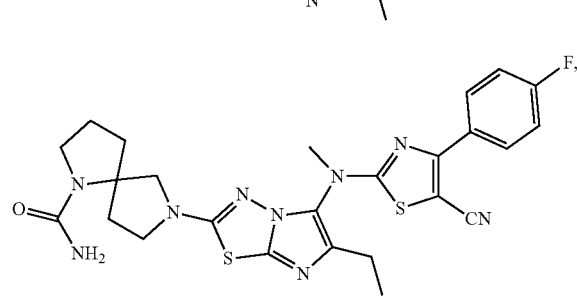

(60)
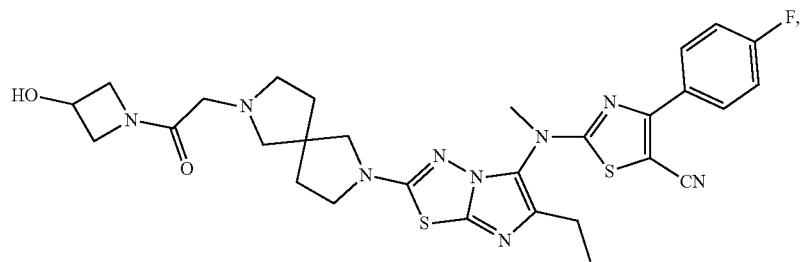
(61)
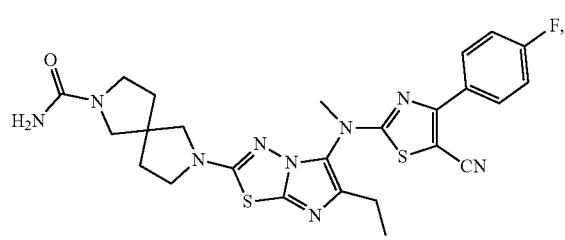
(62)
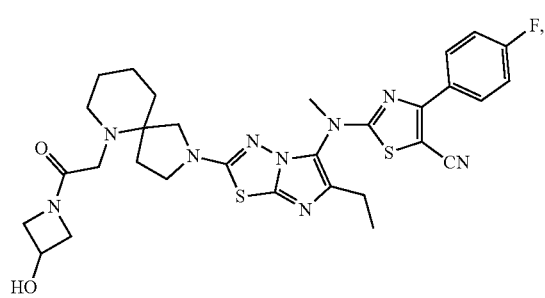
(63)
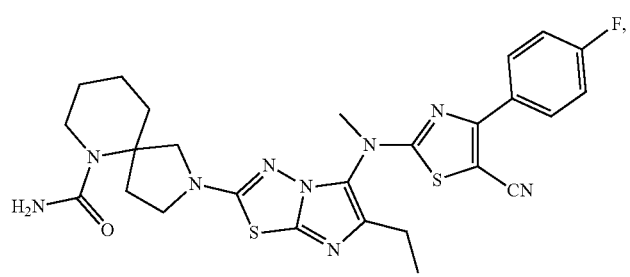
(64)
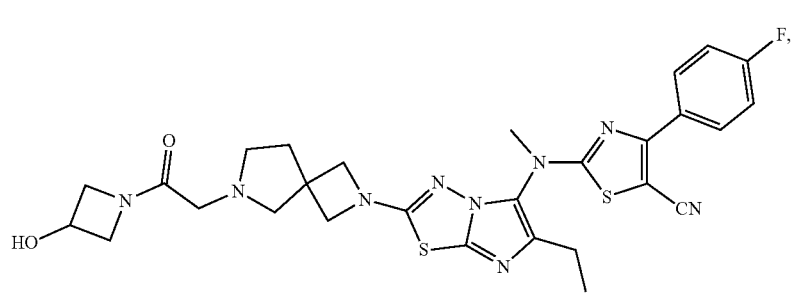
(65)
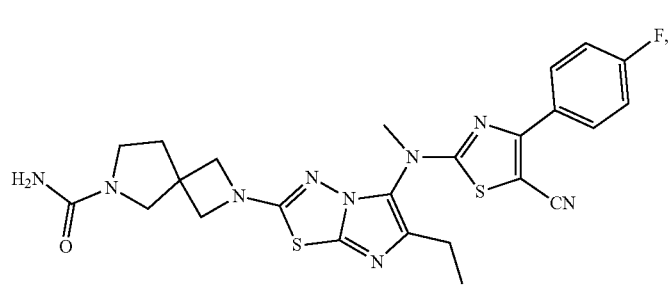

-continued
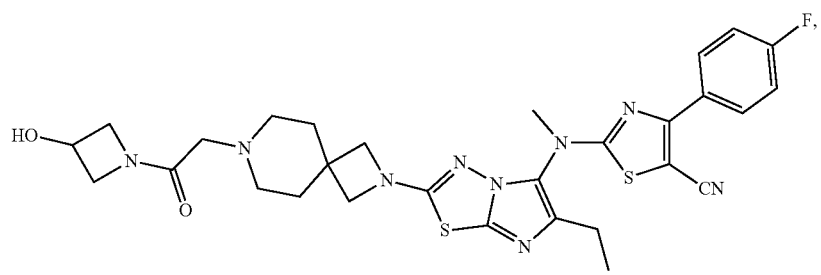
(66)
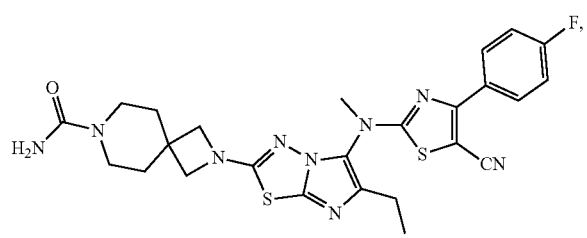
(67)
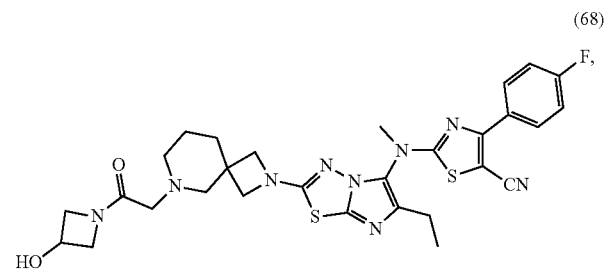
(68)
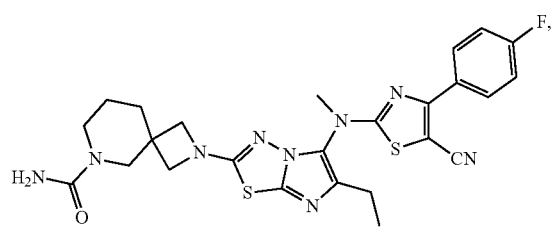
(69)
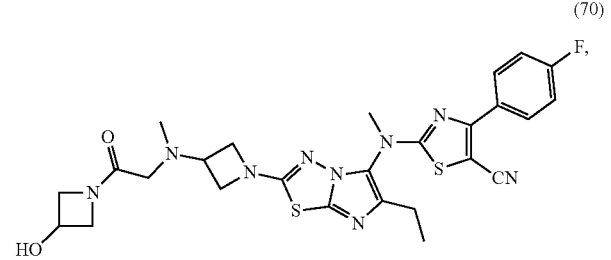
(70)
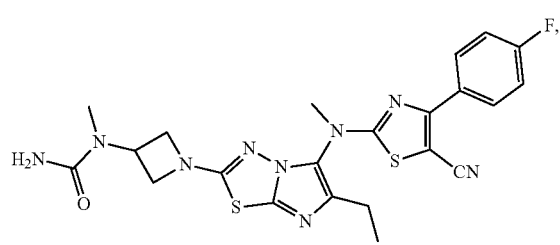
(71)
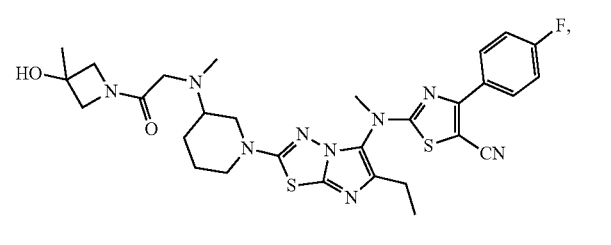
(72)
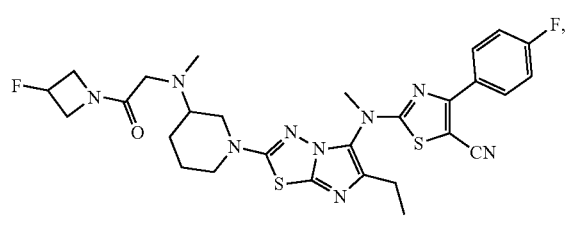
(73)
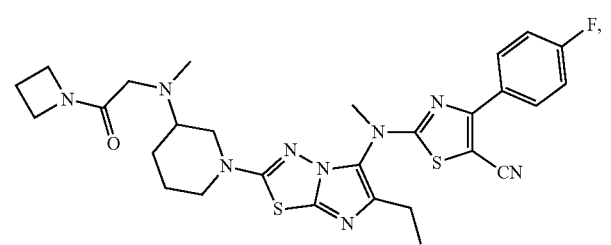
(74)
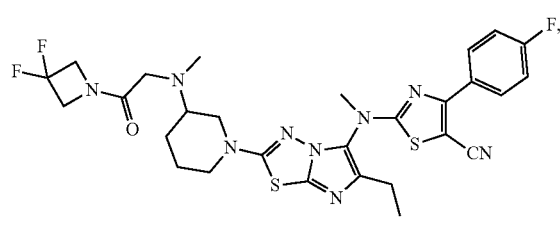
(75)
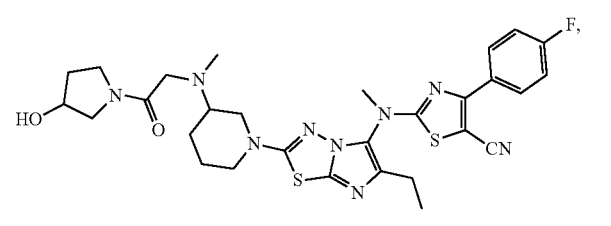
(76)

-continued
(77)
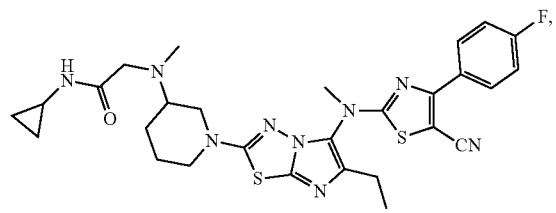
(78)
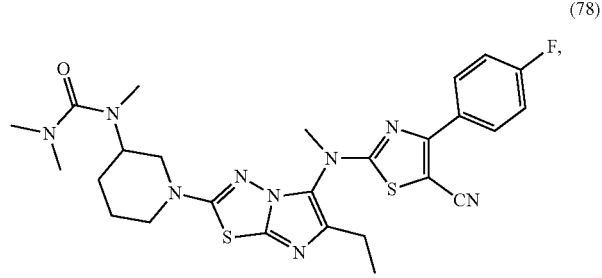
(79)
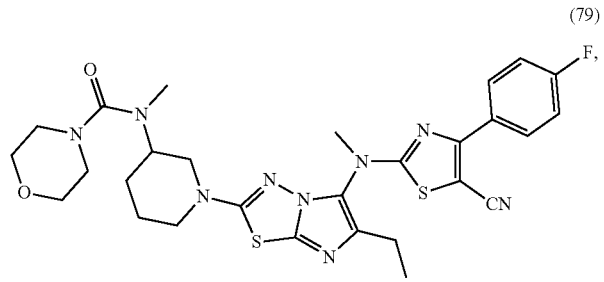
(80)
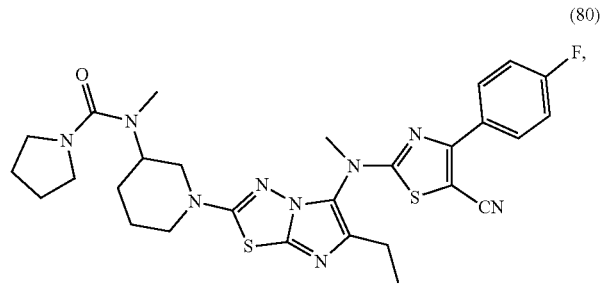
(81)
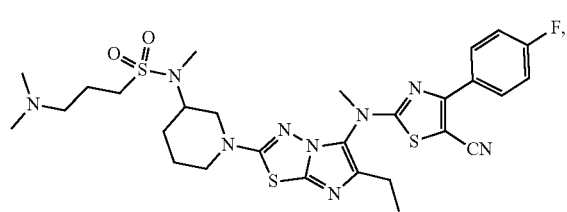
(82)
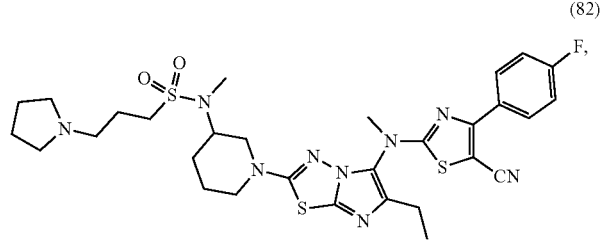
(83)
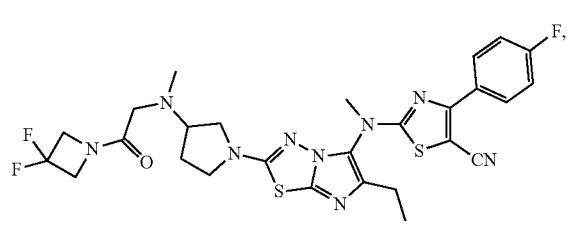
(84)
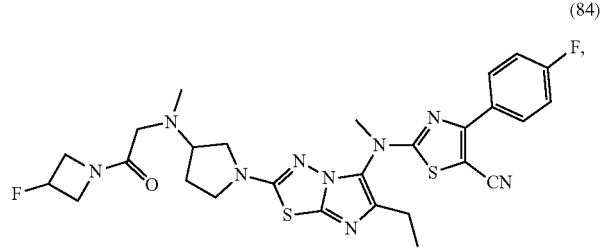
(85)
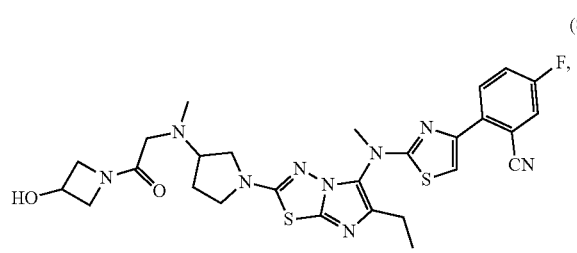
(86)
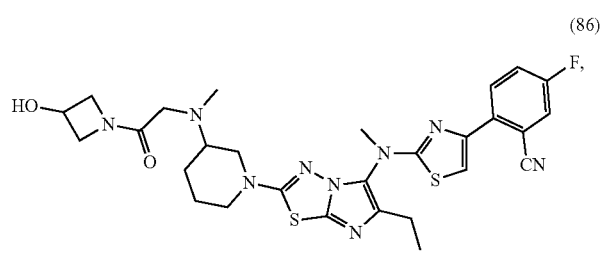
(87)
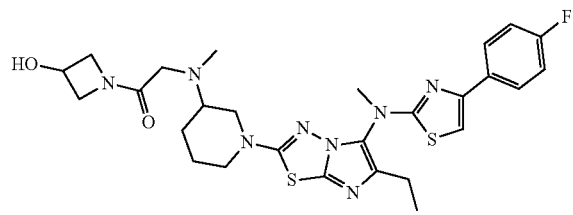
(88)
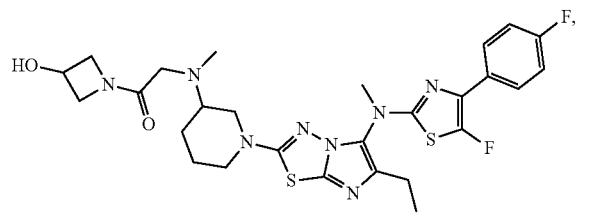

-continued
(89) 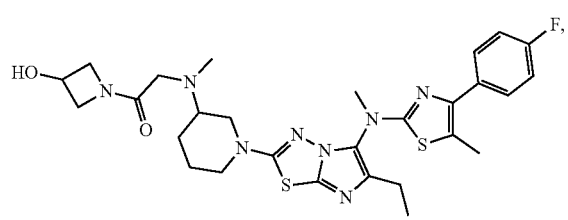
(90) 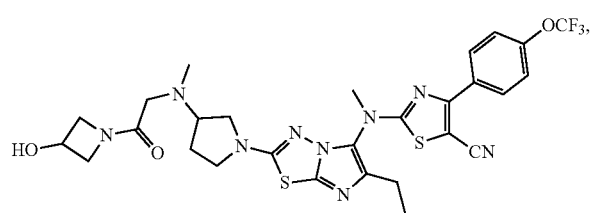
(91) 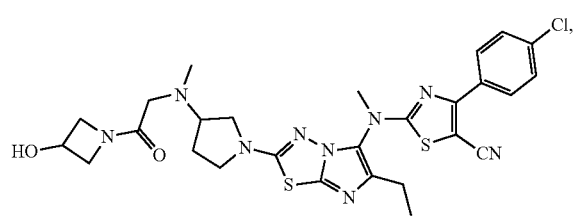
(92) 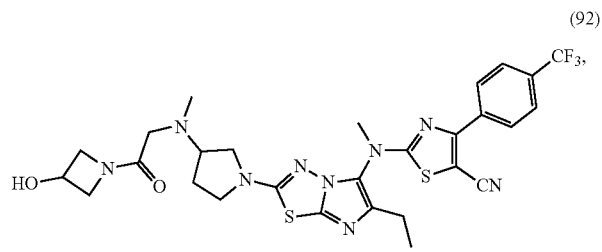
(93) 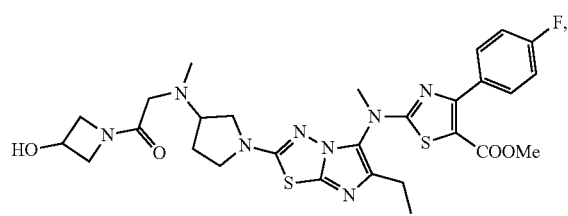
(94) 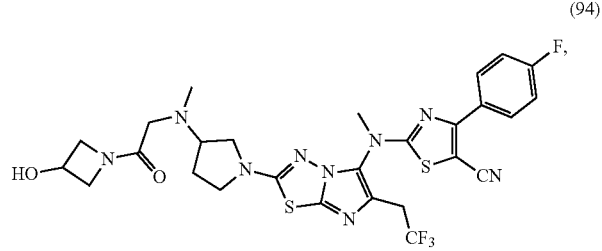
(95) 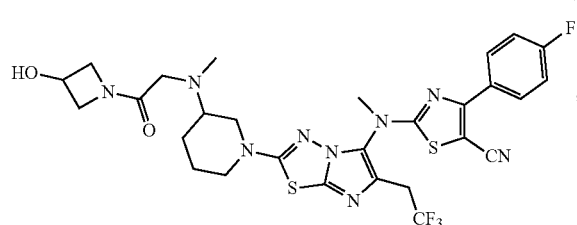
(96) 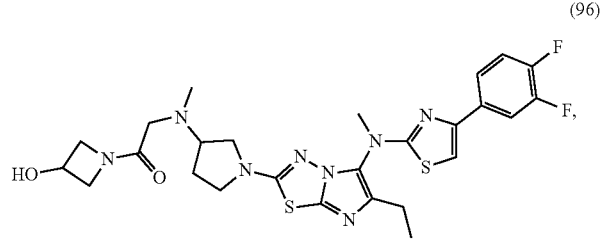
(97) 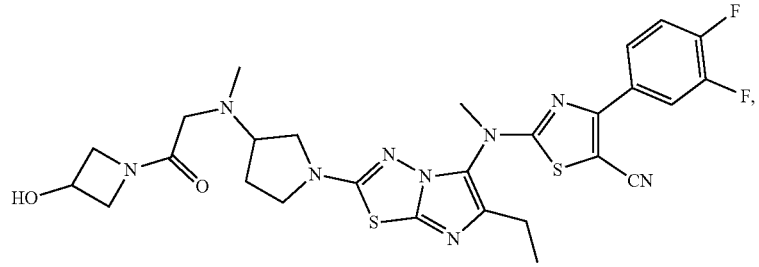
(98) 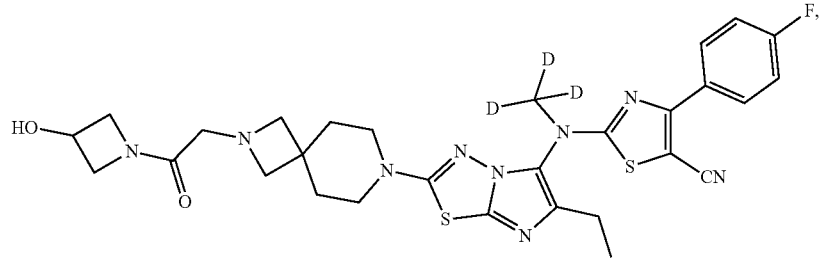

-continued
(99)
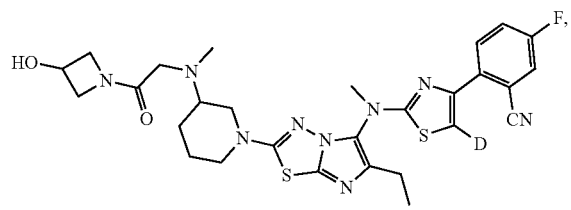
(100)
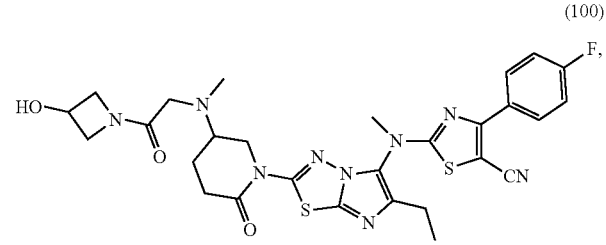
(101)
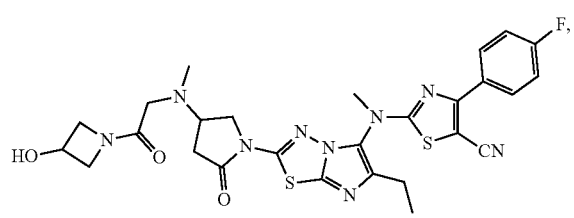
(102)
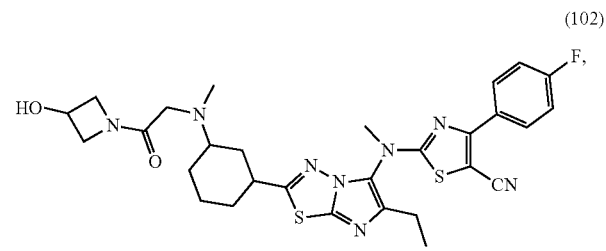
(103)
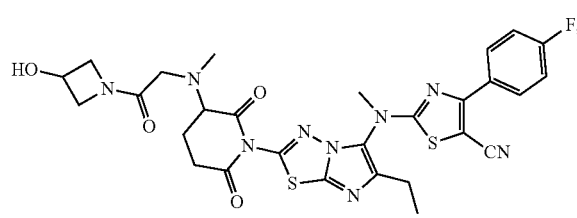
(104)
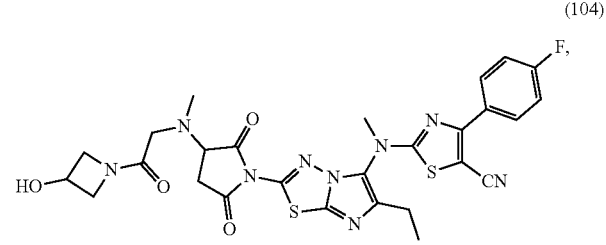
(105)
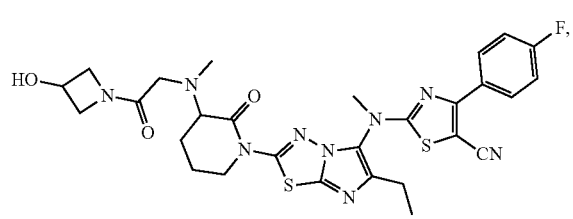
(106)
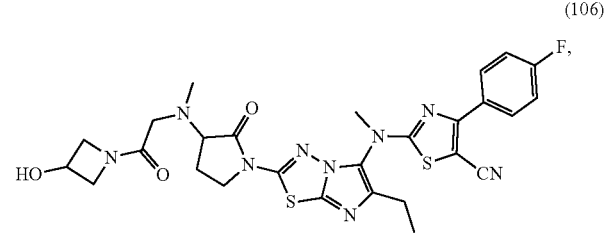
(107)
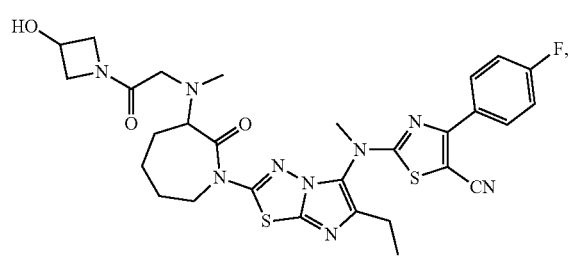
(108)
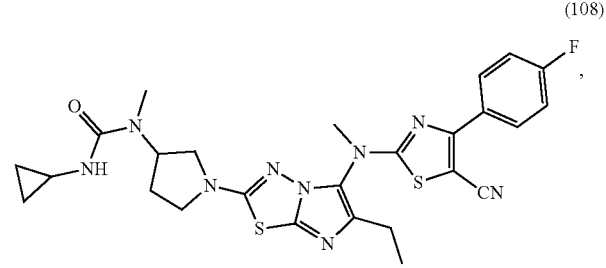
(109)
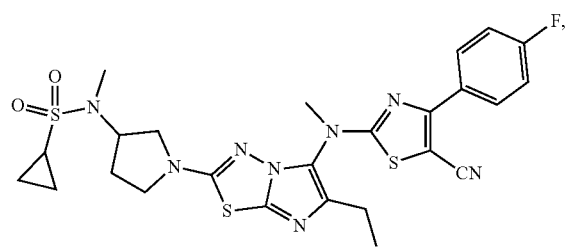
(110)
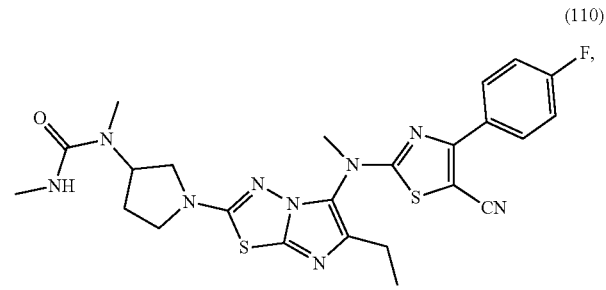

-continued
(111)
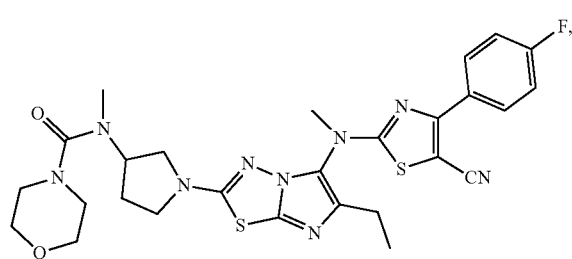
(112)
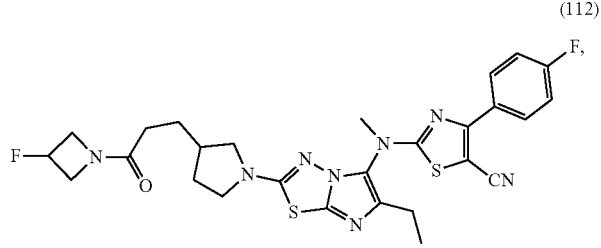
(113)
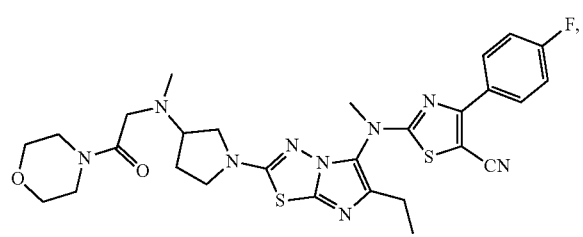
(114)
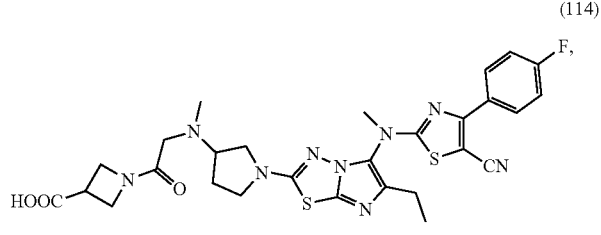
(115)
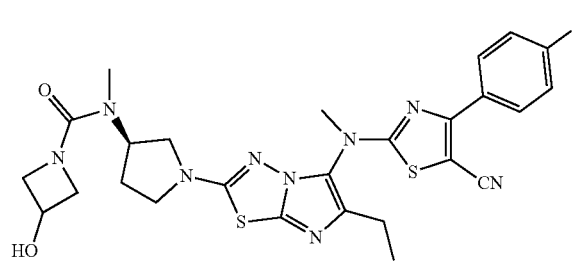
(116)
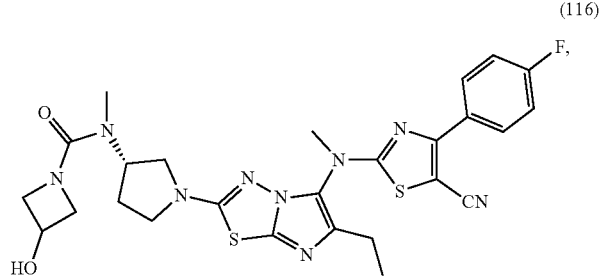
(117)
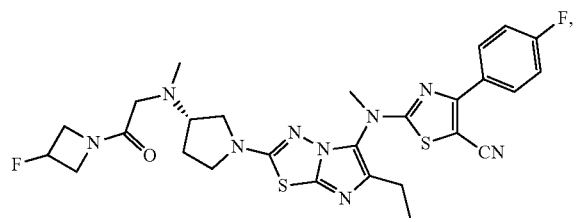
(118)
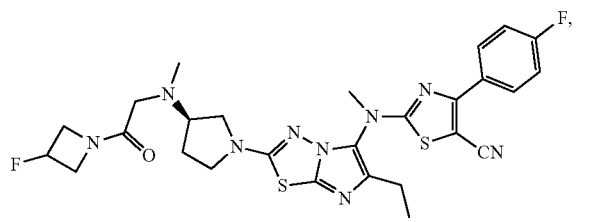
(119)
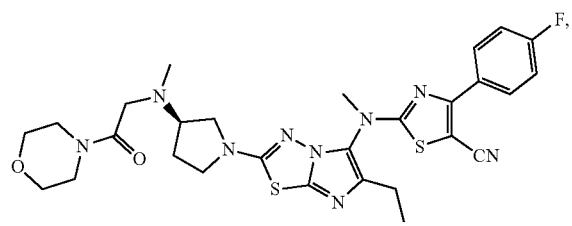
(120)
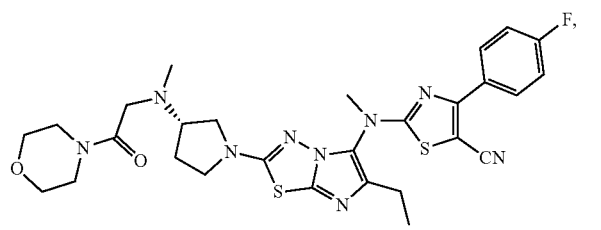
(121)
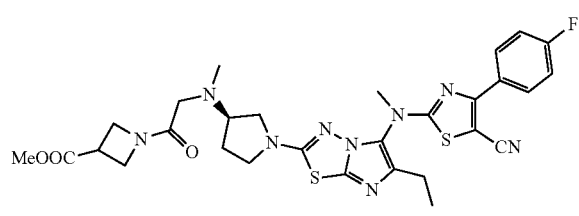
(122)
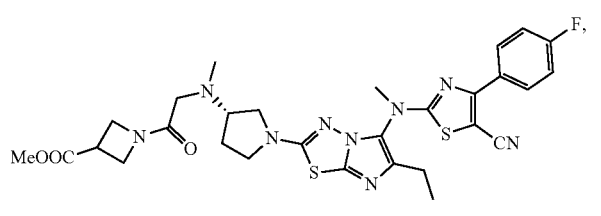

(123)
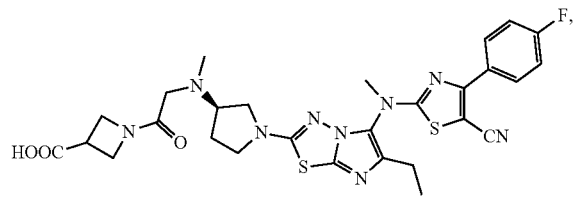
(124)
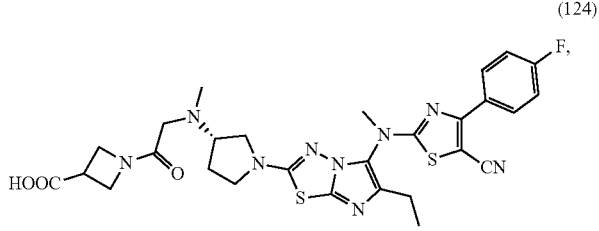
(125)
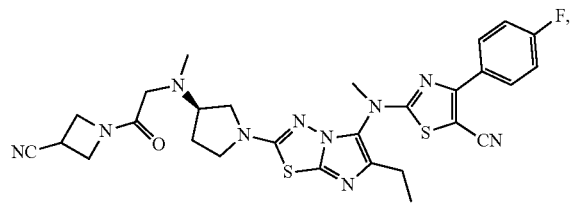
(126)
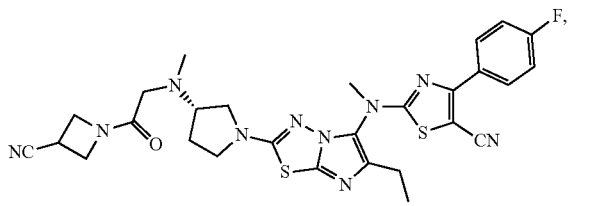
(127)
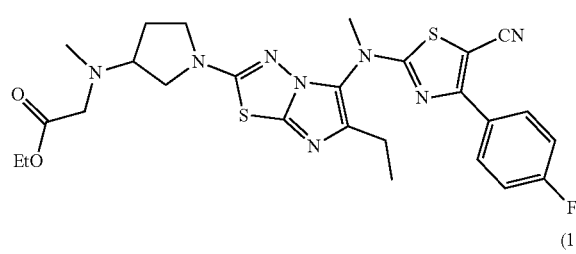
(128)
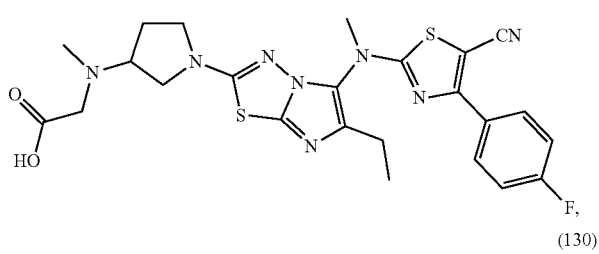
(129)
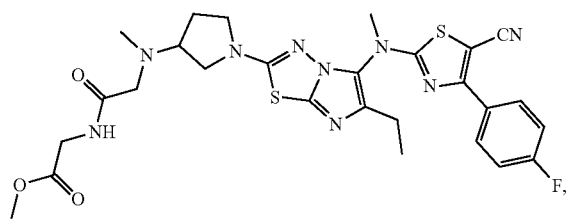
(130)
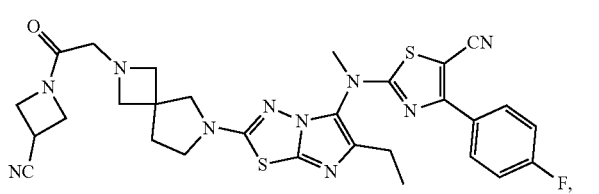
(131)
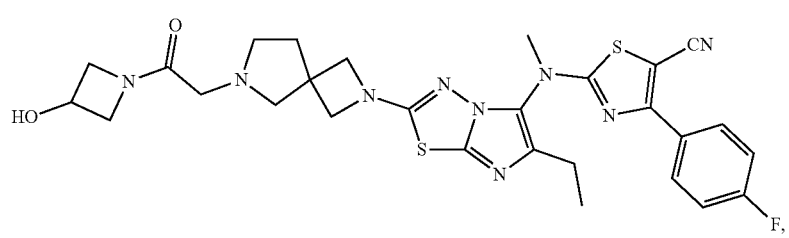
(132)
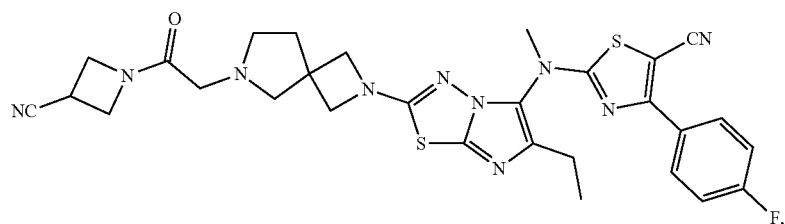
(133)
(134)

-continued
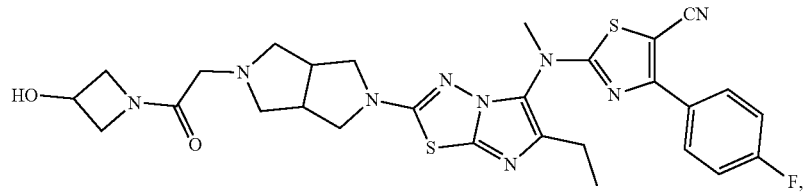
(135)
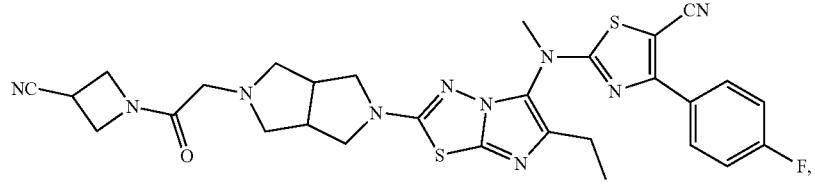
(136)
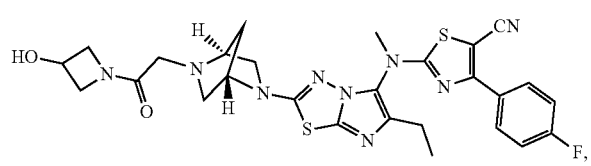
(137)
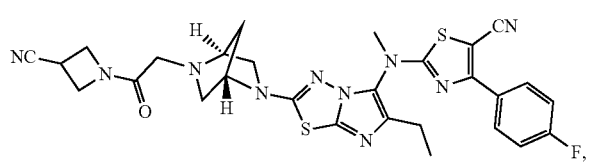
(138)
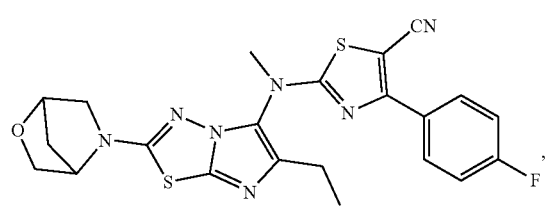
(139)
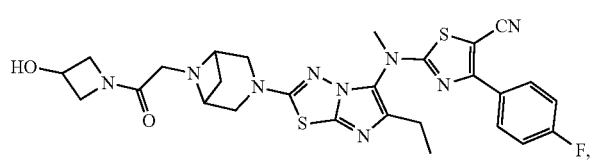
(140)
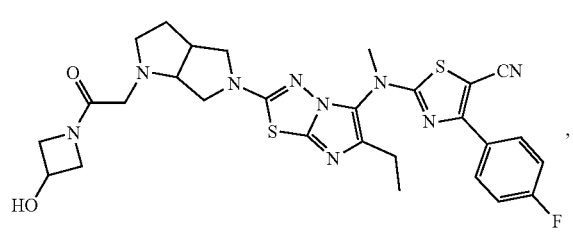
(141)
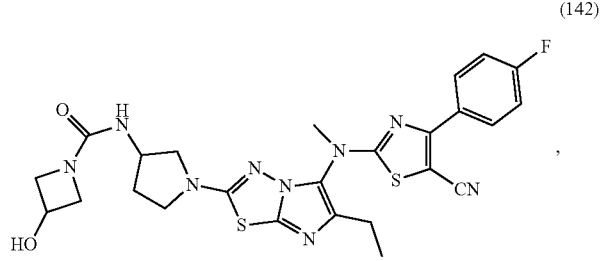
(142)
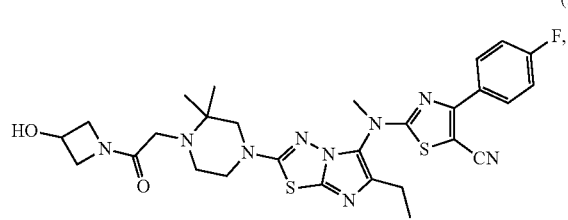
(143)
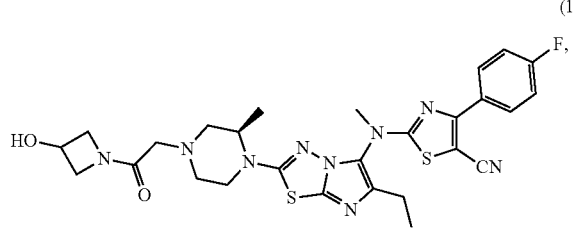
(144)
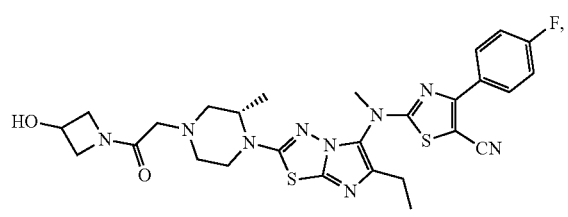
(145)
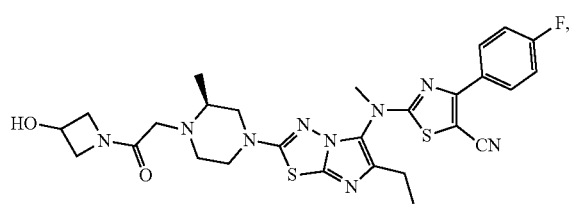
(146)

(147)
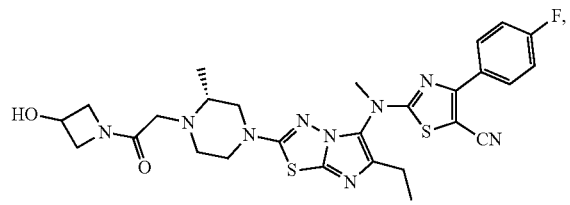
(148)
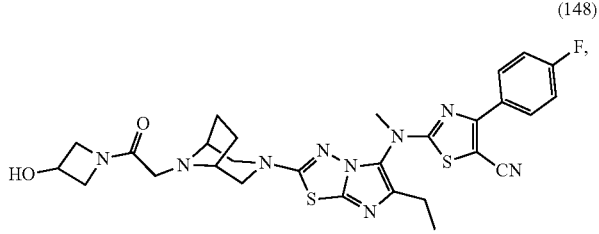
(149)
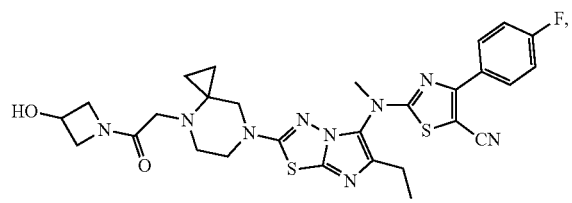
(150)
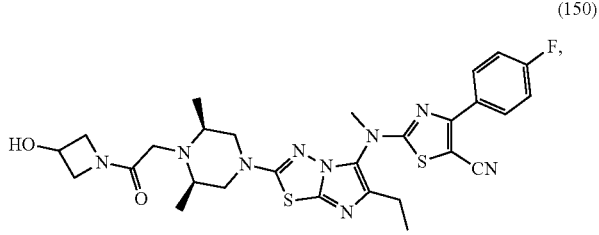
(151)
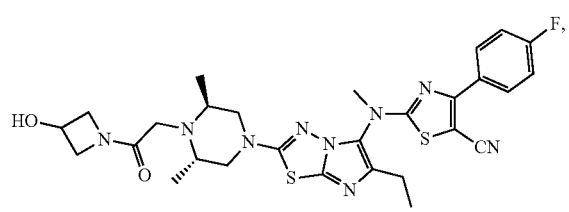
(152)
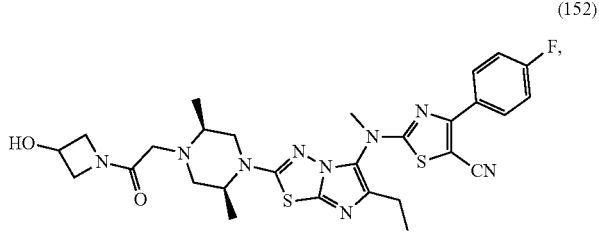
(153)
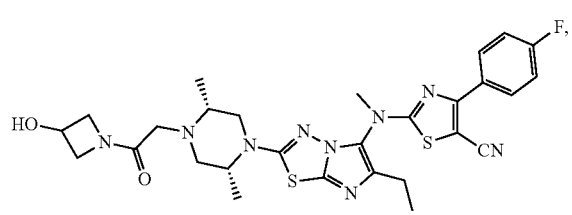
(154)
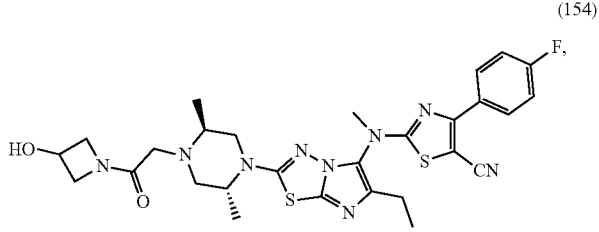
(155)
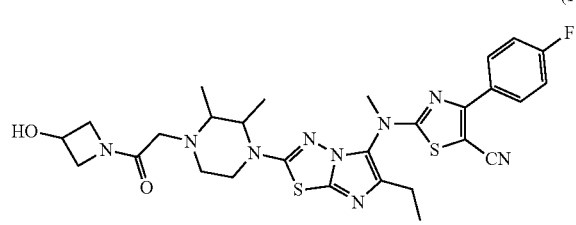
(156)
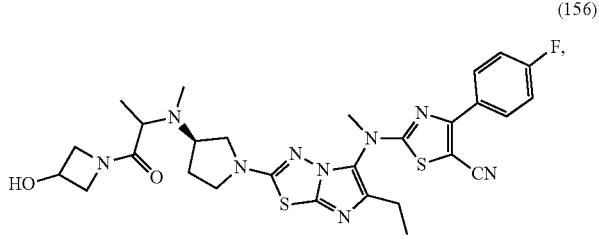
(157)
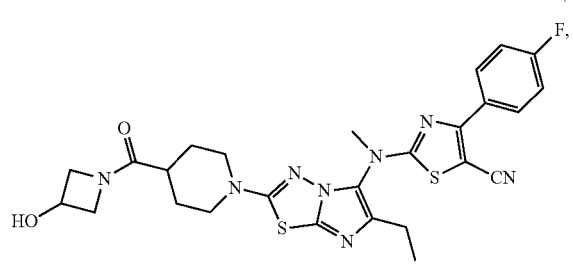
(158)
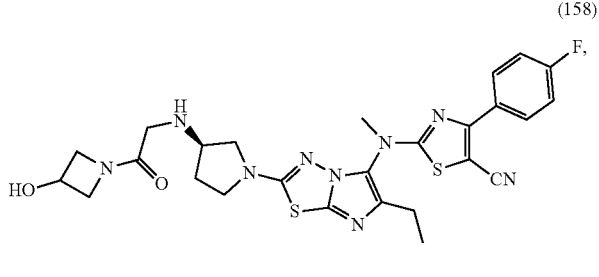

-continued
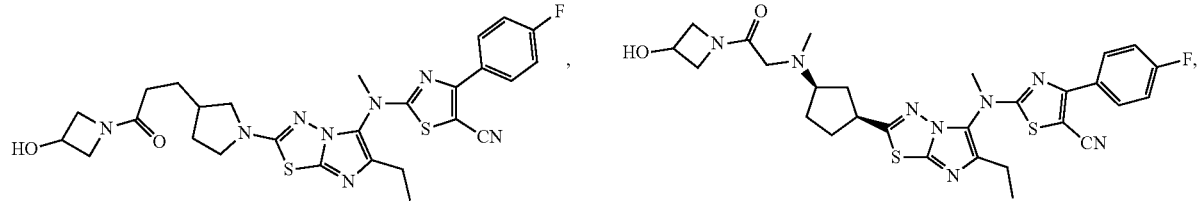
(159), (160)
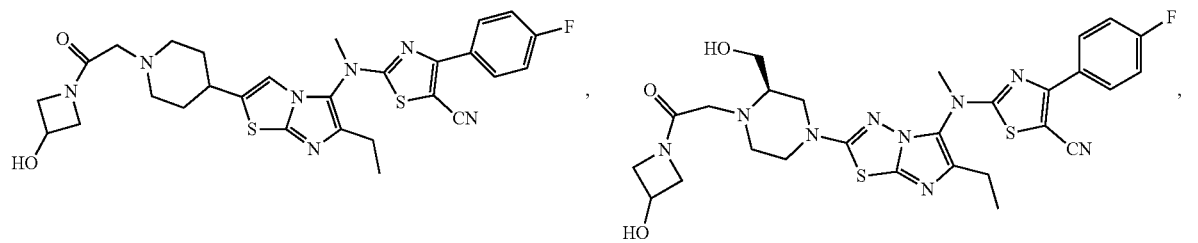
(161), (162)
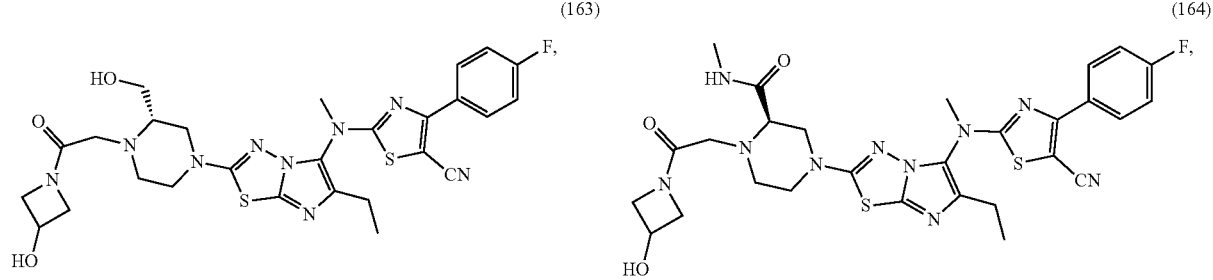
(163), (164)
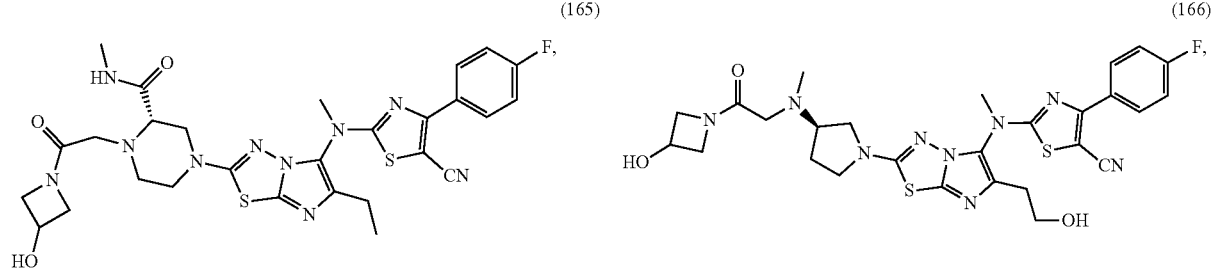
(165), (166)
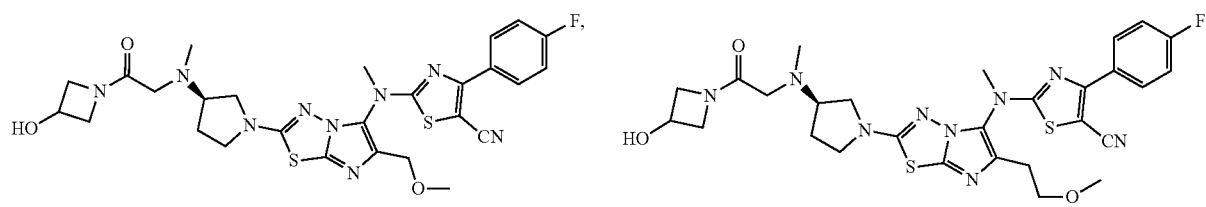
(167), (168)
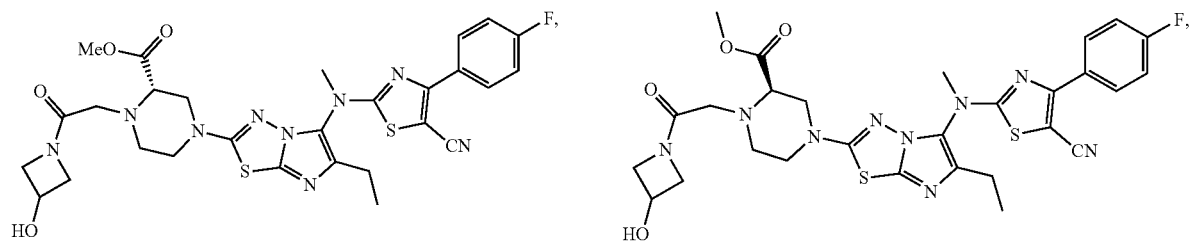
(169), (170)

-continued (171)

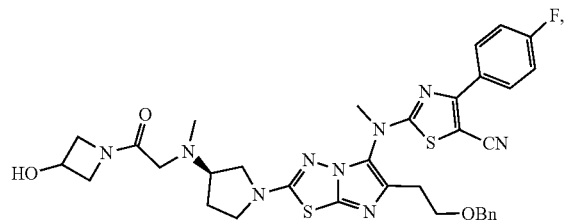

(172)

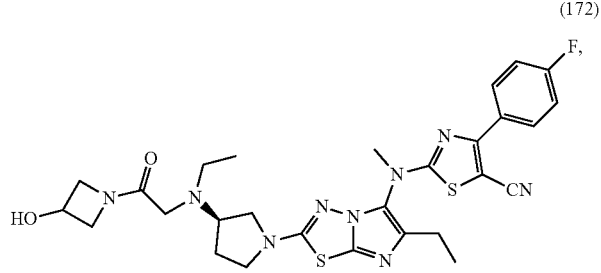

(173)

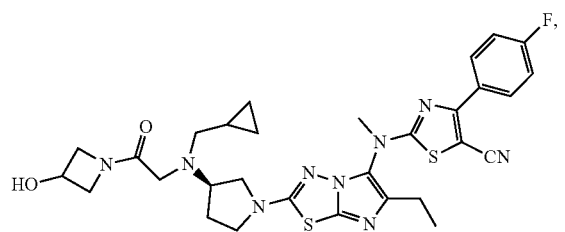

(174)

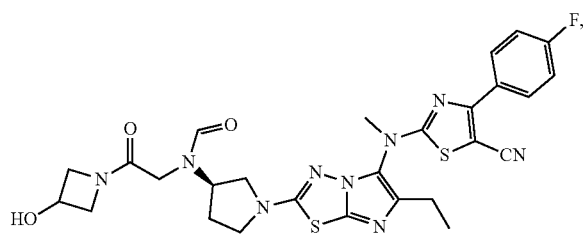

or a pharmaceutically acceptable salt, hydrate, solvate, stereoisomer, tautomer, nitrogen oxide, metabolite, prodrug, or mixture thereof.

It is another aspect to provide a pharmaceutical composition, comprising the compound of the present disclosure or a pharmaceutically acceptable salt, hydrate, solvate, stereoisomer, tautomer, nitrogen oxide, metabolite, prodrug thereof, and a pharmaceutically acceptable excipient, a diluent, or a carrier.

In some examples, the pharmaceutical composition of the present disclosure further comprises an additional therapeutic agent.

In some examples, in the pharmaceutical composition of the present disclosure, the additional therapeutic agent is a therapeutic agent for a disease in relation to fibrotic disease, proliferative disease, inflammatory disease, autoimmune disease, respiratory disease, cardiovascular disease, neurodegenerative disease, dermatologic disorder and/or abnormal vasculogenesis.

In some examples, in the pharmaceutical composition of the present disclosure, the additional therapeutic agent includes, but is not limited to, an immunomodulator, an analgesic, a non-steroidal anti-inflammatory drug, a steroid, a synthetic DMARDS, a proliferative disease drug, a glucocorticoid, a cytostatic agent, an alkylating agent, an antimetabolism agent, a cytotoxic antibiotic, an antibody-based drug, etc.

It is another aspect to provide a use of the compound or the pharmaceutical composition of the present disclosure in the preparation of medicament for preventing or treating a disease with a pathological feature of Autotaxin (ATX) overexpression in a mammal.

In some examples, the disease with a pathological feature of Autotaxin (ATX) overexpression comprises cancer, fibrotic disease, metabolic disease, myelodysplastic syndrome, cardiovascular disease, autoimmune disease, inflammatory disease, nervous system disease, or pain.

In some examples, the disease with a pathological feature of Autotaxin (ATX) overexpression is idiopathic pulmonary fibrosis or hepatic fibrosis. In some examples, the compound or the pharmaceutical composition thereof in the present disclosure can be administrated in combination with other therapeutic agents.

In some examples, the use of the present disclosure comprises administrating an effective amount of the compound or the pharmaceutical composition of the present disclosure to a mammal for preventing or treating.

Pharmaceutical Composition, Preparation and Use

When the compound of the present disclosure is used as a medicament, it is usually administered in a form of a pharmaceutical composition. The composition may be prepared in a well-know manner of pharmaceutical technology and comprises at least one of the compounds according to a formula I, Ia, Ib, Ic, Id, Ie, If, or Ig of the present disclosure. In general, the compound of the present disclosure is administered in a pharmaceutically effective amount. The actual dosage of the compound of the present disclosure will usually be determined by the physician according to relevant conditions, which include symptoms to be treated, a selected administration pathway, an actual compound of the present disclosure administered, the age, weight and response of the individual patients, and symptom severity of the patients, etc.

The pharmaceutical composition of the present disclosure can be administered through various routes, including oral, rectal, transdermal, subcutaneous, intra-articular, intravenous, intramuscular, and intranasal administration, which depends on the intended delivery routes. The compound of embodiments of the invention disclosure is preferably prepared as an injectable or an oral composition, or as an ointment, as a lotion, or as a patch (all for transdermal administration).

In some examples, the composition of the present disclosure is a pharmaceutical composition or a single unit dosage form. The pharmaceutical composition or the single unit dosage form of the present disclosure includes a preventive or therapeutically effective amount of one or more prophylactic or therapeutic agents (for example, the compound or other preventive or therapeutic agents of the present disclosure), and typically one or more pharmaceutically acceptable carriers or excipients. In specific examples and the present disclosure, the term "pharmaceutically acceptable" refers to a medicament approved by supervision organization of federal or state government, or listed in a United State Pharmacopeia or other recognized pharmacopeias for use in animals, especially for humans. The term "carrier" includes diluents, adjuvants (such as, Frend's adjuvant (complete or incomplete)), excipients, intermedium, which are administrated with the therapeutic agent. The pharmaceutical carrier may be sterile solution, such as water and oils including petroleum, animal oil, vegetable oil, or the oils from synthetic sources, such as peanut oil, soybean oil, mineral oil, sesame oil, etc. When the composition is intravenously administrated, water may be used as a carrier. Saline solution, glucose aqueous solution and glycerite may also be used as a liquid carrier, especially for injection solution. Examples of the suitable pharmaceutical carriers are described in Remington: The Science and Practice of Pharmacy; Pharmaceutical Press; $22^{nd}$ edition (Sep. 15, 2012).

Typical pharmaceutical compositions and dosage forms contain one or more excipients. Suitable excipients are known to one skilled in the pharmaceutical field. In some examples, suitable excipients include starch, glucose, lactose, sucrose, gelatin, malt, rice, flour, chalk, silica gel, sodium stearate, glycerin monostearate, talc, sodium chloride, skimmed milk powder, glycerin, propylene, ethylene glycol, water, ethanol, etc. Whether a particular excipient is suitable for incorporation into a pharmaceutical composition or dosage forms depends on many factors well-known in the art, including, but not limited to, the way that the dosage form is administered to the subject, and the specific active ingredients in the dosage. If necessary, the composition or single unit dosage form also contain a little amount of wetting agent, emulgator, or pH buffering agent.

Compositions for oral administration may take the form of bulk liquid solutions or suspensions or bulk powders. However, more generally, the composition is presented in unit dosage form to facilitate precise administration. The term "unit dosage form" refers to a physically discrete unit which is suitable as a unit dosage for humans and other mammals. Each unit contains a predetermined amount of active substance calculated to produce the desired therapeutic effect, together with suitable pharmaceutical excipients, intermedium or carriers, etc. Typical unit dosage forms include pre-filled, predetermined ampoules or syringes for the liquid compositions, or pills, tablets, capsules, etc., for the solid compositions. In the compositions, the compound of the present disclosure having a formula of I, Ia, Ib, Ic, Id, Ie, If, or Ig is usually a minor component (about 0.1 to about 50% by weight, or preferably about 1 to about 40% by weight), the rest are various media or carriers and processing aids that help to form the desired administration form.

It is another aspect to provide a compound of the present disclosure or a pharmaceutical composition including the compound of the present disclosure, for use in a medicament. In specific examples, the present disclosure provides a compound of the present disclosure or a pharmaceutical composition including the compound of the present disclosure for preventing and/or treating a disease in relation to fibrotic disease, proliferative disease, inflammatory disease, autoimmune disease, respiratory disease, cardiovascular disease, neurodegenerative disease, dermatologic disorder and/or abnormal vasculogenesis.

In some examples, the present disclosure provides a compound of the present disclosure or a pharmaceutical composition including the compound of the present disclosure for use in preparation of a medicament for preventing and/or treating a disease in relation to fibrotic disease, proliferative disease, inflammatory disease, autoimmune disease, respiratory disease, cardiovascular disease, neurodegenerative disease, dermatologic disorder and/or abnormal vasculogenesis.

In some examples, the present disclosure provides a compound of the present disclosure or a pharmaceutical composition including the compound of the present disclosure. In specific examples, other therapeutic agents are the therapeutic agents for a disease in relation to fibrotic disease, proliferative disease, inflammatory disease, autoimmune disease, respiratory disease, cardiovascular disease, neurodegenerative disease, dermatologic disorder and/or abnormal vasculogenesis.

In another method of treatment, the present disclosure provides a method of preventing and/or treating a disease, including fibrotic disease, proliferative disease, inflammatory disease, autoimmune disease, respiratory disease, cardiovascular disease, neurodegenerative disease, dermatologic disorder and/or abnormal angiogenesis for mammalian subject, and the method comprises a step of administering an effective amount of one or more of the compounds or pharmaceutical compositions of the present disclosure for treating or preventing the symptoms.

In other examples, the present disclosure provides a compound of embodiments of the present invention or a pharmaceutical composition comprising the compound of the present disclosure for use in the preparation of a medicament for preventing and/or treating fibrotic disease. In a specific example, the fibrotic disease is selected from the group consisting of idiopathic pulmonary fibrosis (IPF), cystic fibrosis, other diffuse parenchymal lung disease of different etiologies (including iatrogenic drug-induced fibrosis, occupational and/or environment-induced fibrosis), granulomatous disease (sarcoidosis, allergic pneumonia), collagen vascular disease, alveolar protein deposition, Langerhans cell granuloma, lymphangiomyotysis, genetic disease (Hermans Chi-Pudlak syndrome, tuberous sclerosis, neurofibroma, metabolic accumulation disorder, familial interstitial lung disease), radiation-induced fibrosis, chronic obstructive pulmonary disease (COPD), scleroderma, Leomycin-induced pulmonary fibrosis, chronic asthma, silicosis, asbestos-induced pulmonary fibrosis, acute respiratory distress syndrome (ARDS), renal fibrosis, renal tubule interstitial fibrosis, glomerulonephritis, localized segment Glomerulosclerosis, IgA nephropathy, hypertension, Alport's disease (Alport), intestinal fibrosis, liver fibrosis, cirrhosis, alcohol-induced liver fibrosis, toxin/drug-induced liver fibrosis, hemochromatosis, non-alcoholic steatohepatitis (NASH), bile duct damage, primary biliary cirrhosis, infection-induced liver fibrosis, virus-induced liver fibrosis and autoimmune hepatitis, corneal scar, hypertrophic scar, Dupuytren disease, scar pimple, skin fibrosis, skin scleroderma, systemic sclerosis, spinal cord injury/fibrosis, bone marrow fibrosis, vascular restenosis, atherosclerosis, arteriosclerosis, Wegener's granulomatosis, Peyronie's disease or chronic lymphocytic. More specifically, the fibrotic disease is idiopathic pulmonary fibrosis (IPF).

A particular aspect of the method of the present disclosure includes administering an effective amount of the compound having a formula I, Ia, Ib, Ic, Id, Ie, If, or Ig of the present disclosure to an individual suffering from a fibrotic disease for a period, which is sufficient to reduce the level of fibrosis in the individual, and preferably to terminate the process that causes said fibrosis. A specific example of the method includes administering an effective amount of a compound having a formula I, Ia, Ib, Ic, Id, Ie, If, or Ig of the disclosure to an individual patient suffering from developing idiopathic pulmonary fibrosis for a period, which is sufficient to reduce or prevent idiopathic pulmonary fibrosis in the patient, and preferably to terminate the process causing the idiopathic pulmonary fibrosis.

The level of injection dose is from about 0.1 mg/kg/h to at least 10 mg/kg/h, all lasting for about 1 to about 120 hours, especially for 24 to 96 hours. A preloaded injection of about 0.1 mg/kg to about 10 mg/kg or more may also be administered to obtain an appropriate steady state. It is not expected that the maximum total dose for 40 to 80 kg human patient will exceed about 1 g/day.

For the prevention and/or treatment of chronic symptoms (such as degenerative symptoms), the treatment regimen is usually extended to many months or years, so that oral administration is preferable for convenience and tolerability of patients. Oral administrations one to four (1-4) times a day in a routine dose, especially one to three (1-3) times a day, usually once or twice a day, and most commonly once a day are representative regimens. Alternatively, for drugs with long-lasting effects, oral administrations once every other week, once a week, and once a day are representative regimens. In particular, the dosage regimen can be every 1 to 14 days, more specifically 1-10 days, even more specifically 1 to 7 days, and most specifically 1 to 3 days.

Each dose provides about 1 to about 1000 mg of the compound of the present disclosure when using these administration patterns, wherein each specific dose provides about 10 to about 500 mg, preferably about 30 to about 250 mg.

When it is used to prevent the onset of a symptom, the compound of the present disclosure will usually be administered to patients who are at risk of developing diseases at the above-mentioned dosage levels under the advice and supervision of a physician. Patients at risk of developing a specific disease generally include patients with a family history of the diseases or patients who have been identified through genetic testing or screening to be particularly prone to develop such diseases.

The compound of the present disclosure may be administered as the sole active agent or it may be administered in combination with other therapeutic agents, including other compounds of the present disclosure that exhibit the same or similar therapeutic activity and are determined to be safe and effective for the combination. In a particular example, the co-administration of two (or more) active agents allows for a significant reduction in the dosage of each active agent used, thereby reducing visible side effects.

In some examples, the compound of the present disclosure or a pharmaceutical composition comprising the compound of the present disclosure is administered as a medicament. In a specific example, the pharmaceutical composition also contains other active substances.

In some examples, the compound of the present disclosure is co-administered with other therapeutic agents for treating and/or preventing inflammatory disease. Specific active agents include, but are not limited to, immunomodulators such as azathioprine, corticosteroids (such as prednisolone or dexamethasone), cyclophosphamide, cyclosporin A, tacrol imus, mycophenolate mofetil, muro monoclonal antibody-CD3 (morolumab-CD3 (OKT3, such as Orthocolone@), ATG, aspirin, acetaminophen, ibuprofen, naproxen and piroxicam.

In some examples, the compound of the present disclosure is co-administered with other therapeutic agents for treating and/or preventing arthritis (such as rheumatic arthritis). Specific active agents include, but are not limited to, analgesic, non-steroidal anti-inflammatory drugs (NASID), steroid, synthetic DMARDS (for example, but being not limited to, methotrexate, leflunomide, sulfasalazine, auranofin, sodium aurothiomalate, penicillamine, chloroquine, hydroxychloroquine, azathioprine, tofaci tinib, barici tinib, fostamatinib and cyclosporin) and biological DMARDS (for example, but beingnot limited to, infliximab, etanercept, adal immumab, rituximab and abatacept)).

In some examples, the compound of the present disclosure is co-administered with other therapeutic agents for treating and/or preventing proliferative disorders. Specific active agents include, but are not limited to, methotrexate, leukovorin, adriamycin, prednisone, bleomycin, cyclophosphamide, 5-fluorouracil, paclitaxel, docetaxel, vincristine, vinblastine, vinorelbine, doxorubicin, tamoxifen, toremifene, megestrol acetate, anastrozole, goserelin, anti-HER2 monoclonal antibody (such as Herceptin™), capecitabine, raloxifene hydrochloride, EGFR inhibitor (such as Iressa, Tarceva, Erbitux), VEGF inhibitor (such as Avastin), protease inhibitors (such as Velcade), Glivec and hsp90 inhibitors (such as 17-AAG). In addition, the compound of the present disclosure having a formula I, Ia, Ib, Ic, Id, or Ie may be co-administered with other treatments which include but are not limited to, radiation therapy or operation. In specific examples, the proliferative disorders are selected from cancer, myeloproliferative disease, or leukemia.

In some examples, the compound of the present disclosure is co-administered with other therapeutic agents for treating and/or preventing autoimmune disease. Specific active agents include, but are not limited to, glucocorticoid, cytostatic inhibitor (such as purine analogue), alkylating agent (such as nitrogen mustard (cyclophosphamide)), nitrosourea, platinum compounds and others of the present disclosure), anti-metabolic agents (such as methotrexate, azathioprine, or purinethol), cytotoxic antibiotic (such as dactinomycin), anthracycline, mitomycin C, bleomycin, or mithramycin)), antibodies (such as anti-CD20, anti-CD25, or anti-CD3 (OTK3) monoclonal antibody, Atgam®, or Tbymoglobuline®), cyclosporine, tacrolimus, rapamycin(sirolimus)), interferon (such as IFN-β), TNF binding proteins (such as Remicade monoclonal antibody, Etanercept or Adalimumab monoclonal antibody), mycophenolate mofetil, fingolimod, or myriocin.

It is apparent for one skilled in the art that co-administration includes delivering two or more therapeutic agents in any forms to patients as part of the same treatment regimen. Although the two or more active agents can be simultaneously administered in a single preparation (i.e. as a single pharmaceutical composition), this is not necessary. The active agents can be also administered in different preparation at different times.

DETAILED DESCRIPTION

In order to describe the present disclosure, examples are listed hereinafter. It should be understood that the present disclosure is not limited to the examples, and only provides methods for practicing the present disclosure.

In general, unless otherwise stated, the compound of the present disclosure can be prepared by the method described herein, wherein the substituents are defined as shown in formula I, Ia, Ib, Ic, Id, or Ie, If, or Ig. The following reaction schemes and examples are used to further illustrate the content of the present disclosure.

It should be recognized by one skilled in the art that the chemical reactions described in the present disclosure can be used to appropriately prepare many other compounds of the present disclosure, and other methods for preparing the compounds are considered to be within the scope of the present disclosure. For example, the synthesis of non-exemplary compounds according to the present disclosure may be successfully prepared by one skilled in the art through modifying methods, such as appropriate protection of interfering groups, by using other well-known reagents in addition to those described in the present disclosure, or regularly modifying some reaction conditions. In addition, the reaction disclosed in the present disclosure or well-known reaction conditions are also recognized to be applicable for the preparation of other compounds of the present disclosure.

In the examples described hereinafter, unless otherwise indicated, all the temperatures are set to degree centigrade. The reagents are commercially available from commercial suppliers, such as Aldrich Chemical Company, Arco Chemical Company and Alfa Chemical Company, and are used without further purifying, unless otherwise indicated. General reagents are purchased from Shantou Xilong Chemical Co., Ltd, Guangdong Guanghua Sci-Tech Co., Ltd., Guangzhou Chemical Reagent Factory, Tianjin Haoyuyu Chemicals Co., Ltd., Tianjin Fuchen Chemical Reagent Factory, Wuhan Xinhuayuan Science and Technology Development Co., Ltd., Qingdao Tenglong Chemical Reagent Co., Ltd., and Qingdao Haiyang Chemical Factory.

Anhydrous tetrahydrofuran, dioxane, methylbenzene, and diethyl ether are obtained by refluxing and drying with metallic sodium. Anhydrous dichloromethane and chloroform are obtained by refluxing and drying with calcium hydride. Ethyl acetate, petroleum ether, n-hexane, N, N'-dimethylacetamide, and N, N'-dimethylformamide are dried with anhydrous sodium sulfate before use.

The following reactions generally perform under a positive pressure of nitrogen gas or argon gas or with a drying tube on anhydrous solvent (unless otherwise indicated). Reaction flasks are plugged with suitable rubber plugs, and substrates are injected by a syringe. Glasswares are all dried.

Chromatographic column uses silica gel. The silica gel (300 to 400 meshes) is purchased from Qingdao Haiyang Chemical Factory.

$^1$H NMR spectrum is recorded by Bruker 400 MHz or 600 MHz nuclear magnetic resonance spectrometer. $^1$H NMR spectrum uses $CDCl_3$, $DMSO-d_6$, $CD_3OD$, or $acetone-d_6$ as solvent (in ppm), and uses TMS (0 ppm) or chloroform (7.26 ppm) as reference. When multiplicities are present, the following abbreviations are used: s (singlet), d (double), t (triplet), m (multiplet), br (broadened), dd (doublet of doublets), dt (doublet of triplets). Coupling constants are used in Hz.

The measurement conditions of low-resolution mass spectrometer (MS) data are: Agilent 6120 quadrupole HPLC-M (column model: Zorbax SB-C18, 2.1×30 mm, 3.5 microns, 6 min, flow rate: 0.6 mL/min. The mobile phase: 5%-95% (the ratio of (0.1% formic acid in $CH_3CN$) to (0.1% formic acid in $H_2O$)), being ionized by electrospray ionization (ESI), and detected by UV at 210 nm/254 nm.

Pure compounds are prepared by Agilent 1260 pre-HPLC or Calesep pump 250 pre-HPLC (column model: NOVASEP 50/80 mm DAC) and are detected by UV at 210 nm/254 nm.

The following abbreviations are used throughout the present disclosure:
$CD_3OD$ methanol-D
$CDCl_3$ chloroform-D
DMF N, N'-dimethyl formamide
$DMSO-d_6$ dimethylsulfoxide-D
g gram
h hour
mL, ml milliliter
RT, rt, r.t. room temperature
Boc tert-butoxycarbonyl
Cbz carbobenzoxy
PMB p-methoxyphenyl
$Pd_2(dba)_3$ tris(dibenzylideneacetone)dipalladium
JohnPhos 2-(Di-tert-butylphosphino)biphenyl The typical synthetic steps for preparing the compounds disclosed in the present disclosure are shown as the following Synthetic Schemes 1, 2 and 3.

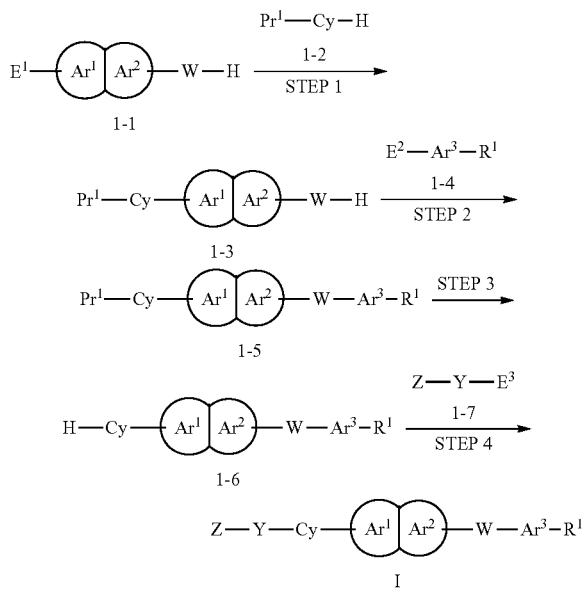

Synthetic Scheme 1 wherein, $E^1$ and $E^2$ are selected from Cl, Br or I; $E^3$ is selected from Cl, Br, I, OMs, OTs or OTf; $Pr^1$ is selected from Boc, Cbz or PMB; Z, Y, Cy, $Ar^1$, $Ar^2$, W, $Ar^3$, and $R^1$ are all defined as described herein.

Intermediate 1-1 is reacted with intermediate 1-2 in the presence of alkali (such as triethylamine, N, N-diisopropylethylamine, potassium carbonate, cesium carbonate, potassium tert-butoxide or sodium tert-butoxide) under a heating condition (50° C. to 150° C.), through nucleophilic substitution reaction to obtain intermediate 1-3; subsequently, the intermediate 1-3 firstly is reacted with strong alkali (such as sodium hydride, potassium tert-butoxide or sodium tert-butoxide) until the reaction is finished, and then is reacted with intermediate 1-4 through nucleophilic substitution reaction to obtain intermediate 1-5; the intermediate 1-5 can react in acid conditions (such as trifluoroacetic acid, chlorine hydride), or be hydrogenated by palladium catalyst, or react with trimethylidosilane to remove the protection group of $Pr^1$, to obtain intermediate 1-6; the intermediate 1-6 is reacted with intermediate 1-7 in presence of alkali (such as triethylamine, N, N-diisopropylethylamine, potassium carbonate, cesium carbonate) under a heating condition (25° C. to 120° C.), through nucleophilic substitution reaction to obtain a compound of formula I.

Synthetic Scheme 2

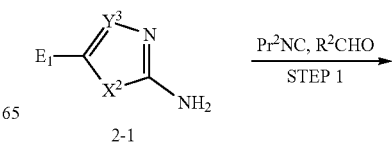

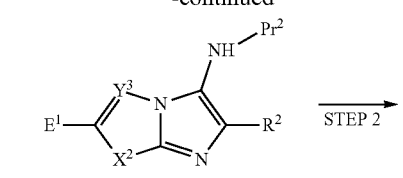

2-2

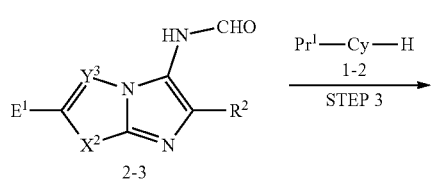

2-3

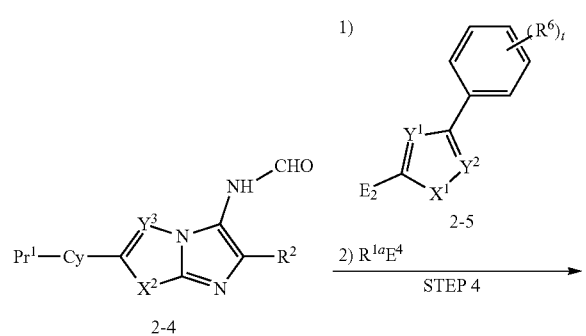

2-4

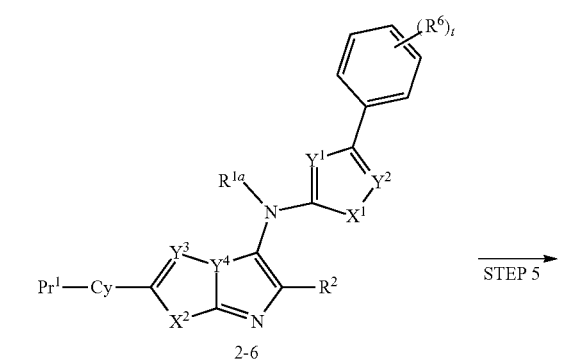

2-6

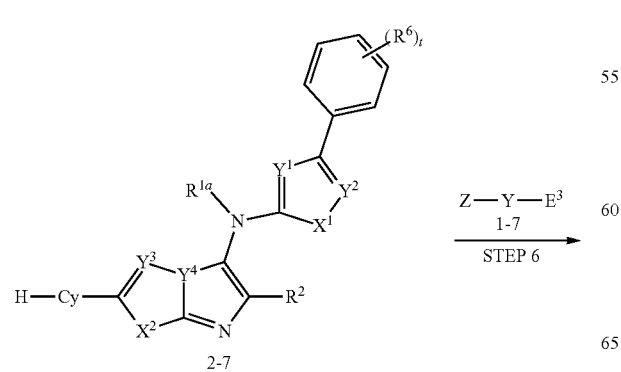

2-7

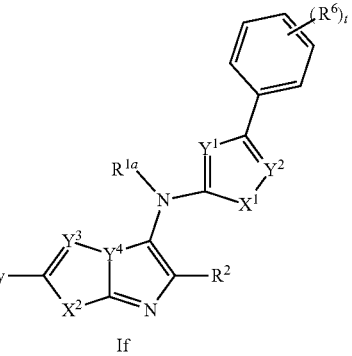

If wherein, $E^1$ and $E^2$ are each independently selected from Cl, Br or I; $E^3$ is selected from Cl, Br, I, OMs, OTs or OTf; $Pr^2$ is selected from tert-butyl, or 2,4,4-trimethylpent-2-yl; $Pr^1$, Z, Y, Cy, $X^1$, $X^2$, $Y^1$, $Y^2$, $Y^3$, $Y^4$, $R^{1a}$, $R^2$, $R^6$, and t are all defined as described herein.

Intermediate 2-1 is reacted with $Pr^2NC$ and aldehyde $R^2CHO$ under the catalysis of lewis acid (such as magnesium chloride) to obtain intermediate 2-2 through a three-component reaction; then the intermediate 2-2 is heated in formic acid to obtain intermediate 2-3; the intermediate 2-3 is reacted with the intermediate 1-2 in the presence of alkali (such as triethylamine, N, N-diisopropylethylamine, potassium carbonate, cesium carbonate, potassium tert-butoxide or sodium tert-butoxide) under a heating condition (50° C. to 150° C.), through nucleophilic substitution reaction to obtain intermediate 2-4; the intermediate 2-4 firstly is reacted with strong alkali (such as sodium hydride, potassium tert-butoxide or sodium tert-butoxide) condition until the reaction is completed, following by reacting with intermediate 2-5 through nucleophilic substitution reaction, and then reacting with substituted alkyl $R^{1a}E^4$ to obtain intermediate 2-6; the intermediate 2-6 can be reacted in acid conditions (such as trifluoroacetic acid, chlorine hydride), or be hydrogenated by palladium catalyst, or be reacted with trimethylidosilane to remove the protection group of $Pr^1$, to obtain intermediate 2-7; the intermediate 2-7 is reacted with intermediate 1-7 in presence of alkali (such as triethylamine, N, N-diisopropylethylamine, potassium carbonate, cesium carbonate) under a heating condition (25° C. to 120° C.), through nucleophilic substitution reaction to obtain a compound of formula If.

Synthetic Scheme 3

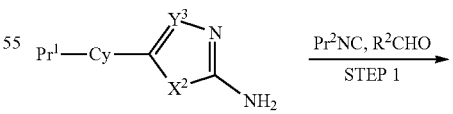

3-1

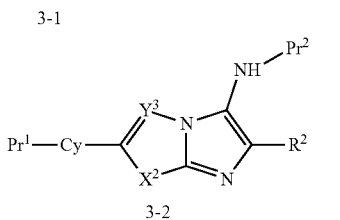

3-2

-continued

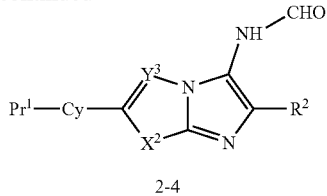

2-4 wherein, Pr² is selected from tert-butyl, or 2,4,4-trimethylpent-2-yl; Pr¹, Cy, X², Y³ and R² are all defined as described herein.

Intermediate 3-1 is reacted with Pr²NC and aldehyde R²CHO under the catalysis of lewis acid (such as magnesium chloride) through a three-component reaction to obtain intermediate 3-2; the intermediate 3-2 in formic acid is heated to obtain intermediate 2-4.

EXAMPLES

Example 1

Preparation of 2-{[6-ethyl-2-(4-methylsulfonyl)piperazin-1-yl)imidazo[2,1-b][1,3,4]thiadiazol-5-yl](methyl)amino}-4-(4-fluorophenyl)thiazole-5-carbonitrile

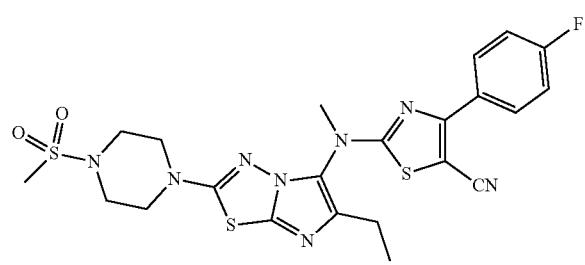 [SMILES: CCc1nc2sc(N3CCN(S(C)(=O)=O)CC3)nn2c1N(C)c1nc(-c2ccc(F)cc2)c(C#N)s1]

STEP 1): 2-bromo-6-ethyl-N-(2,4,5,-trimethylpentane-2-yl)imidazo[2,1-b][1,3,4]thiadiazol-5-amine 2-amino-5-bromo-1,3,4,-thiadiazole (2.0 g, 11.2 mmol) was dissolved in n-butanol (20 mL), followed by adding 1,1,3,3-tetramethylbutylisonitrile (1.56 g, 11.2 mmol), n-propanal (1.6 g, 28 mmol) and anhydrous magnesium chloride (0.5 g, 5.6 mmol), and the mixture was reacted at 120° C. for 4 hours. After solvent evaporation, the reaction mixture was purified by column purification (ethyl acetate: petroleum ether=1:2), to obtain 3.5 g of a brown oily product. Yield: 88%. MS (m/z): 359.1[M+1], 361.1[M+1].

STEP 2): N-(2-bromo-ethylimidazo[2,1-b][1,3,4]thiadiazol-5-yl)carboxamide 2-bromo-6-ethyl-N-(2,4,5,-trimethylpentane-2-yl)imidazo[2,1-b][1,3,4]thiadiazole-5-amine (3.5 g, 9.75 mmol) was added into a reaction flask, then formic acid (20 mL) was added to it, and the mixture was reacted at 80° C. for 3 hours. After the solvent evaporation, the reaction mixture was pulped with petroleum ether, filtered, dried to obtain 2.3 g of a product. Yield: 74%. MS (m/z): 275.0[M+1], 277.0 [M+1].

STEP 3): tert-butyl 4-(6-ethyl-5-formamidoimidazo[2,1-b][1,3,4]thiadiazol-2-yl)piperazine-1-carboxylate N-(2-bromo-ethylimidazo[2,1-b][1,3,4]thiadiazol-5-yl) carboxamide (300 mg, 1.1 mmol) and tert-butyl piperazine-1-carboxylate (305 mg, 1.64 mmol) were dissolved in DMF (5 mL), and potassium carbonate (304 mg, 2.2 mmol) was added and then the mixture reacts at 75° C. for 2 hours. After cooling, the reaction mixture was poured into water, and extracted with ethyl acetate (20 mL×2). The organic layer was washed with saturated saline solution, dried with anhydrous sodium sulfate, evaporated, and purified by column purification (dichloromethane:methanol=40:1), to obtain 200 mg of a light brown foam solid. Yield: 48%. MS (m/z): 381.3[M+1].

STEP 4): tert-butyl 4-{5-[(5-cyano-4-(4-fluorophenyl)thiazol-2-yl)(methyl)amino]-6-ethylimidazo[2,1-b][1,3,4]thiadiazol-2-yl)piperazine-1-carboxylate tert-butyl 4-(6-ethyl-5-formamidoimidazo[2,1-b][1,3,4] thiadiazol-2-yl)piperazine-1-carboxylate (330 mg, 0.87 mmol) was dissolved in tetrahydrofuran (8 mL), and sodium hydride (87 mg, 2.18 mmol) was added. The mixture was stirred for 30 minutes. Then 2-chloro-4-(4-fluorophenyl) thiazole-5-carbonitrile (176 mg, 0.74 mmol) was added to the reaction mixture and the reaction mixture was heated at 70° C. for half an hour. After cooling to room temperature, iodomethane (108 μL, 1.74 mmol) was added to the reaction mixture, which further was reacted at 65° C. for half an hour. After cooling, the reaction mixture was poured into water and extracted with ethyl acetate (15 mL×2). The organic layer was washed with saturated saline solution, dried with anhydrous sodium sulfate, evaporated, and purified by column purification, to obtain 350 mg of a product. Yield: 84%. MS (m/z): 569.3[M+1].

STEP 5): Preparation of 2-{[6-ethyl-2-(piperazin-1-yl)imidazo[2,1-b][1,3,4]thiadiazol-5-yl](methyl) amino}-4-(4-fluorophenyl)-thiazole-5-carbonitrile tert-butyl 4-{5-[(5-cyano-4-(4-fluorophenyl)thiazol-2-yl) (methyl)amino]-6-ethylimidazo[2,1-b][1,3,4]thiadiazol-2-yl)piperazine-1-carboxylate (150 mg, 0.26 mmol) was dissolved in dichloromethane (5 mL), and trifluoroacetic acid (1 mL) was added. The mixture was reacted at room temperature for 2 hours. The reaction mixture was evaporated, and dichloromethane was added. Saturated sodium bicarbonate solution was used for regulating pH to about 8, and then the mixture was extracted with dichloromethane (15 mL×3), washed with saturated saline solution, dried with anhydrous sodium sulfate, evaporated to obtain 112 mg of a foam solid. Yield: 91%. MS (m/z): 469.2[M+1].

STEP 6): 2-{[6-ethyl-2-(4-methylsulfonyl)piperazin-1-yl)imidazo[2,1-b][1,3,4]thiadiazol-5-yl](methyl) amino}-4-(4-fluorophenyl)-thiazole-5-carbonitrile 2-{[6-ethyl-2-(piperazin-1-yl)imidazo[2,1-b][1,3,4]thiadiazol-5-yl](methyl)amino}-4-(4-fluorophenyl)-thiazole-5-carbonitrile (40 mg, 0.085 mmol) was dissolved in dichloromethane (2 mL), and triethylamine (22 μL, 0.16 mmol) and methylsulfonyl chloride (13 μL, 0.16 mmol) were added. The mixture was reacted at room temperature for 1 hour, then was evaporated and purified by preparative plate to obtain 29 mg of a light yellow solid. Yield: 63%. $^1$H NMR (400 MHz, CDCl$_3$) δ: 8.14 (m, 2H), 7.16 (m, 2H), 3.58 (m, 7H), 3.38 (m, 4H), 2.84 (s, 3H), 2.61 (q, J=7.6 Hz, 2H), 1.27 (t, J=7.6 Hz, 3H).

Example 2

Preparation of 2-{[6-ethyl-2-(4-(2-(3-hydroxyazetidin-1-yl)-2-oxoethyl)piperazin-1-yl)imidazo[2,1-b][1,3,4]thiadiazol-5-yl](methyl)amino}-4-(4-fluorophenyl)thiazole-5-carbonitrile

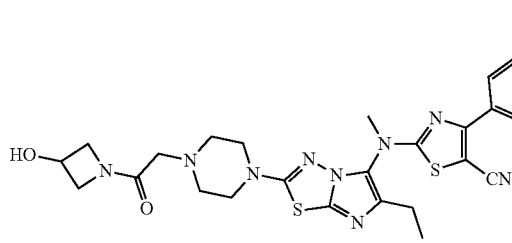

2-{[6-ethyl-2-(piperazin-1-yl)imidazo[2,1-b][1,3,4]thiadiazol-5-yl](methyl)amino}-4-(4-fluorophenyl)thiazole-5-carbonitrile (47 mg, 0.10 mmol) was dissolved in acetonitrile (2 mL), and potassium carbonate (28 mg, 0.20 mmol) and 2-chloro-1-(3-hydorxyazetidin-1-yl) ethanone (15 mg, 0.10 mmol) were added. The mixture was reacted at 70° C. for 1 hour, then was evaporated, and purified by preparative plate (dichloromethane:methanol=10:1), to obtain 26 mg of a white solid. Yield: 45%. $^1$H NMR (400 MHz, CDCl$_3$) δ: 8.13 (m, 2H), 7.15 (m, 2H), 4.69 (m, 1H), 4.41 (m, 1H), 4.28 (m, 1H), 4.05 (m, 1H), 3.91 (m, 1H), 3.57 (s, 3H), 3.49 (m, 4H), 3.08 (m, 2H), 2.65-2.59 (m, 6H), 1.27 (t, J=7.6 Hz, 3H).

Example 3

Preparation of 2-{[6-ethyl-2-(4-(methylsulfonyl)-2,7-diazaspiro[3.5]nonan-7-yl)imidazo[2,1-b][1,3,4]thiadiazol-5-yl](methyl)amino}-4-(4-fluorophenyl)thiazole-5-carbonitrile

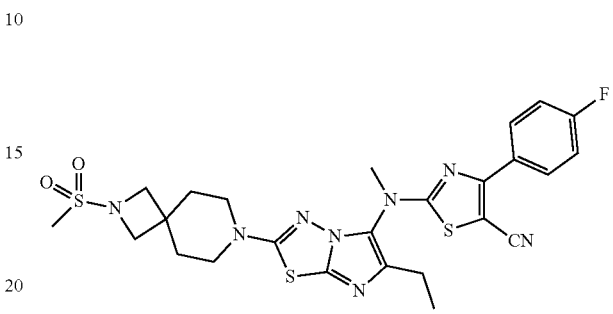

Referring to the Example 1, tert-butyl 2,7-diazaspiro[3.5]nonan-2-carboxylate was used to replace tert-butyl piperazine-1-carboxylate, so that 2-{[6-ethyl-2-(4-(methylsulfonyl)-2,7-diazaspiro[3.5]nonan-7-yl)imidazo[2,1-b][1,3,4]thiadiazol-5-yl](methyl)amino}-4-(4-fluorophenyl)-thiazole-5-carbonitrile was prepared. $^1$H NMR (500 MHz, CDCl$_3$) δ: 8.15 (m, 2H), 7.16 (m, 2H), 3.73 (m, 4H), 3.57 (s, 7H), 3.41 (m, 4H), 2.88 (s, 3H), 2.59 (q, J=7.5 Hz, 2H), 1.93 (m, 4H), 1.28 (t, J=7.5 Hz, 3H).

Example 4

Preparation of 2-{[6-ethyl-2-(2-(2-(3-hydroxyazetidin-1-yl))-2-oxoethyl)-2,7-diazaspiro[3.5]nonan-7-yl)imidazo[2,1-b][1,3,4]thiadiazol-5-yl](methyl)amino}-4-(4-fluorophenyl)-thiazole-5-carbonitrile

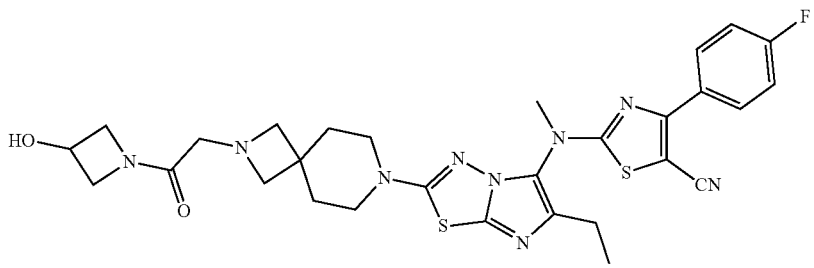 [SMILES: CCc1nc2sc(N3CCC4(CC3)CN(CC(=O)N3CC(O)C3)C4)nn2c1N(C)c1nc(-c2ccc(F)cc2)c(C#N)s1]

Referring to the Example 2, tert-butyl 2,7-diazaspiro[3.5]nonan-2-carboxylate was used to replace tert-butyl piperazin-1-carboxylate, so that 2-{[6-ethyl-2-(2-(2-(3-hydroxyazetidin-1-yl))-2-oxoethyl)-2,7-diazaspiro[3.5]nonan-7-yl)imidazo[2,1-b][1,3,4]thiadiazol-5-yl](methyl)amino}-4-(4-fluorophenyl)-thiazole-5-carbonitrile was prepared. $^1$H NMR (500 MHz, CDCl$_3$) δ: 8.14 (m, 2H), 7.16 (m, 2H), 4.67 (m, 1H), 4.37 (m, 1H), 4.25 (m, 1H), 4.02 (m, 1H), 3.86 (m, 1H), 3.57 (s, 3H), 3.37 (m, 4H), 3.23 (m, 4H), 3.17 (m, 2H), 2.58 (q, J=7.5 Hz, 2H), 1.88 (m, 4H), 1.27 (t, J=7.5 Hz, 3H).

Example 5

Preparation of 2-{[6-ethyl-2-(6-(methylsulfonyl))-2,6-diazaspiro[3.3]heptan-2-yl)imidazo[2,1-b][1,3,4]thiadiazol-5-yl](methyl)amino}-4-(4-fluorophenyl)-thiazole-5-carbonitrile

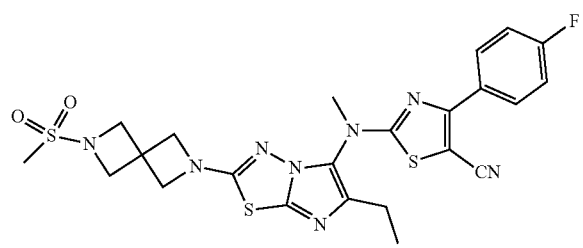 [SMILES: CCc1nc2sc(N3CC4(C3)CN(S(C)(=O)=O)C4)nn2c1N(C)c1nc(-c2ccc(F)cc2)c(C#N)s1]

Referring to the Example 1, tert-butyl 2,6-diazaspiro[3.3]heptan-2-carboxylate hemioxalate was used to replace tert-butyl piperazin-1-carboxylate, so that 2-{[6-ethyl-2-(6-(methylsulfonyl))-2,6-diazaspiro[3.2]heptan-2-yl)imidazo[2,1-b][1,3,4]thiadiazol-5-yl](methyl)amino}-4-(4-fluorophenyl)thiazole-5-carbonitrile was prepared. $^1$H NMR (500 MHz, CDCl$_3$) δ: 8.14 (m, 2H), 7.16 (m, 2H), 4.67 (m, 1H), 4.37 (m, 1H), 4.25 (m, 1H), 4.02 (m, 1H), 3.86 (m, 1H), 3.57 (s, 3H), 3.37 (m, 4H), 3.23 (m, 4H), 3.17 (m, 2H), 2.58 (q, J=7.5 Hz, 2H), 1.88 (m, 4H), 1.27 (t, J=7.5 Hz, 3H).

Example 6

Preparation of 2-{[6-ethyl-2-(6-(2-(3-hydroxyazetidin-1-yl))-2-oxoethyl)-2,6-diazaspiro[3.3]heptan-2-yl)imidazo[2,1-b][1,3,4]thiadiazol-5-yl](methyl)amino}-4-(4-fluorophenyl)-thiazole-5-carbonitrile Referring to the Example 2, tert-butyl 2,6-diazaspiro[3.3]heptan-2-carboxylate hemioxalate was used to replace tert-butyl piperazin-1-carboxylate, so that 2-{[6-ethyl-2-(6-(2-(3-hydroxyazetidin-1-yl))-2-oxoethyl)-2,6-diazaspiro[3.3]heptan-2-yl)imidazo[2,1-b][1,3,4]thiadiazol-5-yl](methyl)amino}-4-(4-fluorophenyl)-thiazole-5-carbonitrile. $^1$H NMR (500 MHz, CDCl$_3$) δ: 8.14 (m, 2H), 7.16 (m, 2H), 4.68 (m, 1H), 4.33 (m, 1H), 4.25 (m, 1H), 4.18 (s, 4H), 3.99 (m, 1H), 3.87 (m, 1H), 3.57 (s, 3H), 3.54 (s, 4H), 3.08 (s, 2H), 2.58 (q, J=7.5 Hz, 2H), 1.27 (t, J=7.5 Hz, 3H).

Example 7

Preparation of 4-{5-[(5-cyano-4-(4-fluorophenyl)thiazol-2-yl)(methyl)amino]-6-ethylimidazo[2,1-b][1,3,4]thiadiazol-2-yl}piperazine-1-carboxamide

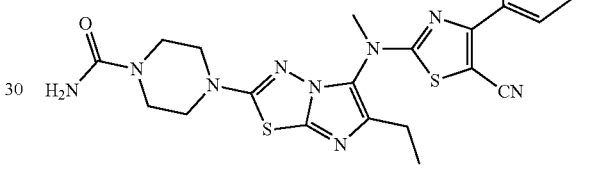

2-{[6-ethyl-2-(piperazin-1-yl)imidazo[2,1-b][1,3,4]thiadiazole-5-yl](methyl)amino}-4-(4-fluorophenyl)-thiazole-5-carbonitrile (40 mg, 0.085 mmol) was dissolved in dichloromethane (2 mL), followed by adding triethylamine (50 μL, 0.36 mmol) and trimethylsilyl isocyanate (30 mg, 0.26 mmol) under the protection of nitrogen gas. The mixture was reacted at room temperature for 3 hours, and then water (0.5 mL) was added, and the mixture was stirred for 20 minutes. After the solvent was evaporated, the reaction mixture was purified through preparative plate (dichloromethane:methanol=20:1), to obtain 18 mg of a white solid. Yield: 39%. $^1$H NMR (400 MHz, CDCl3) δ: 8.14 (m, 2H), 7.16 (m, 2H), 4.55 (s, 2H), 3.58 (m, 7H), 3.48 (m, 4H), 2.59 (q, J=7.6 Hz, 2H), 1.28 (t, J=7.6 Hz, 3H).

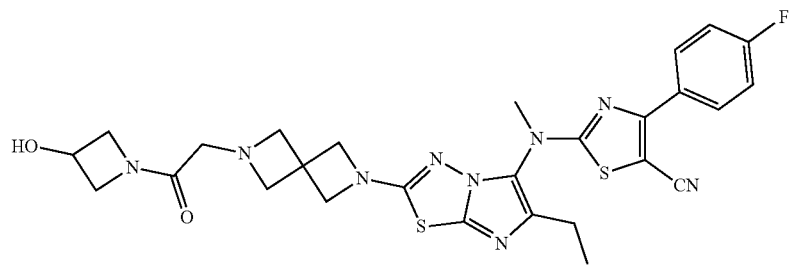 [SMILES: CCc1nc2sc(N3CC4(CN(CC(=O)N5CC(O)C5)C4)C3)nn2c1N(C)c1nc(-c2ccc(F)cc2)c(C#N)s1]

Example 8

Preparation of 7-{5-[5-cyano-4-(4-fluorophenyl)thiazol-2-yl](methyl)amino]-6-ethylimidazo[2,1-b][1,3,4]thiadiazol-2-yl}-2,7-diazaspiro[3.5]nonane-2-carboxamide

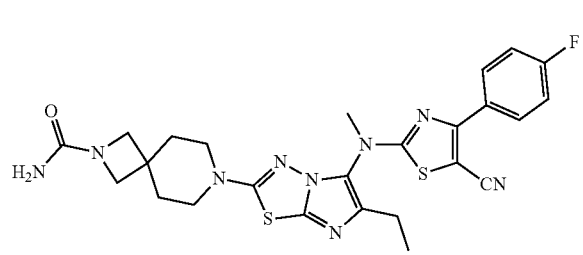 [SMILES: CCc1nc2sc(N3CCC4(CC3)CN(C(N)=O)C4)nn2c1N(C)c1nc(-c2ccc(F)cc2)c(C#N)s1]

Referring to the Example 7, tert-butyl 2,7-diazaspiro[3.5]nonan-2-carboxylate was used to replace tert-butyl piperazin-1-carboxylate, so that 7-{5-[(5-cyano-4-(4-fluorophenyl)thiazol-2-yl)(methyl)amino-6-ethylimidazo[2,1-b][1,3,4]thiadiazol-2-yl}-2,7-diazaspiro[3.5]nonane-2-carboxamide was prepared. $^1$H NMR (400 MHz, CDCl$_3$) δ: 8.14 (m, 2H), 7.16 (m, 2H), 4.32 (s, 2H), 3.75 (s, 4H), 3.57 (s, 3H), 3.42 (m, 4H), 2.59 (q, J=7.6 Hz, 2H), 1.91 (m, 4H), 1.27 (t, J=7.6 Hz, 3H).

Example 9

Preparation of 6-{5-[(5-cyano-4-(4-fluorophenyl)thiazol-2-yl)(methyl)amino]-6-ethylimidazo[2,1-b][1,3,4]thiadiazol-2-yl}-2,6-diazaspiro[3.3]heptane-2-carboxamide

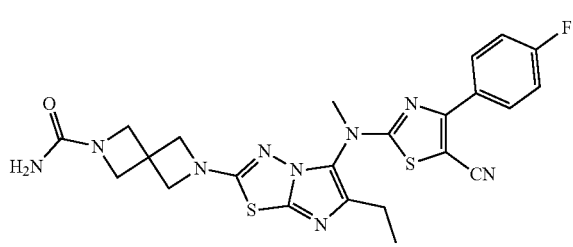 [SMILES: CCc1nc2sc(N3CC4(CN(C(N)=O)C4)C3)nn2c1N(C)c1nc(-c2ccc(F)cc2)c(C#N)s1]

Referring to the Example 7, tert-butyl 2,6-diazaspiro[3.3]heptan-2-carboxylate hemioxalate was used to replace tert-butyl piperazin-1-carboxylate, so that 6-{5-[(5-cyano-4-(4-fluorophenyl)thiazol-2-yl)(methyl)amino]-6-ethylimidazo[2,1-b][1,3,4]thiadiazol-2-yl}-2,6-diazaspiro[3.3]heptane-2-carboxamide was prepared. $^1$H NMR (400 MHz, CDCl$_3$) δ: 8.14 (m, 2H), 7.16 (m, 2H), 4.34 (s, 2H), 4.25 (s, 4H), 4.18 (s, 4H), 3.57 (s, 3H), 2.59 (q, J=7.6 Hz, 2H), 1.27 (t, J=7.6 Hz, 3H).

Example 10

Preparation of N-{1-[5-((5-cyano-4-(4-fluorophenyl)thiazol-2-yl)(methyl)amino)-6-ethylimidazo[2,1-b][1,3,4]thiadiazol-2-yl}pyrrolidin-3-yl]-N-methyl-methanesulfonamide

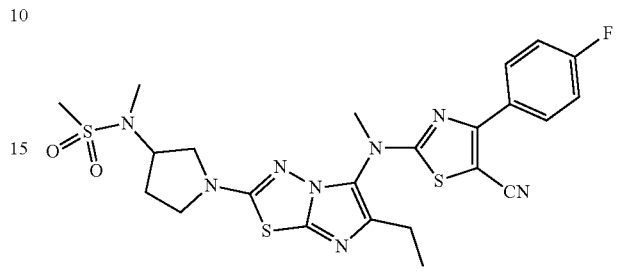

Referring to the Example 1, 3-tert-butoxycarbonylamino-pyrrolidine was used to replace tert-butyl piperazin-1-carboxylate, so that N-{1-[5-((5-cyano-4-(4-fluorophenyl)thiazol-2-yl)(methyl)amino)-6-ethylimidazo[2,1-b][1,3,4]thiadiazol-2-yl]pyrrolidin-3-yl}-N-methylmethanesulfonamide was prepared. $^1$H NMR (400 MHz, CDCl$_3$) δ: 8.14 (m, 2H), 7.16 (m, 2H), 4.73 (m, 1H), 3.68 (m, 2H), 3.58 (s, 3H), 3.46 (m, 2H), 2.89 (m, 6H), 2.61 (m, 2H), 2.28 (m, 2H), 1.27 (m, 3H).

Example 11

Preparation of 2-{[6-ethyl-2-(3-(2-(3-hydroxyazetidin-1-yl))-2-oxoethyl)(methyl)amino)pyrrolidin-1-yl)imidazo[2,1-b][1,3,4]thiadiazol-5-yl](methyl)amino}-4-(4-fluorophenyl)thiazole-5-carbonitrile

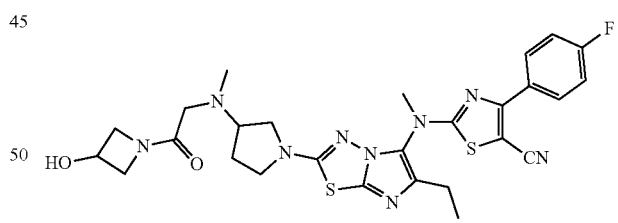

Referring to the Example 2, 3-tert-butoxycarbonylamino-pyrrolidine was used to replace tert-butyl piperazin-1-carboxylate, so that 2-{[6-ethyl-2-(3-((2-(3-hydroxyazetidin-1-yl))-2-oxoethyl)(methyl)amino)pyrrolidin-1-yl)imidazo[2,1-b][1,3,4]thiadiazol-5-yl](methyl)amino}-4-(4-fluorophenyl)thiazole-5-carbonitrile was prepared. $^1$H NMR (400 MHz, CDCl$_3$) δ: 8.14 (m, 2H), 7.16 (m, 2H), 4.68 (m, 1H), 4.41 (m, 1H), 4.28 (m, 1H), 4.06 (m, 1H), 3.89 (m, 1H), 3.65 (m, 1H), 3.59 (m, 3H), 3.47-3.29 (m, 4H), 3.15 (m, 2H), 2.59 (q, J=7.6 Hz, 2H), 2.25 (m, 2H), 1.28 (t, J=7.6 Hz, 3H).

Example 12

Preparation of 1-{1-[5-((5-cyano-4-(4-fluorophenyl)thiazol-2-yl)(methyl)amino)-6-ethylimidazo[2,1-b][1,3,4]thiadiazol-2-yl]pyrrolidin-3-yl}-1-methylurea

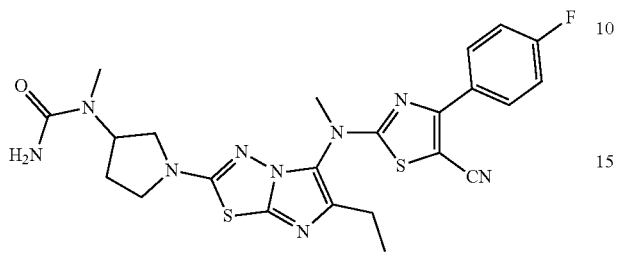

Referring to the Example 7, 3-tert-butoxycarbonylaminopyrrolidine was used to replace tert-butyl piperazin-1-carboxylate, so that 1-{1-[5-((5-cyano-4-(4-fluorophenyl)thiazol-2-yl)(methyl)amino)-6-ethylimidazo[2,1-b][1,3,4]thiadiazol-2-yl]pyrrolidin-3-yl}-1-methylurea was prepared. $^1$H NMR (500 MHz, CDCl$_3$) δ: 8.14 (m, 2H), 7.15 (m, 2H), 5.19 (m, 1H), 4.54 (s, 2H), 3.68-3.58 (m, 5H), 3.45 (m, 1H), 3.33 (m, 1H), 2.85 (s, 3H), 2.59 (q, J=7.5 Hz, 2H), 2.25 (m, 1H), 2.13 (m, 1H), 1.28 (t, J=7.6 Hz, 3H).

Example 13

Preparation of N-{1-[5-((5-cyano-4-(4-fluorophenyl)thiazol-2-yl)(methyl)amino)-6-ethylimidazo[2,1-b][1,3,4]thiadiazol-2-yl]piperidin-3-yl}-N-methylmethanesulfonamide

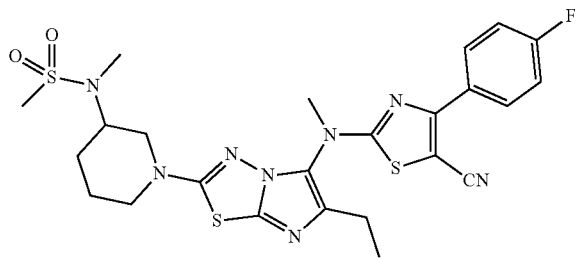 [SMILES: CCc1nc2sc(N3CCCC(N(C)S(C)(=O)=O)C3)nn2c1N(C)c1nc(-c2ccc(F)cc2)c(C#N)s1]

Referring to the Example 1, 3-tert-butoxycarbonylaminopiperdine was used to replace tert-butyl piperazin-1-carboxylate, so that N-{1-[5-((5-cyano-4-(4-fluorophenyl)thiazol-2-yl)(methyl)amino)-6-ethylimidazo[2,1-b][1,3,4]thiadiazol-2-yl]piperidin-3-yl}-N-methylmethanesulfonamide was prepared. $^1$H NMR (500 MHz, CDCl$_3$) δ: 8.15 (m, 2H), 7.16 (m, 2H), 4.00-3.85 (m, 2H), 3.78 (m, 0.5H), 3.66 (m, 0.5H), 3.58 (s, 3H), 3.13-3.02 (m, 2H), 2.87 (m, 6H), 2.59 (q, J=7.5 Hz, 2H), 1.98 (m, 2H), 1.78 (m, 2H), 1.28 (t, J=7.5 Hz, 3H).

Example 14

Preparation of 2-{[6-ethyl-2-(3-((2-(3-hydroxyazetidin-1-yl))-2-oxoethyl)(methyl)amino)piperdin-1-yl)imidazo[2,1-b][1,3,4]thiadiazol-5-yl](methyl)amino}-4-(4-fluorophenyl)-thiazole-5-carbonitrile

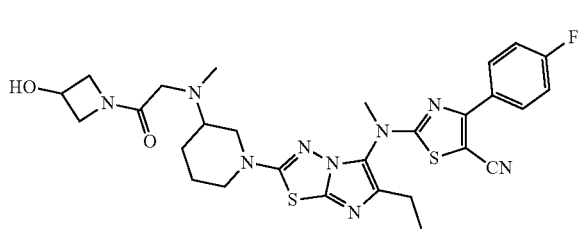 [SMILES: CCc1nc2sc(N3CCCC(N(C)CC(=O)N4CC(O)C4)C3)nn2c1N(C)c1nc(-c2ccc(F)cc2)c(C#N)s1]

Referring to the Example 2, 3-tert-butoxycarbonylaminopiperdine was used to replace tert-butyl piperazin-1-carboxylate, so that 2-{[6-ethyl-2-(3-((2-(3-hydroxyazetidin-1-yl))-2-oxoethyl)(methyl)amino)piperdin-1-yl)imidazo[2,1-b][1,3,4]thiadiazol-5-yl](methyl)amino}-4-(4-fluorophenyl)thiazole-5-carbonitrile was prepared. $^1$H NMR (400 MHz, CDCl$_3$) δ: 8.14 (m, 2H), 7.16 (m, 2H), 4.58 (m, 1H), 4.38 (m, 1H), 4.23 (m, 1H), 4.04 (m, 1H), 3.85 (m, 2H), 3.69 (m, 1H), 3.58 (s, 3H), 3.20 (m, 2H), 3.00 (m, 2H), 2.72 (m, 1H), 2.58 (q, J=7.6 Hz, 2H), 2.00 (m, 1H), 1.86 (m, 1H), 1.51 (m, 2H), 1.27 (t, J=7.6 Hz, 3H).

Example 15

Preparation of 1-{1-[5-((5-cyano-4-(4-fluorophenyl)thiazol-2-yl)(methyl)amino)-6-ethylimidazo[2,1-b][1,3,4]thiadiazol-2-yl]piperidin-3-yl}-1-methylurea

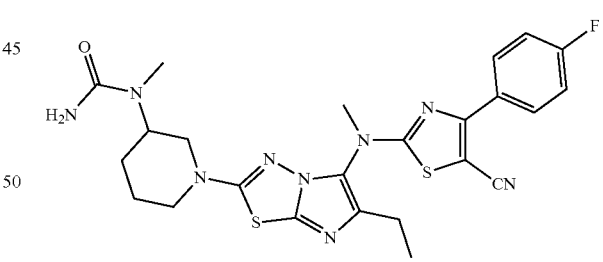

Referring to the example 7, 3-tert-butoxycarbonylaminopiperidine was used to replace tert-butyl piperazin-1-carboxylate, so that 1-{1-[5-((5-cyano-4-(4-fluorophenyl)thiazol-2-yl)(methyl)amino)-6-ethylimidazo[2,1-b][1,3,4]thiadiazol-2-yl]piperidin-3-yl}-1-methylurea was obtained. $^1$H NMR (400 MHz, CDCl$_3$) δ: 8.15 (m, 2H), 7.15 (m, 2H), 4.57 (s, 2H), 4.23 (m, 1H), 3.91 (m, 0.5H), 3.77 (m, 1H), 3.66 (m, 0.5H), 3.57 (s, 3H), 3.00 (m, 2H), 2.84 (s, 3H), 2.59 (q, J=7.6 Hz, 2H), 1.93 (m, 2H), 1.77 (m, 2H), 1.27 (t, J=7.6 Hz, 3H).

Example 16

Preparation of 2-{[6-ethyl-2-(1-(methylsulfonyl)piperidin-4-yl)imidazo[2,1-b][1,3,4]thiadiazol-5-yl](methyl)amino}-4-(4-fluorophenyl)-thiazole-5-carbonitrile

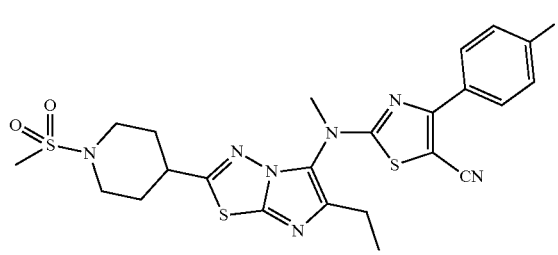

STEP 1):
5-(piperidin-4-yl)-1,2,4-thiadiazole-2-amine 4-piperidinecarboxylic acid (10 g, 77.4 mmol) was dissolved in concentrated hydrochloric acid (150 mL) and water (25 mL), and thiosemicarbazide (14.1 g, 154.8 mmol) was added. The mixture was reacted at 120° C. overnight. A part of solvent was removed by evaporation, and the pH of the reaction mixture was regulated to about 10 with saturated sodium hydroxide solution, followed by stirring for 30 minutes and filtering. Then, filter cake was recrystallized with ethanol, to obtain 2.9 g of a white solid. Yield: 20%. MS (m/z): 185.1 [M+1].

STEP 2): benzyl 4-(5-amino-1,3,4-thiazol-2yl)piperidine-1-carboxylate 5-(piperidin-4-yl)-1,2,4-thiadiazol-2-amine (2.6 g, 14.1 mmol) was dissolved in acetonitrile (30 mL) and water (10 mL), and sodium bicarbonate (1.78 g, 21.2 mmol) was added. The mixture was cooled to 0° C. and dropwise added with CbzCl (2.21 mL, 15.5 mmol), and then was reacted at 0° C. for 2 hours. Water (20 mL) was added to the mixture, which was further extracted with ethyl acetate (50 mL×3). The organic layer was combined, then washed with saturated saline solution (100 mL), dried with anhydrous sodium sulfate, evaporated, and purified by column purification (dichloromethane:methanol=40:1), to obtain 800 mg of a light yellow solid. Yield: 18%. MS (m/z): 319.2 [M+1].

STEP 3): benzyl 4-{5-[(5-cyano-4-(4-fluorophenyl)thiazol-2-yl)(methyl)amino]-6-ethylimidazo[2,1-b][1,3,4]thiadiazol-2-yl}piperidin-1-carboxylate Referring to the method of preparing tert-butyl 4-{5-[(5-cyano-4-(4-fluorophenyl)thiazol-2-yl)(methyl)amino]-6-ethylimidazo[2,1-b][1,3,4]thiadiazol-2-yl]piperazin-1-carboxylate in the Example 1, benzyl 4-(5-amino-1,3,4-thiadiazol-2-yl)piperidine-1-carboxylate was used to replace 2-amino-5-bromo-1,3,4-thiadiazole, so that benzyl 4-{5-[(5-cyano-4-(4-fluorophenyl)thiazol-2-yl)(methyl)amino]-6-ethylimidazo[2,1-b][1,3,4]thiadiazol-2-yl}piperidin-1-carboxylate was prepared. $^1$H NMR (400 MHz, CDCl$_3$) δ: 8.14 (m, 2H), 7.35 (m, 5H), 7.16 (m, 2H), 5.14 (s, 2H), 4.28 (m, 2H), 3.61 (s, 3H), 3.16 (m, 1H), 2.97 (m, 2H), 2.64 (q, J=7.6 Hz, 2H), 2.10 (m, 2H), 1.78 (m, 2H), 1.31 (t, J=7.6 Hz, 3H).

STEP 4): 2-{[6-ethyl-2-(piperidin-4-yl)imidazo[2,1-b][1,3,4]thiadiazol-5-yl](methyl)amino}-4-(4-fluorophenyl)-thiazole-5-carbonitrile benzyl 4-{5-[(5-cyano-4-(4-fluorophenyl)thiazol-2-yl)(methyl)amino]-6-ethylimidazo[2,1-b][1,3,4]thiadiazol-2-yl}piperidine-1-carboxylate (330 mg, 0.55 mmol) was dissolved in dichloromethane (10 mL), and the mixture was cooled to 0° C., followed by adding trimethyliodosilane (220 mg, 1.1 mmol). The mixture was reacted at room temperature for 3 hours, rotated to remove dichloromethane. Then water (20 mL) was added into the mixture, which was extracted with petroleum ether to remove impurities. The aqueous layer was regulated pH to about 8 with sodium bicarbonate solution and the organic layer was extracted with dichloromethane and combined, dried with anhydrous sodium sulfate, evaporated, to obtain 260 mg of a form solid, which will be directly used in the next step without purification. MS (m/z): 468.1 [M+1].

STEP 5): 2-{[6-ethyl-2-(1-(methylsulfonyl)piperidin-4-yl)imidazo[2,1-b][1,3,4]thiadiazol-5-yl](methyl)amino}-4-(4-fluorophenyl)thiazole-5-carbonitrile Referring to the Example 1, 2-{[6-ethyl-2-(piperidin-4-yl)imidazo[2,1-b][1,3,4]thiadiazol-5-yl](methyl)amino}-4-(4-fluorophenyl)thiazole-5-carbonitrile was used to replace 2-{[6-ethyl-2-(piperazin-1-yl)imidazo[2,1-b][1,3,4]thiadiazol-5-yl](methyl)amino}-4-(4-fluorophenyl)thiazole-5-carbonitrile, so that 2-{[6-ethyl-2-(1-(methylsulfonyl)piperidin-4-yl)imidazo[2,1-b][1,3,4]thiadiazol-5-yl](methyl)amino}-4-(4-fluorophenyl)thiazole-5-carbonitrile was prepared. $^1$H NMR (500 MHz, CDCl$_3$) δ: 8.14 (m, 2H), 7.16 (m, 2H), 3.90 (m, 2H), 3.62 (s, 3H), 3.13 (m, 1H), 2.87 (m, 2H), 2.82 (s, 3H), 2.64 (q, J=7.5 Hz, 2H), 2.24 (m, 2H), 1.99 (m, 2H), 1.31 (t, J=7.5 Hz, 3H).

Example 17

Preparation of 2-{[6-ethyl-2-(1-(2-(3-hydroxyazetidin-1-yl)-2oxoethyl)piperidin-4-yl)imidazo[2,1-b][1,3,4]thiadiazol-5-yl](methyl)amino}-4-(4-fluorophenyl)thiazole-5-carbonitrile

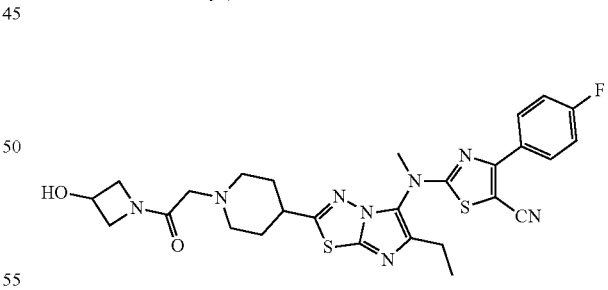

Referring to the Example 2, 2-{[6-ethyl-2-(piperidin-4-yl)imidazo[2,1-b][1,3,4]thiadiazol-5-yl](methyl)amino}-4-(4-fluorophenyl)thiazole-5-carbonitrile was used to replace 2-{[6-ethyl-2-(piperazin-1-yl)imidazo[2,1-b][1,3,4]thiadiazol-5-yl](methyl)amino)}-4-(4-fluorophenyl)thiazole-5-carbonitrile, so that 2-{[6-ethyl-2-(1-(2-(3-hydroxyazetidin-1-yl)-2-oxoethyl)piperidin-4-yl)imidazo[2,1-b][1,3,4]thiadiazol-5-yl](methyl)amino}-4-(4-fluorophenyl)thiazole-5-carbonitrile was prepared. $^1$H NMR (500 MHz, CDCl$_3$) δ: 8.14 (m, 2H), 7.16 (m, 2H), 4.68 (m, 1H), 4.44 (m, 1H), 4.27 (m, 1H), 4.08 (m, 1H), 3.89 (m, 1H), 3.61 (s, 3H), 3.05 (m, 2H), 2.98 (m, 3H), 2.64 (q, J=7.5 Hz, 2H), 2.23 (m, 2H), 2.10 (m, 2H), 1.92 (m, 2H), 1.30 (t, J=7.5 Hz, 3H).

Example 18

Preparation of 4-{5-[(5-cyano-4-(4-fluorophenyl)thiazol-2-yl](methyl)amino]-6-ethylimidazo[2,1-b][1,3,4]thiadiazol-2-yl}piperidine-1-carboxamide

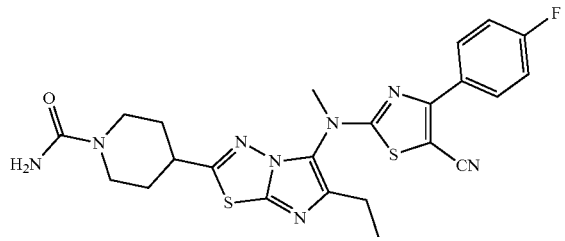 [SMILES: CCc1nc2sc(C3CCN(C(N)=O)CC3)nn2c1N(C)c1nc(-c2ccc(F)cc2)c(C#N)s1]

Referring to the Example 7, 2-{[6-ethyl-2-(piperidin-4-yl)imidazo[2,1-b][1,3,4]thiadiazol-5-yl](methyl)amino}-4-(4-fluorophenyl)thiazole-5-carbonitrile was used to replace 2-{[6-ethyl-2-(piperazin-1-yl) imidazo[2,1-b][1,3,4]thiadiazol-5-yl](methyl)amino}-4-(4-fluorophenyl)thiazole-5-carbonitrile, so that 4-{5-[(5-cyano-4-(4-fluorophenyl)thiazol-2-yl](methyl)amino]-6-ethylimidazo[2,1-b][1,3,4]thiadiazol-2-yl}piperidine-1-carboxamide was prepared. $^1$H NMR (500 MHz, CDCl$_3$) δ: 8.13 (m, 2H), 7.16 (m, 2H), 4.54 (s, 2H), 4.05 (m, 2H), 3.61 (s, 3H), 3.19 (m, 1H), 2.99 (m, 2H), 2.64 (q, J=7.5 Hz, 2H), 2.14 (m, 2H), 1.83 (m, 2H), 1.31 (t, J=7.5 Hz, 3H).

Example 19

Preparation of (R)-1-{1-[5-((5-cyano-4-(4-fluorophenyl)thiazol-2-yl)(methyl)amino)-6-ethylimidazo[2,1-b][1,3,4]thiadiazol-2-yl]pyrrolidin-3-yl}-1-methylurea

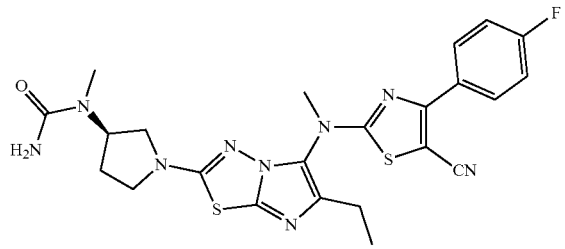 [SMILES: CCc1nc2sc(N3CC[C@@H](N(C)C(N)=O)C3)nn2c1N(C)c1nc(-c2ccc(F)cc2)c(C#N)s1]

Referring to the Example 7, (R)-3-tertbutoxycarbonylaminopyrrolidine was used to replace tert-butyl piperazin-1-carboxylate, so that (R)-1-{1-[5-((5-cyano-4-(4-fluorophenyl)thiazol-2-yl)(methyl)amino)-6-ethylimidazo[2,1-b][1,3,4]thiadiazol-2-yl]pyrrolidin-3-yl}-1-methylurea was prepared. $^1$H NMR (500 MHz, CDCl$_3$) δ: 8.14 (m, 2H), 7.15 (m, 2H), 5.19 (m, 1H), 4.63 (s, 2H), 3.65 (m, 2H), 3.57 (s, 3H), 3.45 (m, 1H), 3.32 (s, 1H), 2.84 (s, 3H), 2.26 (q, J=9.5 Hz, 2H), 2.25 (m, 1H), 2.11 (m, 1H), 1.28 (m, 3H). MS (m/z): 526.2 [M+1].

Example 20

Preparation of (S)-1-{1-[5-((5-cyano-4-(4-fluorophenyl)thiazol-2-yl)(methyl)amino)-6-ethylimidazo[2,1-b][1,3,4]thiadiazol-2-yl]pyrrolidin-3-yl}-1-methylurea

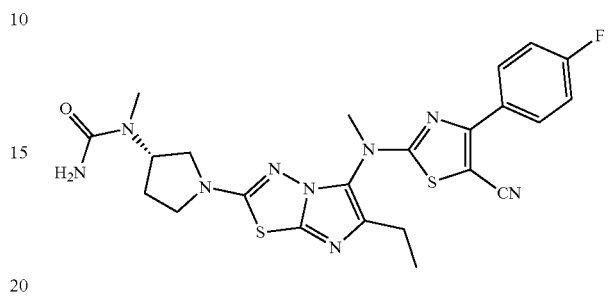

Referring to the Example 7, (S)-3-tertbutoxycarbonylaminopyrrolidine was used to replace tert-butyl piperazin-1-carboxylate, so that (S)-1-{1-[5-((5-cyano-4-(4-fluorophenyl)thiazol-2-yl)(methyl)amino)-6-ethylimidazo[2,1-b][1,3,4]thiadiazol-2-yl]pyrrolidin-3-yl}-1-methylurea was prepared. $^1$H NMR (500 MHz, CDCl$_3$) δ: 8.14 (m, 2H), 7.15 (m, 2H), 5.18 (m, 1H), 4.62 (s, 2H), 3.64 (m, 2H), 3.57 (s, 3H), 3.44 (m, 1H), 3.31 (s, 1H), 2.84 (s, 3H), 2.26 (q, J=9.5 Hz, 2H), 2.26 (m, 1H), 2.10 (m, 1H), 1.28 (m, 3H). MS (m/z): 526.2 [M+1].

Example 21

Preparation of (R)-2-{[6-ethyl-2-(3-((2-(3-hydroxyazetidin-1-yl)-2-oxoethyl)(methyl)amino)pyrrolidin-1-yl)imidazo[2,1-b][1,3,4]thiadiazol-5-yl](methyl)amino}-4-(4-fluorophenyl)thiazole-5-carbonitrile

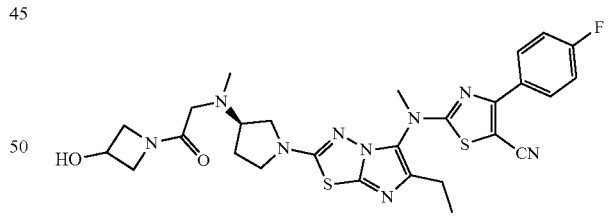

Referring to the Example 2, (R)-3-tertbutoxycarbonylaminopyrrolidine was used to replace tert-butyl piperazin-1-carboxylate, so that (R)-2-{[6-ethyl-2-(3-((2-(3-hydroxyazetidin-1-yl)-2-oxoethyl)(methyl)amino)pyrrolidin-1-yl)imidazo[2,1-b][1,3,4]thiadiazol-5-yl](methyl)amino}-4-(4-fluorophenyl)thiazole-5-carbonitrile was prepared. $^1$H NMR (400 MHz, CDCl$_3$) δ: 8.17 (m, 2H), 7.18 (m, 2H), 4.69 (m, 1H), 4.43 (m, 1H), 4.29 (m, 1H), 4.07 (m, 1H), 3.91 (m, 1H), 3.67 (m, 1H), 3.60 (m, 4H), 3.49-3.31 (m, 3H), 3.16 (m, 2H), 2.61 (q, J=7.6 Hz, 2H), 2.46 (m, 1H), 2.38 (s, 3H), 2.25 (m, 1H), 1.30 (t, J=7.6 Hz, 3H). MS (m/z): 596.2 [M+1].

Example 22

Preparation of (S)-2-{[6-ethyl-2-(3-((2-(3-hydroxyazetidin-1-yl)-2oxoethyl)(methyl)amino)pyrrolidin-1-yl)imidazo[2,1-b][1,3,4]thiadiazol-5-yl](methyl)amino}-4-(4-fluorophenyl)thiazole-5-carbonitrile

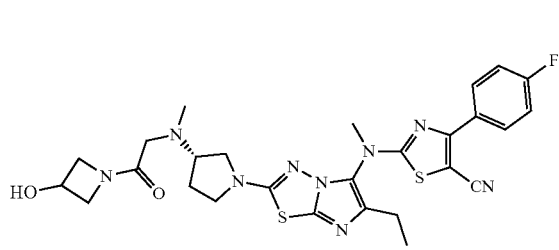 [SMILES: CCc1nc2sc(N3CC[C@H](N(C)CC(=O)N4CC(O)C4)C3)nn2c1N(C)c1nc(-c2ccc(F)cc2)c(C#N)s1]

Referring to the Example 2, (S)-3-tertbutoxycarbonylaminopyrrolidine was used to replace tert-butyl piperazin-1-carboxylate, so that (S)-2-{[6-ethyl-2-(3-((2-(3-hydroxyazetidin-1-yl)-2-oxoethyl)(methyl)amino)pyrrolidin-1-yl)imidazo[2,1-b][1,3,4]thiadiazol-5-yl](methyl)amino}-4-(4-fluorophenyl)thiazole-5-carbonitrile was prepared. $^1$H NMR (400 MHz, CDCl$_3$) δ: 8.17 (m, 2H), 7.18 (m, 2H), 4.70 (m, 1H), 4.44 (m, 1H), 4.29 (m, 1H), 4.08 (m, 1H), 3.91 (m, 1H), 3.67 (m, 1H), 3.60 (m, 4H), 3.49-3.32 (m, 3H), 3.17 (m, 2H), 2.61 (q, J=7.6 Hz, 2H), 2.38 (s, 3H), 2.28 (m, 2H), 1.30 (t, J=7.6 Hz, 3H). MS (m/z): 596.2 [M+1].

Example 23

Preparation of (R)-2-{[6-ethyl-2-(3-((2-(3-hydroxyazetidin-1-yl)-2-oxoethyl)(methyl)amino)piperidin-1-yl)imidazo[2,1-b][1,3,4]thiadiazol-5-yl](methyl)amino}-4-(4-fluorophenyl)thiazole-5-carbonitrile

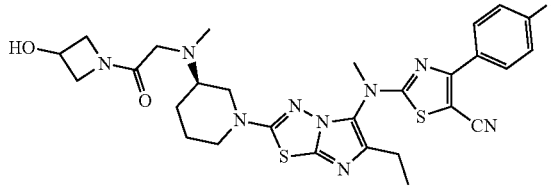

Referring to the Example 2, (R)-3-tertbutoxycarbonylaminopiperidine was used to replace tert-butyl piperazine-1-carboxylate, so that (R)-2-{[6-ethyl-2-(3-((2-(3-hydroxyazetidin-1-yl)-2-oxoethyl)(methyl)amino)piperidin-1-yl)imidazo[2,1-b][1,3,4]thiadiazol-5-yl](methyl)amino}-4-(4-fluorophenyl)thiazole-5-carbonitrile was prepared. $^1$H NMR (400 MHz, CDCl$_3$) δ: 8.16 (m, 2H), 7.18 (m, 2H), 4.60 (m, 1H), 4.39 (m, 1H), 4.25 (m, 1H), 4.07 (m, 1H), 3.86 (m, 2H), 3.69 (m, 1H), 3.60 (s, 3H), 3.22 (m, 2H), 3.03 (m, 2H), 2.74 (m, 1H), 2.60 (q, J=7.6 Hz, 2H), 2.40 (m, 3H), 2.02 (m, 2H), 1.87 (m, 1H), 1.54 (m, 2H), 1.30 (t, J=7.6 Hz, 3H). MS (m/z): 610.2 [M+1].

Example 24

Preparation of (S)-2-{[6-ethyl-2-(3-((2-(3-hydroxyazetidin-1-yl)-2-oxoethyl)(methyl)amino)piperidin-1-yl)imidazo[2,1-b][1,3,4]thiadiazol-5-yl](methyl)amino}-4-(4-fluorophenyl)thiazole-5-carbonitrile

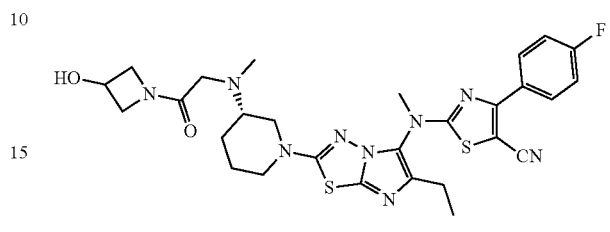

Referring to the Example 2, (S)-3-tertbutoxycarbonylaminopiperidine was used to replace tert-butyl piperazine-1-carboxylate, so that (S)-2-{[6-ethyl-2-(3-((2-(3-hydroxyazetidin-1-yl)-2-oxoethyl)(methyl)amino)piperidin-1-yl)imidazo[2,1-b][1,3,4]thiadiazol-5-yl](methyl)amino}-4-(4-fluorophenyl)thiazole-5-carbonitrile was prepared. $^1$H NMR (400 MHz, CDCl$_3$) δ: 8.16 (m, 2H), 7.18 (m, 2H), 4.61 (m, 1H), 4.40 (m, 1H), 4.26 (m, 1H), 4.08 (m, 1H), 3.87 (m, 2H), 3.69 (m, 1H), 3.60 (s, 3H), 3.22 (m, 2H), 3.03 (m, 2H), 2.74 (m, 1H), 2.61 (q, J=7.6 Hz, 2H), 2.40 (m, 3H), 2.03 (m, 2H), 1.89 (m, 1H), 1.54 (m, 2H), 1.30 (t, J=7.6 Hz, 3H). MS (m/z): 610.2 [M+1].

Example 25

Preparation of 3-tertbutyl-1-{1-[5-((5-cyano-4-(4-fluorophenyl)thiazol-2-yl)(methyl)amino)-6-ethylimidazo[2,1-b][1,3,4]thiadiazol-2-yl]pyrrolidin-3-yl}-1-methylurea

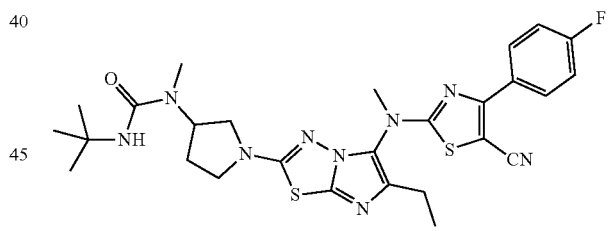

STEP 1): Preparation of 2-{[6-ethyl-2-(3-(methylamino)pyrrolidin-1-yl)imidazo[2,1-b][1,3,4]thiadiazol-5-yl](methyl)amino}-4-(4-fluorophenyl)thiazole-5-carbonitrile Referring to the Example 1, 3-tertbutoxycarbonylaminopyrrolidine was used to replace tert-butyl piperazine-1-carboxylate, so that 2-{[6-ethyl-2-(3-(methylamino)pyrrolidin-1-yl)imidazo[2,1-b][1,3,4]thiadiazol-5-yl](methyl)amino}-4-(4-fluorophenyl)thiazole-5-carbonitrile was obtained. MS (m/z): 483.2 [M+1].

STEP 2): preparation of 3-tertbutyl-1-{1-[5-((5-cyano-4-(4-fluorophenyl)thiazol-2-yl) (methyl)amino)-6-ethylimidazo[2,1-b][1,3,4]thiadiazol-2-yl]pyrrolidin-3-yl}-1-methylurea 2-{[6-ethyl-2-(3-(methylamino)pyrrolidin-1-yl)imidazo[2,1-b][1,3,4]thiadiazol-5-yl](methyl)amino}-4-(4-fluorophenyl)thiazole-5-carbonitrile (48 mg, 0.10 mmol) was dissolved in tetrahydrofuran, and tertbutylisocyanate (15 mg, 0.15 mmol) was added. The mixture was reacted at 50° C. for 3 hours, evaporated and purified by thick preparative plate to obtain 41 mg of a white solid, yield: 71%.1H NMR (400 MHz, CDCl$_3$) δ: 8.15 (m, 2H), 7.17 (m, 2H), 4.31 (m, 1H), 3.76 (m, 1H), 3.67-3.60 (m, 5H), 3.47 (m, 1H), 3.28 (m, 1H), 2.78 (s, 3H), 2.63 (m, 2H), 2.24 (m, 1H), 2.10 (m, 1H), 1.37 (s, 9H), 1.27 (m, 3H). MS (m/z): 582.2 [M+1].

Example 26

Preparation of 3-tert-butyl-1-{1-[5-((5-cyano-4-(4-fluorophenyl)thiazol-2-yl)(methyl)amino)-6-ethyl-imidazo[2,1-b][1,3,4]thiadiazol-2-yl]piperidin-3-yl}-1-methylurea

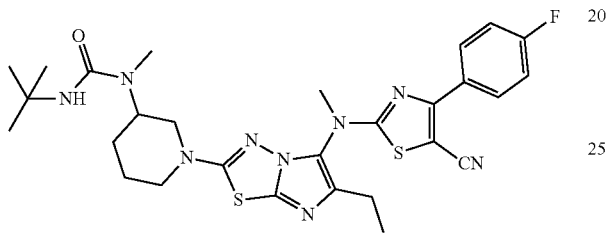

Referring to the Example 25, 3-tertbutoxycarbonylaminopiperidine was used to replace 3-tertbutoxycarbonylaminopyrrolidine, so that 3-tertbutyl-1-{1-[5-((5-cyano-4-(4-fluorophenyl)thiazol-2-yl)(methyl)amino)-6-ethylimidazo[2,1-b][1,3,4]thiadiazol-2-yl]piperidin-3-yl}-1-methylurea was prepared. $^1$H NMR (400 MHz, CDCl$_3$) δ: 8.16 (m, 2H), 7.17 (m, 2H), 4.26 (s, 1H), 3.88-3.65 (m, 3H), 3.60 (s, 3H), 2.97 (m, 2H), 2.78 (s, 3H), 2.62 (m, 2H), 1.91 (m, 2H), 1.78 (m, 2H), 1.37 (s, 9H), 1.27 (m, 3H).

Example 27

Preparation of 1-{1-[5-((5-cyano-4-(4-fluorophenyl)thiazol-2-yl)(methyl)amino)-6-ethylimidazo[2,1-b][1,3,4]thiadiazol-2-yl}pyrrolidin-3-yl}-3-cyclopropyl-1-methylurea

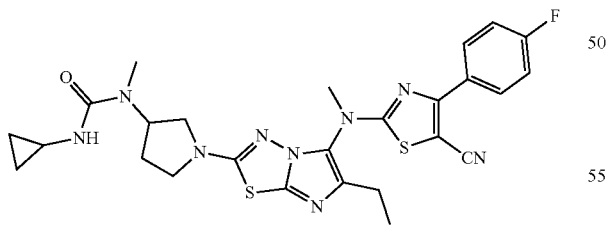

Triphosgene (24.5 mg, 0.083 mmol) was added into the flask, followed by adding dichloromethane (2 mL) under the protection of nitrogen gas, and then the mixture was cooled to 0° C. Cyclopropylamine (17 L, 0.25 mmol), triethylamine (86 μL, 0.62 mmol) and dichloromethane (1 mL) were added into another flask to perform reaction, and then the reaction solution was added to the first flask. The mixture was reacted at 0° C. for half an hour, and 2-{[6-ethyl-2-(3-(methylamino)pyrrolidin-1-yl)imidazo[2,1-b][1,3,4]thiadiazol-5-yl](methyl)amino}-4-(4-fluorophenyl)thiazole-5-carbonitrile (30 mg, 0.062 mmol) was added. The temperature gradually increased to room temperature, and the mixture was reacted overnight, then evaporated and purified through thick preparative plate (dichloromethane:methanol=20:1), to obtain 26 mg of a light-yellow solid, yield: 74%. $^1$H NMR (500 MHz, CDCl$_3$) δ: 8.16 (m, 2H), 7.18 (m, 2H), 5.23 (m, 1H), 4.70 (s, 1H), 3.72-3.60 (m, 5H), 3.48 (m, 1H), 3.32 (m, 1H), 2.78 (s, 3H), 2.68-2.58 (m, 3H), 2.26 (m, 1H), 2.14 (m, 1H), 1.30 (t, J=7.2 Hz, 3H), 0.76 (m, 2H), 0.50 (m, 2H). MS (m/z): 566.4 [M+1].

Example 28

Preparation of N-{1-[5-((5-cyano-4-(4-fluorophenyl)thiazol-2-yl)(methyl)amino)-6-ethylimidazo[2,1-b][1,3,4]thiadiazol-2-yl}pyrrolidin-3-yl}-N-methyl-cyclopropanesulfonamide

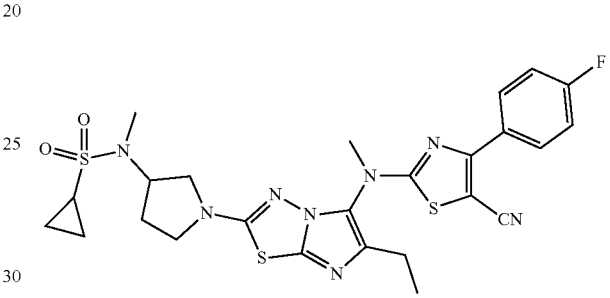

2-{[6-ethyl-2-(3-(methylamino)pyrrolidin-1-yl)imidazo[2,1-b][1,3,4]thiadiazol-5-yl](methyl)amino}-4-(4-fluorophenyl)thiazole-5-carbonitrile (30 mg, 0.062 mmol) was dissolved in dichloromethane (2 mL), followed by adding cloyclopropanesulfonyl chloride (19 μL, 0.19 mmol) and triethylamine (34 μL, 0.25 mmol). The mixture was reacted at room temperature for 2 hours, evaporated and purified through thick preparative plate (dichloromethane:methanol=30:1) to obtain 21 mg of a white solid, yield 58%. $^1$HNMR (500 MHz, CDCl$_3$) δ: 8.17 (m, 2H), 7.18 (m, 2H), 4.77 (m, 1H), 3.72-3.61 (m, 5H), 3.49 (m, 2H), 2.92 (s, 3H), 2.63 (q, J=7.6 Hz, 2H), 2.33 (m, 3H), 1.31 (t, J=7.6 Hz, 3H), 1.23 (m, 2H), 1.06 (m, 2H). MS (m/z): 587.3 [M+1].

Example 29

Preparation of 1-{1-[5-((5-cyano-4-(4-fluorophenyl)thiazol-2-yl)(methyl)amino)-6-ethylimidazo[2,1-b][1,3,4]thiadiazol-2-yl}pyrrolidin-3-yl}-1,3-dimethylurea

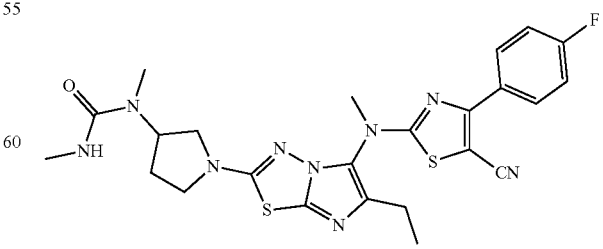

Referring to the Example 27, methylamine tetrahydrofuran solution was used to replace cyclopropylamine solution, so that 1-{1-[5-((5-cyano-4-(4-fluorophenyl)thiazol-2-yl)(methyl)amino)-6-ethylimidazo[2,1-b][1,3,4]thiadiazol-2-yl]pyrrolidin-3-yl}-1,3-dimethylurea was obtained. ¹H NMR (500 MHz, CDCl₃) δ: 8.16 (m, 2H), 7.18 (m, 2H), 5.25 (m, 1H), 4.45 (m, 1H), 3.70-3.60 (m, 5H), 3.48 (m, 1H), 3.32 (m, 1H), 2.85 (d, J=4.4 Hz, 3H), 2.82 (s, 3H), 2.62 (q, J=7.6 Hz, 2H), 2.25 (m, 1H), 2.13 (m, 1H), 1.30 (t, J=7.6 Hz, 3H). MS (m/z): 540.3 [M+1]

Example 30

Preparation of N-{1-[5-((5-cyano-4-(4-fluorophenyl)thiazol-2-yl)(methyl)amino)-6-ethylimidazo[2,1-b][1,3,4]thiadiazol-2-yl}pyrrolidin-3-yl}-3-hydroxy-N-methylazetidine-1-carboxamide

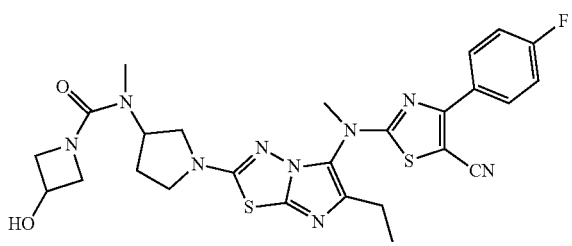 [SMILES: CCc1nc2sc(N3CCC(N(C)C(=O)N4CC(O)C4)C3)nn2c1N(C)c1nc(-c2ccc(F)cc2)c(C#N)s1]

Triphosgene (13.4 mg, 0.045 mmol) was added into a flask, followed by adding dichloromethane (2 mL) under the protection of nitrogen gas, and then the mixture was cooled to 0° C. 2-{[6-ethyl-2-(3-(methylamino)pyrrolidin-1-yl)imidazo[2,1-b][1,3,4]thiadiazol-5-yl](methyl)amino}-4-(4-fluorophenyl)thiazole-5-carbonitrile (27 mg, 0.057 mmol), triethylamine (39 µL, 0.28 mmol) and dichloromethane (1 mL) were added into another flask and performed reaction, and the reaction mixture was dropwise added to the first flask. The mixture was reacted at 0° C. for half an hour. Azetidine-3-ol hydrochloride (31 mg, 0.28 mmol) and triethylamine (39 µL, 0.28 mmol) were added. While the temperature gradually increased to room temperature, the mixture was reacted overnight, then evaporated and purified through thick preparative plate (dichloromethane:methanol=16:1) to obtain 21 mg of a white solid, yield 65%. ¹H NMR (400 MHz, CDCl₃) δ: 8.17 (m, 2H), 7.18 (m, 2H), 4.87 (m, 1H), 4.64 (m, 1H), 4.23 (m, 2H), 3.88 (m, 2H), 3.72-3.60 (m, 5H), 3.48 (m, 1H), 3.36 (m, 1H), 2.80 (s, 3H), 2.62 (q, J=7.6 Hz, 2H), 2.26-2.14 (m, 3H), 1.30 (t, J=7.6 Hz, 3H). MS (m/z): 582.4 [M+1].

Example 31

Preparation of 1-{1-[5-((5-cyano-4-(4-fluorophenyl)thiazol-2-yl)(methyl)amino)-6-ethylimidazo[2,1-b][1,3,4]thiadiazol-2-yl]pyrrolidin-3-yl}-1,3,3-trimethylurea

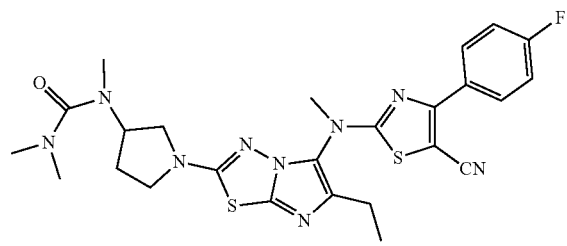 [SMILES: CCc1nc2sc(N3CCC(N(C)C(=O)N(C)C)C3)nn2c1N(C)c1nc(-c2ccc(F)cc2)c(C#N)s1]

2-{[6-ethyl-2-(3-(methylamino)pyrrolidin-1-yl)imidazo[2,1-b][1,3,4]thiadiazol-5-yl](methyl)amino}-4-(4-fluorophenyl)thiazole-5-carbonitrile (25 mg, 0.052 mmol) was dissolved in tetrahydrofuran (2 mL), under the protection of nitrogen gas, followed by stirring and cooling to 0° C. Triethylamine (22 µL, 0.16 mmol) was added, and then dimethylaminocarbonyl chloride (7 mg, 0.067 mmol) was added dropwise. The mixture was reacted at 0° C. for 15 minutes, and it was reacted overnight after gradually increasing temperature to room temperature. The mixture was evaporated and purified through thick preparative plate (dichloromethane:methanol=25:1) to obtain 24 mg of a white solid, yield 83%.1H NMR (400 MHz, CDCl₃) δ:8.17 (m, 2H), 7.18 (m, 2H), 4.43 (m, 1H), 3.81 (m, 1H), 3.65 (m, 1H), 3.60 (m, 3H), 3.49 (m, 1H), 3.37 (m, 1H), 2.87 (s, 6H), 2.80 (s, 3H), 2.62 (q, J=7.6 Hz, 2H), 2.32 (m, 1H), 2.18 (m, 1H), 1.29 (m, 3H). MS (m/z): 554.36[M+1].

Example 32

Preparation of N-{1-[5-((5-cyano-4-(4-fluorophenyl)thiazol-2-yl)(methyl)amino)-6-ethylimidazo[2,1-b][1,3,4]thiadiazol-2-yl}pyrrolidin-3-yl}-N-methylmorpholine-4-carboxamide

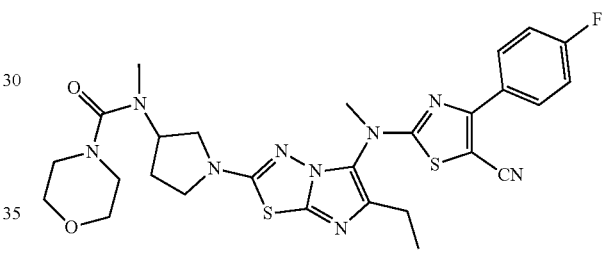

Referring to the Example 31, 4-morpholinecarbonyl chloride was used to replace dimethylcarbamyl chloride, so that N-{1-[5-((5-cyano-4-(4-fluorophenyl)thiazol-2-yl)(methyl)amino)-6-ethylimidazo[2,1-b][1,3,4]thiadiazol-2-yl}pyrrolidin-3-yl}-N-methylmorpholine-4-carboxamide was obtained. ¹H NMR (400 MHz, CDCl₃) δ: 8.16 (m, 2H), 7.18 (m, 2H), 4.52 (m, 1H), 3.18 (m, 1H), 3.72-3.64 (m, 5H), 3.60 (s, 3H), 3.50 (m, 1H), 3.38 (m, 1H), 3.30 (m, 4H), 2.85 (s, 3H), 2.63 (q, J=7.6 Hz 2H), 2.33 (m, 1H), 2.19 (m, 1H), 1.29 (s, 3H). MS (m/z): 596.38 [M+1].

Example 33

Preparation of 2-{[6-ethyl-2-(3-((2-(3-fluoroazetidin-1-yl)-2-oxoethyl)(methyl)amino)pyrrolidin-1-yl)imidazo[2,1-b][1,3,4]thiadiazol-5-yl](methyl)amino}-4-(4-fluorophenyl)thiazole-5-carbonitrile

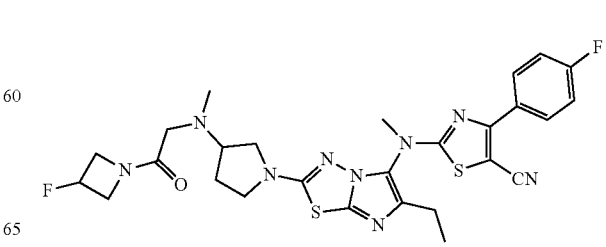

Referring to the Example 11, 2-chloro-1-(3-fluoroazetidin-1-yl) ethanone was used to replace 2-chloro-1-(3-hydroxyazetidin-1-yl)ethanone, so that 2-{[6-ethyl-2-(3-((2-(3-fluoroazetidin-1-yl)-2-oxoethyl)(methyl)amino)pyrrolidin-1-yl)imidazo[2,1-b][1,3,4]thiadiazol-5-yl](methyl)amino}-4-(4-fluorophenyl)thiazole-5-carbonitrile was prepared. H NMR (500 MHz, CDCl$_3$) δ: 8.18 (m, 2H), 7.18 (m, 2H), 5.40-5.26 (m, 1H), 5.51 (m, 1H), 4.36 (m, 2H), 4.17 (m, 1H), 3.68-3.61 (m, 5H), 3.50-3.31 (m, 3H), 3.20 (s, 2H), 2.63 (q, J=9.5 Hz, 2H), 2.38 (s, 3H), 2.27 (m, 1H), 2.04 (m, 1H). MS (m/z): 598.3 [M+1].

Example 34

Preparation of 2-{[6-ethyl-2-(3-(methyl(2-mophlin-2-oxoethyl)amino)pyrrolidin-1-yl)imidazo[2,1-b][1,3,4]thiadiazol-5-yl](methyl)amino}-4-(4-fluorophenyl)thiazole-5-carbonitrile

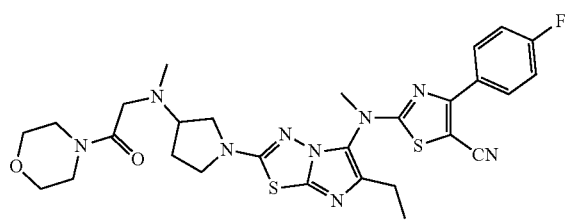 [SMILES: CCc1nc2sc(N3CCC(N(C)CC(=O)N4CCOCC4)C3)nn2c1N(C)c1nc(-c2ccc(F)cc2)c(C#N)s1]

Referring to the Example 11, 2-chloro-1-morpholin ethanone was used to replace 2-chloro-1-(3-hydroxyazetidin-1-yl)ethanone, so that 2-{[6-ethyl-2-(3-(methyl(2-mophlin-2-oxoethyl)amino)pyrrolidin-1-yl)imidazo[2,1-b][1,3,4]thiadiazol-5-yl](methyl)amino}-4-(4-fluorophenyl)thiazole-5-carbonitrile was prepared. $^1$H NMR (400 MHz, CDCl$_3$) δ: 8.16 (m, 2H), 7.18 (m, 2H), 3.73-3.67 (m, 6H), 3.65-3.60 (m, 8H), 3.50-3.43 (m, 2H), 3.32-3.29 (m, 3H), 2.62 (q, J=7.6 Hz, 2H), 2.40 (s, 3H), 2.26 (m, 1H), 2.05 (m, 1H), 1.30 (m, 3H). MS (m/z): 610.4 [M+1].

Example 35

Preparation of 1-{2-[(1-(5-((5-cyano-4-(4-fluorophenyl)thiazol-2-yl)(methyl)amino)-6-ethylimidazo[2,1-b][1,3,4]thiadiazol-2-yl)pyrrolidin-3-yl)(methyl)amino]acetyl}azetidine-3-carboxylic acid

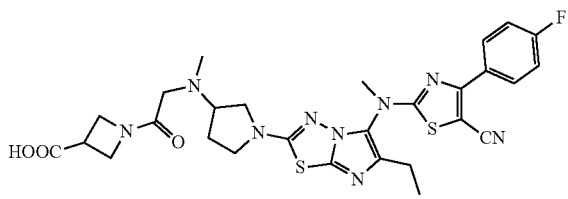 [SMILES: CCc1nc2sc(N3CCC(N(C)CC(=O)N4CC(C(=O)O)C4)C3)nn2c1N(C)c1nc(-c2ccc(F)cc2)c(C#N)s1]

2-{[6-ethyl-2-(3-(methylamino)pyrrolidin-1-yl)imidazo[2,1-b][1,3,4]thiadiazol-5-yl](methyl)amino}-4-(4-fluorophenyl)thiazole-5-carbonitrile (110 mg, 0.228 mmol) was dissolved in acetonitrile (5 mL), followed by adding triethylamine (95 μL, 0.685 mmol) under the protection of nitrogen gas. The mixture was stirred and cooled to 0° C., and methyl 1-(2-acetylchloride) azetidine-3-carboxylate (65 mg, 0.342 mmol) was added. The mixture was reacted at 0° C. for 10 minutes, and it was reacted overnight after gradually increasing temperature to 80° C. Methyl 1-(2-acetylchloride)azetidine-3-carboxylate (33 mg, 0.171 mmol) was re-added. The mixture continued to react for 5 hours until the reaction was completed. The mixture was evaporated and purified through thick preparative plate (dichloromethane:methanol=15:1) to obtain 84 mg of a white solid. The white solid was dissolved in THF (2 mL) and stirred. After cooling to 0° C., 0.5 N sodium hydroxide solution (0.5 mL) was gradually added dropwise. The mixture was reacted 30 minutes and rotated to remove THF, and the water (5 mL) was added. The mixture was regulated pH to about 5 to precipitate a white solid product. After filtration, the filter cake was purified through thick preparative plate (dichloromethane:methanol=12:1) to obtain 31 mg of a white solid, yield 22%. $^1$H NMR (400 MHz, CD$_3$OD) &: 8.12 (m, 2H), 7.24 (m, 2H), 4.44 (m, 2H), 4.14 (m, 2H), 3.70 (m, 1H), 3.62 (m, 1H), 3.58 (s, 3H), 3.49-3.37 (m, 4H), 3.23 (s, 2H), 2.58 (q, J=7.6 Hz, 2H), 2.35 (s, 3H), 2.27 (m, 1H), 2.06 (m, 1H), 1.29 (m, 3H). MS (m/z): 624.3 [M+1].

Example 36

Preparation of (R)—N-{1-[5-((5-cyano-4-(4-fluorophenyl)thiazol-2-yl)(methyl)amino)-6-ethylimidazo[2,1-b][1,3,4]thiadiazol-2-yl]pyrrolidin-3-yl}-3-hydroxy-N-methylazetidine-1-carboxamide

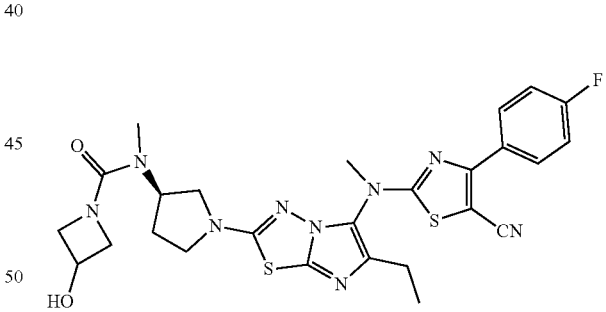

Referring to the Example 30, (R)-3-tertbutoxycarbonylaminopyrrolidine was used to replace 3-tertbutoxycarbonylaminopyrrolidine, so that (R)—N-{1-[5-((5-cyano-4-(4-fluorophenyl)thiazol-2-yl)(methyl)amino)-6-ethylimidazo[2,1-b][1,3,4]thiadiazol-2-yl]pyrrolidin-3-yl}-3-hydroxy-N-methylazetidine-1-carboxamide was prepared. $^1$H NMR (400 MHz, CDCl$_3$) δ: $^1$H NMR (400 MHz, CDCl$_3$) &: 8.16 (m, 2H), 7.18 (m, 2H), 4.88 (m, 1H), 4.63 (m, 1H), 4.22 (m, 2H), 3.88 (m, 2H), 3.71-3.60 (m, 5H), 3.48 (m, 1H), 3.36 (m, 1H), 2.80 (s, 3H), 2.61 (q, J=7.6 Hz, 2H), 2.40 (m, 1H), 2.26 (m, 1H), 2.17 (m, 1H), 1.30 (t, J=7.6 Hz, 3H). MS (m/z): 582.2 [M+1]

Example 37

Preparation of (S)—N-{1-[5-((5-cyano-4-(4-fluoro-phenyl)thiazol-2-yl)(methyl)amino)-6-ethylimidazo[2,1-b][1,3,4]thiadiazol-2-yl]pyrrolidin-3-yl}-3-hydroxy-N-methylazetidine-1-carboxamide

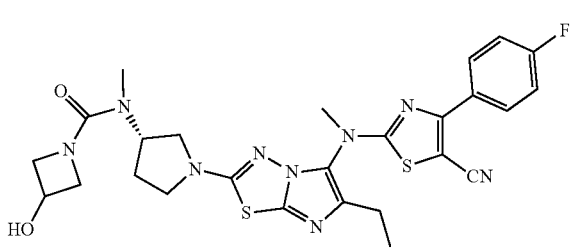 [SMILES: CCc1nc2sc(N3CC[C@H](N(C)C(=O)N4CC(O)C4)C3)nn2c1N(C)c1nc(-c2ccc(F)cc2)c(C#N)s1]

Referring to the Example 30, (S)-3-tertbutoxycarbonylaminopyrrolidine was used to replace 3-tertbutoxycarbonylaminopyrrolidine, so that (S)—N-{1-[5-((5-cyano-4-(4-fluorophenyl)thiazol-2-yl)(methyl)amino)-6-ethylimidazo[2,1-b][1,3,4]thiadiazol-2-yl]pyrrolidin-3-yl}-3-hydroxy-N-methylazetidine-1-carboxamide was obtained. ¹HNMR (400 MHz, CDCl₃) δ: ¹H NMR (400 MHz, CDCl₃) δ: 8.16 (m, 2H), 7.18 (m, 2H), 4.87 (m, 1H), 4.63 (m, 1H), 4.23 (m, 2H), 3.88 (m, 2H), 3.71-3.60 (m, 5H), 3.48 (m, 1H), 3.36 (m, 1H), 2.80 (s, 3H), 2.61 (q, J=7.6 Hz, 2H), 2.41 (m, 1H), 2.26 (m, 1H), 2.18 (m, 1H), 1.30 (t, J=7.6 Hz, 3H). MS (m/z): 582.2 [M+1].

Example 38

Preparation of (S)-2-{[6-ethyl-2-(3-((2-(3-fluoroazetidin-1-yl)-2-oxoethyl)(methyl)amino)pyrrolidin-1-yl)imidazo[2,1-b][1,3,4]thiadiazol-5-yl](methyl)amino}-4-(4-fluorophenyl)thiazole-5-carbonitrile

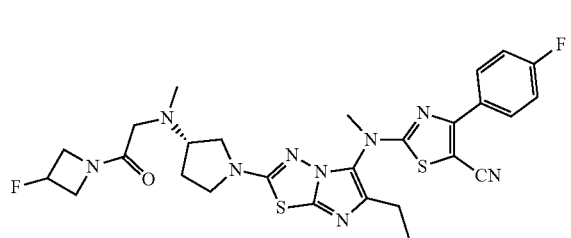 [SMILES: CCc1nc2sc(N3CC[C@H](N(C)CC(=O)N4CC(F)C4)C3)nn2c1N(C)c1nc(-c2ccc(F)cc2)c(C#N)s1]

Referring to the Example 33, (S)-3-tertbutoxycarbonylaminopyrrolidine was used to replace 3-tertbutoxycarbonylaminopyrrolidine, so that (S)-2-{[6-ethyl-2-(3-((2-(3-fluoroazetidin-1-yl)-2-oxoethyl)(methyl)amino)pyrrolidin-1-yl)imidazo[2,1-b][1,3,4]thiadiazol-5-yl](methyl)amino}-4-(4-fluorophenyl)thiazole-5-carbonitrile was prepared. ¹H NMR (400 MHz, CDCl₃) δ: 8.15 (m, 2H), 7.16 (m, 2H), 5.37-5.22 (m, 1H), 4.48 (m, 1H), 4.32 (m, 2H), 4.14 (m, 1H), 3.68-3.58 (m, 5H), 3.48-3.28 (m, 3H), 3.17 (s, 2H), 2.60 (q, J=7.6 Hz, 2H), 2.36 (s, 3H), 2.24 (m, 1H), 2.01 (m, 1H), 1.28 (m, 3H). MS (m/z): 598.3 [M+1].

Example 39

Preparation of (R)-2-{[6-ethyl-2-(3-((2-(3-fluoroazetidin-1-yl)-2-oxoethyl)(methyl)amino)pyrrolidin-1-yl)imidazo[2,1-b][1,3,4]thiadiazol-5-yl](methyl)amino}-4-(4-fluorophenyl)thiazole-5-carbonitrile

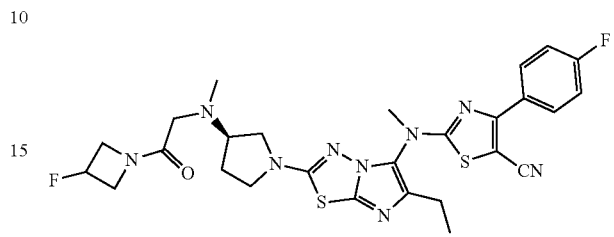

Referring to the Example 33, (R)-3-tertbutoxycarbonylamino pyrrolidine was used to replace 3-tertbutoxycarbonylaminopyrrolidine, so that (R)-2-{[6-ethyl-2-(3-((2-(3-fluoroazetidin-1-yl)-2-oxoethyl)(methyl)amino)pyrrolidin-1-yl)imidazo[2,1-b][1,3,4]thiadiazol-5-yl](methyl)amino}-4-(4-fluorophenyl)thiazole-5-carbonitrile was prepared. ¹H NMR (400 MHz, CDCl₃) δ: 8.17 (m, 2H), 7.18 (m, 2H), 5.40-5.25 (m, 1H), 4.51 (m, 1H), 4.34 (m, 2H), 4.16 (m, 1H), 3.70-3.59 (m, 5H), 3.52-3.31 (m, 3H), 3.19 (s, 2H), 2.61 (q, J=7.2 Hz, 2H), 2.38 (s, 3H), 2.27 (m, 1H), 2.03 (m, 1H), 1.30 (m, 3H). MS (m/z): 598.2 [M+1].

Example 40

Preparation of (R)-2-{[6-ethyl-2-(3-(methyl(2-morpholino-2-oxoethyl)amino)pyrrolidin-1-yl)imidazo[2,1-b][1,3,4]thiadiazol-5-yl](methyl)amino}-4-(4-fluorophenyl)thiazole-5-carbonitrile

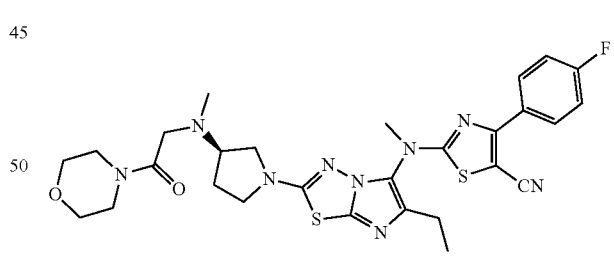

Referring to the Example 34, (R)-3-tertbutoxycarbonylaminopyrrolidine was used to replace 3-tertbutoxycarbonylaminopyrrolidine, so that (R)-2-{[6-ethyl-2-(3-(methyl(2-morpholino-2-oxoethyl)amino)pyrrolidin-1-yl)imidazo[2,1-b][1,3,4]thiadiazol-5-yl](methyl)amino}-4-(4-fluorophenyl)thiazole-5-carbonitrile was prepared. ¹H NMR (400 MHz, CDCl₃) δ: 8.15 (m, 2H), 7.16 (m, 2H), 3.66 (m, 5H), 3.60-3.57 (m, 8H), 3.48-3.41 (m, 2H), 3.36-3.29 (m, 3H), 2.60 (q, J=7.6 Hz, 2H), 2.37 (s, 3H), 2.25 (m, 1H), 2.03 (m, 1H), 1.28 (m, 3H). MS (m/z): 610.3 [M+1].

Example 41

Preparation of (S)-2-{[6-ethyl-2-(3-(methyl(2-morpholino-2-oxoethyl)amino)pyrrolidin-1-yl)imidazo[2,1-b][1,3,4]thiadiazol-5-yl](methyl)amino}-4-(4-fluorophenyl)thiazole-5-carbonitrile

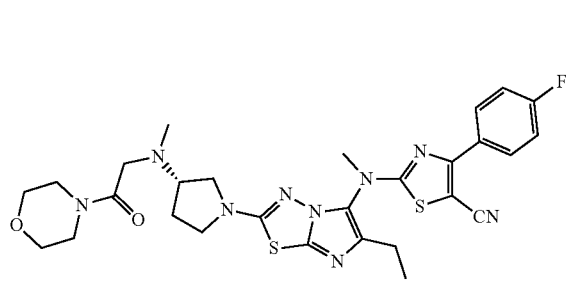 [SMILES: CCc1nc2sc(N3CC[C@H](N(C)CC(=O)N4CCOCC4)C3)nn2c1N(C)c1nc(-c2ccc(F)cc2)c(C#N)s1]

Referring to the example 34, (S)-3-tertbutoxycarbonylaminopyrrolidine was used to replace 3-tertbutoxycarbonylaminopyrrolidine, so that (S)-2-{[6-ethyl-2-(3-(methyl(2-morpholino-2-oxoethyl)amino)pyrrolidin-1-yl)imidazo[2,1-b][1,3,4]thiadiazol-5-yl](methyl)amino}-4-(4-fluorophenyl)thiazole-5-carbonitrile was prepared. $^1$H NMR (400 MHz, CDCl$_3$) δ: 8.17 (m, 2H), 7.18 (m, 2H), 3.69 (m, 5H), 3.65-3.60 (m, 8H), 3.50-3.46 (m, 2H), 3.38-3.31 (m, 3H), 2.62 (q, J=7.2 Hz, 2H), 2.40 (s, 3H), 2.26 (m, 1H), 2.05 (m, 1H), 1.31 (m, 3H). MS (m/z): 610.4[M+1].

Example 42

Preparation of methyl (R)-1-{2-[(1-(5-((5-cyano-4-(4-fluorophenyl)thiazol-2-yl)(methyl)amino)-6-ethylimidazo[2,1-b][1,3,4]thiadiazol-2-yl)pyrrolidin-3-yl)(methyl)amino]acetyl}azetidine-3-carboxylate

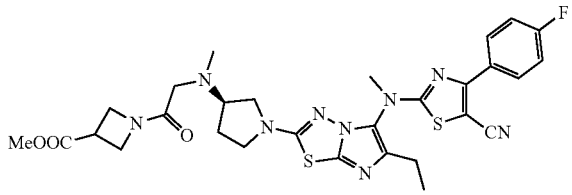 [SMILES: CCc1nc2sc(N3CC[C@@H](N(C)CC(=O)N4CC(C(=O)OC)C4)C3)nn2c1N(C)c1nc(-c2ccc(F)cc2)c(C#N)s1]

Referring to the Example 21, methyl 1-(2-chloroacetyl)azetidin-3-carboxylate was used to replace 2-chloro-1-(3-hydroxyazetidine-1-yl)ethanone, so that (R)-1-{2-[(1-(5-((5-cyano-4-(4-fluorophenyl)thiazol-2-yl)(methyl)amino)-6-ethylimidazo[2,1-b][1,3,4]thiadiazol-2-yl}pyrrolidin-3-yl)(methyl)amino]acetyl}azetidine-3-carboxylate was prepared. MS (m/z): 638.3 [M+1].

Example 43

Preparation of methyl (S)-1-{2-[(1-(5-((5-cyano-4-(4-fluorophenyl)thiazol-2-yl)(methyl)amino)-6-ethylimidazo[2,1-b][1,3,4]thiadiazol-2-yl)pyrrolidin-3-yl)(methyl)amino]acetyl}azetidine-3-carboxylate

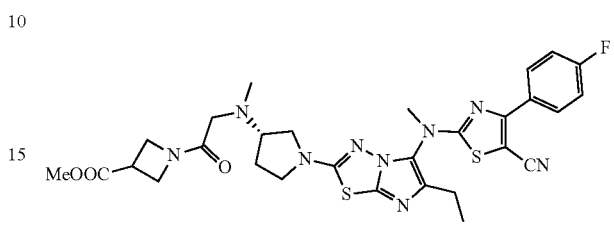

Referring to the Example 22, methyl 1-(2-chloroacetyl)azetidin-3-carboxylate was used to replace 2-chloro-1-(3-hydroxyazetidine-1-yl)ethanone, so that (S)-1-{2-[(1-(5-((5-cyano-4-(4-fluorophenyl)thiazol-2-yl)(methyl)amino)-6-ethylimidazo[2,1-b][1,3,4]thiadiazol-2-yl}pyrrolidin-3-yl)(methyl)amino]acetyl}azetidine-3-carboxylate was prepared. MS (m/z): 638.3 [M+1].

Example 44

Preparation of (R)-1-{2-[(1-(5-((5-cyano-4-(4-fluorophenyl)thiazol-2-yl)(methyl)amino)-6-ethylimidazo[2,1-b][1,3,4]thiadiazol-2-yl}pyrrolidin-3-yl)(methyl)amino]acetyl}azetidine-3-carboxylic acid

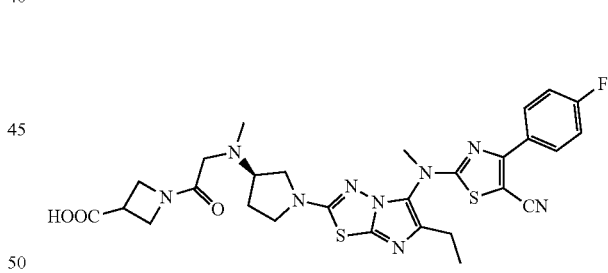

Referring to the Example 35, (R)-3-tertbutoxycarbonylaminopyrrolidine was used to replace 3-tertbutoxycarbonylaminopyrrolidine, so that (R)-1-{2-[(1-(5-((5-cyano-4-(4-fluorophenyl)thiazol-2-yl)(methyl)amino)-6-ethylimidazo[2,1-b][1,3,4]thiadiazol-2-yl}pyrrolidin-3-yl)(methyl)amino]acetyl}azetidine-3-carboxylic acid was prepared. $^1$H NMR (500 MHz, CD$_3$OD) &: 8.13 (m, 2H), 7.24 (m, 2H), 4.52 (t, 1H), 4.38 (m, 1H), 4.18 (m, 1H), 4.09 (m, 1H), 3.71 (m, 1H), 3.63 (m, 1H), 3.59 (s, 3H), 3.51-3.37 (m, 4H), 3.24 (s, 2H), 2.60 (q, J=7.5 Hz, 2H), 2.36 (s, 3H), 2.27 (m, 1H), 2.07 (m, 1H), 1.28 (m, 3H). MS (m/z): 624.3 [M+1].

Example 45

Preparation of (S)-1-{2-[(1-(5-((5-cyano-4-(4-fluorophenyl)thiazol-2-yl)(methyl)amino)-6-ethylimidazo[2,1-b][1,3,4]thiadiazol-2-yl}pyrrolidin-3-yl)(methyl)amino]acetyl}azetidine-3-carboxylic acid

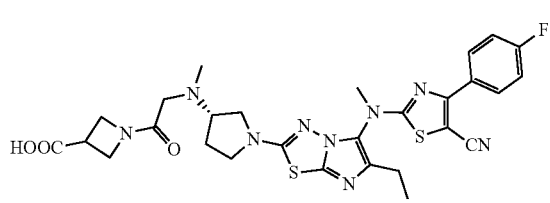 [SMILES: CCc1nc2sc(N3CC[C@H](N(C)CC(=O)N4CC(C(=O)O)C4)C3)nn2c1N(C)c1nc(-c2ccc(F)cc2)c(C#N)s1]

Referring to the Example 35, (S)-3-tertbutoxycarbonylaminopyrrolidine was used to replace 3-tertbutoxycarbonyaminopyrrolidine, so that (S)-1-{2-[(1-(5-((5-cyano-4-(4-fluorophenyl)thiazol-2-yl)(methyl)amino)-6-ethylimidazo[2,1-b][1,3,4]thiadiazol-2-yl}pyrrolidin-3-yl)(methyl)amino]acetyl}azetidine-3-carboxylic acid was prepared. $^1$H NMR (500 MHz, CD$_3$OD) δ: 8.15 (m, 2H), 7.26 (m, 2H), 4.45 (t, 1H), 4.38 (m, 1H), 4.19 (m, 1H), 4.10 (m, 1H), 3.74 (m, 1H), 3.64 (m, 1H), 3.59 (s, 3H), 3.52-3.41 (m, 4H), 3.34 (s, 2H), 2.60 (q, J=7.5 Hz, 2H), 2.43 (s, 3H), 2.30 (m, 1H), 2.11 (m, 1H), 1.27 (m, 3H). MS (m/z): 624.3 [M+1].

Example 46

Preparation of (R)-2-{[2-(3-((2-(3-cyanoazetidin-1-yl)-2-oxoethyl)(methyl)amino)pyrrolidin-1-yl)-6-ethylimidazo[2,1-b][1,3,4]thiadiazol-5-yl](methyl)amino}-4-(4-fluorophenyl)thiazole-5-carbonitrile

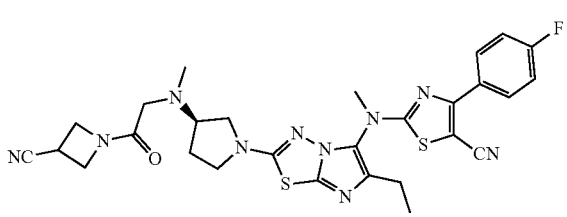 [SMILES: CCc1nc2sc(N3CC[C@@H](N(C)CC(=O)N4CC(C#N)C4)C3)nn2c1N(C)c1nc(-c2ccc(F)cc2)c(C#N)s1]

Referring to the Example 21, 2-chloro-1-(3-cyanoazetidin-1-yl) ethanone was used to replace 2-chloro-1-(3-hydroxyazetidin-1-yl)ethanone, so that (R)-2-{[2-(3-((2-(3-cyanoazetidin-1-yl)-2-oxoethyl)(methyl)amino)pyrrolidin-1-yl)-6-ethylimidazo[2,1-b][1,3,4]thiadiazol-5-yl](methyl)amino}-4-(4-fluorophenyl)-thiazole-5-carbonitrile was prepared. $^1$HNMR (500 MHz, CDCl$_3$) δ: 8.15 (m, 2H), 7.16 (m, 2H), 4.55 (t, 1H), 4.49 (m, 1H), 4.33 (t, 1H), 4.26 (m, 1H), 3.66 (m, 1H), 3.59 (m, 4H), 3.52-3.43 (m, 2H), 3.39-3.29 (m, 2H), 3.18 (q, J=6.0 Hz, 2H), 2.60 (q, J=7.5 Hz, 2H), 2.35 (s, 3H), 2.24 (m, 1H), 2.00 (m, 1H), 1.28 (t, 3H). MS (m/z): 605.3 [M+1].

Example 47

Preparation of (S)-2-{[2-(3-((2-(3-cyanoazetidin-1-yl)-2-oxoethyl)(methyl)amino)pyrrolidin-1-yl)-6-ethylimidazo[2,1-b][1,3,4]thiadiazol-5-yl](methyl)amino}-4-(4-fluorophenyl)-thiazole-5-carbonitrile

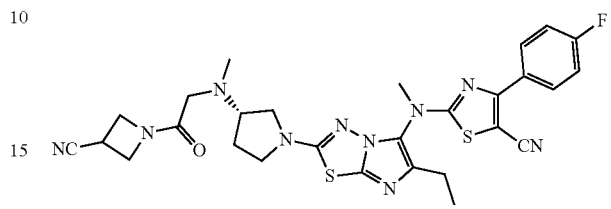

Referring to the example 22, 2-chloro-1-(3-cyanoazetidin-1-yl)ethanone was used to replace 2-chloro-1-(3-hydroxyazetidin-1-yl)ethanone, so that (S)-2-{[2-(3-((2-(3-cyanoazetidin-1-yl)-2-oxoethyl)(methyl)amino)pyrrolidin-1-yl)-6-ethylimidazo[2,1-b][1,3,4]thiadiazol-5-yl](methyl)amino}-4-(4-fluorophenyl)-thiazole-5-carbonitrile was prepared. $^1$HNMR (500 MHz, CDCl$_3$) δ: 8.15 (m, 2H), 7.16 (m, 2H), 4.55 (t, 1H), 4.50 (m, 1H), 4.33 (t, 1H), 4.26 (m, 1H), 3.66 (m, 1H), 3.59 (m, 4H), 3.52-3.43 (m, 2H), 3.32-3.29 (m, 2H), 3.18 (q, J=6.0 Hz, 2H), 2.60 (q, J=7.5 Hz, 2H), 2.35 (s, 3H), 2.24 (m, 1H), 2.00 (m, 1H), 1.28 (t, 3H). MS (m/z): 605.4 [M+1].

Example 48

Preparation of ethyl 2-{[1-(5-((5-cyano-4-(4-fluorophenyl)thiadiazol-2-yl) (methyl)amino)-6-ethylimidazo[2,1-b][1,3,4]thiadiazol-2-yl)pyrrolidin-3-yl](methyl)amino}acetate

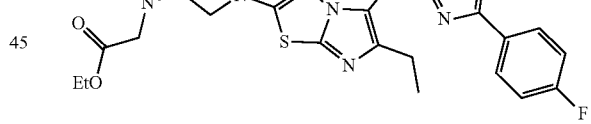

2-{[6-ethyl-2-(3-(methylamino)pyrrolidin-1-yl)imidazo[2,1-b][1,3,4]thiadiazol-5-yl](methyl)amino}-4-(4-fluorophenyl)thiazole-5-carbonitrile (1.03 g, 2.14 mmol) was dissolved in acetonitrile (25 mL), followed by adding potassium carbonate (1.18 g, 8.56 mmol). The mixture was stirred at room temperature for 15 minutes, and then it was reacted at room temperature for 3 hours after ethyl bromoacetate (536 mg, 3.21 mmol) was added. The reaction mixture was filtered and washed. The filtrate was evaporated and dissolved with ethyl acetate (60 mL), and then washed with water and saturated saline solution in succession. The organic layer was dried with anhydrous sodium sulfate, filtered, evaporated, and purified by column purification (petroleum ether: ethyl acetate=1:1), to obtain 760 mg of a yellow thick product, yield:62%. $^1$H-NMR (400 MHz, CDCl$_3$) δ: 8.17 (m, 2H), 7.17 (m, 2H), 4.21 (q, J=7.2 Hz, 2H), 3.72-3.60 (m, 2H), 3.60 (s, 3H), 3.55-3.50 (m, 1H), 3.49-3.41 (m, 1H), 3.37 (m, 2H), 3.33-3.30 (m, 1H), 2.62 (q, J=7.6 Hz, 2H), 2.48 (s, 3H), 2.30-2.22 (m, 1H), 2.09-1.98 (m, 1H), 1.32-1.28 (in, 3H). MS (m/z): 569.3 [M+1].

Example 49

Preparation of 2-{[1-(5-((5-cyano-4-(4-fluorophenyl)thiazol-2-yl)(methyl)amino)-6-ethylimidazo[2,1-b][1,3,4]thiadiazol-2-yl)pyrrolidin-3-yl](methyl)amino}acetic acid

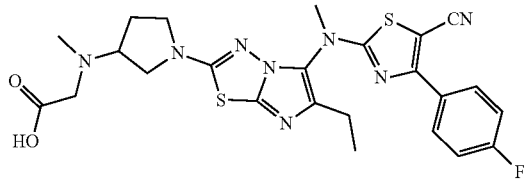 [SMILES: CCc1nc2sc(N3CCC(N(C)CC(=O)O)C3)nn2c1N(C)c1nc(-c2ccc(F)cc2)c(C#N)s1]

Ethyl 2-{[1-(5-((5-cyano-4-(4-fluorophenyl)thiazol-2-yl)(methyl)amonio)-6-ethylimidazo[2,1-b][1,3,4]thiadiazol-2-yl)pyrrolidin-3-yl](methyl)amino}acetate (660 mg, 1.16 mmol) was dissolved in tetrahydrofuran (6 mL) and methanol (6 mL), water (3 mL) and lithium hydroxide monohydrate (243 mg, 5.80 mmol) were added. The mixture was reacted at room temperature for 16 hours and evaporated, and then water (25 mL) was added to the mixture, to dissolve and stir well. The mixture was regulated pH to about 3 to 4, to precipitate a white solid, and filtered. The filter cake was washed with water and dried through vacuum, so that 610 mg of a white solid product was obtained, yield: 97%. $^1$H-NMR (400 MHz, DMSO) &: 8.08 (m, 2H), 7.42 (m, 2H), 3.67-3.58 (m, 2H), 3.54 (s, 3H), 3.46-3.38 (m, 2H), 3.35 (s, 2H), 3.30-3.25 (m, 1H), 2.54-2.48 (m, 2H), 2.39 (s, 3H), 2.22-2.14 (m, 1H), 2.00-1.91 (m, 1H), 1.19 (t, J=7.6 Hz, 3H). MS (m/z): 541.3[M+1].

Example 50

Preparation of methyl 2-{2-[1-(5-((5-cyano-4-(4-fluorophenyl)thiazol-2-yl)(methyl)amino)-6-ethylimidazo[2,1-b][1,3,4]thiadiazol-2-yl)pyrrolidin-3-yl](methyl)amino]acetamido}acetate

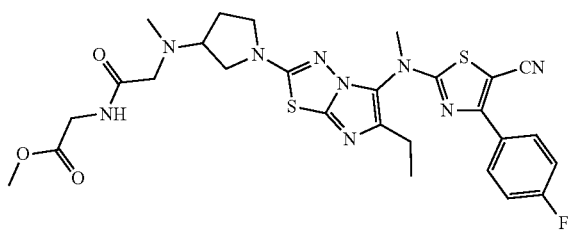 [SMILES: CCc1nc2sc(N3CCC(N(C)CC(=O)NCC(=O)OC)C3)nn2c1N(C)c1nc(-c2ccc(F)cc2)c(C#N)s1]

Methyl glycinate hydrochloride (70 mg, 0.56 mmol) was suspended in dichloromethane (20 mL), and triethylamine (112 mg, 1.12 mmol) was added. The mixture was stirred at room temperature for 30 minutes. Then, 2-{[1-(5-((5-cyano-4-(4-fluorophenyl)thiazol-2-yl)(methyl)amino)-6-ethylimidazo[2,1-b][1,3,4]thiadiazol-2-yl)pyrrolidin-3-yl](methyl)amino}acetic acid (200 mg, 0.37 mmol) and HATU (169 mg, 0.44 mmol) were added, then the mixture was reacted at room temperature for 16 hours. The reaction mixture was poured into the water, and extracted with dichloromethane (30 mL×3). The organic layer was combined and washed with saturated saline solution, dried with anhydrous sodium sulfate, filtered, evaporated and purified by column purification (petroleum ether: ethyl acetate=1:1), to obtain 180 mg of a white solid product, yield 80%. $^1$H-NMR (400 MHz, CDCl$_3$) δ: 8.18 (m, 2H), 7.56 (s, 1H), 7.20 (m, 2H), 4.11 (s, 2H), 3.79 (s, 3H), 3.72 (m, 1H), 3.65 (m, 1H), 3.63 (s, 3H), 3.55-3.46 (m, 1H), 3.45-3.35 (m, 2H), 3.20 (m, 2H), 2.62 (m, 2H), 2.45 (s, 3H), 2.34-2.24 (m, 1H), 2.09 (m, 1H), 1.32 (m, 3H). MS (m/z): 612.3 [M+1].

Example 51

Preparation of 2-{2-[1-(5-((5-cyano-4-(4-fluorophenyl)thiazol-2-yl)(methyl)amino)-6-ethylimidazo[2,1-b][1,3,4]thiadiazol-2-yl)pyrrolidin-3-yl](methyl)amino]acetamido}acetic acid

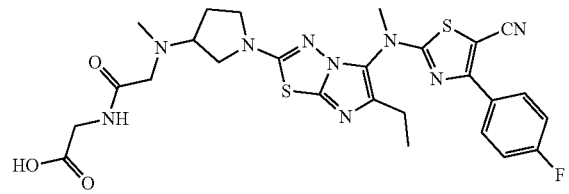 [SMILES: CCc1nc2sc(N3CCC(N(C)CC(=O)NCC(=O)O)C3)nn2c1N(C)c1nc(-c2ccc(F)cc2)c(C#N)s1]

Methyl 2-{[1-(5-((5-cyano-4-(4-fluorophenyl)thiazol-2-yl)(methyl)amonio)-6-ethylimidazo[2,1-b][1,3,4]thiadiazol-2-yl)pyrrolidin-3-yl](methyl)amino]acetamido}acetate (80 mg, 0.13 mmol) was dissolved in tetrahydrofuran (2 mL) and methanol (2 mL), water (1 mL) and lithium hydroxide monohydrate (30 mg, 0.65 mmol) were added. The mixture was reacted at room temperature for 1 hour and evaporated, and then water (10 mL) was added to the mixture, to dissolve and stir well. The mixture was regulated pH to about 3 to 4, to precipitate a solid, and filtered. The filter cake was washed with water and dried through vacuum, so that 60 mg of a grey solid product was obtained, yield: 77%. $^1$H-NMR (400 MHz, CDCl$_3$) δ: 8.16 (m, 2H), 7.60 (s, 1H), 7.18 (m, 2H), 4.11 (s, 2H), 3.69 (m, 2H), 3.60 (s, 3H), 3.54-3.48 (m, 1H), 3.43 (m, 2H), 3.27-3.14 (m, 2H), 2.62 (m, 2H), 2.43 (s, 3H), 2.24 (m, 1H), 2.15 (m, 1H), 1.28 (m, 3H). MS (m/z): 598.3 [M+1].

Example 52

Preparation of 2-{[6-ethyl-2-(6-(2-(3-hydroxyazetidin-1-yl)-2-oxoethyl)-2,6-diazaspiro[3.4]octan-2-yl)imidazo[2,1-b][1,3,4]thiadiazol-5-yl](methyl)amino}-4-(4-fluorophenyl)thiazole-5-carbonitrile

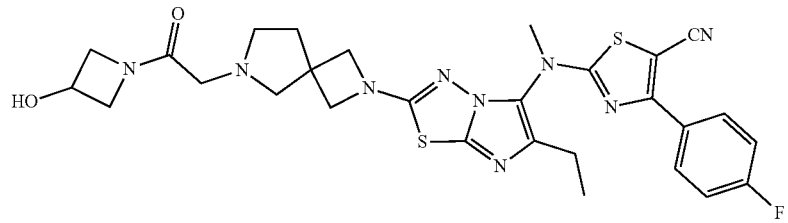 [SMILES: CCc1nc2sc(N3CC4(CCN(CC(=O)N5CC(C#N)C5)C4)C3)nn2c1N(C)c1nc(-c2ccc(F)cc2)c(C#N)s1]

Referring to the Example 2, tert-butyl 2,6-dizazspiro[3.4]octane-6-carboxylate hemioxalate was used to replace tert-butyl piperazine-1-carboxylate, so that 2-{[6-ethyl-2-(6-(2-(3-hydroxyazetidin-1-yl)-2-oxoethyl)-2,6-diazaspiro[3.4]octan-2-yl)imidazo[2,1-b][1,3,4]thiadiazol-5-yl](methyl)amino}-4-(4-fluorophenyl)thiazole-5-carbonitrile was prepared. $^1$H-NMR (400 MHz, CDCl$_3$) δ: 8.16 (m, 2H), 7.17 (m, 2H), 4.69 (m, 1H), 4.40-4.36 (m, 1H), 4.30-4.26 (m, 1H), 4.08-4.01 (m, 5H), 3.91-3.88 (m, 1H), 3.59 (s, 3H), 3.18 (m, 2H), 2.95 (m, 2H), 2.75 (t, J=7.2 Hz, 2H), 2.61 (q, J=7.6 Hz, 2H), 2.17 (t, J=7.2 Hz, 2H), 1.29 (t, J=7.6 Hz, 3H). MS (m/z): 608.2 [M+1].

Example 53

Preparation of 2-{[6-ethyl-2-(6-(2-(3-cyanoazetidin-1-yl)-2-oxoethyl)-2,6-diazaspiro[3.4]octane-2-yl)imidazo[2,1-b][1,3,4]thiadiazol-5-yl](methyl)amino}-4-(4-fluorophenyl)thiazole-5-carbonitrile

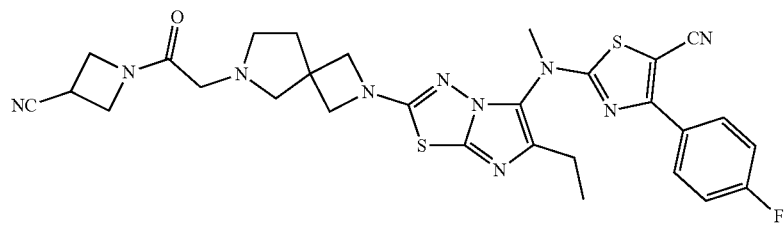

Referring to the Example 52, 2-chloro-1-(3-cyanoazetidin-1-yl)-ethanone was used to replace 2-chloro-1-(3-hydroxyazetidin-1-yl)-ethanone, so that 2-{[6-ethyl-2-(6-(2-(3-cyanoazetidin-1-yl)-2-oxoethyl)-2,6-diazaspiro[3.4]octane-2-yl)imidazo[2,1-b][1,3,4]thiadiazol-5-yl](methyl)amino}-4-(4-fluorophenyl)thiazole-5-carbonitrile was prepared. $^1$H-NMR (400 MHz, CDCl$_3$) δ: 8.16 (m, 2H), 7.18 (m, 2H), 4.54-4.44 (m, 2H), 4.38-4.33 (m, 1H), 4.29-4.25 (m, 1H), 4.06 (m, 2H), 4.05 (m, 2H), 3.59 (s, 3H), 3.54-3.49 (m, 1H), 3.21 (s, 2H), 2.93 (s, 2H), 2.73 (t, J=7.2 Hz, 2H), 2.62 (q, J=7.6 Hz, 2H), 2.18 (t, J=7.2 Hz, 2H), 1.29 (t, J=7.6 Hz, 3H). MS (m/z): 617.2 [M+1].

Example 54

Preparation of 2-{[6-ethyl-2-(2-(2-(3-hydroxyazetidin-1-yl)-2-oxoethyl)-2,6-diazaspiro[3.4]octane-6-yl)imidazo[2,1-b][1,3,4]thiadiazol-5-yl](methyl)amino}-4-(4-fluorophenyl)thiazole-5-carbonitrile

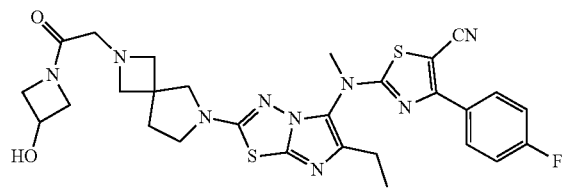 [SMILES: CCc1nc2sc(N3CCC4(CN(CC(=O)N5CC(C#N)C5)C4)C3)nn2c1N(C)c1nc(-c2ccc(F)cc2)c(C#N)s1]

Referring to the Example 2, tert-butyl 2,6-dizazspiro[3.4]octane-6-carboxylate was used to replace tert-butyl piperazine-1-carboxylate, so that 2-{[6-ethyl-2-(2-(2-(3-hydroxyazetidin-1-yl)-2-oxoethyl)-2,6-diazaspiro[3.4]octane-6-yl)imidazo[2,1-b][1,3,4]thiadiazol-5-yl](methyl)amino}-4-(4-fluorophenyl)thiazole-5-carbonitrile was prepared. $^1$H-NMR (400 MHz, CDCl$_3$) δ: 8.18 (m, 2H), 7.18 (m, 2H), 4.69 (m, 1H), 4.39 (m, 1H), 4.29-4.25 (m, 1H), 4.07-4.03 (m, 1H), 3.91-3.86 (m, 1H), 3.62 (m, 2H), 3.60 (s, 3H), 3.51-3.48 (m, 2H), 3.47-3.42 (m, 4H), 3.20 (m, 2H), 2.62 (q, J=7.6 Hz, 2H), 2.29 (m, 2H), 1.30 (m, 3H). MS (m/z): 608.2 [M+1].

Example 55

Preparation of 2-{[6-ethyl-2-(2-(2-(3-cyanoazetidin-1-yl)-2-oxoethyl)-2,6-diazaspiro[3.4]octane-6-yl)imidazo[2,1-b][1,3,4]thiadiazol-5-yl](methyl)amino}-4-(4-fluorophenyl)thiazole-5-carbonitrile

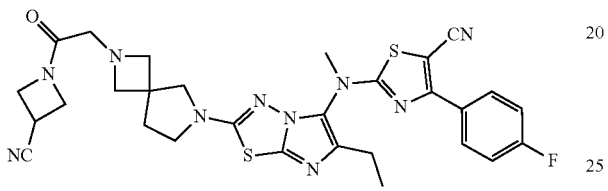

Referring to the Example 54, 2-chloro-1-(3-cyanoazetidin-1-yl)ethanone was used to replace 2-chloro-1-(3-hydroxyazetidin-1-yl)ethanone, so that 2-{[6-ethyl-2-(2-(2-(3-cyanoazetidin-1-yl)-2-oxoethyl)-2,6-diazaspiro[3.4]octane-6-yl)imidazo[2,1-b][1,3,4]thiadiazol-5-yl](methyl)amino}-4-(4-fluorophenyl)thiazole-5-carbonitrile was prepared. $^1$H-NMR (400 MHz, CDCl$_3$) δ: 8.18 (m, 2H), 7.18 (m, 2H), 4.57-4.52 (m, 1H), 4.50-4.46 (m, 1H), 4.36-4.31 (m, 1H), 4.27-4.22 (m, 1H), 3.60 (m, 5H), 3.55-3.51 (m, 1H), 3.50-3.47 (m, 2H), 3.37 (m, 4H), 3.18 (s, 2H), 2.62 (q, J=7.6 Hz, 2H), 2.27 (m, 2H), 1.30 (m, 3H). MS (m/z 617.2): [M+1].

Example 56

Preparation of 2-{[6-ethyl-2-(5-(2-(3-hydroxyazetidin-1-yl)-2-oxoethyl)hexahydropyrrolo[3,4-c]pyrrol-2(1H)-yl)imidazo[2,1-b][1,3,4]thiadiazol-5-yl](methyl)amino}-4-(4-fluorophenyl)thiazole-5-carbonitrile

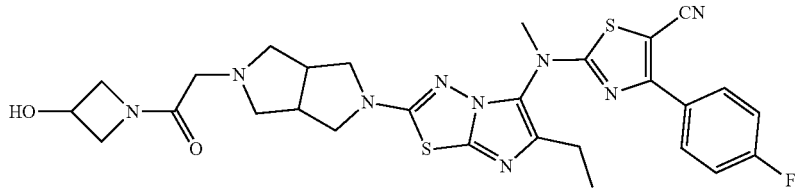 [SMILES: CCc1nc2sc(N3CC4CN(CC(=O)N5CC(O)C5)CC4C3)nn2c1N(C)c1nc(-c2ccc(F)cc2)c(C#N)s1]

Referring to the Example 2, tert-butyl hexahydropyrrolo[3,4-c]pyrrol-2(1H)-carboxylate was used to replace tert-butyl piperazine-1-carboxylate, so that 2-{[6-ethyl-2-(5-(2-(3-hydroxyazetidin-1-yl)-2-oxoethyl)hexahydropyrrolo[3,4-c]pyrrol-2(1H)-yl)imidazo[2,1-b][1,3,4]thiadiazol-5-yl](methyl)amino}-4-(4-fluorophenyl)thiazole-5-carbonitrile was prepared. $^1$H-NMR (400 MHz, CDCl$_3$) δ: 8.16 (m, 2H), 7.18 (m, 2H), 4.65 (m, 1H), 4.39-4.34 (m, 1H), 4.28-4.24 (m, 1H), 4.04-3.99 (m, 1H), 3.90-3.85 (m, 1H), 3.70-3.66 (m, 2H), 3.60 (s, 3H), 3.41-3.33 (m, 2H), 3.19-3.11 (m, 2H), 3.07-3.00 (m, 2H), 2.79-2.72 (m, 2H), 2.70-2.65 (m, 2H), 2.64-2.59 (m, 2H), 1.29 (m, 3H). MS (m/z): 608.3[M+1].

Example 57

Preparation of 2-{[6-ethyl-2-(5-(2-(3-cyanoazetidin-1-yl)-2-oxoethyl)hexahydropyrrolo[3,4-c]pyrrol-2(1H)-yl) imidazo[2,1-b][1,3,4]thiadiazol-5-yl](methyl)amino}-4-(4-fluorophenyl)thiazole-5-carbonitrile

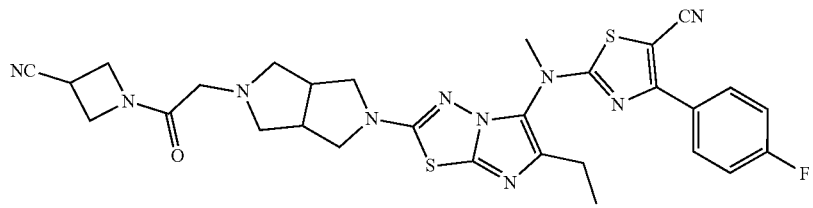 [SMILES: CCc1nc2sc(N3CC4CN(CC(=O)N5CC(C#N)C5)CC4C3)nn2c1N(C)c1nc(-c2ccc(F)cc2)c(C#N)s1]

Referring to the Example 56, 2-chloro-1-(3-cyanoazetidin-1-yl)ethanone was used to replace 2-chloro-1-(3-hydroxyazetidin-1-yl)ethanone, so that 2-{[6-ethyl-2-(5-(2-(3-cyanoazetidin-1-yl)-2-oxoethyl)hexahydropyrrolo[3,4-c]pyrrol-2(1H)-yl)imidazo[2,1-b][1,3,4]thiadiazol-5-yl](methyl)amino}-4-(4-fluorophenyl)thiazole-5-carbonitrile was obtained. ¹H-NMR (400 MHz, CDCl₃) δ: 8.17 (m, 2H), 7.18 (m, 2H), 4.52-4.42 (m, 2H), 4.37-4.32 (m, 1H), 4.28-4.24 (m, 1H), 3.69 (m, 2H), 3.60 (s, 3H), 3.52-3.46 (m, 1H), 3.36 (m, 2H), 3.19 (s, 2H), 3.06 (m, 2H), 2.84-2.74 (m, 2H), 2.66 (m, 2H), 2.64 (m, 2H), 1.28 (m, 3H). MS (m/z): 617.3 [M+1].

Example 58

Preparation of 2-{[6-ethyl-2-((1S,4S)-5-(2-(3-hydroxyazetidin-1-yl)-2-oxoethyl)-2,5-diazabicyclo[2.2.1]heptan-2-yl)imidazo[2,1-b][1,3,4]thiadiazol-5-yl](methyl)amino}-4-(4-fluorophenyl)thiazole-5-carbonitrile

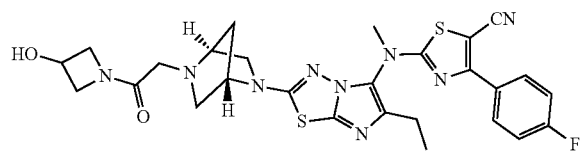

Referring to the Example 2, tert-butyl (1S,4S)-2,5-diazabicyclo[2.2.1]heptan-2-carboxylate was used to replace tert-butyl piperazine-1-carboxylate, so that 2-{[6-ethyl-2-((1S,4S)-5-(2-(3-hydroxyazetidin-1-yl)-2-oxoethyl)-2,5-diazabicyclo[2.2.1]heptan-2-yl)imidazo[2,1-b][1,3,4]thiadiazol-5-yl](methyl)amino}-4-(4-fluorophenyl)thiazole-5-carbonitrile was prepared. ¹H-NMR (400 MHz, CDCl₃) δ: 8.17 (m, 2H), 7.18 (m, 2H), 4.70 (m, 1H), 4.45-4.35 (m, 1H), 4.33-4.25 (m, 2H), 4.04 (m, 1H), 3.91-3.87 (m, 1H), 3.76 (m, 1H), 3.61 (s, 3H), 3.60-3.53 (m, 1H), 3.46-3.39 (m, 1H), 3.29-3.22 (m, 2H), 3.16-3.05 (m, 1H), 2.85-2.77 (m, 1H), 2.64 (q, J=7.2 Hz, 2H), 2.11-2.04 (m, 1H), 1.96-1.91 (m, 1H), 1.29 (m, 3H). MS (m/z): 594.3 [M+1].

Example 59

Preparation of 2-{[6-ethyl-2-((1S,4S)-5-(2-(3-cyanoazetidin-1-yl)-2-oxoethyl)-2,5-diazabicyclo[2.2.1]heptan-2-yl)imidazo[2,1-b][1,3,4]thiadiazol-5-yl](methyl)amino}-4-(4-fluorophenyl)thiazole-5-carbonitrile

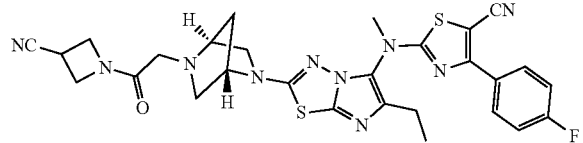 [SMILES: CCc1nc2sc(N3C[C@@H]4C[C@H]3CN4CC(=O)N3CC(C#N)C3)nn2c1N(C)c1nc(-c2ccc(F)cc2)c(C#N)s1]

Referring to the Example 58, 2-chloro-1-(3-cyanoazetidin-1-yl)ethanone was used to replace 2-chloro-1-(3-hydroxyazetidin-1-yl)ethanone, so that 2-{[6-ethyl-2-((1S,4S)-5-(2-(3-cyanoazetidin-1-yl)-2-oxoethyl)-2,5-diazabicyclo[2.2.1]heptan-2-yl)imidazo[2,1-b][1,3,4]thiadiazol-5-yl](methyl)amino}-4-(4-fluorophenyl)thiazole-5-carbonitrile was prepared. ¹H-NMR (400 MHz, CDCl₃) δ: 8.17 (m, 2H), 7.18 (m, 2H), 4.59-4.46 (m, 2H), 4.38-4.31 (m, 2H), 4.29-4.24 (m, 1H), 3.71 (m, 1H), 3.61 (s, 3H), 3.56-3.52 (m, 1H), 3.51-3.49 (m, 1H), 3.47-3.42 (m, 1H), 3.30 (m, 2H), 3.11-3.01 (m, 1H), 2.89-2.79 (m, 1H), 2.69-2.57 (m, 2H), 2.07-2.02 (m, 1H), 1.99-1.93 (m, 1H), 1.28 (m, 3H). MS (m/z): 603.3 [M+1].

Example 60

Preparation of 2-{[2-(2-oxa-5-azabicyclo[2.2.1]heptan-5-yl)-6-ethylimidazo[2,1-b][1,3,4]thiadiazol-5-yl](methyl)amino}-4-(4-fluorophenyl)thiazole-5-carbonitrile

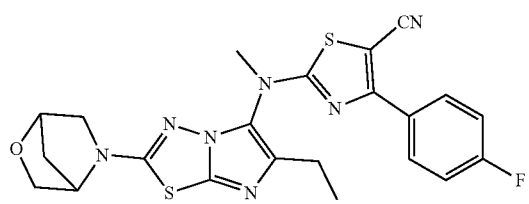 [SMILES: CCc1nc2sc(N3CC4CC3CO4)nn2c1N(C)c1nc(-c2ccc(F)cc2)c(C#N)s1]

Referring to the synthetic method of tert-butyl 4-{5-[(5-cyano-4-(4-fluorophenyl)thiazol-2-yl)(methyl)amino]-6-ethylimidazo[2,1-b][1,3,4]thiadiazol-2-yl}piperazine-1-carboxylate in Example 1, 2-oxa-5-azabicyclo[2.2.1]heptane was used to replace tert-butyl piperazine-1-carboxylate, so that 2-{[2-(2-oxa-5-azabicyclo[2.2.1]heptan-5-yl)-6-ethylimidazo[2,1-b][1,3,4]thiadiazol-5-yl](methyl)amino}-4-(4-fluorophenyl)thiazole-5-carbonitrile was prepared. ¹H-NMR (400 MHz, CDCl₃) δ: 8.17 (m, 2H), 7.18 (m, 2H), 4.75 (m, 1H), 4.56-4.50 (m, 1H), 4.02 (m, 1H), 3.90 (m, 1H), 3.60 (s, 3H), 3.54 (m, 1H), 3.45 (m, 1H), 2.62 (q, J=7.6 Hz, 2H), 2.05 (m, 2H), 1.30 (t, J=7.6 Hz, 3H). MS (m/z): 482.2 [M+1].

Example 61

Preparation of 2-{[6-ethyl-2-(6-(2-(3-hydroxyazetidin-1-yl)-2-oxoethyl)-3,6-diazabicyclo[3.1.1]heptan-3-yl)imidazo[2,1-b][1,3,4]thiadiazol-5-yl](methyl)amino}-4-(4-fluorophenyl)thiazole-5-carbonitrile

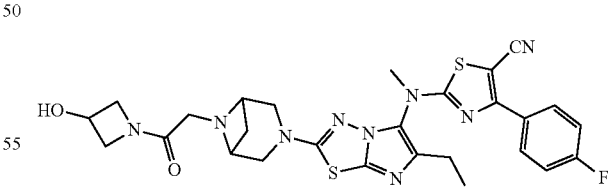

Referring to Example 2, tert-butyl 3,6-diazabicyclo[3.1.1]heptan-carboxylate was used to replace tert-butyl piperazine-1-carboxylate, so that 2-{[6-ethyl-2-(6-(2-(3-hydroxyazetidin-1-yl)-2-oxoethyl)-3,6-diazabicyclo[3.1.1]heptan-3-yl)imidazo[2,1-b][1,3,4]thiadiazol-5-yl](methyl)amino}-4-(4-fluorophenyl)thiazole-5-carbonitrile was prepared. ¹H-NMR (400 MHz, CDCl₃) δ: 8.17 (m, 2H), 7.18 (m, 2H), 4.69 (m, 1H), 4.40 (m, 1H), 4.28-4.24 (m, 1H), 4.08-4.04 (m, 1H), 3.92-3.85 (m, 3H), 3.81-3.75 (m, 2H), 3.62 (s, 3H), 3.48 (m, 2H), 3.09 (s, 2H), 2.82-2.76 (m, 1H), 2.62 (q, J=7.6 Hz, 2H), 1.68 (m, 1H), 1.31 (t, J=7.6 Hz, 3H). MS (m/z): 594.2 [M+1].

Example 62

Preparation of 2-{[6-ethyl-2-(1-(2-(3-hydroxyazetidin-1-yl)-2-oxoethyl)hexahydropyrrolo[3,4-b]pyrrol-5(1H)-yl)imidazo[2,1-b][1,3,4]thiadiazol-5-yl](methyl)amino}-4-(4-fluorophenyl)thiazole-5-carbonitrile

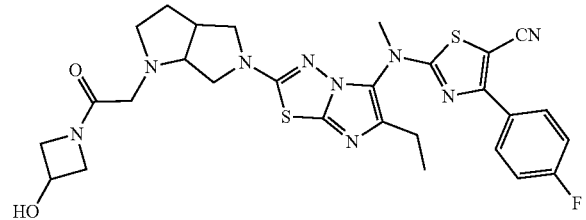 [SMILES: CCc1nc2sc(N3CC4CCN(CC(=O)N5CC(O)C5)C4C3)nn2c1N(C)c1nc(-c2ccc(F)cc2)c(C#N)s1]

Referring to Example 2, tert-butyl hexahydropyrrolo[3,4-b]pyrrol-5(1H)-carboxylate was used to replace tert-butyl piperazine-1-carboxylate, so that 2-{[6-ethyl-2-(1-(2-(3-hydroxyazetidin-1-yl)-2-oxoethyl)hexahydropyrrolo[3,4-b]pyrrol-5(1H)-yl)imidazo[2,1-b][1,3,4]thiadiazol-5-yl](methyl)amino}-4-(4-fluorophenyl)thiazole-5-carbonitrile was prepared. $^1$H-NMR (400 MHz, CDCl$_3$) δ: 8.17 (m, 2H), 7.18 (m, 2H), 4.69-4.62 (m, 1H), 4.40-4.33 (m, 1H), 4.31-4.23 (m, 2H), 4.06-3.98 (m, 1H), 3.91-3.84 (m, 1H), 3.64-3.57 (m, 1H), 3.60 (s, 3H), 3.55-3.49 (m, 1H), 3.18-3.10 (m, 2H), 3.08-3.0(m, 2H), 2.82-2.75 (m, 1H), 2.67-2.56 (m, 4H), 2.27-2.18 (m, 1H), 2.03-1.96 (m, 1H), 1.29 (m, 3H). MS (m/z): 608.2 [M+1].

Example 63

Preparation of 2-{[6-ethyl-2-(3-((2-(3-hydroxyazetidin-1-yl)-2-oxoethyl)(methyl)amino)imidazo[2,1-b][1,3,4]thiadiazol-5-yl](methyl)amino}-4-(4-fluorophenyl)thiazole-5-carbonitrile

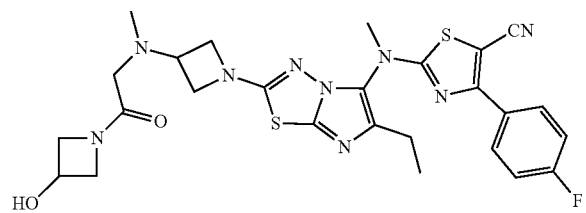 [SMILES: CCc1nc2sc(N3CC(N(C)CC(=O)N4CC(O)C4)C3)nn2c1N(C)c1nc(-c2ccc(F)cc2)c(C#N)s1]

Referring to Example 2, 3-tert-butoxycarbonylamino-azatidine was used to replace tert-butyl piperazine-1-carboxylate, so that 2-{[6-ethyl-2-(3-((2-(3-hydroxyazetidin-1-yl)-2-oxoethyl)(methyl)amino)imidazo[2,1-b][1,3,4]thiadiazol-5-yl](methyl)amino}-4-(4-fluorophenyl)thiazole-5-carbonitrile was prepared. $^1$H-NMR (400 MHz, CDCl$_3$) δ: 8.16 (m, 2H), 7.18 (m, 2H), 4.70 (m, 1H), 4.41 (m, 1H), 4.30-4.26 (m, 1H), 4.15 (m, 2H), 4.08-4.02 (m, 3H), 3.93-3.89 (m, 1H), 3.78 (m, 1H), 3.59 (s, 3H), 3.08 (s, 2H), 2.62 (q, J=7.2 Hz, 2H), 2.34 (s, 3H), 1.30-1.28 (m, 3H). MS (m/z): 582.2 [M+1].

Example 64

Preparation of N-{1-[5-((5-cyano-4-(4-fluorophenyl)thiazol-2-yl)(methyl)amino)-6-ethylimidazo[2,1-b][1,3,4]thiadiazol-2-yl]pyrrolidin-3-yl}-3-hydroxyazadetin-1-carboxamide

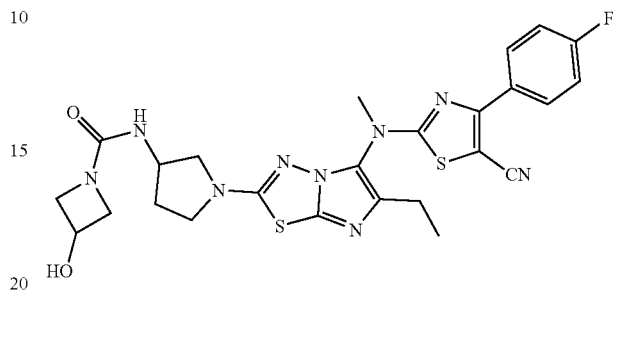

STEP 1) tert-butyl (1-(6-ethyl-5-carboxamidimidazo[2,1-b][1,3,4]thiadiazol-2-yl)pyrrolidin-3-yl) carbamate Referring to the synthetic method of tert-butyl 4-(6-ethyl-5-carboxamidimidazo[2,1-b][1,3,4]thiadiazol-2-yl)pyrrolidin-2-yl)piperazin-1-carboxylate in Example 1, 3-tert-butoxycarbonylaminopyrrolidine was used to replace tert-butyl piperazine-1-carboxylate, so that tert-butyl (1-(6-ethyl-5-carboxamidimidazo[2,1-b][1,3,4]thiadiazol-2-yl)pyrrolidin-3-yl)carbamate was prepared. MS (m/z): 381.2 [M+1].

STEP 2) tert-butyl {1-[5-((5-cyano-4-(4-fluorophenyl)thiazol-2-yl)amino)$_6$-ethylimidazo[2,1-b][1,3,4]thiadiazol-2-yl]pyrrolidin-3-yl}carbamate (1-(6-ethyl-5-carboxamidimidazo[2,1-b][1,3,4]thiadiazol-2-yl]pyrrolidin-3-yl)carbamate (300 mg, 0.79 mmol) was dissolved in DMF (3 mL), and potassium tert-butoxide (256 mg, 2.28 mmol) was added. The mixture was stirred for 5 minutes, followed by adding N-(2-bromo-6-ethylimidazo[2,1-b][1,3,4]thiadiazol-5-yl)carboxamide (181 mg, 0.76 mmol). When the temperature increased to room temperature, the mixture was reacted for 30 minutes. LC-MS detection indicated that the reaction was completed. Then the reaction mixture was poured into water and extracted with ethyl acetate (20 mL×3). The organic layer was combined, washed with saturated saline solution, dried with anhydrous sodium sulfate, evaporated, and purified by column purification (petroleum ether: ethyl acetate=1:1), to obtain 260 mg of a white solid product, yield:62%. MS (m/z): 555.2 [M+1].

STEP 3) tert-butyl {1-[5-((5-cyano-4-(4-fluorophenyl)thiazol-2-yl)(methyl)amino)-6-ethylimidazo[2,1-b][1,3,4]thiadiazol-2-yl]pyrrolidin-3-yl}-carbamate tert-butyl {1-[5-((5-cyano-4-(4-fluorophenyl)thiazol-2-yl)amino)-6-ethylimidazo[2,1-b][1,3,4]thiadiazol-2-yl]pyrrolidin-3-yl}-carbamate (200 mg, 0.36 mmol) was dissolved in tetrahydrofuran (4 mL). When the temperature decreased to –10° C., potassium tert-butoxide (44 mg, 0.40 mmol) was added. The mixture was stirred for 10 minutes, and iodomethane (62 mg, 0.43 mmol) was added into it. The temperature was kept for 6 hours, and LC-MS detection indicated that the reaction was completed. The reaction mixture was poured into water and extracted with ethyl acetate (20 mL×3). The organic layer was combined, washed with saturated saline solution, dried with anhydrous sodium sulfate, evaporated, and purified with column purification (petroleum ether: ethyl acetate=1:1), to obtain 176 mg of a white solid product, yield:86%. MS (m/z): 569.2 [M+1].

STEP 4) 2-{[2-(3-aminopyrrolidin-1-yl)-6-ethylimidazo[2,1-b][1,3,4]thiadiazol-5-yl](methyl)amino}-4-(4-fluorophenyl)thiazol-5-carbonitrile tert-butyl {1-[5-((5-cyano-4-(4-fluorophenyl)thiazol-2-yl)(methyl)amino)-6-ethylimidazo[2,1-b][1,3,4]thiadiazol-2-yl]pyrrolidin-3-yl}-carbamate (176 mg, 0.36 mmol) was dissolved in 1,4-dioxane (2 mL). After the temperature decreased to 0 to 5° C., 4N HCl/1,4-dioxane (2 mL) was dropwise added. After 10 minutes, the mixture was reacted at room temperature for 3 hours and LC-MS detection indicated that the reaction was completed. Then the mixture was evaporated, and stirred for 30 minutes after adding ethyl acetate (4 mL). The mixture was filtered and then the filter cake was dissolved with M methanol (5 mL), followed by adding sodium bicarbonate (80 mg), stirring for 30 minutes and evaporation. Dichloromethane (5 mL) was added to dissolve the mixture, which was filtered then. The filtrate was combined, dried with anhydrous sodium sulfate, and evaporated to obtain 140 mg of a white solid product, yield: 96%. MS (m/z): 469.2 [M+1].

STEP 5) N-{1-[5-((5-cyano-4-(4-fluorophenyl)thiazol-2-yl)(methyl)amino)-6-ethylimidazo[2,1-b][1,3,4]thiadiazol-2-yl]pyrrolidin-3-yl}-3-hydroxyazadetin-1-carboxamide Referring to Example 30, 2-{[2-(3-aminopyrrolidin-1-yl)-6-ethylimidazo[2,1-b][1,3,4]thiadiazol-5-yl](methyl)amino}-4-(4-fluorophenyl)thiazol-5-carbonitrile was used to replace 2-{[6-ethyl-2-(3-(methylamino)pyrrolidin-1-yl)imidazo[2,1-b][1,3,4]thiadiazol-5-yl](methyl)amino}-4-(4-fluorophenyl)thiazol-5-carbonitrile, so that N-{1-[5-((5-cyano-4-(4-fluorophenyl)thiazol-2-yl)(methyl)amino)-6-ethylimidazo[2,1-b][1,3,4]thiadiazol-2-yl]pyrrolidin-3-yl}-3-hydroxyazadetin-1-carboxamide was prepared. ¹H NMR (400 MHz, CDCl₃) δ: 8.14 (m, 2H), 7.16 (m, 2H), 4.65 (m, 1H), 4.50 (m, 1H), 4.23 (m, 1H), 4.16 (m, 2H), 3.84-3.74 (m, 3H), 3.58-3.53 (m, 5H), 3.31 (m, 1H), 2.60 (m, 3H), 2.36 (s, 1H), 2.02 (m, 1H), 2.03 (m, 1H), 1.28 (m, 3H). MS (m/z): 568.2 [M+1].

Example 65

Preparation of 2-{[6-ethyl-2-(4-(2-(3-hydroxyazetidin-1-yl)-2-oxoethyl)-3,3-dimethylpiperazin-1-yl)imidazo[2,1-b][1,3,4]thiadiazol-5-yl](methyl)amino}-4-(4-fluorophenyl)thiazole-5-carbonitrile

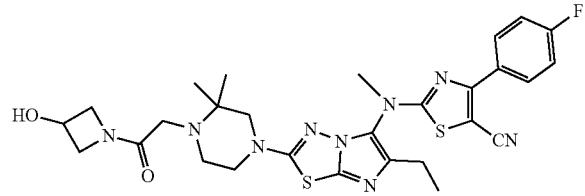 [SMILES: CCc1nc2sc(N3CCN(CC(=O)N4CC(O)C4)C(C)(C)C3)nn2c1N(C)c1nc(-c2ccc(F)cc2)c(C#N)s1]

Referring to Example 2, 2,2-dimethylpiperazin-1-carboxylate was used to replace tert-butyl piperazine-1-carboxylate, so that 2-{[6-ethyl-2-(4-(2-(3-hydroxyazetidin-1-yl)-2-oxoethyl)-3,3-dimethylpiperazin-1-yl)imidazo[2,1-b][1,3,4]thiadiazol-5-yl](methyl)amino}-4-(4-fluorophenyl)thiazole-5-carbonitrile was prepared. ¹H NMR (400 MHz, CDCl₃) δ: 8.16 (m, 2H), 7.17 (m, 2H), 4.68 (m, 1H), 4.50 (m, 1H), 4.27 (m, 1H), 4.15 (m, 1H), 3.90 (m, 1H), 3.59 (s, 3H), 3.50 (m, 2H), 3.31 (m, 1H), 3.21 (m, 2H), 3.13 (m, 2H), 2.73 (m, 2H), 2.60 (q, J=7.6 Hz, 2H), 1.29 (t, J=7.6 Hz, 3H), 1.12 (s, 6H). MS (m/z): 610.2 [M+1].

Example 66

Preparation of (R)-2-{[6-ethyl-2-(4-(2-(3-hydroxyazetidin-1-yl)-2-oxoethyl)-2-methylpiperazin-1-yl)imidazo[2,1-b][1,3,4]thiadiazol-5-yl](methyl)amino}-4-(4-fluorophenyl)thiazole-5-carbonitrile

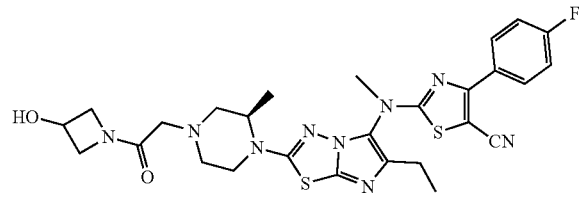 [SMILES: CCc1nc2sc(N3CCN(CC(=O)N4CC(O)C4)C[C@H]3C)nn2c1N(C)c1nc(-c2ccc(F)cc2)c(C#N)s1]

Referring to Example 2, tert-butyl (R)-3-methylpiperazine-1-carboxylate was used to replace tert-butyl piperazine-1-carboxylate, so that (R)-2-{[6-ethyl-2-(4-(2-(3-hydroxyazetidin-1-yl)-2-oxoethyl)-2-methylpiperazin-1-yl)imidazo[2,1-b][1,3,4]thiadiazol-5-yl](methyl)amino}-4-(4-fluorophenyl)thiazole-5-carbonitrile was prepared. ¹H NMR (400 MHz, CDCl₃) δ: 8.16 (m, 2H), 7.18 (m, 2H), 4.72 (m, 1H), 4.47 (m, 1H), 4.31 (m, 1H), 4.12 (m, 1H), 3.93 (m, 2H), 3.60 (s, 4H), 3.44 (m, 1H), 3.08 (m, 2H), 2.93 (m, 1H), 2.79 (m, 1H), 2.61 (m, 2H), 2.50 (m, 1H), 2.35 (m, 1H), 1.43 (m, 3H), 1.29 (m, 3H). MS (m/z): 596.2 [M+1].

Example 67

Preparation of (S)-2-{[6-ethyl-2-(4-(2-(3-hydroxyazetidin-1-yl)-2-oxoethyl)-2-methylpiperazin-1-yl)imidazo[2,1-b][1,3,4]thiadiazol-5-yl](methyl)amino}-4-(4-fluorophenyl)thiazole-5-carbonitrile

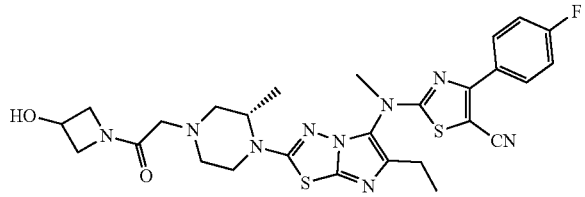 [SMILES: CCc1nc2sc(N3CCN(CC(=O)N4CC(O)C4)C[C@@H]3C)nn2c1N(C)c1nc(-c2ccc(F)cc2)c(C#N)s1]

Referring to Example 2, tert-butyl (S)-3-methylpiperazin-1-carboxylate was used to replace tert-butyl piperazin-1-carboxylate, so that (S)-2-{[6-ethyl-2-(4-(2-(3-hydroxyazetidin-1-yl)-2-oxoethyl)-2-methylpiperazin-1-yl)imidazo[2,1-b][1,3,4]thiadiazol-5-yl](methyl)amino}-4-(4-fluorophenyl)thiazole-5-carbonitrile was prepared. ¹H NMR (400 MHz, CDCl₃) δ: 8.16 (m, 2H), 7.18 (m, 2H), 4.72 (m, 1H), 4.46 (m, 1H), 4.31 (m, 1H), 4.12 (m, 1H), 3.93 (m, 2H), 3.60 (s, 4H), 3.44 (m, 1H), 3.07 (m, 2H), 2.93 (m, 1H), 2.79 (m, 1H), 2.62 (m, 2H), 2.50 (m, 1H), 2.34 (m, 1H), 1.42 (m, 3H), 1.28 (m, 3H). MS (m/z): 596.2 [M+1].

Example 68

Preparation of (S)-2-{[6-ethyl-2-(4-(2-(3-hydroxyazetidin-1-yl)-2-oxoethyl)-3-methylpiperazin-1-yl)imidazo[2,1-b][1,3,4]thiadiazol-5-yl](methyl)amino}-4-(4-fluorophenyl)thiazole-5-carbonitrile

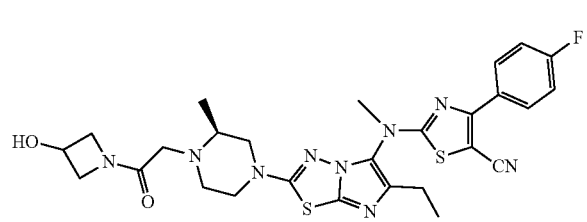 [SMILES: CCc1nc2sc(N3CCN(CC(=O)N4CC(O)C4)[C@@H](C)C3)nn2c1N(C)c1nc(-c2ccc(F)cc2)c(C#N)s1]

Referring to Example 2, tert-butyl (S)-2-methylpiperazin-1-carboxylate was used to replace tert-butyl piperazin-1-carboxylate, so that (S)-2-{[6-ethyl-2-(4-(2-(3-hydroxyazetidin-1-yl)-2-oxoethyl)-3-methylpiperazin-1-yl)imidazo[2,1-b][1,3,4]thiadiazol-5-yl](methyl)amino}-4-(4-fluorophenyl)thiazole-5-carbonitrile was prepared. $^1$H NMR (400 MHz, CDCl$_3$) δ: 8.17 (m, 2H), 7.18 (m, 2H), 4.71 (m, 1H), 4.45 (m, 1H), 4.29 (m, 1H), 4.10 (m, 1H), 3.91 (m, 1H), 3.60 (m, 5H), 3.45-3.32 (m, 2H), 3.02-2.92 (m, 3H), 2.76 (m, 1H), 2.66-2.58 (m, 4H), 1.30 (t, J=7.6 Hz, 3H), 1.14 (d, J=6.0 Hz, 3H). MS (m/z): 596.2 [M+1].

Example 69

Preparation of (R)-2-{[6-ethyl-2-(4-(2-(3-hydroxyazetidin-1-yl)-2-oxoethyl)-3-methylpiperazin-1-yl)imidazo[2,1-b][1,3,4]thiadiazol-5-yl](methyl)amino}-4-(4-fluorophenyl)thiazole-5-carbonitrile

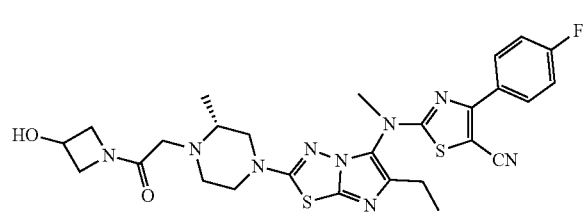 [SMILES: CCc1nc2sc(N3CCN(CC(=O)N4CC(O)C4)[C@H](C)C3)nn2c1N(C)c1nc(-c2ccc(F)cc2)c(C#N)s1]

Referring to Example 2, tert-butyl (R)-2-methylpiperazin-1-carboxylate was used to replace tert-butyl piperazin-1-carboxylate, so that (R-2-{[6-ethyl-2-(4-(2-(3-hydroxyazetidin-1-yl)-2-oxoethyl)-3-methylpiperazin-1-yl)imidazo[2,1-b][1,3,4]thiadiazol-5-yl](methyl)amino}-4-(4-fluorophenyl)thiazole-5-carbonitrile was prepared. $^1$H NMR (400 MHz, CDCl$_3$) δ: 8.17 (m, 2H), 7.18 (m, 2H), 4.71 (m, 1H), 4.46 (m, 1H), 4.30 (m, 1H), 4.11 (m, 1H), 3.91 (m, 1H), 3.60 (m, 5H), 3.45-3.32 (m, 2H), 3.02-2.92 (m, 3H), 2.76 (m, 1H), 2.66-2.58 (m, 3H), 2.47 (m, 1H), 1.30 (t, J=7.6 Hz, 3H), 1.15 (d, J=5.6 Hz, 3H). MS (m/z): 596.2 [M+1].

Example 70

Preparation of 2-{[6-ethyl-2-(8-(2-(3-hydroxyazetidin-1-yl)-2-oxoethyl)-3,8-diazabicyclo[3.2.1]octan-3-yl)imidazo[2,1-b][1,3,4]thiadiazol-5-yl](methyl)amino}-4-(4-fluorophenyl)thiazole-5-carbonitrile

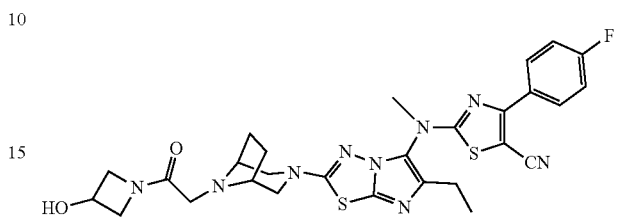

Referring to Example 2, tert-butyl 3,8-diazabicyclo[3.2.1]octan-8-carboxylate was used to replace tert-butyl piperazine-1-carboxylate, so that 2-{[6-ethyl-2-(8-(2-(3-hydroxyazetidin-1-yl)-2-oxoethyl)-3,8-diazabicyclo[3.2.1]octan-3-yl)imidazo[2,1-b][1,3,4]thiadiazol-5-yl](methyl)amino}-4-(4-fluorophenyl)thiazole-5-carbonitrile was prepared. $^1$H NMR (400 MHz, CDCl$_3$) δ: 8.15 (m, 2H), 7.16 (m, 2H), 4.68 (m, 1H), 4.50 (m, 1H), 4.29 (m, 1H), 4.19 (m, 1H), 3.94 (m, 1H), 3.57-3.37 (m, 9H), 3.12 (m, 2H), 2.60 (m, 2H), 2.06 (m, 2H), 1.80-1.71 (m, 2H), 1.28 (m, 3H). MS (m/z): 608.16 [M+1].

Example 71

Preparation of 2-{[6-ethyl-2-(4-(2-(3-hydroxyazetidin-1-yl)-2-oxoethyl)-4,7-diazaspiro[2.5]octan-7-yl)imidazo[2,1-b][1,3,4]thiadiazol-5-yl](methyl)amino}-4-(4-fluorophenyl)thiazole-5-carbonitrile

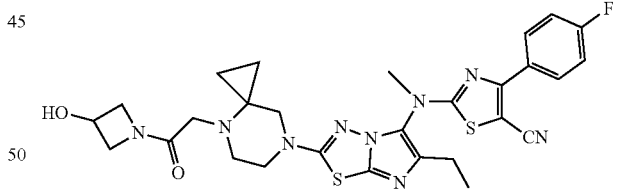

Referring to Example 2, tert-butyl 4,7-diazaspiro[2.5]octan-4-carboxylate was used to replace tert-butyl piperazine-1-carboxylate, so that 2-{[6-ethyl-2-(4-(2-(3-hydroxyazetidin-1-yl)-2-oxoethyl)-4,7-diazaspiro[2.5]octan-7-yl)imidazo[2,1-b][1,3,4]thiadiazol-5-yl](methyl)amino}-4-(4-fluorophenyl)thiazole-5-carbonitrile was prepared. $^1$H-NMR (400 MHz, CDCl$_3$) δ: 8.17 (m, 2H), 7.18 (m, 2H), 4.69 (m, 1H), 4.41-4.36 (m, 1H), 4.30-4.26 (m, 1H), 4.05-4.02 (m, 1H), 3.91-3.88 (m, 1H), 3.59 (s, 3H), 3.50-3.40 (m, 4H), 3.25 (s, 2H), 3.16 (m, 2H), 2.62 (q, J=7.2 Hz, 2H), 1.28 (t, J=7.2 Hz, 3H), 0.81 (m, 2H), 0.68 (m, 2H). MS (m/z): 608.4 [M+1].

Example 72

Preparation of cis-2-{[6-ethyl-2-(4-(2-(3-hydroxyazetidin-1-yl)-2-oxoethyl)-3,5-dimethylpiperazin-1-yl)imidazo[2,1-b][1,3,4]thiadiazol-5-yl](methyl)amino}-4-(4-fluorophenyl)thiazole-5-carbonitrile

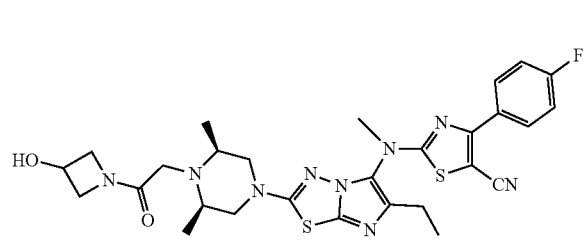 [SMILES: CCc1nc2sc(N3C[C@@H](C)N(CC(=O)N4CC(O)C4)[C@@H](C)C3)nn2c1N(C)c1nc(-c2ccc(F)cc2)c(C#N)s1]

Referring to Example 2, tert-butyl cis-3,5-dimethylpiperazin-1-yl-carboxylate was used to replace tert-butyl piperazine-1-carboxylate, so that cis-2-{[6-ethyl-2-(4-(2-(3-hydroxyazetidin-1-yl)-2-oxoethyl)-3,5-dimethylpiperazin-1-yl)imidazo[2,1-b][1,3,4]thiadiazol-5-yl](methyl)amino}-4-(4-fluorophenyl)thiazole-5-carbonitrile was prepared. $^1$H NMR (400 MHz, CDCl$_3$) δ: 8.17 (m, 2H), 7.18 (m, 2H), 4.71 (m, 1H), 4.41 (m, 1H), 4.28 (m, 1H), 4.05 (m, 1H), 3.90 (m, 1H), 3.60 (m, 5H), 3.43 (m, 2H), 3.28 (m, 2H), 2.88 (m, 2H), 2.61 (q, J=7.6 Hz, 2H), 1.30 (m, 3H), 1.15 (m, 6H). MS (m/z): 610.3 [M+1].

Example 73

Preparation of trans-2-{[6-ethyl-2-(4-(2-(3-hydroxyazetidin-1-yl)-2-oxoethyl)-3,5-dimethylpiperazin-1-yl)imidazo[2,1-b][1,3,4]thiadiazol-5-yl](methyl)amino}-4-(4-fluorophenyl)thiazole-5-carbonitrile

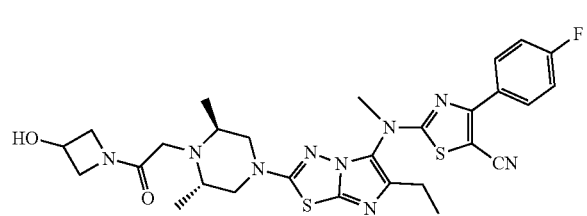 [SMILES: CCc1nc2sc(N3C[C@H](C)N(CC(=O)N4CC(O)C4)[C@@H](C)C3)nn2c1N(C)c1nc(-c2ccc(F)cc2)c(C#N)s1]

Referring to Example 2, tert-butyl trans-3,5-dimethylpiperazin-1-yl-carboxylate was used to replace tert-butyl piperazine-1-carboxylate, so that trans-2-{[6-ethyl-2-(4-(2-(3-hydroxyazetidin-1-yl)-2-oxoethyl)-3,5-dimethylpiperazin-1-yl)imidazo[2,1-b][1,3,4]thiadiazol-5-yl](methyl)amino}-4-(4-fluorophenyl)thiazole-5-carbonitrile was prepared. $^1$H-NMR (400 MHz, CDCl$_3$) δ: 8.17 (m, 2H), 7.18 (m, 2H), 4.75-4.67 (m, 1H), 4.57-4.47 (m, 1H), 4.34-4.27 (m, 1H), 4.22-4.12 (m, 1H), 3.94-3.88 (m, 1H), 3.60 (m, 3H), 3.58-3.50 (m, 2H), 3.45-3.36 (m, 1H), 3.24-3.15 (m, 2H), 3.14-3.03 (m, 3H), 2.64 (m, 2H), 1.28 (m, 3H), 1.10 (m, 6H). MS (m/z): 610.3 [M+1].

Example 74

Preparation of 2-{[6-ethyl-2-((2S,5S)-4-(2-(3-hydroxyazetidin-1-yl)-2-oxoethyl)-2,5-dimethylpiperazin-1-yl)imidazo[2,1-b][1,3,4]thiadiazol-5-yl](methyl)amino}-4-(4-fluorophenyl)thiazole-5-carbonitrile

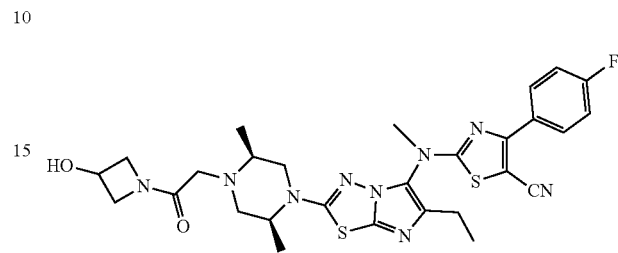

Referring to Example 2, tert-butyl trans(2S,5S)-2,5-dimethylpiperazin-1-yl-carboxylate was used to replace tert-butyl piperazine-1-carboxylate, so that 2-{[6-ethyl-2-((2S,5S)-4-(2-(3-hydroxyazetidin-1-yl)-2-oxoethyl)-2,5-dimethylpiperazin-1-yl)imidazo[2,1-b][1,3,4]thiadiazol-5-yl](methyl)amino}-4-(4-fluorophenyl)thiazole-5-carbonitrile was prepared. $^1$H NMR (400 MHz, CDCl$_3$) δ: 8.17 (m, 2H), 7.18 (m, 2H), 4.72 (m, 1H), 4.48 (m, 1H), 4.30 (m, 1H), 4.13 (m, 1H), 3.91 (m, 2H), 3.60 (s, 3H), 3.48 (m, 2H), 3.03 (m, 1H), 2.92 (m, 1H), 2.74 (m, 2H), 2.61 (m, 3H), 2.45 (m, 1H), 1.40 (m, 3H), 1.30 (t, J=7.6 Hz, 3H), 1.16 (m, 3H). MS (m/z): 610.2 [M+1].

Example 75

Preparation of 2-{[6-ethyl-2-((2R,5R)-4-(2-(3-hydroxyazetidin-1-yl)-2-oxoethyl)-2,5-dimethylpiperazin-1-yl)imidazo[2,1-b][1,3,4]thiadiazol-5-yl](methyl)amino}-4-(4-fluorophenyl)thiazole-5-carbonitrile

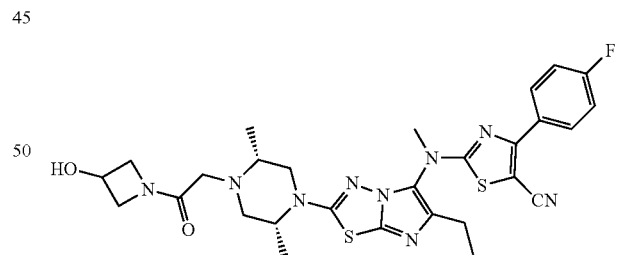

Referring to Example 2, tert-butyl trans(2R,5R)-2,5-dimethylpiperazin-1-yl-carboxylate was used to replace tert-butyl piperazine-1-carboxylate, so that 2-{[6-ethyl-2-((2R,5R)-4-(2-(3-hydroxyazetidin-1-yl)-2-oxoethyl)-2,5-dimethylpiperazin-1-yl)imidazo[2,1-b][1,3,4]thiadiazol-5-yl](methyl)amino}-4-(4-fluorophenyl)thiazole-5-carbonitrile was prepared. $^1$H NMR (400 MHz, CDCl$_3$) δ: 8.17 (m, 2H), 7.18 (m, 2H), 4.70 (m, 1H), 4.47 (m, 1H), 4.28 (m, 1H), 4.11 (m, 1H), 3.91 (m, 2H), 3.60 (s, 3H), 3.47 (m, 2H), 3.06-2.90 (m, 3H), 2.75 (m, 2H), 2.60 (m, 3H), 1.40 (m, 3H), 1.29 (m, 3H), 1.16 (m, 3H). MS (m/z): 610.3 [M+1].

Example 76

Preparation of trans-2-{[6-ethyl-2-(4-(2-(3-hydroxyazetidin-1-yl)-2-oxoethyl)-2,5-dimethylpiperazin-1-yl)imidazo[2,1-b][1,3,4]thiadiazol-5-yl](methyl)amino}-4-(4-fluorophenyl)thiazole-5-carbonitrile

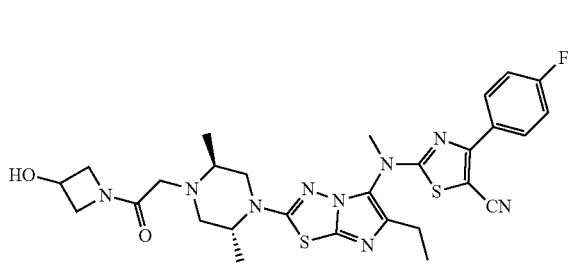 [SMILES: CCc1nc2sc(N3C[C@H](C)N(CC(=O)N4CC(O)C4)C[C@H]3C)nn2c1N(C)c1nc(-c2ccc(F)cc2)c(C#N)s1]

Referring to Example 2, tert-butyl trans-2,5-dimethylpiperazin-1-yl-carboxylate was used to replace tert-butyl piperazine-1-carboxylate, so that trans-2-{[6-ethyl-2-(4-(2-(3-hydroxyazetidin-1-yl)-2-oxoethyl)-2,5-dimethylpiperazin-1-yl)imidazo[2,1-b][1,3,4]thiadiazol-5-yl](methyl)amino}-4-(4-fluorophenyl)thiazole-5-carbonitrile was prepared. $^1$H NMR (400 MHz, CDCl$_3$) δ: 8.17 (m, 2H), 7.18 (m, 2H), 4.72 (m, 1H), 4.47 (m, 1H), 4.30 (m, 1H), 4.12 (m, 1H), 3.93 (m, 2H), 3.60 (s, 4H), 3.36 (m, 1H), 3.19-3.06 (m, 3H), 2.94 (m, 1H), 2.70-2.59 (m, 3H), 2.49 (m, 1H), 1.41 (m, 3H), 1.30 (t, J=7.6 Hz, 3H), 1.07 (m, 3H). MS (m/z): 610.2 [M+1].

Example 77

Preparation of 2-{[6-ethyl-2-(4-(2-(3-hydroxyazetidin-1-yl)-2-oxoethyl)-2,3-dimethylpiperazin-1-yl)imidazo[2,1-b][1,3,4]thiadiazol-5-yl](methyl)amino}-4-(4-fluorophenyl)thiazole-5-carbonitrile

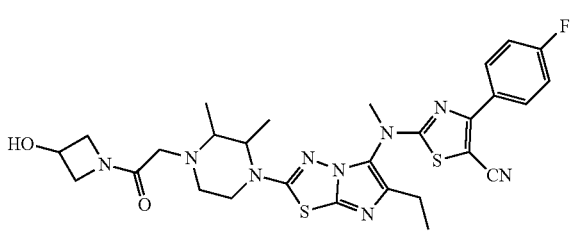 [SMILES: CCc1nc2sc(N3CCN(CC(=O)N4CC(O)C4)C(C)C3C)nn2c1N(C)c1nc(-c2ccc(F)cc2)c(C#N)s1]

Referring to Example 2, tert-butyl 2,3-dimethylpiperazin-1-yl-carboxylate was used to replace tert-butyl piperazin-1-carboxylate, so that 2-{[6-ethyl-2-(4-(2-(3-hydroxyazetidin-1-yl)-2-oxoethyl)-2,3-dimethylpiperazin-1-yl)imidazo[2,1-b][1,3,4]thiadiazol-5-yl](methyl)amino}-4-(4-fluorophenyl)thiazole-5-carbonitrile was prepared. $^1$H NMR (400 MHz, CDCl$_3$) δ: 8.14 (m, 2H), 7.16 (m, 2H), 4.71 (m, 1H), 4.48 (m, 1H), 4.30 (m, 1H), 4.16 (m, 1H), 3.97-3.90 (m, 2H), 3.65-3.58 (m, 4H), 3.41 (s, 1H), 3.15 (m, 2H), 2.92 (m, 1H), 2.77 (m, 1H), 2.56 (m, 3H), 1.43 (m, 3H), 1.28 (m, 3H), 1.09 (m, 3H). MS (m/z): 610.23 [M+1].

Example 78

Preparation of 2-{[6-ethyl-2-((3R)-3-((1-(3-hydroxyazetidin-1-yl)-1-oxopropan-2-yl)(methyl)amino)pyrrolidin-1-yl)imidazo[2,1-b][1,3,4]thiadiazol-5-yl](methyl)amino}-4-(4-fluorophenyl)thiazol-5-carbonitrile

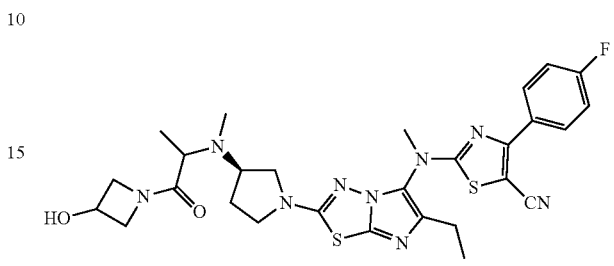

Referring to Example 21, 2-chloro-1-(3-hydroxyazetidin-1-yl)acetone was used to replace 2-chloro-1-(3-hydroxyazetidin-1-yl)ethanone, so that 2-{[6-ethyl-2-((3R)-3-((1-(3-hydroxyazetidin-1-yl)-1-oxopropan-2-yl)(methyl)amino)pyrrolidin-1-yl)imidazo[2,1-b][1,3,4]thiadiazol-5-yl](methyl)amino}-4-(4-fluorophenyl)thiazole-5-carbonitrile was prepared. $^1$H NMR (400 MHz, CDCl$_3$) δ: 8.15 (m, 2H), 7.16 (m, 2H), 4.67 (m, 1H), 4.57 (m, 1H), 4.36 (m, 1H), 4.26 (m, 2H), 4.01 (m, 1H), 3.89 (m, 1H), 3.64-3.50 (m, 5H), 3.44 (m, 1H), 3.30 (m, 1H) 2.60 (q, J=7.6 Hz, 2H), 2.30-2.21 (m, 4H), 2.03 (m, 2H), 1.28 (m, 3H), 1.19 (m, 3H). MS (m/z): 610.33 [M+1].

Example 79

Preparation of 2-{[6-ethyl-2-(4-(3-hydroxyazetidin-1-carbonyl)piperidin-1-yl)imidazo[2,1-b][1,3,4]thiadiazol-5-yl](methyl)amino}-4-(4-fluorophenyl)thiazole-5-carbonitrile

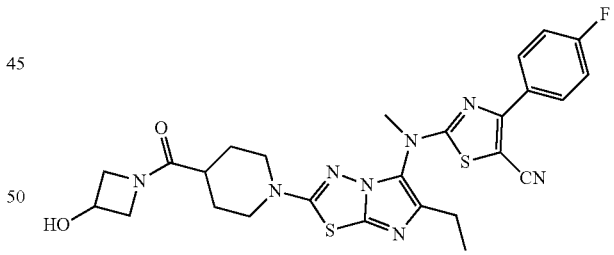

STEP 1) methyl 1-{5-[(5-cyano-4-(4-fluorophenyl)thiazol-2-yl)(methyl)amino]-6-ethylimidazo[2,1-b][1,3,4]thiadiazol-2-yl}piperidine-4-carboxylate Referring to the synthetic method of tert-butyl 4-{5-[(5-cyano-4-(4-fluorophenyl)thiazol-2-yl)(methyl)amino]-6-ethylimidazo[2,1-b][1,3,4]thiadiazol-2-yl}piperazine-1-carboxylate in Example 1, methyl piperidinr-4-carboxylate was used to replace tert-butyl piperazinr-1-carboxylate, so that methyl 1-{5-[(5-cyano-4-(4-fluorophenyl)thiazol-2-yl)(methyl)amino]-6-ethylimidazo[2,1-b][1,3,4]thiadiazol-2-yl}piperidine-4-carboxylate was prepared. MS (m/z): 526.2 [M+1].

STEP 2) 1-{5-[(5-cyano-4-(4-fluorophenyl)thiazol-2-yl)(methyl)amino]-6-ethylimidazo[2,1-b][1,3,4]thiadiazol-2-yl}piperidin-4-carboxylic acid methyl 1-{5-[(5-cyano-4-(4-fluorophenyl)thiazol-2-yl)(methyl)amino]-6-ethylimidazo[2,1-b][1,3,4]thiadiazol-2-yl}piperidin-4-carboxylate (509 mg, 0.97 mmol) was dissolved in tetrahydrofuran (3 mL) and water (2 mL), followed by adding lithium hydrate (122 mg, 2.91 mmol). The mixture was reacted at room temperature for 3 hours, and LC-MS detection indicated that the reaction was completed. The mixture was evaporated, and further it was stirred and dissolved after addition of water (6 mL). Then the mixture was regulated pH with 1N hydrogen chloride solution to about 3, to precipitate a white solid. After filtration, the filter cake was dried through vacuum, so that 421 mg of a white solid product was obtained, yield: 85%. MS (m/z): 512.2 [M+1].

Step 3) 2-{[6-ethyl-2-(4-(3-hydroxyazetidin-1-carbonyl)piperidin-1-yl)imidazo[2,1-b][1,3,4]thiadiazol-5-yl](methyl)amino}-4-(4-fluorophenyl)thiazole-5-carbonitrile 1-{5-[(5-cyano-4-(4-fluorophenyl)thiazol-2-yl)(methyl)amino]-6-ethylimidazo[2,1-b][1,3,4]thiadiazol-2-yl}piperidine-4-carboxylic acid (60 mg, 0.12 mmol) was dissolved in dichloromethane (2 mL), HATU (53 mg, 0.14 mmol) and triethylamine (48 mg, 0.47 mmol) were added. After stirring for 10 minutes, 3-hydroxyazacyclobutane hydrochloride (25 mg, 0.23 mmol) was added. The mixture was reacted at room temperature overnight. The reaction mixture was poured into water, and extracted with dichloromethane (15 mL×3). The organic layer was combined, dried with anhydrous sodium sulfate, evaporated, and purified through a preparative plate (dichloromethane:methanol=15:1), to obtain 53 mg of a white solid product, yield: 80%. $^1$H NMR (400 MHz, CDCl$_3$) δ: 8.14 (m, 2H), 7.16 (m, 2H), 4.71 (m, 1H), 4.39 (m, 1H), 4.25 (m, 1H), 4.04 (m, 1H), 3.94-3.80 (m, 3H), 3.58 (s, 3H), 3.11 (m, 2H), 2.58 (q, J=7.6 Hz, 2H), 2.42 (m, 1H), 1.94-1.75 (m, 4H), 1.28 (m, 3H). MS (m/z): 567.4 [M+1].

Example 80

Preparation of (R)-2-{[6-ethyl-2-(3-((2-(3-hydroxyazetidin-1-yl)-2-oxoethyl)amino)pyrrolidin-1-yl)imidazo[2,1-b][1,3,4]thiadiazol-5-yl](methyl)amino}-4-(4-fluorophenyl)thiazol-5-carbonitrile

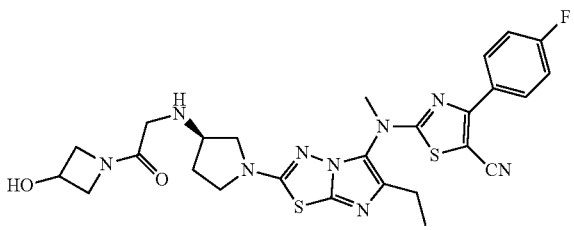 [SMILES: CCc1nc2sc(N3CC[C@@H](NCC(=O)N4CC(O)C4)C3)nn2c1N(C)c1nc(-c2ccc(F)cc2)c(C#N)s1]

STEP 1) 2-{[2-bromo-6-ethylimidazo[2,1-b][1,3,4]thiadiazol-5-yl](methyl)amino}-4-(4-fluorophenyl)thiazol-5-carbonitrile N-(2-bromo-6-ethylimidazo[2,1-b][1,3,4]thiadiazol-5-yl]carboxamide (525 mg, 1.91 mmol) was dissolved in tetrahydrofuran (THF, 8 mL), and the mixture was cooled in an ice bath before 60% sodium hydride (229 mg, 5.73 mmol) was added. The mixed solution was stirred for 15 minutes, and then a solution of 2-chloro-4-(4-fluorophenyl)thiazole-5-carbonitrile (454 mg, 1.91 mmol) in tetrahydrofuran (3 mL) was dripped. After the temperature increased to room temperature, the mixture was reacted for 30 minutes. Then thin layer plate detection indicated that the reaction was completed. Subsequently, iodomethane (542 mg, 3.82 mmol) was added to the mixture, and was reacted at room temperature for 2 hours. LC-MS detection indicated that the reaction was completed. Water was dropwise added to the reaction solution and performed quenched reaction. After addition of water (30 mL), the mixture was extracted with ethyl acetate (30 mL×3). The organic layer was combined, washed with sodium saline solution, dried with anhydrous sodium sulfate, evaporated, and purified with column purification (petroleum ether: ethyl acetate=2:1), to obtain 603 mg of a white solid product, yield 68%.

STEP 2) tert-butyl (R)-{1-[5-((5-cyano-4-(4-fluorophenyl)thiazol-2-yl)(methyl)amino)-6-ethylimidazo[2,1-b][1,3,4]thiadiazol-2-yl]pyrrolidin-3-yl}carboxylate (R)-3-tertbutoxycarbonylamidepyrrolidine (100 mg, 0.537 mmol) was dissolved in DMF (6 mL), and potassium carbonate (222 mg, 1.61 mmol) and 2-{[2-bromo-6-ethylimidazo[2,1-b][1,3,4]thiadiazol-5-yl](methyl)amino}-4-(4-fluorophenyl)thiazol-5-carbonitrile (248 mg, 0.537 mmol) were added. The mixture was heated to 65° C. and was reacted for 3 hours, and LC-MS detection indication that the reaction was completed. Then the reaction mixture was poured into water (20 mL), and further extracted with ethyl acetate (20 mL×3). The organic layer was combined, washed with saturated saline solution, dried with anhydrous sodium sulfate, evaporated and purified with column purification (petroleum ether: ethyl acetate=1.5:1), to obtain 275 mg of a white solid product, yield:90%.

STEP 3) (R)-2-{[6-ethyl-2-(3-((2-(3-hydroxyazetidin-1-yl)-2-oxoethyl)amino)pyrrolidin-1-yl) imidazo[2,1-b][1,3,4]thiadiazol-5-yl](methyl)amino}-4-(4-fluorophenyl)thiazol-5-carbonitrile Referring to Example 2, tert-butyl (R)-{1-[5-((5-cyano-4-(4-fluorophenyl)thiazol-2-yl)(methyl)amino)-6-ethylimidazo[2,1-b][1,3,4]thiadiazol-2-yl]pyrrolidin-3-yl}carboxylate was used to replace tert-butyl 4-{5-[(5-cyano-4-(4-fluorophenyl)thiazol-2-yl)(methyl)amino]-6-ethylimidazo[2,1-b][1,3,4]thiadiazol-2-yl}piperazin-1-carboxylate, so that (R)-2-{[6-ethyl-2-(3-((2-(3-hydroxyazetidin-1-yl)-2-oxoethyl)amino)pyrrolidin-1-yl)imidazo[2,1-b][1,3,4]thiadiazol-5-yl](methyl)amino}-4-(4-fluorophenyl)thiazole-5-carbonitrile was prepared. $^1$H NMR (400 MHz, CDCl$_3$) δ: 8.15 (m, 2H), 7.18 (m, 2H), 4.70 (m, 1H), 4.30 (m, 2H), 3.99 (m, 1H), 3.91 (m, 1H), 3.64-3.46 (m, 7H), 3.33-3.16 (m, 3H), 2.60 (q, J=7.6 Hz, 2H), 2.22 (m, 1H), 1.99 (m, 2H), 1.28 (m, 3H). MS (m/z): 582.2 [M+1].

Example 81

Preparation of methyl (S)-4-{5-[(5-cyano-4-(4-fluorophenyl)thiazol-2-yl)(methyl)amino]-6-ethylimidazo[2,1-b][1,3,4]thiadiazol-2-yl}-1-(2-(3-hydroxyazetidin-1-yl)-2-oxoethyl)piperazine-2-carboxylate

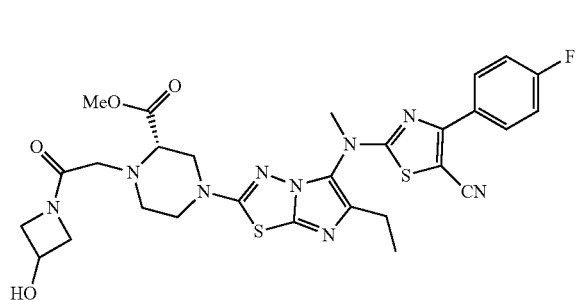 [SMILES: CCc1nc2sc(N3CCN(CC(=O)N4CC(O)C4)[C@H](C(=O)OC)C3)nn2c1N(C)c1nc(-c2ccc(F)cc2)c(C#N)s1]

Referring to Example 80, methyl (S)-1-Boc-2-piperazinecarboxylate was used to replace (R)-3-tertbutoxycarbonylaminopyrrolidine, so that methyl (S)-4-{5-[(5-cyano-4-(4-fluorophenyl)thiazol-2-yl)(methyl)amino]-6-ethylimidazo[2,1-b][1,3,4]thiadiazol-2-yl}-1-(2-(3-hydroxyazetidin-1-yl)-2-oxoethyl)piperazine-2-carboxylate was prepared. $^1$H NMR (400 MHz, CDCl$_3$) δ: 8.16 (m, 2H), 7.18 (m, 2H), 4.69 (m, 1H), 4.42 (m, 1H), 4.28 (m, 1H), 4.07 (m, 1H), 3.89 (m, 2H), 3.76-3.64 (m, 6H), 3.59 (s, 3H), 3.47-3.36 (m, 3H), 3.21 (m, 1H), 2.78 (m, 1H), 2.60 (q, J=7.6 Hz, 2H), 1.29 (d, J=7.6 Hz, 3H). MS (m/z): 640.2[M+1].

Example 82

Preparation of (S)-2-{[6-ethyl-2-(4-(2-(3-hydroxyazetidin-1-yl)-2-oxoethyl)-3-(hydroxymethyl)piperazin-1-yl)imidazo[2,1-b][1,3,4]thiadiazol-5-yl](methyl)amino}-4-(4-fluorophenyl)thiazole-5-carbonitrile

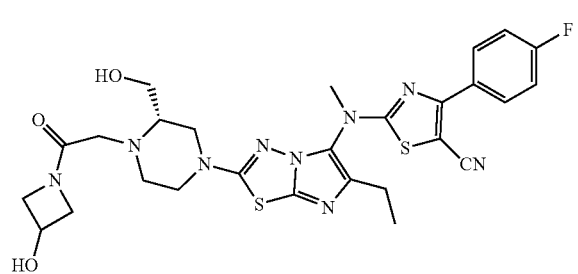 [SMILES: CCc1nc2sc(N3CCN(CC(=O)N4CC(O)C4)[C@H](CO)C3)nn2c1N(C)c1nc(-c2ccc(F)cc2)c(C#N)s1]

Lithium bromide (4 mg, 0.47 mmol) and sodium borohydride (16 mg, 0.48 mmol) were added to methyl (S)-4-{5-[(5-cyano-4-(4-fluorophenyl)thiazol-2-yl)(methyl)amino]-6-ethylimidazo[2,1-b][1,3,4]thiadiazol-2-yl}-1-(2-(3-hydroxyazetidin-1-yl)-2-oxoethyl)piperazine-2-carboxylate (100 mg, 0.14 mmol) in tetrahydrofuran (1 mL) and ethanol (3 mL). The mixture was stirred at room temperature for 3 hours, then evaporated, and purified through thick preparative plate, to obtain 10 mg of a white solid product, yield: 11%. MS (m/z): 626.2[M+1].

Example 83

Preparation of (S)-4-{5-[(5-cyano-4-(4-fluorophenyl)thiazol-2-yl)(methyl)amino]-6-ethylimidazo[2,1-b][1,3,4]thiadiazol-2-yl}-1-(2-(3-hydroxyazetidin-1-yl)-2-oxoethyl)-N-methylpiperazine-2-carboxamide

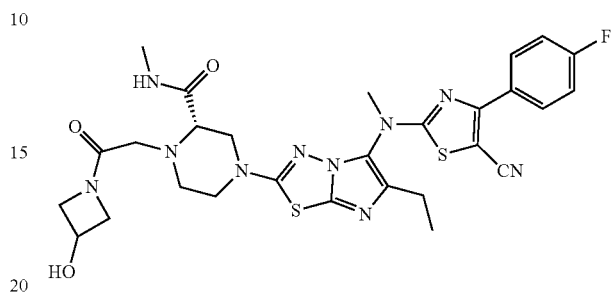

1) (S)-4-{5-[(5-cyano-4-(4-fluorophenyl)thiazol-2-yl)(methyl)amino]-6-ethylimidazo[2,1-b][1,3,4]thiadiazol-2-yl}-1-(2-(3-hydroxyazetidin-1-yl)-2-oxoethyl)piperazine-2-carboxylic acid Lithium hydroxide (5 mg, 0.12 mmol) were added to methyl (S)-4-{5-[(5-cyano-4-(4-fluorophenyl)thiazol-2-yl)(methyl)amino]-6-ethylimidazo[2,1-b][1,3,4]thiadiazol-2-yl}-1-(2-(3-hydroxyazetidin-1-yl)-2-oxoethyl)piperazine-2-carboxylate (50 mg, 0.07 mmol) in tetrahydrofuran (2 mL) and water (1 mL). The mixture was reacted under stirring at room temperature for 3 hours and evaporated, and then water (3 mL) was added. 1N HCl was used for regulating pH to about 5. The mixture was filtered and dried to obtain 47 mg of a grey white solid product. MS (m/z): 626.2 [M+1].

2) (S)-4-{5-[(5-cyano-4-(4-fluorophenyl)thiazol-2-yl)(methyl)amino]-6-ethylimidazo[2,1-b][1,3,4]thiadiazol-2-yl}-1-(2-(3-hydroxyazetidin-1-yl)-2-oxoethyl)-N-methylpiperazine-2-carboxamide (S)-4-{5-[(5-cyano-4-(4-fluorophenyl)thiazol-2-yl)(methyl)amino]-6-ethylimidazo[2,1-b][1,3,4]thiadiazol-2-yl}-1-(2-(3-hydroxyazetidin-1-yl)-2-oxoethyl)piperazine-2-carboxylic acid (34 mg, 0.05 mmol) was dissolved in tetrahydrofuran (4 mL), followed by adding HATU (23 mg, 0.06 mmol) and triethylamine (0.02 mL, 0.15 mmol). The mixture was stirred for 15 minutes and then methylamine hydrochloride (5.5 mg, 0.08 mmol) was added. After stirring at room temperature for 4 hours, LC-MS detection indicated that the reaction was completed. The solvent was evaporated and the residue was purified through a thick preparative plate to obtain 30 mg of a white solid product, yield: 89%. MS (m/z): 639.2[M+1].

Example 84

Preparation of methyl (R)-4-{5-[(5-cyano-4-(4-fluorophenyl)thiazol-2-yl)(methyl)amino]-6-ethylimidazo[2,1-b][1,3,4]thiadiazol-2-yl}-1-(2-(3-hydroxyazetidin-1-yl)-2-oxoethyl)piperazine-2-carboxylate

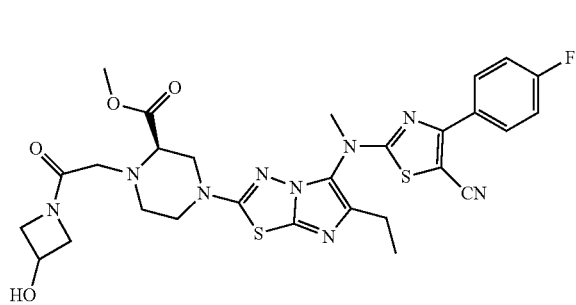 [SMILES: CCc1nc2sc(N3CCN(CC(=O)N4CC(O)C4)[C@@H](C(=O)OC)C3)nn2c1N(C)c1nc(-c2ccc(F)cc2)c(C#N)s1]

Referring to Example 80, methyl (R)-1-Boc-2-piperazinecarboxylate was used to replace (R)-3-tertbutoxycarbonyl pyrrolidine, so that methyl (R)-4-{5-[(5-cyano-4-(4-fluorophenyl)thiazol-2-yl)(methyl)amino]-6-ethylimidazo[2,1-b][1,3,4]thiadiazol-2-yl}-1-(2-(3-hydroxyazetidin-1-yl)-2-oxoethyl)piperazine-2-carboxylate was prepared. $^1$H NMR (400 MHz, CDCl$_3$) δ: 8.16 (m, 2H), 7.18 (m, 2H), 4.70 (m, 1H), 4.42 (m, 1H), 4.30 (m, 1H), 4.08 (m, 1H), 3.89 (m, 2H), 3.76-3.64 (m, 6H), 3.59 (s, 3H), 3.46-3.36 (m, 3H), 3.22 (m, 1H), 2.79 (m, 2H), 2.60 (q, J=7.6 Hz, 2H), 1.29 (d, J=7.6 Hz, 3H). MS (m/z): 640.2[M+1].

Example 85

Preparation of (R)-2-{[6-ethyl-2-(4-(2-(3-hydroxyazetidin-1-yl)-2-oxoethyl)-3-(hydroxymethyl)piperazin-1-yl)imidazo[2,1-b][1,3,4]thiadiazol-5-yl](methyl)amino}-4-(4-fluorophenyl)thiazole-5-carbonitrile

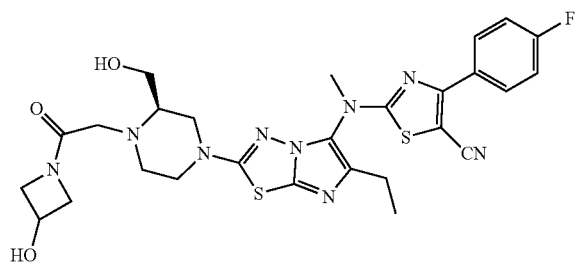 [SMILES: CCc1nc2sc(N3CCN(CC(=O)N4CC(O)C4)[C@@H](CO)C3)nn2c1N(C)c1nc(-c2ccc(F)cc2)c(C#N)s1]

Referring to Example 82, methyl (R)-1-Boc-2-piperazinecarboxylate was used to replace methyl (S)-1-Boc-2-piperazine-carboxylate, so that (R)-2-{[6-ethyl-2-(4-(2-(3-hydroxyazetidin-1-yl)-2-oxoethyl)-3-(hydroxymethyl)piperazin-1-yl)imidazo[2,1-b][1,3,4]thiadiazol-5-yl](methyl)amino}-4-(4-fluorophenyl)thiazole-5-carbonitrile was prepared. MS (m/z): 612.2 [M+1].

Example 86

Preparation of (R)-2-{[6-2-((benzyloxy)ethyl-2-(3-((2-(3-hydroxyazetidin-1-yl)-2-oxoethyl)(methyl)amino)pyrrolidin-1-yl)imidazo[2,1-b][1,3,4]thiadiazol-5-yl](methyl)amino}-4-(4-fluorophenyl)thiazole-5-carbonitrile

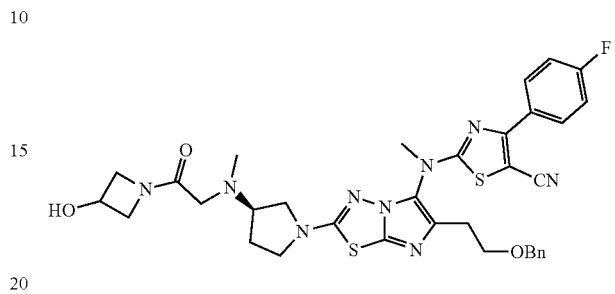

STEP 1) 6-[2-(benzyloxy)ethyl]-2-bromo-N-(tert-butyl)imidazo[2,1-b][1,3,4]thiadiazole-5-amine 3-(benzyloxy)n-propanal (6.9 g, 42.07 mmol) was added to 5-bromo-1,3,4-thiadiazole-2-amine (4.7 g, 26.26 mmol) in n-butanol (60 mL). The mixture was stirred at room temperature for 10 minutes until the temperature decreased to 0° C. Magnesium chloride (1.28 g, 13.47 mmol) and butyl isocyanide (2.28 g, 27.47 mmol) were added. After the temperature increased to 70° C., the mixture was reacted for 5 hours and LC-MS detection indicated that the reaction was completed. The reaction mixture was evaporated and water (60 mL) was added to it, which was further extracted with ethyl acetate (60 mL×2). The organic layer was combined, washed with saturated saline solution, dried with anhydrous sodium sulfate, evaporated, and purified through column purification (petroleum ether: ethyl acetate=3:1), to obtain 4.1 g of an oily product, yield: 38%. MS (m/z): 409.1, 411.1 [M+1].

STEP 2) N-{6-[2-(benzyloxy)ethyl]-2-bromoimidazo[2,1-b][1,3,4]thiadiazole-5-acetamide 6-[2-(benzyloxy)ethyl]-2-bromo-N-(tert-butyl)imidazo[2,1-b][1,3,4]thiadiazole-5-amine (3.89 g, 9.5 mmol) was dissolved in acetic acid (30 mL), and then the mixture was stirred at room temperature. After p-toluenesulfonic acid monohydrate (1.39 g, 7.3 mmol) was added, the mixture was reacted for 2.5 hours with the temperature increasing to 110° C. LC-MS detection indicated that the reaction was completed. Subsequently, the mixture was evaporated and water (60 mL) was added, and then the mixture was extracted with ethyl acetate (60 mL×3). The organic layer was combined, washed with saturated saline solution, dried with anhydrous sodium sulfate, evaporated, and purified with column purification (petroleum ether:ethyl acetate=2:1), to obtain 3.09 g of a white solid product, yield: 82%. MS (m/z): 395.0, 397.0 [M+1].

STEP 3) 2-{[6-(2-(benzyloxy)ethyl]-2-bromoimidazo[2,1-b][1,3,4]thiadiazol-5-yl](methyl)amino}-4-(4-fluorophenyl)thiazole-5-carbonitrile N-{6-[2-(benzyloxy)ethyl]-2-bromoimidazo[2,1-b][1,3,4]thiadiazole-5-acetamide (580 mg, 1.472 mmol) was dissolved in tetrahydrofuran (15 mL), under the protection of nitrogen gas, 60% NaH (151 mg, 3.77 mmol) was added to the mixture in an ice bath. The solution was stirred for 15 minutes, and 2-chloro-4-(4-fluorophenyl)thiazole-5-carbonitrile (324 mg, 1.36 mmol) in tetrahydrofuran (3 mL) was dropwise added to the solution. After the addition was finished, the mixture was reacted for 30 minutes with the temperature increasing to room temperature. Thin plate detection indicated the reaction was completed. Iodomethane (321 mg, 2.26 mmol) was added to the mixture. After the reaction continued for 2 hours, LC-MS detection indicated the reaction was completed. The reaction mixture performed quenched reaction and was added with water (20 mL), extracted with ethyl acetate (20 mL×3). The organic layer was combined, washed with saturated saline solution, dried with anhydrous sodium sulfate, evaporated, and purified with column purification (petroleum ether:ethyl acetate=5:1), to obtain 481 mg of a white solid product, yield: 85%. MS (m/z): 569.1, 571.1 [M+1].

STEP 4) tert-butyl (R)-{1-[6-2-((benzyloxy)ethyl)-5-((5-cyano-4-(4-fluorophenyl)thiazol-2-yl)(methyl)amino)imidazo[2,1-b][1,3,4]thiadiazol-2-yl]pyrrolidin-3-yl}(methyl)carbamate (R)-3-tertbutoxycarbonyl pyrrolidine (149 mg, 0.75 mmol) was dissolved in DMF (6 mL), and potassium carbonate (295 mg, 2.14 mmol) and 2-{[6-(2-(benzyloxy)ethyl)-2-bromoimidazo[2,1-b][1,3,4]thiadiazol-5-yl](methyl)amino}-4-(4-fluorophenyl)thiazol-5-carbonitrile (481 mg, 0.85 mmol) were added into it. The mixture was heated to 70° C. and was reacted for 3 hours, and LC-MS detection indicated that the reaction was completed. The reaction mixture was poured into water (20 mL), and then extracted with ethyl acetate (20 mL×3). The organic layer was combined, washed with saturated saline solution, dried with anhydrous sodium sulfate, evaporated and purified with column purification (petroleum ether:ethyl acetate=1:2), to obtain 409 mg of a white solid product, yield: 70%. MS (m/z): 689.3 [M+1].

Referring to Example 2, tert-butyl (R)-1-{[6-2-((benzyloxy)ethyl)-((5-cyano-4-(4-fluorophenyl)thiazol-2-yl)(methyl)amino)imidazo[2,1-b][1,3,4]thiadiazol-2-yl]pyrrolidin-3-yl}(methyl)carboxylate was used to replace tert-butyl 4-{5-[(5-cyano-4-(4-fluorophenyl)thiazol-2-yl)(methyl)amino]-6-ethylimidazo[2,1-b][1,3,4]thiadiazol-2-yl]piperizine-1-carboxylate, so that (R)-2-{[6-2-((benzyloxy)ethyl-2-(3-((2-(3-hydroxyazetidin-1-yl)-2-oxoethyl)(methyl)amino)pyrrolidin-1-yl)imidazo[2,1-b][1,3,4]thiadiazol-5-yl](methyl)amino}-4-(4-fluorophenyl)thiazole-5-carbonitrile was prepared. ¹H NMR (400 MHz, CDCl₃) δ: 8.13 (m, 2H), 7.30-7.24 (m, 5H), 7.16 (m, 2H), 4.65 (m, 1H), 4.51 (s, 2H), 4.40 (m, 1H), 4.26 (m, 1H), 4.06 (m, 1H), 3.89 (m, 1H), 3.79 (m, 2H), 3.67-3.52 (m, 5H), 3.43 (m, 2H), 3.33 (m, 1H), 3.16 (m, 2H), 2.87 (m, 2H), 2.38 (s, 3H), 2.24 (m, 1H), 2.09 (m, 1H). MS (m/z): 702.6 [M+1].

Example 87

Preparation of (R)-4-(4-fluorophenyl)-2-{[2-(3-((2-(3-hydroxyazetidin-1-yl)-2-oxoethyl)(methyl)amino)pyrrolidin-1-yl)-6-(2-hydroxyethyl)imidazo[2,1-b][1,3,4]thiadiazol-5-yl](methyl)amino}thiazole-5-carbonitrile

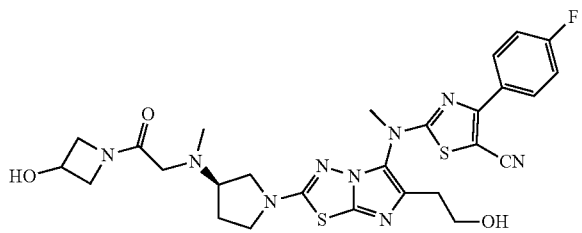 [SMILES: CN(c1nc(-c2ccc(F)cc2)c(C#N)s1)c1c(CCO)nc2sc(N3CC[C@@H](N(C)CC(=O)N4CC(O)C4)C3)nn12]

(R)-2-{[6-2-((benzyloxy)ethyl)-2-(3-((2-(3-hydroxyazetidin-1-yl)-2-oxoethyl)(methyl)amino)pyrrolidin-1-yl)imidazo[2,1-b][1,3,4]thiadiazol-5-yl](methyl)amino}-4-(4-fluorophenyl)thiazole-5-carbonitrile (50 mg, 0.071 mmol) was dissolved in dichloromethane (10 mL). The mixture was stirred under the protection of nitrogen gas until the temperature decreased to 0-5° C. Then, titanium tetrachloride (32 mg, 0.168 mmol) was dropwise added until addition was completed. The solution was stirred for 15 minutes, and then was reacted for 30 minutes after the temperature increased to room temperature. LC-MS detection indicated the reaction was completed. 1N HCl (1 mL) was dropwise added for performing quenched reaction. After stirring the mixture for 15 minutes, saturated sodium bicarbonate solution was used for regulating pH to about 10. Then, the mixture was filtered, and extracted with dichloromethane (20 mL×3). The organic layer was combined, dried with anhydrous sodium sulfate, evaporated, and purified through thick preparative plate (dichloromethane:methanol=12:1), to obtain 33 mg of a white solid product, yield: 77%. ¹H NMR (400 MHz, CDCl₃) δ: 8.13 (m, 2H), 7.15 (m, 2H), 4.68 (m, 1H), 4.40 (m, 1H), 4.27 (m, 1H), 4.08 (m, 1H), 3.91 (m, 3H), 3.68-3.59 (m, 6H), 3.47 (s, 2H), 3.24 (m, 2H), 2.78 (m, 2H), 2.47 (s, 3H), 2.01 (m, 1H), 2.27 (m, 1H), 2.14 (m, 1H). MS (m/z): 612.68 [M+1].

Example 88

Preparation of (R)-4-(4-fluorophenyl)-2-{[2-(3-((2-(3-hydroxyazetidin-1-yl)-2-oxoethyl)(methyl)amino)pyrrolidin-1-yl)-6-(2-methoxyethyl)imidazo[2,1-b][1,3,4]thiadiazol-5-yl](methyl)amino}thiazole-5-carbonitrile

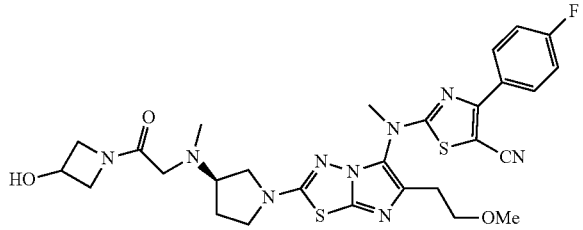 [SMILES: COCCc1nc2sc(N3CC[C@@H](N(C)CC(=O)N4CC(O)C4)C3)nn2c1N(C)c1nc(-c2ccc(F)cc2)c(C#N)s1]

STEP 1) 2-{[2-bromo-6-(2-hydroxyethyl)imidazo[2,1-b][1,3,4]thiadiazol-5-yl](methyl)amino}-4-(4-fluorophenyl)thiazole-5-carbonitrile 2-{[6-(2-(benzyloxy)ethyl)-2-bromoimidazo[2,1-b][1,3,4]thiadiazol-5-yl](methyl)amino}-4-(4-fluorophenyl)thiazole-5-carbonitrile (1.4 g, 2.465 mmol) was dissolved in dichloromethane (25 mL), the mixture was cooled in an ice bath under the protection of nitrogen gas. After the temperature decreased to 0-5° C., titanium tetrachloride (32 mg, 2.93 mmol) was dropwise added until addition was completed. After the temperature increased to room temperature and the mixture was reacted for 30 minutes, LC-MS detection indicated the reaction was completed. 1N HCl (15 mL) was dripped to the mixture for performing quenched reaction. After stirring the mixture for 15 minutes, the mixture was separated. The aqueous phase remained and was added with water (50 mL), regulated pH to about 7 with saturated sodium bicarbonate solution, and then filtered. Subsequently, the aqueous phase was continually regulated pH to about 10 with sodium hydroxide solution and extracted with dichloromethane (100 mL×3). The organic layer was combined, dried with anhydrous sodium sulfate, evaporated, and purified with column purification (dichloromethane:methanol=20:1), to obtain 898 mg of a white solid product, yield: 76%. MS (m/z): 479.0, 481.0 [M+1].

STEP 2) tert-butyl (R)-{1-5-[(5-cyano-4-(4-fluorophenyl)thiazol-2-yl)(methyl)amino]-6-(2-methoxyethyl)imidazo[2,1-b][1,3,4]thiadiazol-2-yl]pyrrolidin-3-yl}(methyl) carbamate (R)-3-tertbutoxycarbonyl pyrrolidine (90 mg, 0.45 mmol) was dissolved in DMF (6 mL), and potassium carbonate (186 mg, 1.35 mmol) and 2-{[2-bromo-6-(2-hydroxyethyl)imidazo[2,1-b][1,3,4]thiadiazol-5-yl](methyl)amino}-4-(4-fluorophenyl)thiazole-5-carbonitrile (140 mg, 0.293 mmol) were added. The mixture was heated to 70° C. and was reacted for 3 hours. LC-MS detection indicated the reaction was completed. 60% NaH (28 mg, 0.68 mmol) was added after the mixture was cooled in an ice bath. Then, iodomethane (128 mg, 0.9 mmol) was added to the mixture which was further stirred for 10 minutes, and the reaction continued for 3 hours and LC-MS detection indicated that the reaction was completed. The reaction mixture was poured into water (15 mL), and extracted with ethyl acetate (15 mL×3). The organic layer was combined, washed with saturated saline solution, dried with anhydrous sodium sulfate, evaporated, and purified with column purification (petroleum ether: ethyl acetate=1:2), to obtain 110 mg of a white solid product, yield: 61%.

STEP 3) (R)-4-(4-fluorophenyl)-2-{[2-(3-((2-(3-hydroxyazetidin-1-yl)-2-oxoethyl)(methyl)amino)pyrrolidin-1-yl)-6-(2-methoxyethyl)imidazo[2,1-b][1,3,4]thiadiazol-5-yl](methyl)amino}thiazole-5-carbonitrile Referring to Example 2, tert-butyl (R)-{1-5-[(5-cyano-4-(4-fluorophenyl)thiazol-2-yl) (methyl)amino]-6-(2-methoxyethyl)imidazo[2,1-b][1,3,4]thiadiazol-2-yl]pyrrolidin-3-yl}(methyl)carbamate was used to replace tert-butyl 4-{5-[(5-cyano-4-(4-fluorophenyl)thiazol-2-yl) (methyl)amino]-6-ethylimidiazo[2,1-b][1,3,4]thiadiazol-2-yl}piperazine-1-carboxylate, so that (R)-4-(4-fluorophenyl)-2-{[2-(3-((2-(3-hydroxyazetidin-1-yl)-2-oxoethyl)(methyl)amino)pyrrolidin-1-yl)-6-(2-methoxyethyl)imidazo[2,1-b][1,3,4]thiadiazol-5-yl](methyl)amino}thiazole-5-carbonitrile was prepared. $^1$H NMR (400 MHz, CDCl$_3$) δ: 8.15 (m, 2H), 7.16 (m, 2H), 4.68 (m, 1H), 4.40 (m, 1H), 4.28 (m, 1H), 4.08 (m, 1H), 3.91 (m, 1H), 3.70-3.59 (m, 8H), 3.46 (s, 2H), 3.33-3.28 (m, 5H), 2.83 (m, 2H), 2.51 (s, 3H), 2.28 (m, 1H), 2.18 (m, 1H). MS (m/z): 626.28 [M+1].

Example 89

Preparation of (R)-2-{[6-ethyl-2-(3-(ethyl(2-(3-hydroxyazetidin-1-yl)-2-oxoethyl)amino)pyrrolidin-1-yl)imidazo[2,1-b][1,3,4]thiadiazol-5-yl](methyl)amino}-4-(4-fluorophenyl)thiazole-5-carbonitrile

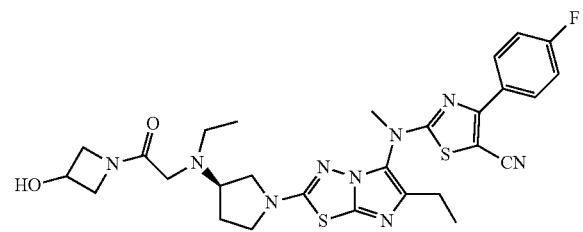 [SMILES: CCc1nc2sc(N3CC[C@@H](N(CC)CC(=O)N4CC(O)C4)C3)nn2c1N(C)c1nc(-c2ccc(F)cc2)c(C#N)s1]

(R)-2-{[6-ethyl-2-(3-((2-(3-hydroxyazetidin-1-yl)-2-oxoethyl)amino)pyrrolidin-1-yl)imidazo[2,1-b][1,3,4]thiadiazol-5-yl](methyl)amino}-4-(4-fluorophenyl)thiazole-5-carbonitrile (40 mg, 0.069 mmol) was dissolved in acetonitrile, followed by adding iodoethane (22 mg, 0.14 mmol) and potassium carbonate (29 mg, 0.21 mmol). The mixture was heated to 75° C. and was reacted overnight. After the reaction mixture was cooled, it was filtered, evaporated, and purified with thin preparative plate (dichloromethane: methanol=20:1), to obtain 26 mg of a white solid product, yield: 62%. $^1$H NMR (400 MHz, CDCl$_3$) δ: 8.17 (m, 2H), 7.18 (m, 2H), 4.71 (m, 1H), 4.43 (m, 1H), 4.28 (m, 1H), 4.11 (m, 1H), 3.92 (m, 1H), 3.73-3.41 (m, 9H), 2.94 (m, 3H), 2.61 (m, 2H), 2.31 (m, 2H), 1.30 (m, 3H), 1.21 (m, 3H). MS (m/z): 610.2 [M+1].

Example 90

Preparation of (R)-2-{[6-ethyl-2-(3-((cyclopropylmethyl(2-(3-hydroxyazetidin-1-yl)-2-oxoethyl)amino)pyrrolidin-1-yl)imidazo[2,1-b][1,3,4]thiadiazol-5-yl](methyl)amino}-4-(4-fluorophenyl)thiazole-5-carbonitrile

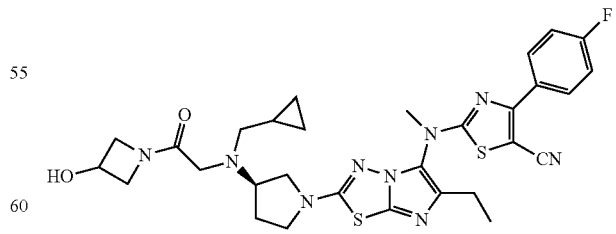

Referring to Example 89, bromomethylcyclopropane was used to replace iodoethane, so that (R)-2-{[6-ethyl-2-(3-((cyclopropylmethyl(2-(3-hydroxyazetidin-1-yl)-2-oxoethyl)amino)pyrrolidin-1-yl)imidazo[2,1-b][1,3,4]thiadiazol-5-yl](methyl)amino}-4-(4-fluorophenyl)thiazole-5- carbonitrile was prepared. ¹H NMR (400 MHz, CDCl₃) δ: 8.15 (m, 2H), 7.16 (m, 2H), 4.69 (m, 1H), 4.42 (m, 1H), 4.26 (m, 1H), 4.09 (m, 1H), 3.89 (m, 1H), 3.70-3.42(m, 10H), 2.72 (m, 2H), 2.59 (m, 2H), 2.27 (m, 2H), 1.28 (m, 3H), 0.93 (m, 1H), 0.59 (m, 2H), 0.20 (m, 2H). MS (m/z): 636.3 [M+1].

Example 91

Preparation of (R)—N-{1-[5-((5-cyano-4-(4-fluorophenyl)thiazol-2-yl)(methyl)amino)-6-ethylimidazo[2,1-b][1,3,4]thiadiazol-2-yl]pyrrolidin-3-yl}-N-(2-(3-hydroxyazetidin-1-yl)-2-oxoethyl)formamide

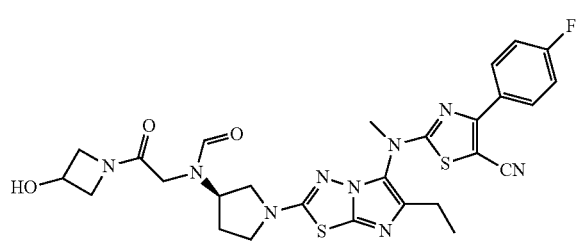 [SMILES: CCc1nc2sc(N3CC[C@@H](N(C=O)CC(=O)N4CC(O)C4)C3)nn2c1N(C)c1nc(-c2ccc(F)cc2)c(C#N)s1]

(R)-2-{[6-ethyl-2-(3-((2-(3-hydroxyazetidin-1-yl)-2-oxoethyl)amino)pyrrolidin-1-yl)imidazo[2,1-b][1,3,4]thiadiazol-5-yl](methyl)amino}-4-(4-fluorophenyl)thiazol-5-carbonitrile (40 mg, 0.069 mmol) was dissolved in dichloromethane (3 mL), followed by adding formic acid (9.5 mg, 0.21 mmol), HATU (80 mg, 0.21 mmol) and triethylamine (30 mg, 0.3 mmol). The mixture was reacted at room temperature for 2 days. Then, the reaction mixture was poured into water (10 mL), and extracted with dichloromethane (10 mL×3). The organic layer was combined, dried with anhydrous sodium sulfate, evaporated, and purified with thin preparative plate (dichloromethane:methanol=20:1), to obtain 23 mg of a white solid product, yield: 55%. ¹H NMR (400 MHz, CDCl₃) δ: 12.05 (br, 1H), 8.15 (m, 2H), 7.18 (m, 2H), 4.70 (m, 1H), 4.48 (m, 1H), 4.28 (m, 1H), 4.14 (m, 1H), 3.92 (m, 1H), 3.84-3.74 (m, 2H), 3.66-3.51 (m, 6H), 3.12 (m, 2H), 2.61 (m, 2H), 2.41-2.34 (m, 2H), 1.30 (m, 3H). MS (m/z): 610.2 [M+1].

Biological Test

Analysis In Vitro: LPC was Used as Substrate for Screening Enzyme Activity

Principle: Lysophosphatidylcholine (LPC) as substrate is hydrolyzed by using the activity of lysoPLD enzyme, to produce lysophosphatidic acid (LPA) and choline, which is oxidized to produce $H_2O_2$ under the action of choline oxidase. In presence of horse radish peroxidase (HPR), Amplex Red reagent is reacted with $H_2O_2$ in a quantitative chemistry ratio of 1 to 1, to produce strong fluorescence products, which are detected by a fluorescent quantitative test.

Experimental procedures: the compounds to be tested were dissolved in DMSO, to prepare 10 mM of stock solution, which was diluted in a gradient concentration of 3 times with DMSO from 10 mM, to generate 10 concentration gradients. The reaction buffer solution was used for preparing a mixed solution 1 of 2 ng/μl ATX, 2 U/ml HRP and 0.2 U/ml choline oxidase in a final concentration. 20 μl of the above mixed solution 1 was added to each hole of an experiment board, with 10 nl/hole. The compounds diluted with DMSO were transferred into an experiment board with Echo550. The reaction buffer solution was used for preparing a mixed solution 2 of 60 mM LPC and 400 μM Amplex Red in a final concentration. 20 μl of the above mixed solution 2 was added to each hole of the experiment board.

After addition, the experiment board was shook for 30 seconds on a shaker, and incubated for 30 minutes. Envision was used to read the fluorescence signals with an exciting light at 530 nm and emitted light at 590 nm. Inhibition ratio of the compounds to enzyme reaction was calculated according to the ratio of fluorescence, and $IC_{50}$ of the compounds was analyzed and calculated by software, seeing Table 1.

TABLE 1

INHIBITORY ACTIVITY ANALYSIS OF THE COMPOUNDS AGAINST ATX, WITH LPC AS SUBSTRATE

| COMPOUNDS TESTED | LPC - $IC_{50}$ | COMPOUNDS TESTED | LPC - $IC_{50}$ |
|---|---|---|---|
| Example 1 | + | Example 2 | +++ |
| Example 3 | ++ | Example 4 | +++ |
| Example 5 | ++ | Example 6 | +++ |
| Example 7 | ND | Example 8 | +++ |
| Example 9 | ND | Example 10 | ++++ |
| Example 11 | ++++ | Example 12 | ++++ |
| Example 13 | +++ | Example 14 | ++++ |
| Example 15 | ++++ | Example 16 | + |
| Example 17 | +++ | Example 18 | +++ |
| Example 19 | ++++ | Example 20 | ++++ |
| Example 21 | ++++ | Example 22 | ++++ |
| Example 23 | +++ | Example 24 | ++++ |
| Example 25 | +++ | Example 26 | + |
| Example 27 | +++ | Example 28 | +++ |
| Example 29 | ++++ | Example 30 | ++++ |
| Example 31 | +++ | Example 32 | +++ |
| Example 33 | ++++ | Example 34 | ++++ |
| Example 35 | ++++ | Example 36 | ++++ |
| Example 37 | ++++ | Example 38 | ++++ |
| Example 39 | +++ | Example 40 | +++ |
| Example 41 | ++++ | Example 42 | +++ |
| Example 43 | ++++ | Example 44 | +++ |
| Example 45 | ++++ | Example 46 | +++ |
| Example 47 | ++++ | Example 48 | ND |
| Example 49 | ND | Example 50 | ND |
| Example 51 | ND | Example 52 | ND |
| Example 53 | ND | Example 54 | ND |
| Example 55 | ND | Example 56 | ND |
| Example 57 | ND | Example 58 | ND |
| Example 59 | ND | Example 60 | ND |
| Example 61 | ND | Example 62 | ND |
| Example 63 | ND | Example 64 | ND |
| Example 65 | ND | Example 66 | ND |
| Example 67 | ND | Example 68 | ND |
| Example 69 | ND | Example 70 | ND |
| Example 71 | ND | Example 72 | ND |
| Example 73 | ND | Example 74 | ND |
| Example 75 | ND | Example 76 | ND |
| Example 77 | ND | Example 78 | ND |
| Example 79 | ND | Example 80 | ND |
| Example 81 | ++++ | Example 82 | +++ |
| Example 83 | ++ | Example 84 | +++ |
| Example 85 | ++ | Example 86 | + |
| Example 87 | ++ | Example 88 | +++ |
| Example 89 | +++ | Example 90 | + |
| Example 91 | ++++ | | |

+: ≥1000 Nm; ++: 500-1000 nM; +++: 100-500 nM; ++++: 0.01-100 nM
NOTE:
ND means not detected According to Table 1, the compounds of the present disclosure have a good inhibitory activity against ATX, and $IC_{50}$ values for most of the compounds are below 500 nM, even below 100 nM.

Analysis In Vitro: Detection of LPA in Human Plasma for Screening Activity

Principle: LPC in plasma being used as a substrate, the produced LPA 18:2 (LPA 17:0 as an internal standard) is detected by LC/MS/MS quantitative analysis. At different concentrations of the compounds to be tested, the percentage of residual activity is obtained by the ratio of the production of LPA18:2 to that in the absence of the compounds to be tested, thereby calculating $IC_{50}$ values.

Experiment procedures: blank plasma was derived from at least 6 individual people. The compounds to be tested were diluted from stock solution in 3-fold dilution gradient, to produce 8 concentrations of working solution (with zero) in series. 10 μL of the melting blank plasma samples were taken and iced methanol solution containing internal standard (LPA 17:0) was added to it, so that the mixture directedly performed protein precipitation, which served as a system control sample. 2 μL of the working solution in different concentration was taken and 198 μL of blank human plasma was added, which was incubated with a concentration of 0 to 10 μM. The samples were placed at an incubater containing 5% $CO_2$ at 37° C., and incubated for 2 hours. When the incubation was completed, 10 μL of plasma sample was taken and appropriate volume of iced methanol solution containing internal standard (LPA 17:0) was added into it, so that the mixture directedly performed protein precipitation. The precipitation was centrifuged to take supernatant. LPA 18:2 was detected by LC/MS/MS and $IC_{50}$ values were analyzed and calculated by software, seeing Table 2.

TABLE 2

ANALYSIS OF $IC_{50}$ VALUES OF THE COMPOUND OF THE PRESENT DISCLOSURE IN HUMAN WHOLE BLOOD

| COMPOUNDS TESTED | PLASMA ACTIVITY $IC_{50}$ | COMPOUNDS TESTED | PLASMA ACTIVITY $IC_{50}$ |
| --- | --- | --- | --- |
| Example 1 | ND | Example 2 | +++ |
| Example 3 | ND | Example 4 | ++++ |
| Example 5 | ND | Example 6 | ND |
| Example 7 | ++ | Example 8 | +++ |
| Example 9 | ++ | Example 10 | ++++ |
| Example 11 | ++++ | Example 12 | ++++ |
| Example 13 | ND | Example 14 | ++++ |
| Example 15 | ++++ | Example 16 | ND |
| Example 17 | ++++ | Example 18 | ND |
| Example 19 | +++ | Example 20 | ++++ |
| Example 21 | ++++ | Example 22 | ++++ |
| Example 23 | +++ | Example 24 | ++++ |
| Example 25 | ND | Example 26 | ND |
| Example 27 | ND | Example 28 | ND |
| Example 29 | ND | Example 30 | ND |
| Example 31 | ND | Example 32 | ND |
| Example 33 | ND | Example 34 | ND |
| Example 35 | ND | Example 36 | +++ |
| Example 37 | +++ | Example 38 | +++ |
| Example 39 | ND | Example 40 | ND |
| Example 41 | +++ | Example 42 | ND |
| Example 43 | ND | Example 44 | ND |
| Example 45 | +++ | Example 46 | ND |
| Example 47 | ++++ | Example 48 | +++ |
| Example 49 | ++ | Example 50 | +++ |
| Example 51 | +++ | Example 52 | +++ |
| Example 53 | ++++ | Example 54 | +++ |
| Example 55 | +++ | Example 56 | ++++ |
| Example 57 | +++ | Example 58 | ++++ |
| Example 59 | +++ | Example 60 | + |
| Example 61 | +++ | Example 62 | +++ |
| Example 63 | ++++ | Example 64 | ++++ |
| Example 65 | ++++ | Example 66 | ++++ |
| Example 67 | ++++ | Example 68 | ++++ |
| Example 69 | +++ | Example 70 | +++ |
| Example 71 | +++ | Example 72 | +++ |
| Example 73 | +++ | Example 74 | ++++ |
| Example 75 | +++ | Example 76 | ++++ |
| Example 77 | ++++ | Example 78 | ++++ |
| Example 79 | +++ | Example 80 | ++++ |

+: ≥1000 nM; ++: 500-1000 nM; +++: 100-500 nM; ++++: 0.01-100 nM
NOTE:
ND means not detected According to Table 2, the compound of the present disclosure also effectively inhibits ATX in human plasma, so that LPC is inhibited to be hydrolyzed to LPA, and the $IC_{50}$ values for most of the compounds are below 100 nM.

In conclusion, the compound of the present disclosure has a great inhibitory activity, excellent efficacy in vivo and pharmacokinetic properties, and well clinical application prospect.

Although the present invention has been disclosed in the form of preferred embodiments and variations thereon, it will be understood that numerous additional modifications and variations could be made thereto without departing from the scope of the invention.

For the sake of clarity, it is to be understood that the use of 'a' or 'an' throughout this application does not exclude a plurality, and 'comprising' does not exclude other steps or elements.

The invention claimed is:
1. A compound of formula (Ic), or a pharmaceutically acceptable salt, stereoisomer, tautomer, or mixture thereof:

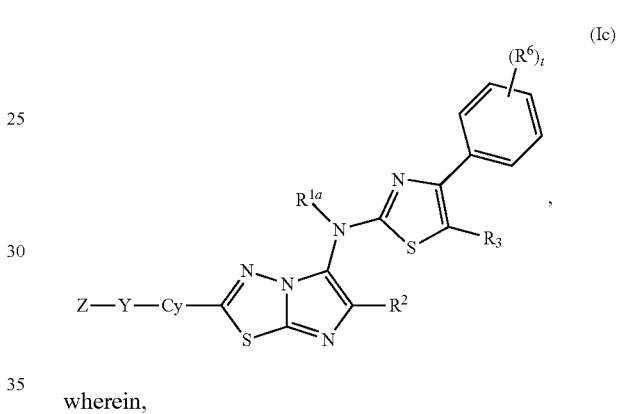

wherein,
t is 1 or 2;
Cy is

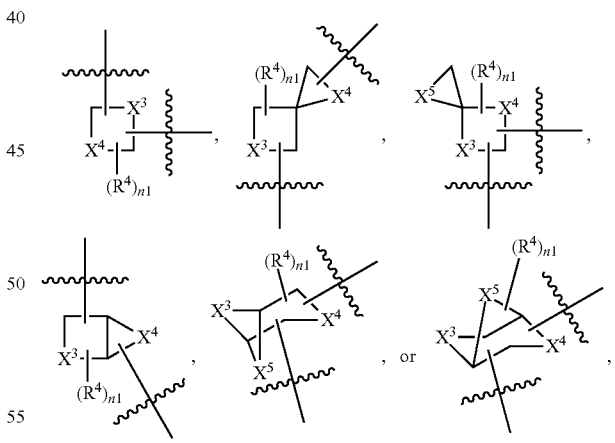

wherein,
each of $X^3$, $X^4$, and $X^5$ is independently —NH—, —$(CH_2)_{m1}$—NH—$(CH_2)_{m2}$—, or —$(CH_2)_{m3}$—;
each m1 is independently 1, 2, or 3;
each m2 is independently 0, 1, 2, or 3;
each m3 is independently 1, 2, or 3; and
n1 is 0, 1, 2, 3, or 4;
Y is -$(L^1$-$W^1)_m$-$L^2$-;
$L^1$ is absent, or $L^1$ is —N($R^t$)—;
$W^1$ is $C_{1-4}$ alkylene;

L² is absent, or L² is —C(=O)—, —N(R^b)—, —C(=O)N(R^c)—, —N(R^c)C(=O)—, —C(=O)N(R^c)—R^15—C(=O)O—, —N(R^d)C(=O)N(R^c)—, —S(=O)_{0-2}—, —S(=O)_{1-2}N(R^e)—, or —N(R^f)S(=O)_{1-2}—;

Z is H, C_{1-4} alkyl, C_{2-4} alkenyl, C_{2-4} alkynyl, C_{3-8} cycloalkyl, or C_{2-7} heterocyclyl, wherein each of C_{1-4} alkyl, C_{2-4} alkenyl, C_{2-4} alkynyl, C_{3-8} cycloalkyl, or C_{2-7} heteroCyClyl is optionally substituted with one or more R⁵;

m is 0, or 1;

R^{1a} is H, C_{1-4} alkyl;

each R² is independently C_{1-6} alkyl, C_{2-6} alkenyl, C_{2-6} alkynyl, C_{1-6} haloalkyl, C_{1-6} hydroxyalkyl, C_{1-6} alkoxy-C_{1-6} alkyl, or C_{6-10} aryloxy- C_{1-6} alkyl;

each R³ is independently H, —CN, F, Cl, Br, I, C_{1-6} alkyl;

each R⁴ is independently oxo (C=O), C_{1-6} alkyl, C_{2-6} alkenyl, C_{2-6} alkynyl, C_{1-6} hydroxyalkyl, —C(=O)OR^{8a}, or —C(=O)NR^{9a}R⁹;

each R⁵ is independently —CN, —OH, F, Cl, Br, I, C_{1-6} alkyl, C_{2-6} alkenyl, C_{2-6} alkynyl, C_{1-6} alkoxyl, —OC(=O)R^{8a}, or —C(=O)OR^{8a};

each R⁶ is independently —CN, F, Cl, Br, I, or C_{1-6} haloalkyl;

R^{8a}, R⁹ are, independently in each instance, H, C_{1-6} alkyl, C_{2-6} alkenyl, or C_{2-6} alkynyl;

R^{9a} is independently H, C_{1-6} alkyl, C_{2-6} alkenyl, or C_{2-6} alkynyl;

R^15 is C_{1-6} alkylene;

R^16 is H; and

R^c, R^d, R^e, R^f and R^i are, independently in each instance, H, C_{1-6} alkyl, C_{2-6} alkenyl, R^16—C(=O)—, or C_{3-8} cycloalkyl-C_{1-4} alkyl.

2. The compound of claim 1, wherein,
R^{1a} is methyl, ethyl, propyl.

3. The compound of claim 1, wherein,
R^{8a}, R⁹ are, independently in each instance, H, C_{1-4} alkyl, C_{2-4} alkenyl, or C_{2-4} alkynyl;
R^{9a} is independently in each instance, H, C_{1-4} alkyl, C_{2-4} alkenyl, or C_{2-4} alkynyl.

4. The compound of any one of claim 1, wherein Cy is

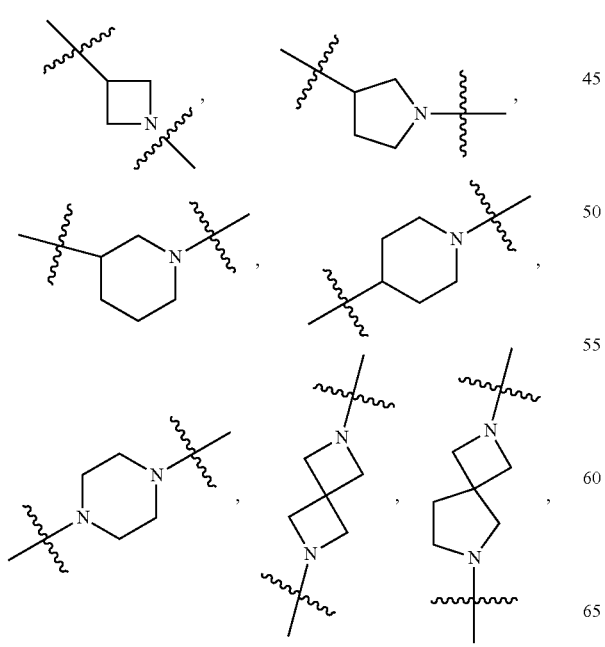

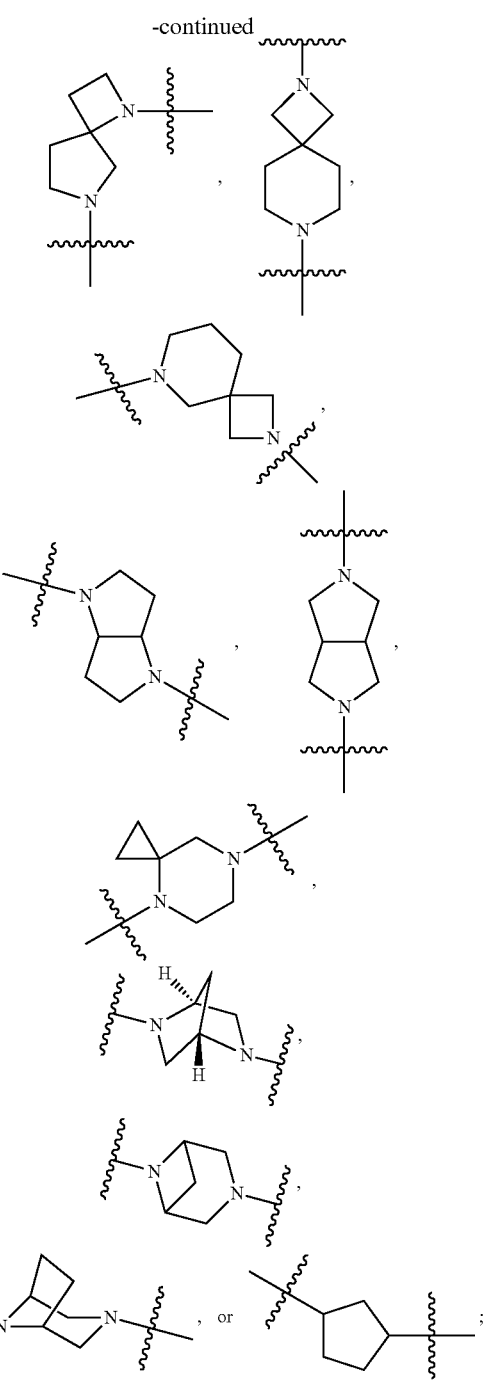

wherein Cy is optionally substituted with 1, 2, 3, or 4 R⁴.

5. The compound of claim 1, wherein
R^c, R^d, R^e, R^f, and R^i are, independently in each instance, H, or C_{1-4} alkyl, C_{2-4} alkenyl, R^16—C(=O)—, or C_{3-6} cycloalkyl-C_{1-4} alkyl.

6. The compound of claim 1, wherein Z is H, methyl, ethyl, propyl, or tert-butyl, or Z is:

-continued

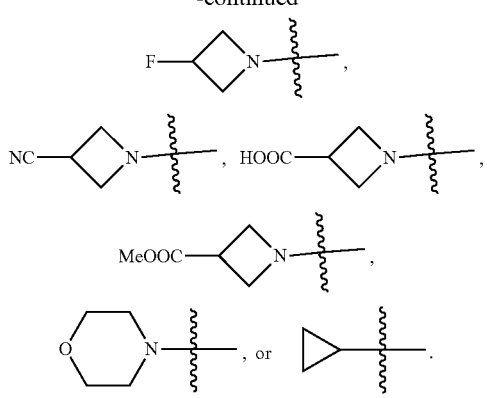

7. The compound of claim 1, wherein, each $R^2$ is independently $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ alkoxy-$C_{1-4}$ alkyl, or $C_{6-10}$ aryloxy-$C_{1-4}$ alkyl.

8. The compound of claim 1, wherein, each $R^2$ is independently methyl, ethyl, propyl, methoxymethyl, methoxyethyl, methoxypropyl, ethoxymethyl, ethoxyethyl, benzyloxymethyl, or benzyloxyethyl, —$CH_2CH_2OH$, or —$CH_2CF_3$.

9. The compound of claim 1, wherein, each $R^3$ is independently H, —CN, F, or $C_{1-4}$ alkyl.

10. The compound of claim 1, wherein, each $R^4$ is independently oxo (C=O), $C_{1-4}$ alkyl, $C_{2-4}$ alkenyl, $C_{2-4}$ alkynyl, $C_{1-4}$ hydroxyalkyl-C(=O)$OR^{8a}$, or —C(=O)$NR^{9a}R^9$.

11. The compound of claim 1, wherein, each $R^5$ is independently —CN, —OH, F, $C_{1-4}$ alkoxy, —OC(=O)$R^{8a}$, or —C(=O)$OR^{8a}$.

12. The compound of claim 1, wherein, each $R^6$ is independently —CN, F, Cl, Br, I, or $C_{1-4}$ haloalkyl.

13. The compound of claim 1, wherein, $R^{8a}$, $R^9$ are, independently in each instance, H, or $C_{1-4}$ alkyl;

$R^{9a}$ is independently in each instance, H, or $C_{1-4}$ alkyl.

14. A compound having a structure of one of formulas (Id) to (Ig):

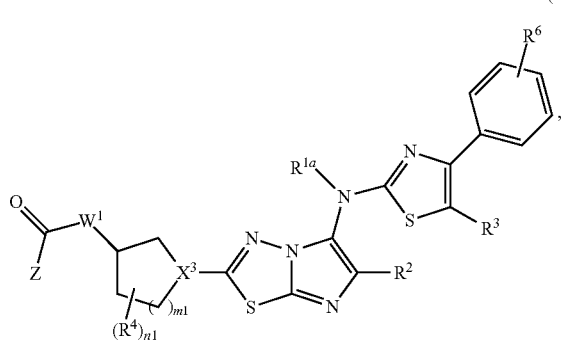

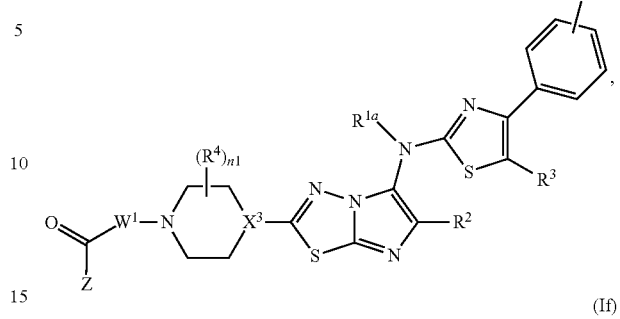

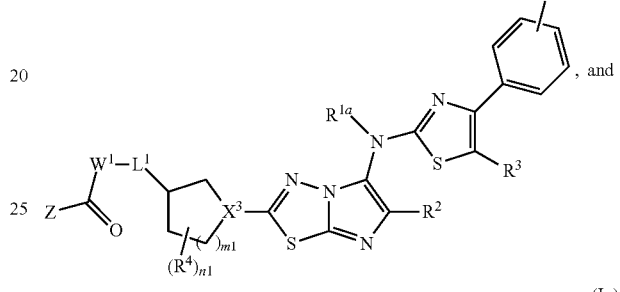

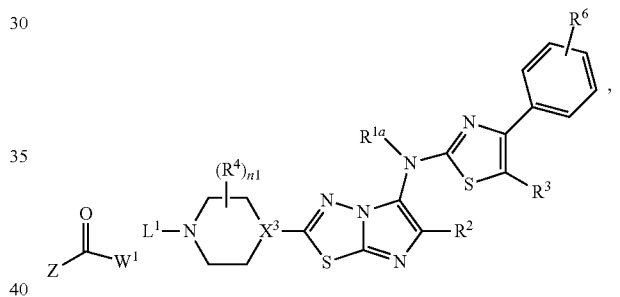

wherein,

Z is H, $C_{1-4}$ alkyl, $C_{2-4}$ alkenyl, $C_{2-4}$ alkynyl, $C_{3-8}$ cycloalkyl, $C_{2-7}$ heterocyclyl, wherein each of $C_{1-4}$ alkyl, $C_{2-4}$ alkenyl, $C_{2-4}$ alkynyl, $C_{3-8}$ cycloalkyl, or $C_{2-7}$ heterocyclyl is optionally substituted with one or more $R^5$;

$R^{1a}$ is H, methyl, or —$CF_3$;

$R^2$ is independently ethyl, or —$CH_2CF_3$, —$CH_2CH_2OH$, or benzyloxyethyl;

$R^3$ is independently H, —CN, F, methyl, ethyl, methoxymethyl, methoxyethyl, methoxypropyl, ethoxymethyl, ethoxyethyl, —$CF_3$, —$CH_2CF_3$, or —$CH_2CH_2OH$;

$R^4$ is oxo (=O), methyl, ethyl, —$CH_2OH$, —C(=O)$OCH_3$, or —NHC(=O)$CH_3$;

each $R^5$ is independently —CN, —OH, F, Cl, Br, I $C_{1-6}$ alkyl, $C_{1-6}$ alkoxyl, —OC(=O)$R^{8a}$, or —C(=O)$OR^{8a}$;

$R^6$ is —CN, F, Cl, —$CF_3$, or —$CH_2CF_3$, or —C(=O)$CF_3$;

$X^3$ is N, or CH;

$L^1$ is absent, or $L^1$ is —N($R^i$);

$W^1$ is $C_{1-4}$ alkylene;

$R^{8a}$ is $C_{1-4}$ alkyl;

$R^i$ is independently H, or methyl;

m1 is 1, or 2; and n1 is 0, 1, or 2;

or a pharmaceutically acceptable salt, stereoisomer, tautomer, or mixture thereof.

15. The compound of claim 1, wherein the compound is a compound having one of the following structures:
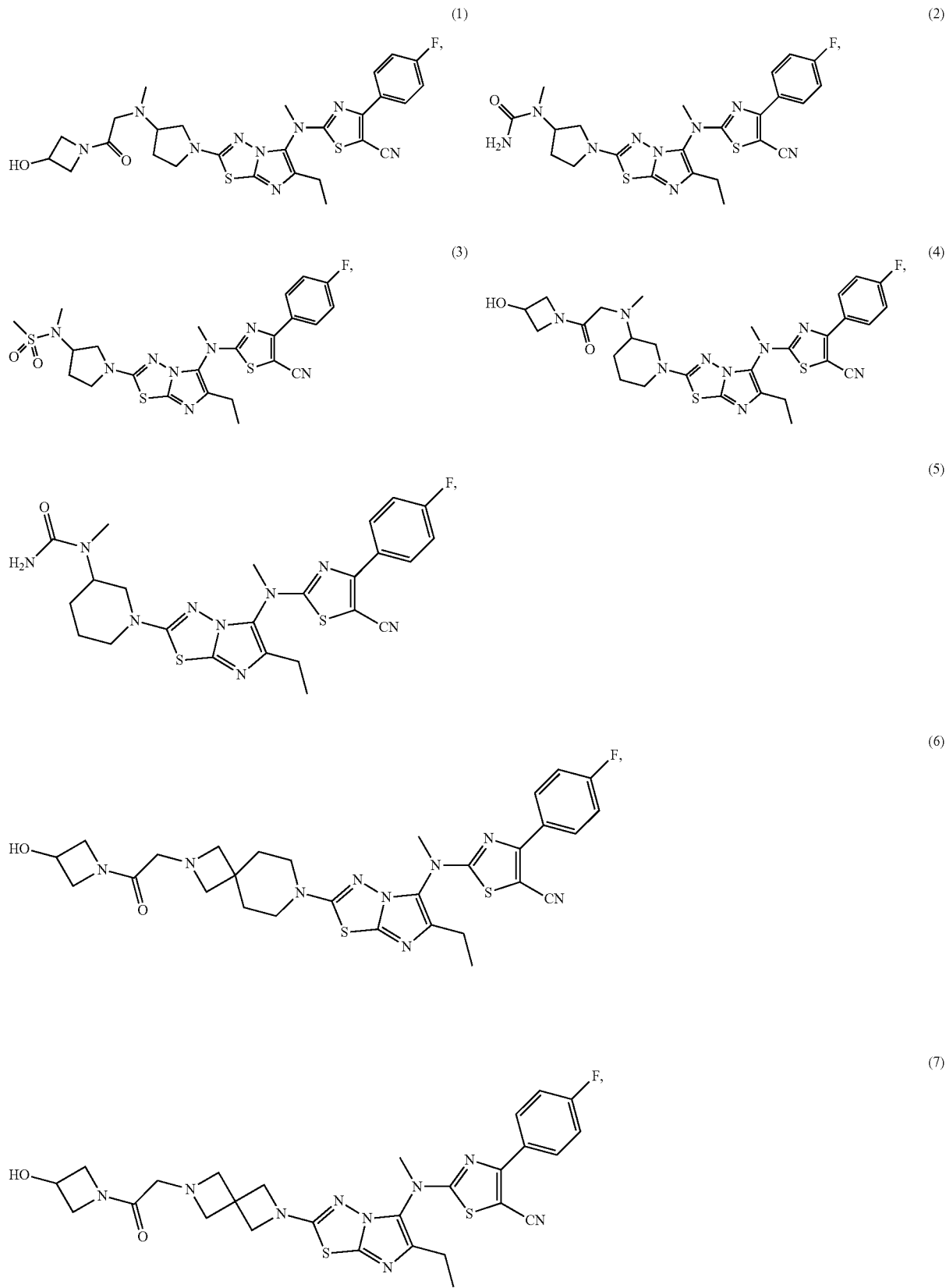

-continued
(8)
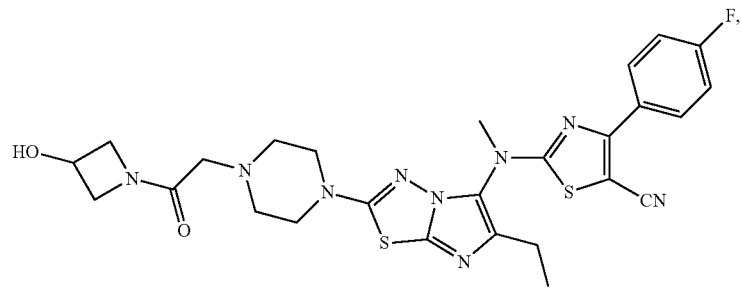
(9)
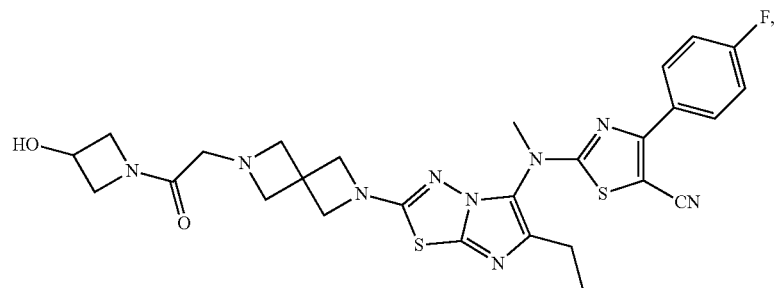
(10)
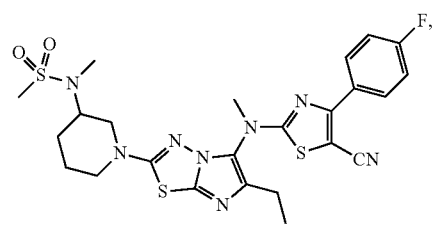
(11)
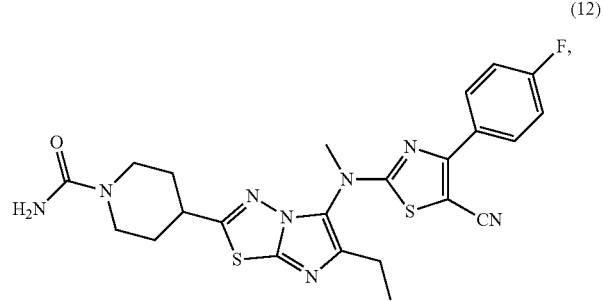
(12)
(13)
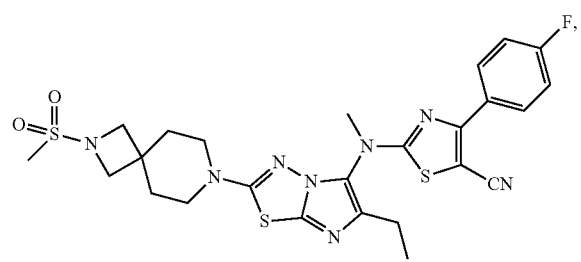
(14)
(15)
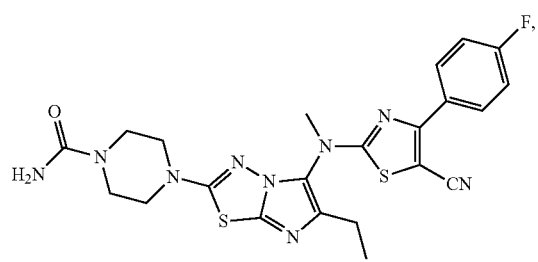

-continued
(16)
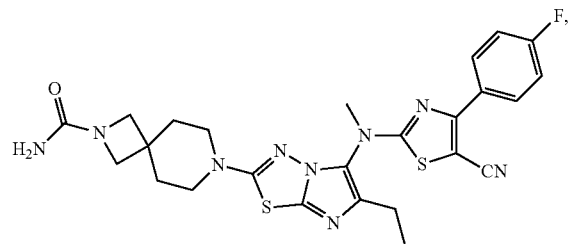
(17)
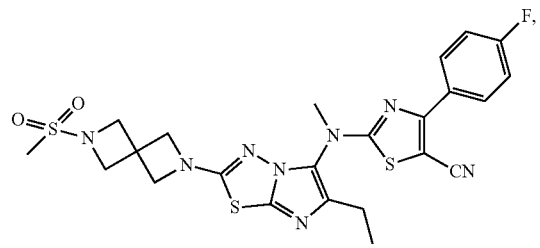
(18)
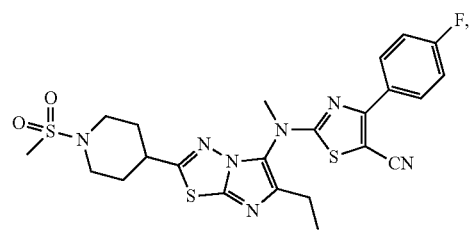
(19)
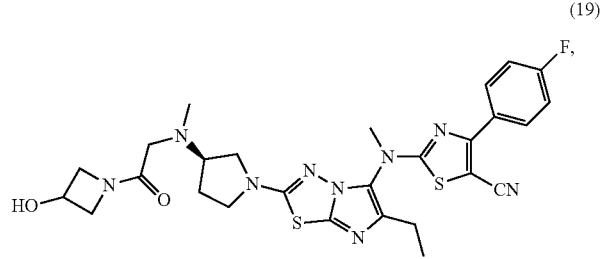
(20)
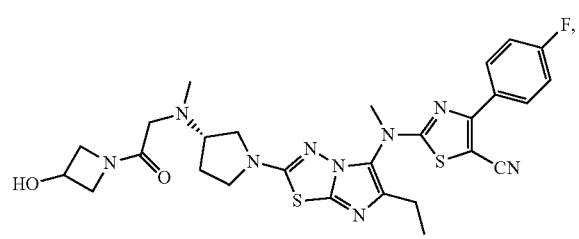
(21)
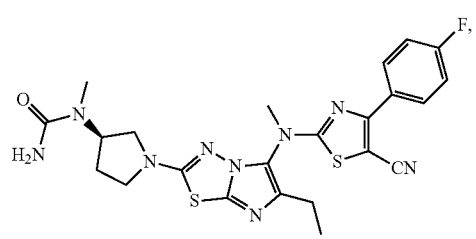
(22)
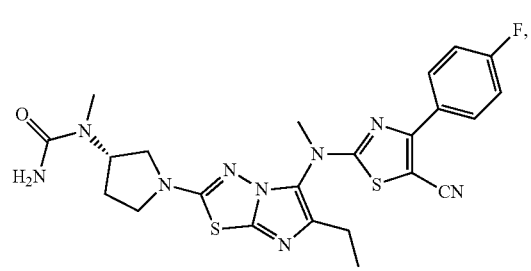
(23)
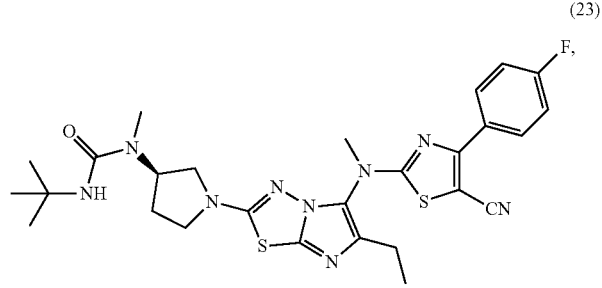
(24)
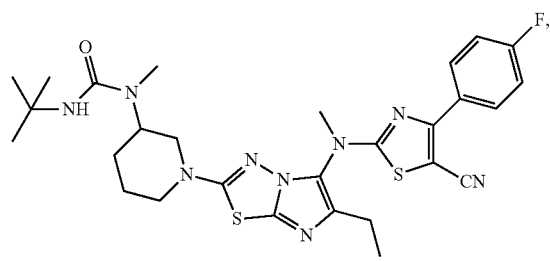
(26)
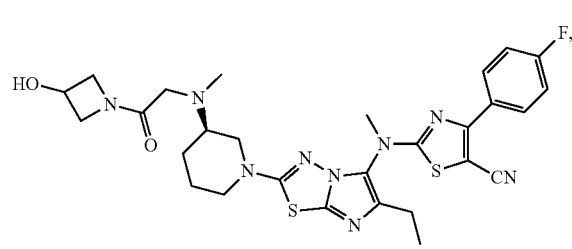
(27)
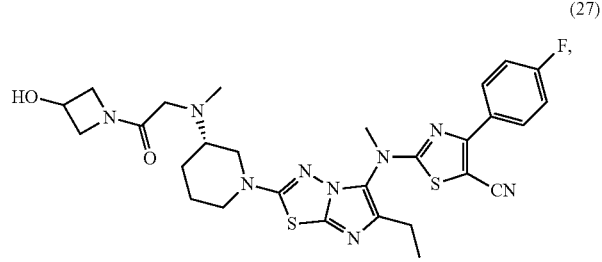

-continued
(28)
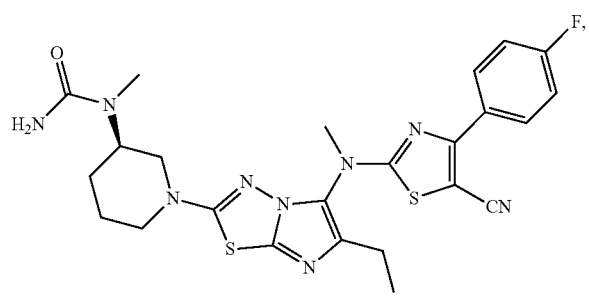
(29)
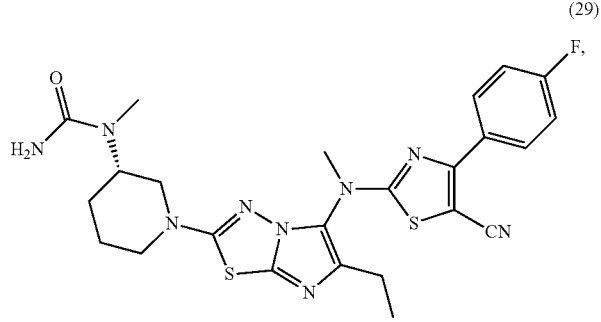
(30)
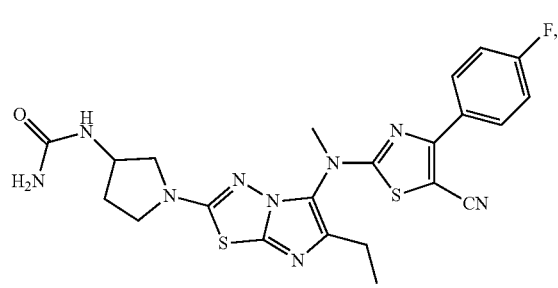
(31)
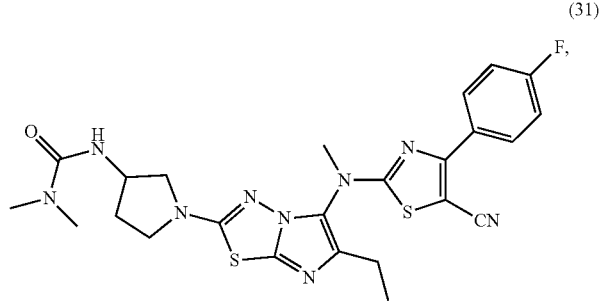
(32)
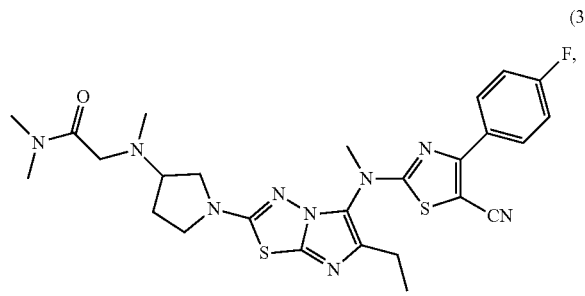
(33)
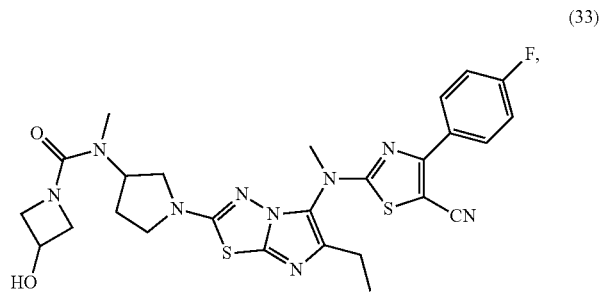
(56)
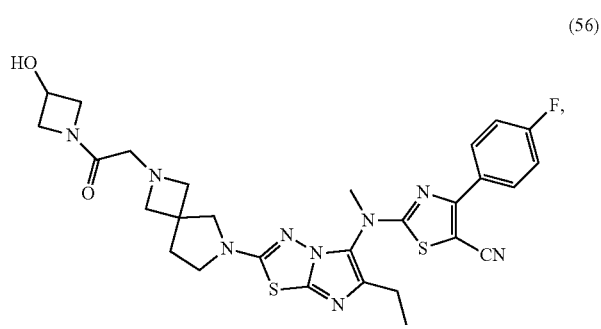 [SMILES: CCc1nc2sc(N3CCC4(CN(CC(=O)N5CC(O)C5)C4)C3)nn2c1N(C)c1nc(-c2ccc(F)cc2)c(C#N)s1]
(64)
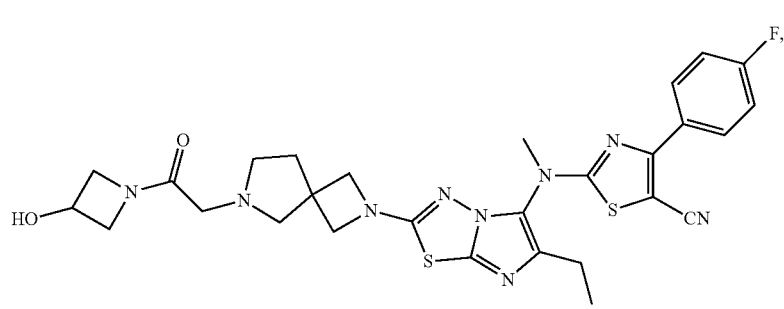

(70)
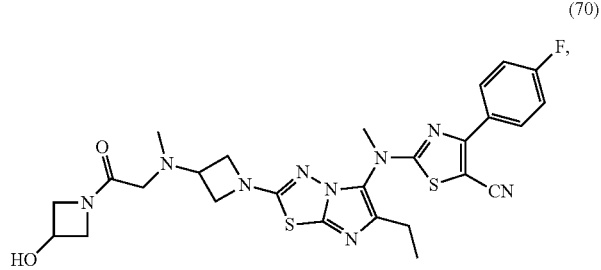
(71)
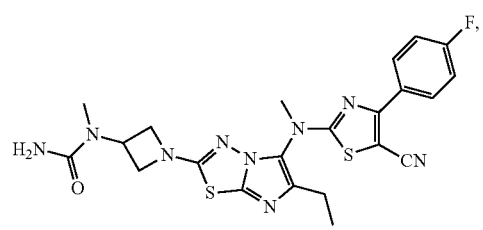
(72)
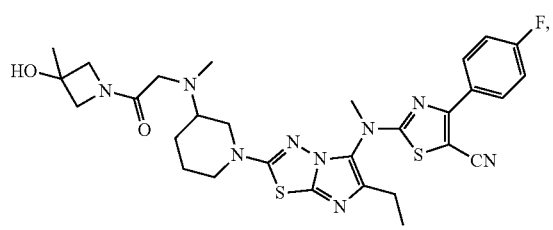
(78)
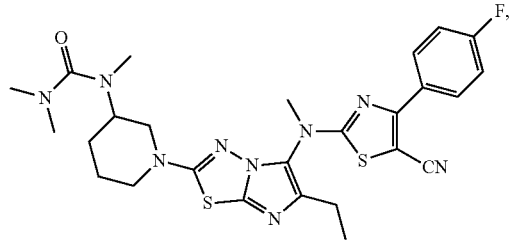
(83)
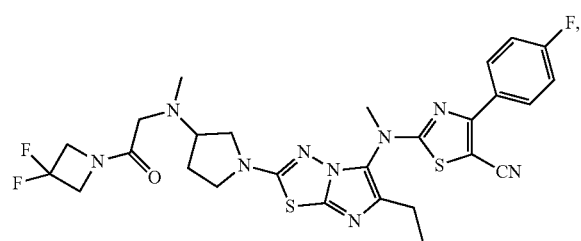
(84)
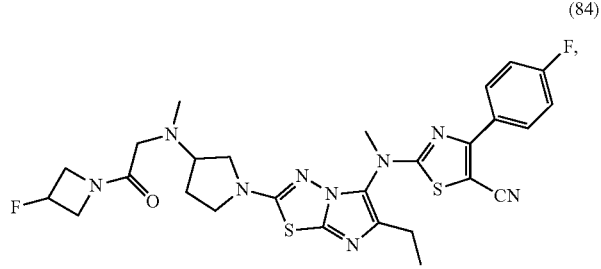
(85)
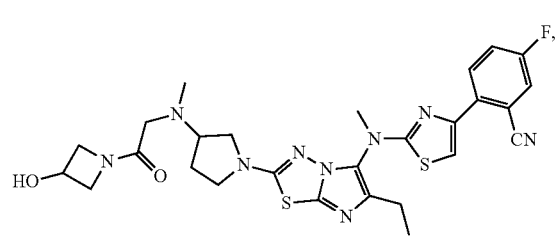
(87)
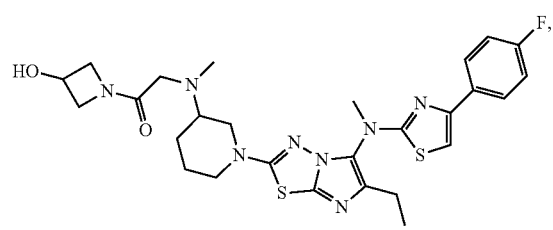
(88)
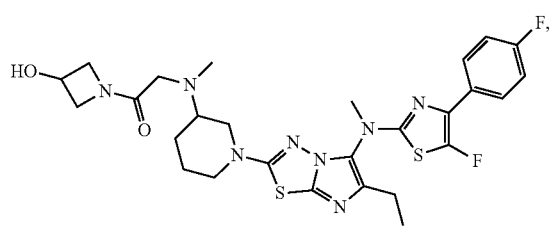

-continued
(89)
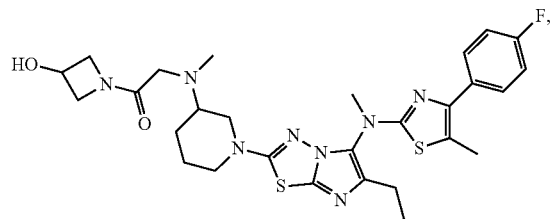
(91)
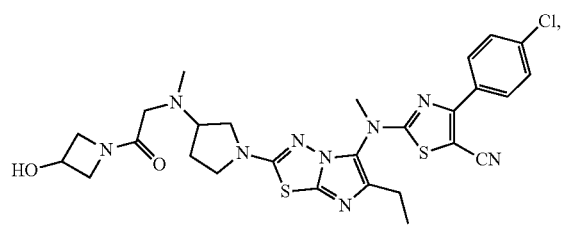
(92)
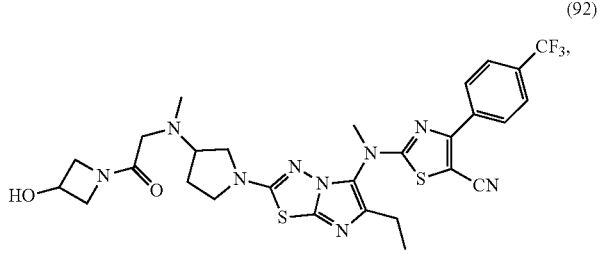
(94)
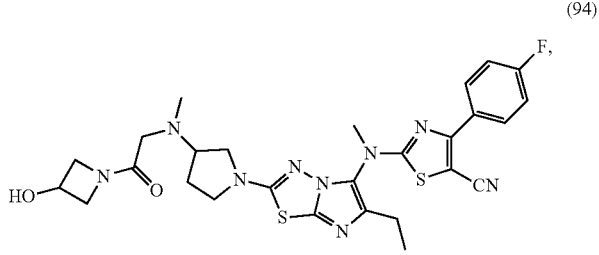
(95)
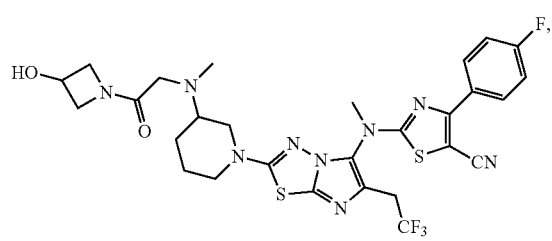
(108)
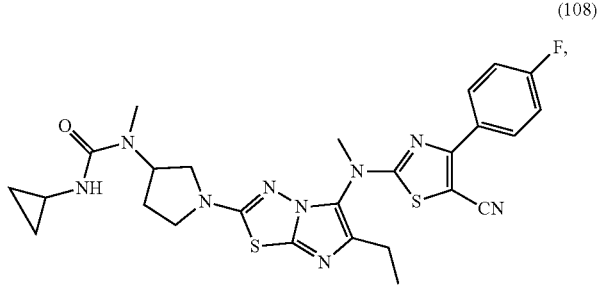
(109)
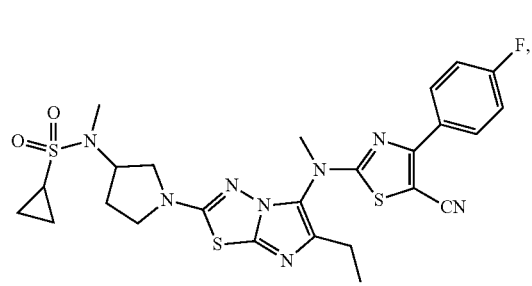
(110)
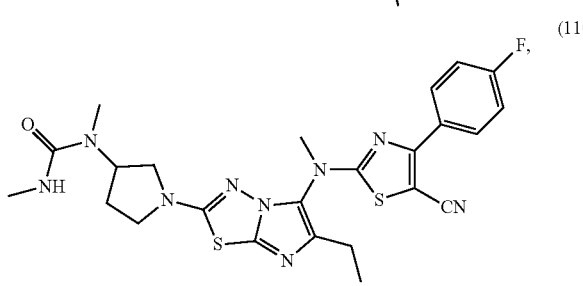

-continued
(111)
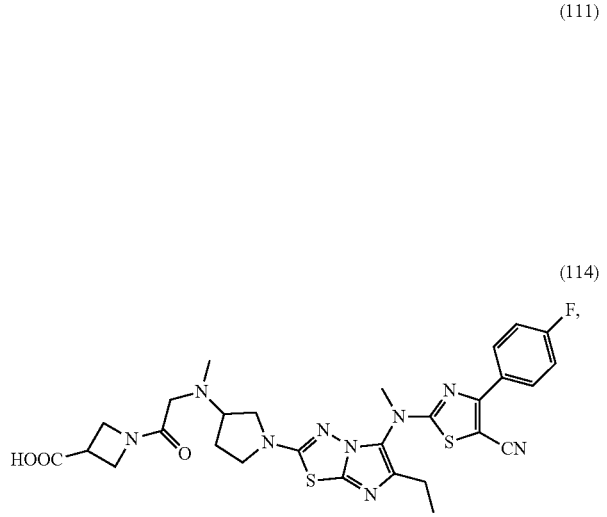
(113)
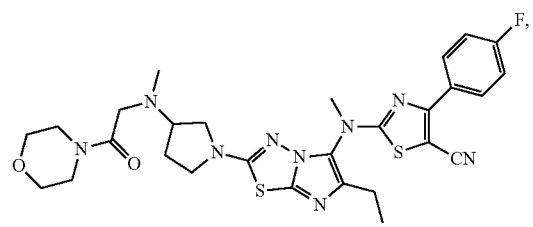
(114)
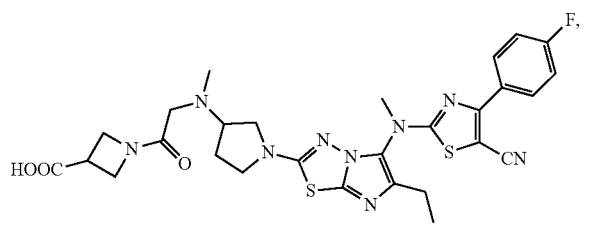
(115)
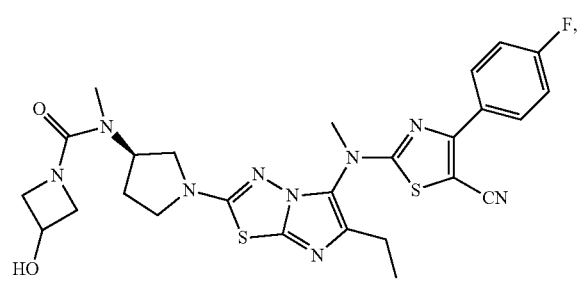
(116)
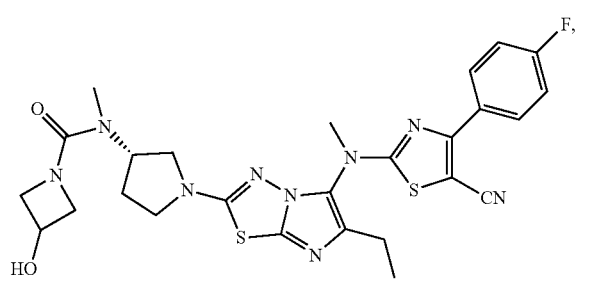
(117)
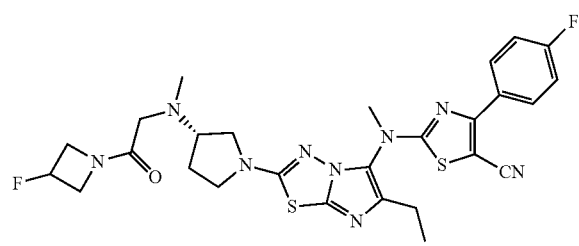
(118)
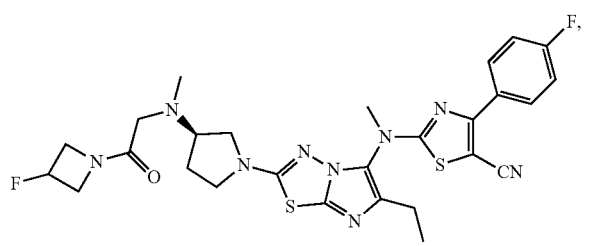
(119)
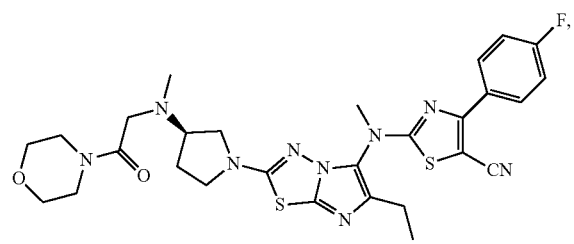
(120)
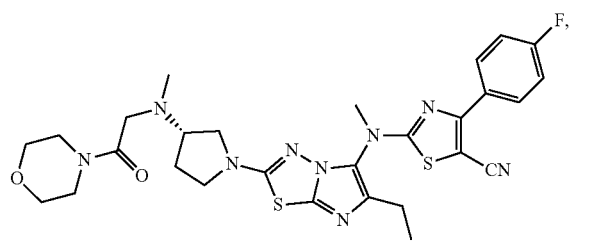
(121)
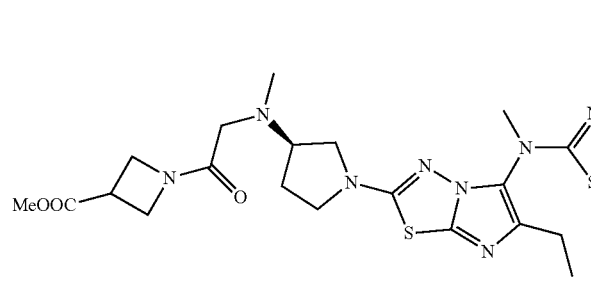

-continued
(122)
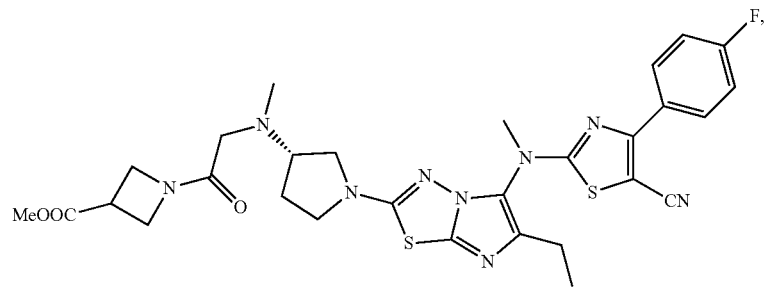
(123)
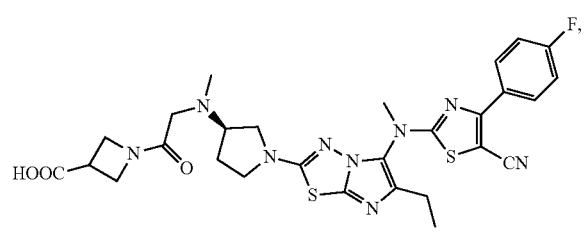
(124)
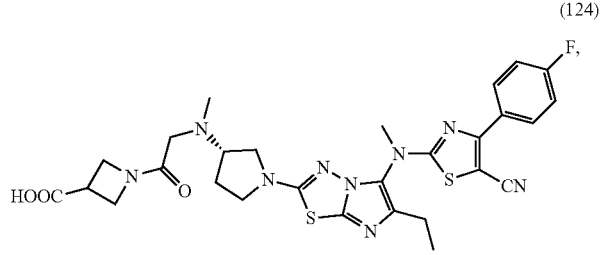
(125)
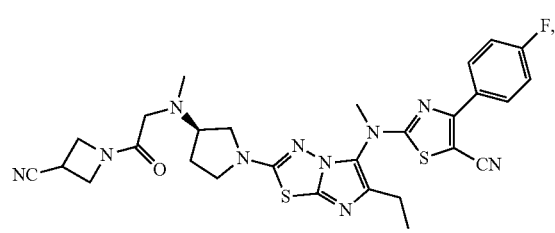
(126)
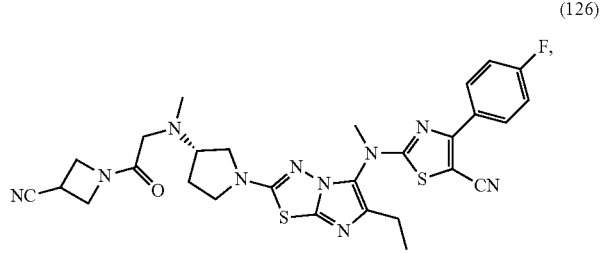
(127)
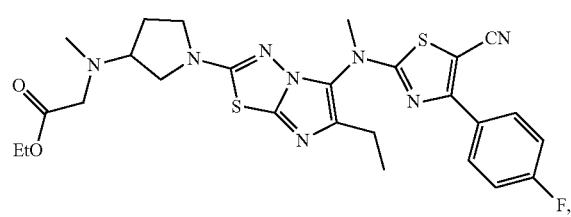
(128)
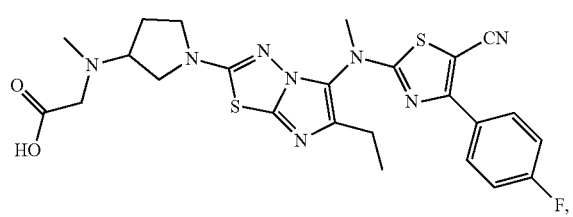
(129)
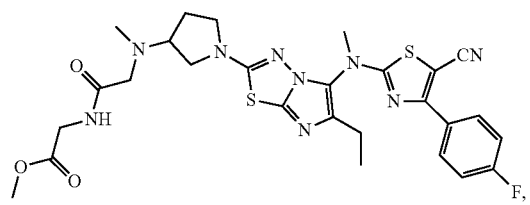
(130)
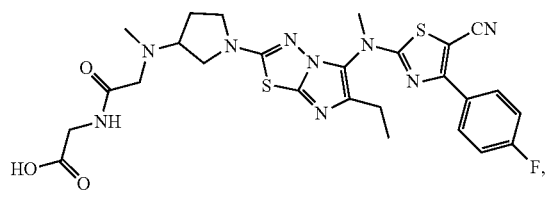
(131)
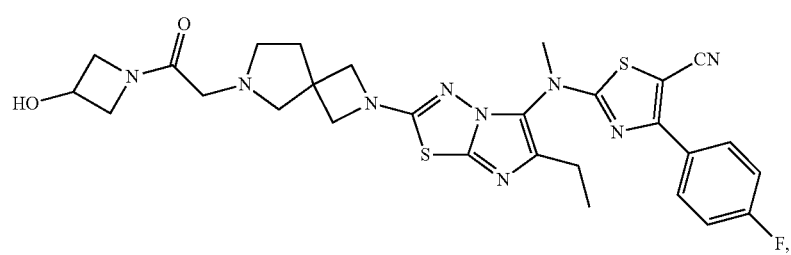

-continued
(132)
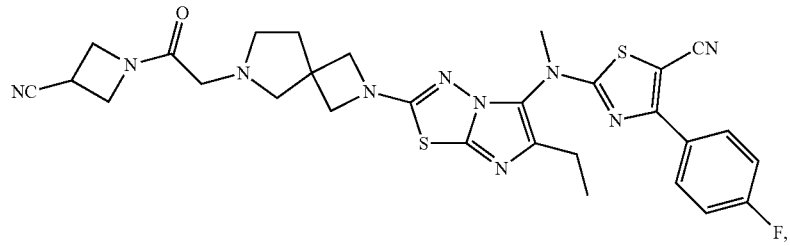
(133)
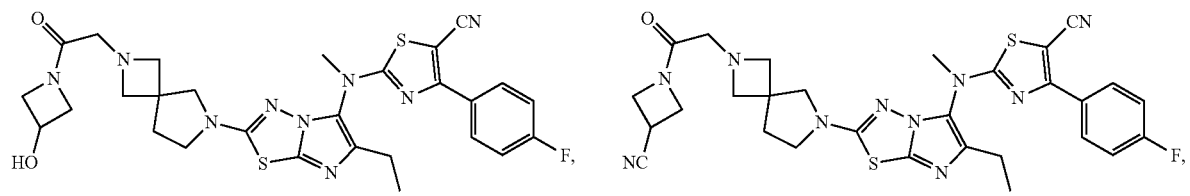
(134)
(135)
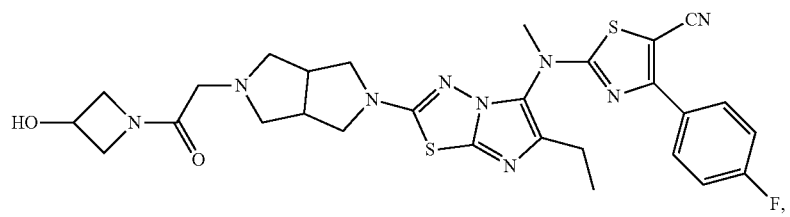
(136)
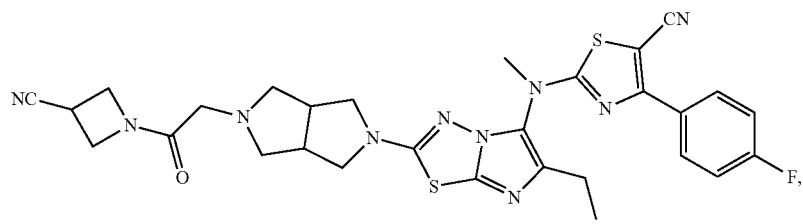
(137)
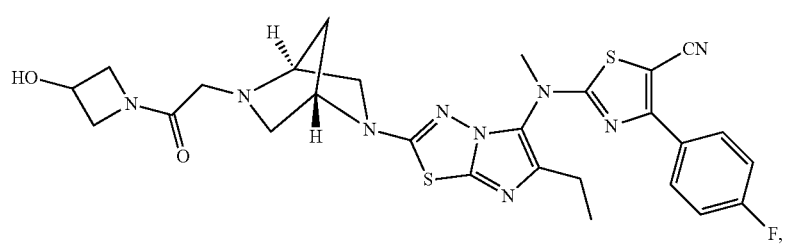
(138)
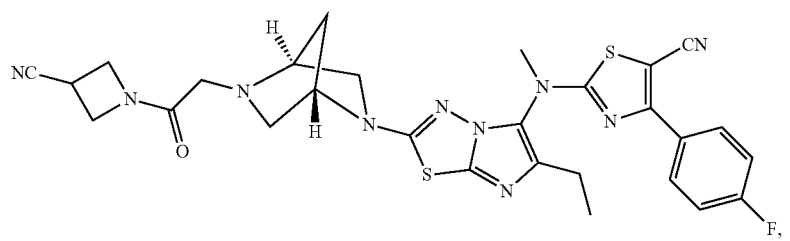
(139)
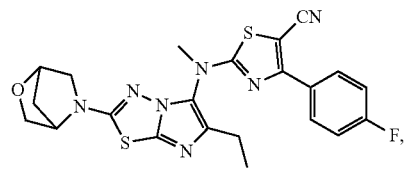
(140)
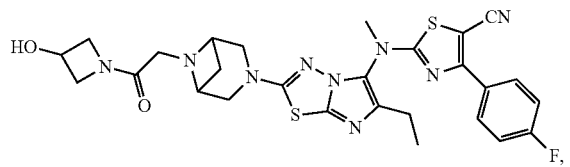

-continued
(141)
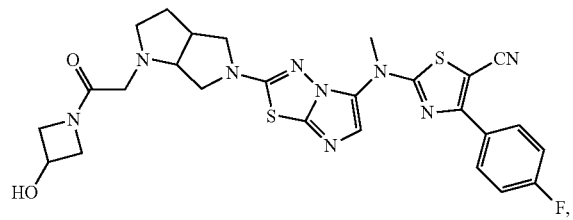
(142)
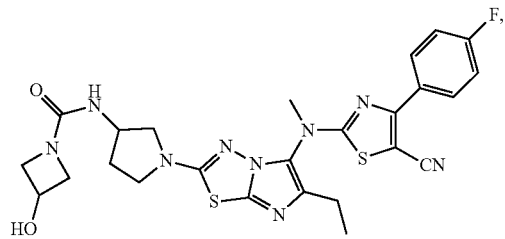
(143)
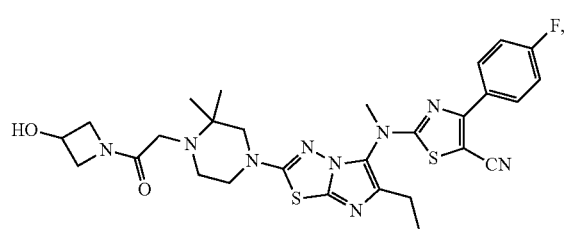
(144)
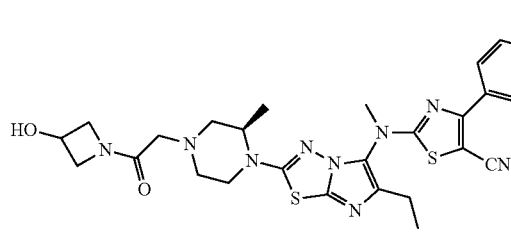
(145)
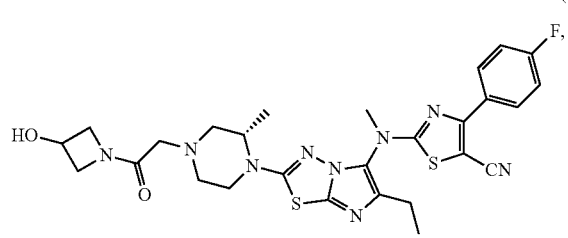
(146)
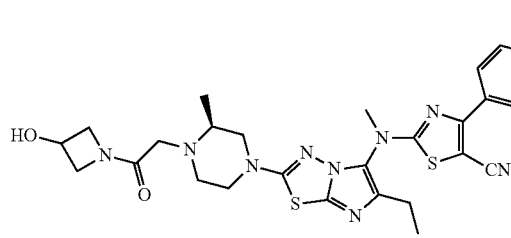
(147)
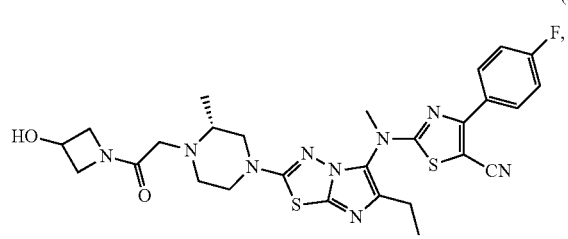
(148)
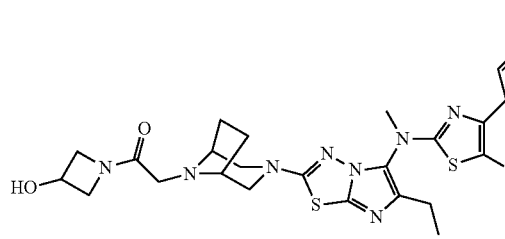
(149)
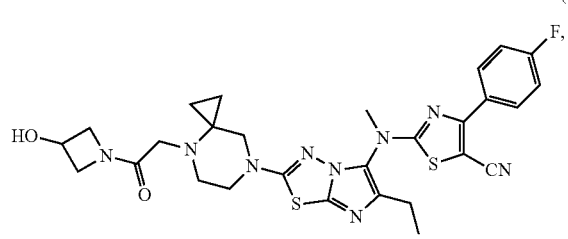
(150)
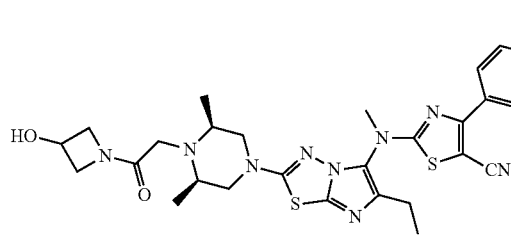
(151)
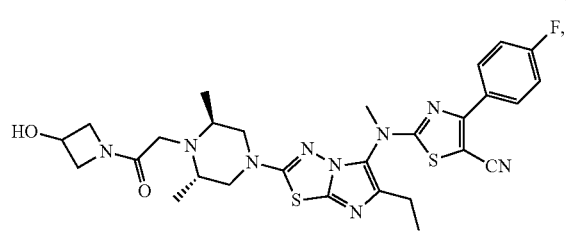
(152)
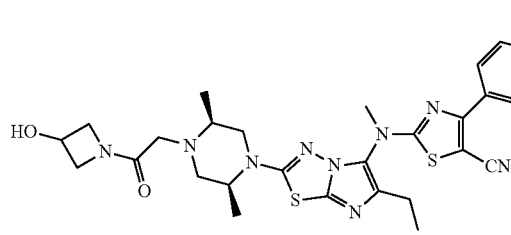

-continued
(153)
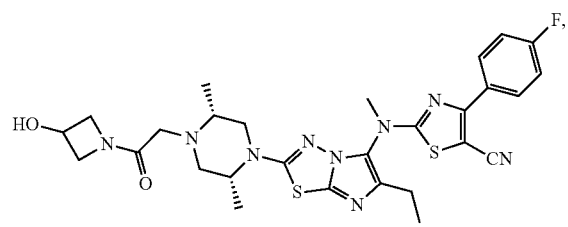
(154)
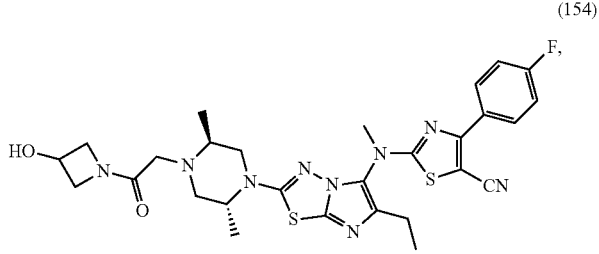
(155)
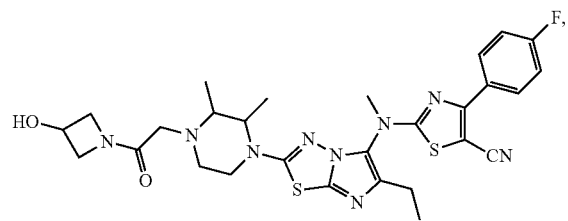
(156)
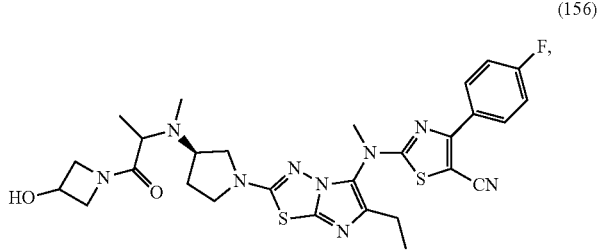
(157)
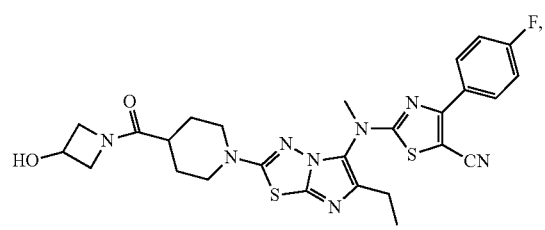
(158)
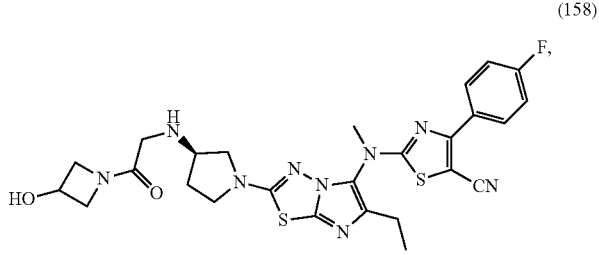
(161)
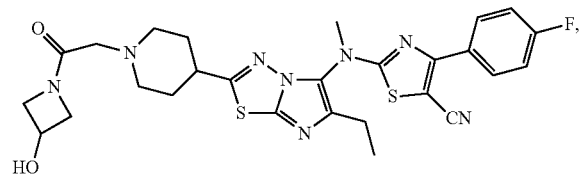
(162)
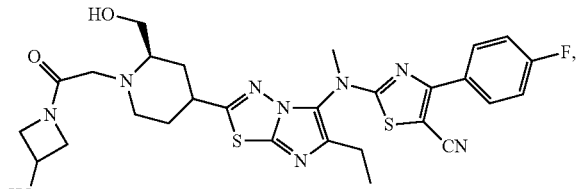
(163)
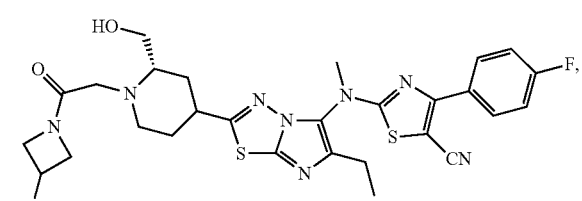
(164)
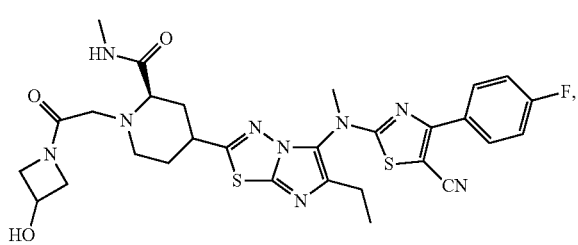
(165)
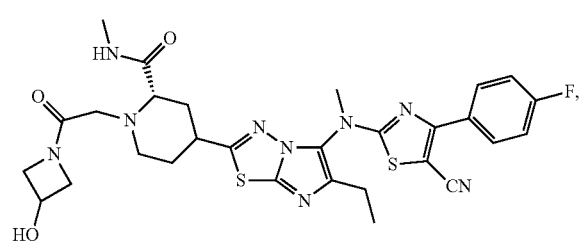
(166)
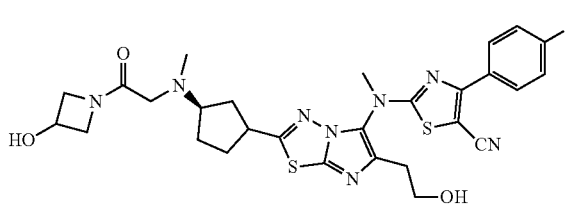

-continued

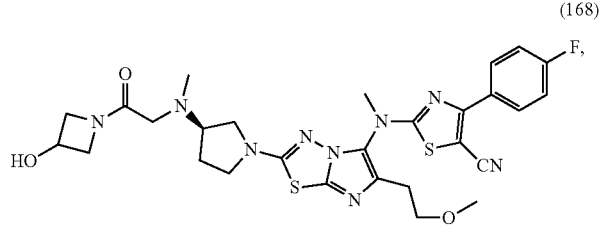
(168)

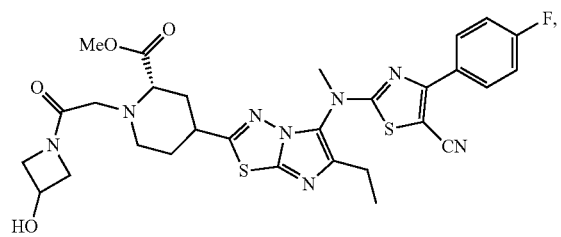
(169)

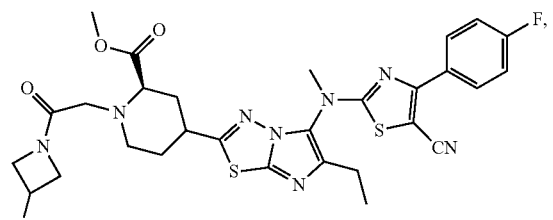
(170)

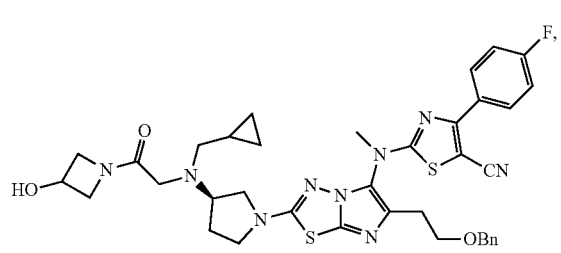
(171)

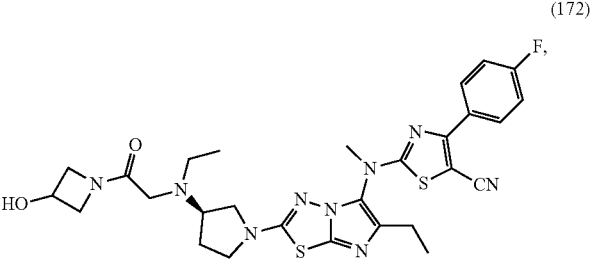
(172)

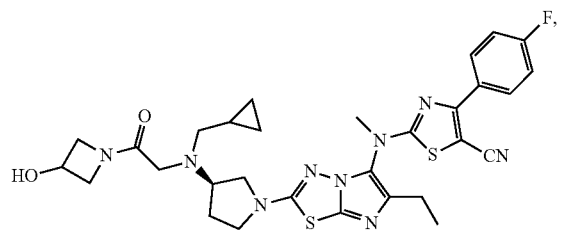
(173)

or or a pharmaceutically acceptable salt, stereoisomer, tautomer, or mixture thereof.

16. A pharmaceutical composition, comprising the compound of claim 1, and a pharmaceutically acceptable excipient, diluent, or carrier.

17. The pharmaceutical composition of claim 16, further comprising an additional therapeutic agent.

18. A method of preventing or treating a fibrotic disease in a mammal, the method comprising administering a therapeutic amount of at least one of the compound of claim 1 and a pharmaceutical composition comprising the compound of claim 1.

19. The method of claim 18, wherein the fibrotic disease is idiopathic pulmonary fibrosis or hepatic fibrosis.

* * * * *